(12) United States Patent
Suh et al.

(10) Patent No.: US 9,879,081 B2
(45) Date of Patent: Jan. 30, 2018

(54) PROTEIN COMPLEX, BISPECIFIC ANTIBODY INCLUDING THE PROTEIN COMPLEX, AND METHOD OF PREPARATION THEREOF

(71) Applicant: Samsung Electronics Co., Ltd., Suwon-si, Gyeonggi-do (KR)

(72) Inventors: Hye Young Suh, Hwaseong-si (KR); Jae Il Lee, Yongin-si (KR); Su-Jeong Hwang, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/315,068

(22) Filed: Jun. 25, 2014

(65) Prior Publication Data

US 2014/0378664 A1    Dec. 25, 2014

(30) Foreign Application Priority Data

Jun. 25, 2013  (KR) .................. 10-2013-0073358
Jun. 25, 2013  (KR) .................. 10-2013-0073361

(51) Int. Cl.
*C07K 16/00* (2006.01)
*C07K 16/28* (2006.01)
*C07K 16/32* (2006.01)
*C07K 16/46* (2006.01)
*C07K 16/22* (2006.01)

(52) U.S. Cl.
CPC .......... *C07K 16/22* (2013.01); *C07K 16/2863* (2013.01); *C07K 16/32* (2013.01); *C07K 16/468* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 6,121,424 A | 9/2000 | Whitlow et al. | |
| 7,262,276 B2 | 8/2007 | Huang et al. | |
| 7,498,024 B2 | 3/2009 | Fang et al. | |
| 7,696,320 B2 | 4/2010 | Ignatovich et al. | |
| 7,951,917 B1 | 5/2011 | Arathoon et al. | |
| 8,034,905 B2 | 10/2011 | Kavlie et al. | |
| 8,227,577 B2 | 7/2012 | Klein et al. | |
| 8,394,943 B2 | 3/2013 | Kavlie et al. | |
| 8,475,766 B2 | 7/2013 | Collinson et al. | |
| 2003/0077282 A1 | 4/2003 | Bigler et al. | |
| 2003/0105000 A1* | 6/2003 | Pero ................. | A61K 38/06 514/19.3 |
| 2005/0079184 A1 | 4/2005 | Hsing-Chang et al. | |
| 2005/0255115 A1 | 11/2005 | Huang et al. | |
| 2006/0088529 A1 | 4/2006 | Leung et al. | |
| 2006/0099686 A1 | 5/2006 | Fiedler et al. | |
| 2008/0138339 A1 | 6/2008 | Huang et al. | |
| 2008/0171851 A1 | 7/2008 | Fiedler et al. | |
| 2009/0169553 A1* | 7/2009 | Day .................. | C12N 9/647 424/139.1 |
| 2009/0175791 A1 | 7/2009 | Kavile et al. | |
| 2009/0175851 A1 | 7/2009 | Klein et al. | |
| 2010/0015133 A1 | 1/2010 | Igawa et al. | |
| 2010/0254988 A1* | 10/2010 | Bossenmaier ..... | C07K 16/2863 424/136.1 |
| 2011/0104176 A1* | 5/2011 | Cheong ............. | C07K 16/2863 424/152.1 |
| 2011/0236388 A1 | 9/2011 | Baehner et al. | |
| 2011/0287009 A1* | 11/2011 | Scheer ............... | C07K 16/244 424/136.1 |
| 2012/0064001 A1 | 3/2012 | Kavlie et al. | |
| 2012/0134993 A1 | 5/2012 | Pan et al. | |
| 2013/0149238 A1 | 6/2013 | Kavlie et al. | |
| 2013/0196377 A1* | 8/2013 | Lee .................. | C07K 16/468 435/69.6 |

(Continued)

FOREIGN PATENT DOCUMENTS

| | | |
|---|---|---|
| EP | 1394253 A1 | 3/2004 |
| JP | 2011-201893 A | 10/2011 |
| KR | 2008-0013875 A | 2/2008 |

(Continued)

OTHER PUBLICATIONS

Burgess et al. (J of Cell Bio. 111:2129-2138, 1990).*
Rudikoff et al. (PNAS USA, 1982, 79: 1979-1983).*
Coleman et al. (Research in Immunology, 1994; 145(1): 33-36).*
Abaza et al. (Journal of Protein Chemistry, vol. 11, No. 5, 1992, pp. 433-444).*
Gussow et al. (1991, Methods in Enzymology 203:99-121).*
Ibragimova and Wade (Biophysical Journal, Oct. 1999, vol. 77, pp. 2191-2198).*

(Continued)

*Primary Examiner* — Peter J Reddig
(74) *Attorney, Agent, or Firm* — Leydig, Voit & Mayer, Ltd.

(57) ABSTRACT

A protein complex comprising a first polypeptide comprising a first antigen-binding region; a second polypeptide comprising a second antigen-binding region; and a linker connecting the first polypeptide and the second polypeptide, wherein the first antigen-binding region is a single stranded polypeptide comprising a first light chain antigen-binding region and a first heavy chain antigen-binding region, the second antigen-binding region is a single stranded polypeptide comprising a second light chain antigen-binding region and a second heavy chain antigen-binding region, and the linker connects the C-terminal of the first polypeptide and the N-terminal of the second polypeptide, and comprises a tag including a cleavable amino acid sequence at one terminal or both terminals of the linker; as well as a bispecific antibody derived from the protein complex, and related compositions and methods.

18 Claims, 42 Drawing Sheets

(56) References Cited

U.S. PATENT DOCUMENTS

2014/0081002 A1* 3/2014 Lee .................... C07K 16/468
530/387.3
2014/0127210 A1* 5/2014 Kim .................... C07K 16/468
424/136.1

FOREIGN PATENT DOCUMENTS

| KR | 2008-0074231 A | 8/2008 |
| KR | 2010-0087397 A | 8/2010 |
| KR | 2010-0102110 A | 9/2010 |
| KR | 2011-0068814 A | 6/2011 |
| KR | 2013-0074348 A | 7/2013 |
| WO | WO 2010/111625 A1 | 9/2010 |

OTHER PUBLICATIONS

Ridgway et al, "'Knobs-into-holes' engineering of antibody $C_H3$ domains for heavy chain heterodimerization", *Protein Engineering*, 9(7): 617-621 (1996).

* cited by examiner

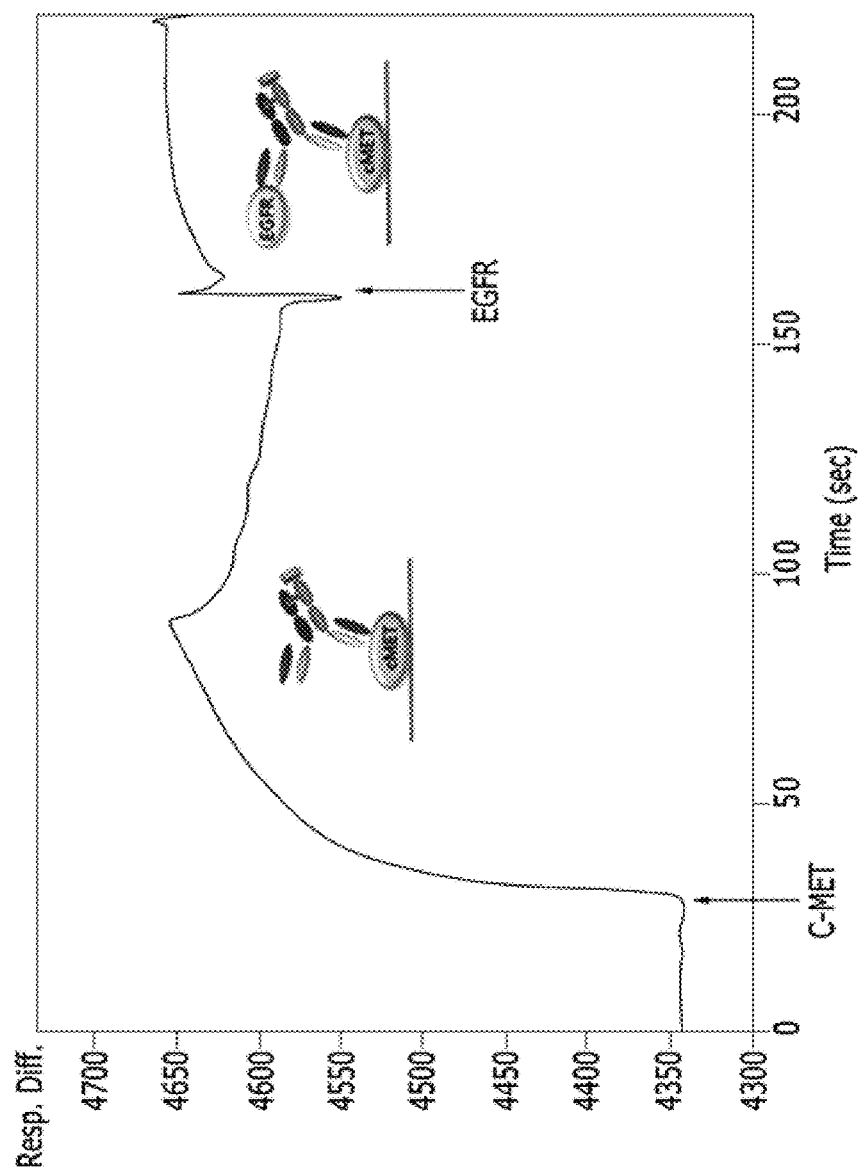

FIG. 10B

| | Ka (1 / Ms) | Kd (1 / s) | KD (M) | |
|---|---|---|---|---|
| C-MET | 1.281E+5 | 2.296E-8 | 1.792E-13 | MxM |
| | Ka (1 / Ms) | Kd (1 / s) | KD (M) | |
| | 1.072E+5 | 1.877E-8 | 1.750E-13 | M kinetics (MxE) |

| | Ka (1 / Ms) | Kd (1 / s) | KD (M) | |
|---|---|---|---|---|
| EGFR | 4.837E+4 | 3.290E-8 | 6.802E-9 | ExE |
| | Ka (1 / Ms) | Kd (1 / s) | KD (M) | |
| | 7.294E+4 | 3.395E-4 | 4.654E-9 | E kinetics (ExE) |

FIG. 19

| Sample | $K_D$ (nM) | $K_a$ (1/Ms) | $K_d$ (1/s) | Chi$^2$ | U-Value | T ($k_a$) | T ($k_d$) |
|---|---|---|---|---|---|---|---|
| M x M | <0.01 | 1.281 x 10$^5$ | 2.296 x 10$^{-8}$ | 1.54 | 95 | 3.8 x 10$^2$ | 0.89 |

| Sample | $K_D$ (nM) | $K_a$ (1/Ms) | $K_d$ (1/s) | $Chi^2$ | U-Value | $T(k_a)$ | $T(k_d)$ |
|---|---|---|---|---|---|---|---|
| M x M | <0.1 | 3.809 x $10^5$ | 8.280 x $10^{-8}$ | 2.93 | 95 | 2.1 x $10^2$ | 0.85 |

FIG. 28

```
                        edge,interface
                        ---------------
                     B i B I B I    B i
     IgG   G Q P R E P Q V Y T L P P S R E E M T K N Q
     IgA   G N T F R P Q V H L L P P P S E ELA L B Z L
     IgD   Q A P V K L G L N L L A S S D P - - P E A A
     IgE   G P R A A P E V Y A F A T P E W P G S R D K
     IgM   - D Z B T A I R V F A I P P S F ASIFL T K S
                            350                 360 middle,interface              exterior
        -----------------           -----------
        B I B I B I B i             B   B   B
     IgG V S L T C L V K G F Y P S D I A V E W E S N
     IgA V T L T C L A R G F S P K D V L V R W L Q G
     IgD S W L L C B V S G F S P P N I L L M W L EDQ
     IgE R T L A C L I Q N F M P E D I S V Q W L H N
     IgM T K L T C L V T D L T T Y BSV T I S W T R Z
                     370                   380 edge,interface
                        ---------------------
                          I          i       I
     IgG   D - G Q P E N N Y K T T P P V/M L D S D G S
     IgA   S Q E L P R E K Y L T W A S R   Q Z PSQGTTT
     IgD   R E V N T S G F A P A R P P P   Q P G S T T
     IgE   E V Q L P D A R H S T T Q P R   K T K G S G
     IgM   D - - G E A V K T H T B I S Z   S H P B A T
                        390                 400 middle,interface                       exterior
        -----------------                    ------------
        B I B I B I   B i B           B      B   B   B
     IgG P F L Y S K/R L T V D K S R W Q Q G N V F S C S V M
     IgA F A V T S I   L R V A A E D W K K G D T F S C M V G
     IgD F W A W S V   L R V P A P P S P Q P A T Y T C V V S
     IgE F F V P S R   L E V T R A E W E Q K D E F I C R A V
     IgM F S A V G E   A S I C E B B W B S G E R F T C T V T
                      410                   420 exterior
                    ---------------
        B             b   b   b
     IgG H E A L H N H Y T Q K S L S L S P G K
     IgA H E A L P L A F T Q K T I D R L A G K
     IgD H E D - S R T L L N A S R S L E V S Y
     IgE H E A ASP S Q T V Q R A V S V N P G K
     IgM H T D L P S P L K Q T I S R P K - - -
         430               440
```

PROTEIN COMPLEX, BISPECIFIC ANTIBODY INCLUDING THE PROTEIN COMPLEX, AND METHOD OF PREPARATION THEREOF

CROSS-REFERENCE TO RELATED APPLICATIONS

This application claims the benefit of Korean Patent Application No. 10-2013-0073358, filed on Jun. 25, 2013, in the Korean Intellectual Property Office, and Korean Patent Application No. 10-2013-0073361, filed on Jun. 25, 2013, in the Korean Intellectual Property Office, the entire disclosures of which are hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 307,762 Bytes ASCII (Text) file named "716609_ST.25.TXT," created on Jun. 25, 2014.

BACKGROUND

1. Field

A protein complex including two different antigen-binding regions, a bispecific antibody obtained from the protein complex, and a method of the same are provided.

2. Description of the Related Art

As monoclonal antibodies have emerged as strong candidates of new drug markets, they have been developed into therapeutic agents against various targets. However, they have failed to show satisfactory drug efficacy on many occasions, and antibody production can be very expensive. Thus, developing new drugs based on such antibodies can be challenging. As one of the methods for solving such problems, research on bispecific antibodies has been steadily conducted since the mid-1980s but despite numerous efforts, a leading technology has not yet materialized.

Producing homogeneous bispecific antibodies in large quantities using existing methods for preparing bispecific antibodies has proven difficult, and due to their low efficacy and side effects, there have been difficulties in their practical use. Lately, competitive new antibody platforms have emerged utilizing antibody engineering technology, but they are still in the verification stage.

Therefore, there is need of developing bispecific antibodies having excellent efficacy and little side effects, and more efficient methods for preparing them.

SUMMARY

Provided is a protein complex including a first polypeptide including a first antigen-binding region; a second polypeptide including a second antigen-binding region; and a linker connecting the first polypeptide and the second polypeptide. The first antigen-binding region is a polypeptide including a first light chain antigen-binding region and a first heavy chain antigen-binding region, and the second antigen-binding region is a polypeptide including a second light chain antigen-binding region and a second heavy chain antigen-binding region. The linker connects the C-terminal of the first polypeptide and the N-terminal of the second polypeptide, and includes a tag including a cleavable amino acid sequence at one terminal or both terminals of the linker.

In an embodiment, one of the first polypeptide and the second polypeptide includes at least one amino acid residue forming at least one knob on a site not located within the antigen-binding region, and the other of the first or second polypeptide includes at least one amino acid residue forming at least one hole on a site not located within the antigen-binding region. The knob and hole can be coupled to one another.

Also provided is a bispecific antibody that can be obtained by cleaving the tag of the protein complex. Thus, the bispecific antibody includes a first polypeptide including a first antigen-binding region and a second polypeptide including a second antigen-binding region, wherein the first antigen-binding region is a polypeptide including a first light chain antigen-binding region and a first heavy chain antigen-binding region and the second antigen-binding region is a polypeptide including a second light chain antigen-binding region and a second heavy chain antigen-binding region. One of the first polypeptide and the second polypeptide includes at least one amino acid residue forming at least one knob on a site not located within the antigen-binding region, and the other of the first or second polypeptide includes at least one amino acid residue forming at least one hole on a site not located within the antigen-binding region, such that the knob of one polypeptide is coupled to the hole of the other polypeptide.

A polynucleotide encoding the protein complex, as well as a method of preparing the protein complex or bispecific antibody, and related compositions and methods, also are provided.

BRIEF DESCRIPTION OF THE DRAWINGS

FIG. 10A is a graph and illustration showing the binding affinity result of the bispecific antigen-antibody reaction of an anti c-Met/EGFR bispecific antibody produced from a c-Met/EGFR double binding protein complex according to one embodiment, measured by Surface Plasmon Resonance (SPR) methods;

FIG. 10B are graphs showing the binding affinity results of an anti c-Met/EGFR bispecific antibody (M×E) according to one embodiment toward EGFR and c-Met, compared to a monovalent antibody (M×M or E×E, wherein M: c-Met, E: EGFR);

FIG. 19 is a table showing the affinity result of a c-Met/Ang2 bispecific antibody produced from a c-Met/Ang2 double binding protein complex toward c-Met (M×M: anti-cMet monospecific bivalent Ab);

FIG. 28 shows the interface residues of the CH3 domain of the immunoglobulins IgG (SEQ ID NO: 147), IgA (SEQ ID NO: 148), IgD (SEQ ID NO: 149), IgE (SEQ ID NO: 150) and IgM (SEQ ID NO: 151).

DETAILED DESCRIPTION

Figure 1:
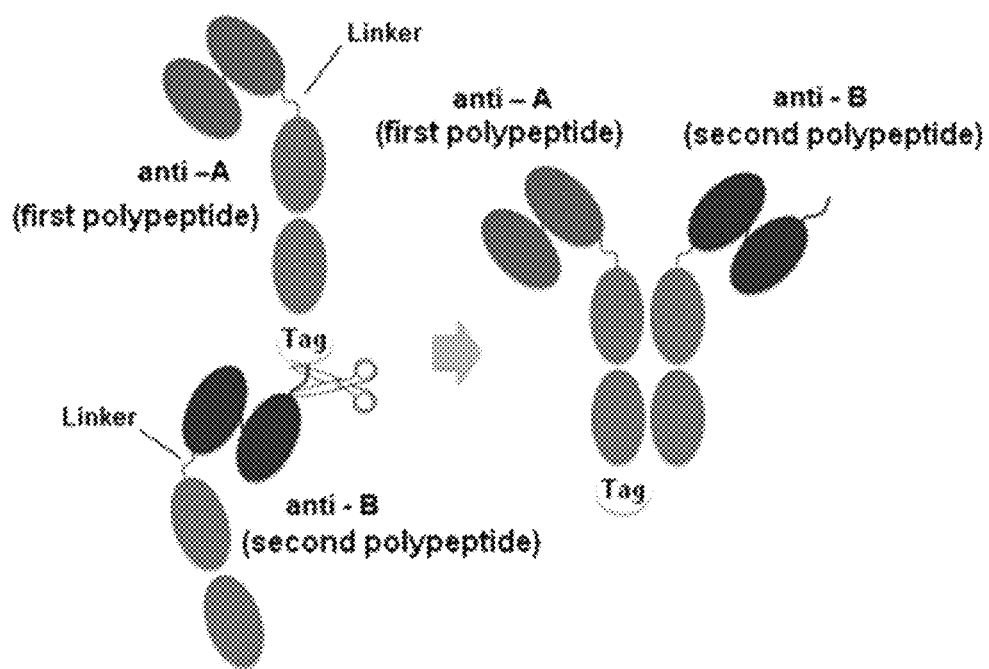
FIG. 1 illustrates the preparation of a bispecific antibody using a single stranded first polypeptide, a second polypeptide, a linker, and a tag.

A dimer is formed via Fc regions during the general formation process of an antibody. The formation rate of a bispecific antibody having a right and left asymmetric structure (heterodimer) can be low in comparison to a bispecific antibody having a symmetric structure (homodimer).

Accordingly, the present disclosure provides a technology of preparing a scFv-Fc bispecific antibody that, in at least some embodiments, yields an improved heterodimer formation rate.

One embodiment provides a protein complex, wherein the protein complex may include a first polypeptide including a first antigen-binding region; a second polypeptide including a second antigen-binding region; and a first linker connecting the first polypeptide and the second polypeptide.

The first antigen-binding region may include a first light chain antigen-binding region or a first heavy chain antigen-binding region, or may be a single stranded polypeptide including the first light chain antigen-binding region and the first heavy chain antigen-binding region, where the first light chain antigen-binding region and the first heavy chain antigen-binding region are linked. The first antigen-binding region may be located at the N-terminal of the first polypeptide.

The second antigen-binding region may include a second light chain antigen-binding region or a second heavy chain antigen-binding region, or may be a single stranded polypeptide including the second light chain antigen-binding region and the second heavy chain antigen-binding region, where the second light chain antigen-binding region and the second heavy chain antigen-binding region are linked. The second antigen-binding region may be located at the N-terminal of the second polypeptide.

The first linker may connect the C-terminal of the first polypeptide and the N-terminal of the second polypeptide. The first linker may be linked to a tag including a cleavable amino acid sequence (e.g., cleavage site to be cleaved by enzymes such as proteases) at one terminal or both terminals of the linker, that is, toward either one terminal linked to the C-terminal of the first polypeptide and the N-terminal of the second polypeptide or toward both terminals.

In particular, the protein complex may include a first polypeptide, a second polypeptide linked toward the C-terminal of the first polypeptide, and a first linker connecting the C-terminal of the first polypeptide and the N-terminal of the second polypeptide.

The term "linked toward" as used in the specification may refer to being directly linked to the terminal or indirectly linked via a linker, etc.

The first antigen-binding region of the first polypeptide may be a polypeptide in a single stranded form (scFv; single-chain variable-region fragment) where a first light chain antigen-binding region and a first heavy chain antigen-binding region are linked. The first light chain antigen-binding region and the first heavy chain antigen-binding region may be linked at any position and/or in any order. The first light chain antigen-binding region and the first heavy chain antigen-binding region may be linked via a linker (hereafter, referred to as a second linker) or without it (e.g., directly). For example, the first polypeptide may be a form where the C-terminal of the first light chain antigen-binding region and the N-terminal of the first heavy chain antigen-binding region are linked via the second linker or without it, or a form where the C-terminal of the first heavy chain antigen-binding region and the N-terminal of the first light chain antigen-binding region are linked via the second linker or without it. In other words, the first antigen-binding region of the first polypeptide may include the first light chain antigen-binding region toward its N-terminal and the first heavy chain antigen-binding region toward its C-terminal, or include the first heavy chain antigen-binding region toward its N-terminal and the first light chain antigen-binding region toward its C-terminal, and optionally include the second linker connecting them.

Likewise, the second antigen-binding region of the second polypeptide may be a polypeptide in a single stranded form (scFv) where a second light chain antigen-binding region and a second heavy chain antigen-binding region are linked. The second light chain antigen-binding region and the second heavy chain antigen-binding region may be linked at any position and/or in any order. The second light chain antigen-binding region and the second heavy chain antigen-binding region may be linked via a linker (hereafter, referred to as a third linker) or without it. For example, the second polypeptide may be a form where the C-terminal of the second light chain antigen-binding region and the N-terminal of the second heavy chain antigen-binding region are linked through the third linker or without it, or a form where the C-terminal of the second heavy chain antigen-binding region and the N-terminal of the second light chain antigen-binding region are linked via the third linker or without it. In other words, the second antigen-binding region of the second polypeptide may include the second light chain antigen-binding region toward its N-terminal and the second heavy chain antigen-binding region toward its C-terminal, or include the second heavy chain antigen-binding region toward its N-terminal and the second light chain antigen-binding region toward its C-terminal, and optionally include the third linker connecting them.

The first linker, the second linker, and the third linker may be peptide linkers identical to or different from one another. The first linker may be linked to a tag including a cleavable amino acid sequence inside the linker toward either one end terminal (toward the C-terminal of the first polypeptide or toward the N-terminal of the second polypeptide) or toward both terminals, and the cleavable amino acid sequence may refer to a cleavage site to be cleaved by enzymes such as proteases.

Further, the remaining regions of the protein complex (excluding the first antigen-binding region and the second antigen-binding region of the first polypeptide and the second polypeptide) may include all or part of the heavy chain constant regions of an antibody, for example, all or part of Fc region (e.g., CH3 domain and/or CH2 domain) and/or a hinge region connecting the first antigen-binding region and the second antigen-binding region, respectively to all or part of the Fc region. The Fc region can be of any immunoglobulin subtype.

In one embodiment, the first polypeptide and the second polypeptide in the protein complex may contain some mutations of amino acid residues to the region of the protein complex excluding (i.e., not located within) the first antigen-binding region and the second antigen-binding region such that the first polypeptide and the second polypeptide can form a dimer. Such mutations can be introduced to the heavy chain constant regions of each polypeptide, for example, the Fc region (e.g., CH3 domain) of immunoglobulin.

The design of such mutations can be informed, for example, through the introduction of a "knob-into-hole" principle. Specifically, the first polypeptide and the second polypeptide may include amino acid residues that form one or more knobs or one or more holes which can be mutually coupled in the region of the protein complex excluding (i.e., not located within) the first antigen-binding region and the second antigen-binding region (all or part of the heavy chain constant regions), for example, the Fc region (e.g., CH3 domain). For example, the knobs may be formed in the all or part of the heavy chain constant regions of any one polypeptide of the first polypeptide and the second polypeptide, for example, the Fc region (e.g., CH3 domain), the holes may be formed in the all or part of the heavy chain constant regions of the other polypeptide, for example, the Fc region (e.g., CH3 domain), and in particular, the knobs and the holes may be formed at mutually corresponding locations on the Fc region of each polypeptide (e.g., CH3 domain). One or more knob-hole pairs may be included in the region of the protein complex excluding (i.e., not including) each antigen-binding region of the first polypeptide and the second polypeptide.

As described above, the first polypeptide and the second polypeptide may include amino acid residues that form one or more knobs or holes in the region of the protein complex excluding (i.e., not including) the first antigen-binding region and the second antigen-binding region (all or part of the heavy chain constant regions), for example, the Fc region, particularly CH3 domain, and form a dimer (heterodimer) by being mutually coupled through them. For example, the Fc region of any one polypeptide of the first polypeptide and the second polypeptide (e.g., CH3 domain) include one or more knobs, the Fc region of the other polypeptide (e.g., CH3 domain) include one or more holes, and they are mutually coupled, whereby a bispecific antibody having a right and left asymmetric structure can be formed.

In general, when an antibody is formed in the cells, two heavy chain Fc regions are mutually coupled to form a dimer. In particular, as in the process of preparing a bispecific antibody, the chances that homodimers and heterodimers are to be formed are similar according to the above general antibody production method, the formation rate of a bispecific antibody having a right and left asymmetric structure (heterodimer) can become low.

The protein complex according to one embodiment of the present invention includes amino acid residues that form one or more knobs or one or more holes which can be mutually coupled to each other in the region of the first polypeptide and the second polypeptide excluding the first antigen-binding region and the second antigen-binding region (e.g., Fc regions, specifically CH3 domain), thereby forming a knob-hole binding to increase the formation rate of heterodimers so that it can improve the production efficiency of a bispecific antibody having a right and left asymmetric structure.

The terms "knob" and "hole" as used in the specification refer to structures in relatively protruding (knob) or indented (hole) forms on the three dimensional structure of a protein complex, which are formed by the mutation of amino acid residues on the remainder region except the antigen-binding regions of the first polypeptide or the second polypeptide, preferably, on CH3 domain of each polypeptide.

The knob-into-hole principle is a technology of increasing the formation rate of an antibody in an intended heterodimer form by mutating at least one (e.g., about 1 to about 20, about 1 to about 16, about 1 to about 10, about 1 to about 6, or about 1 to about 3) residue present at contact surfaces (interfaces) between the constant regions of each heavy chain, for example, Fc regions, particularly CH3 domain, wherein the mutations may be each carried out differently on each heavy chain constant region of the first polypeptide and the second polypeptide, for example, Fc regions, particularly, CH3 domain. In detail, the Fc region of any one of the first polypeptide and the second polypeptide, particularly CH3 domain may be mutated to include residues having relatively larger (protruding) side chains than neighboring amino acid residues, and the Fc region of the other, particularly CH3 domain may be mutated to include residues having relatively smaller (indented) side chains than neighboring amino acid residues. The knobs and holes may be present at locations corresponding to each other in each Fc region of the first polypeptide and the second polypeptide, particularly CH3 domain, such that the knob of one polypeptide is coupled to the hole of the other polypeptide. More than one knob/hole pair can be present.

The knob is formed (or created) by replacing at least one (e.g., about 1 to about 20, about 1 to about 16, about 1 to about 10, about 1 to about 6, or about 1 to about 3) amino acid within Fc region (e.g., CH3 domain) of one polypeptide with at least one amino acid residue forming a protruding structure by having relatively larger side chains than neighboring amino acid residues on the three dimensional structure of a protein and for example, the amino acid residue having larger side chains may be one or more selected from the group consisting of Arg, Phe, Tyr, and Trp. The hole is formed (or created) by replacing at least one (e.g., about 1 to about 20, about 1 to about 16, about 1 to about 10, about 1 to about 6, or about 1 to about 3) amino acid within Fc region (e.g., CH3 domain) of the other polypeptide with at least one amino acid residue forming an indented structure by having relatively smaller side chains than neighboring amino acid residues on the three dimensional structure of a protein and preferably, the amino acid residue having smaller side chains may be one or more selected from the group consisting of Ala, Ser, Thr, Gly and Val. The amino acid residues may be selected from natural or non-natural amino acids. The protein complex may comprise at least one knob/hole pair, for example, about 1 to about 20, about 1 to about 10, about 1 to about 5, or about 1 to about 3 knob/hole pairs. The knob and hole may be naturally or non-naturally occurring. The Fc region (e.g., CH3 domain) may be from any immunoglobulin subtype, for example, an immunoglobulin selected from the group consisting of IgG (e.g., a subtype selected from the group consisting of IgG1, IgG2a, IgG2b, IgG3 and IgG4), IgA, IgD, IgE and IgM. The contact residue to be replaced on the first or second polypeptide can correspond to at least one IgG residue selected from the group consisting of amino acid residues 347, 349, 350, 351, 366, 368, 370, 392, 394, 395, 397, 398, 399, 405, 407 and 409, for example, selected from the group consisting of amino acid residues 366, 368, 370, 405, 407 and 409, according to the amino acid numbering as shown in FIG. 28.

FIG. 28 shows the interface residues of the CH3 domain of the immunoglobulins IgG (SEQ ID NO: 147), IgA (SEQ ID NO: 148), IgD (SEQ ID NO: 149), IgE (SEQ ID NO: 150) and IgM (SEQ ID NO: 151). The CH3 domain of each of these immunoglobulins is made up of a "β-sandwich", which is comprised of two separate and parallel "β-sheets". One of the β-sheets provides the interface residues, the other is the "exterior β-sheet". The β-sheet forming the interface is formed from four "β-strands". The residues of each of the seven β-strands of the CH3 domain of the various immunoglobulins are identified by dashed overlining. The residues in the middle and edge β-strands of the interface are identified, as are those of the exterior β-sheet. Residue numbering is according to Fc crystal structure. The residues buried in the interior of the CH3 domain are identified with a "B", those which are partially buried in the interior of the CH3 domain are identified with a "b", those "contact" residues which are partially buried at the interface (i.e. 26%-10% exposed) are identified with an "i" and those which are buried at the interface (i.e. <6% exposed) are identified with an "I". The bold residues are optimal candidate original residues for replacement with import residues. The amino acids forming the knob and hole can be any combinations of amino acids as long as the amino acid residues can be mutually coupled to each other. For example, the pair of the amino acid sequences forming the knob and hole, respectively, may be Arg/Ala (knob/hole), Phe/Ser(knob/hole), Tyr/Thr(knob/hole), or Trp/Val(knob/hole), but is not limited thereto.

Figure 2:
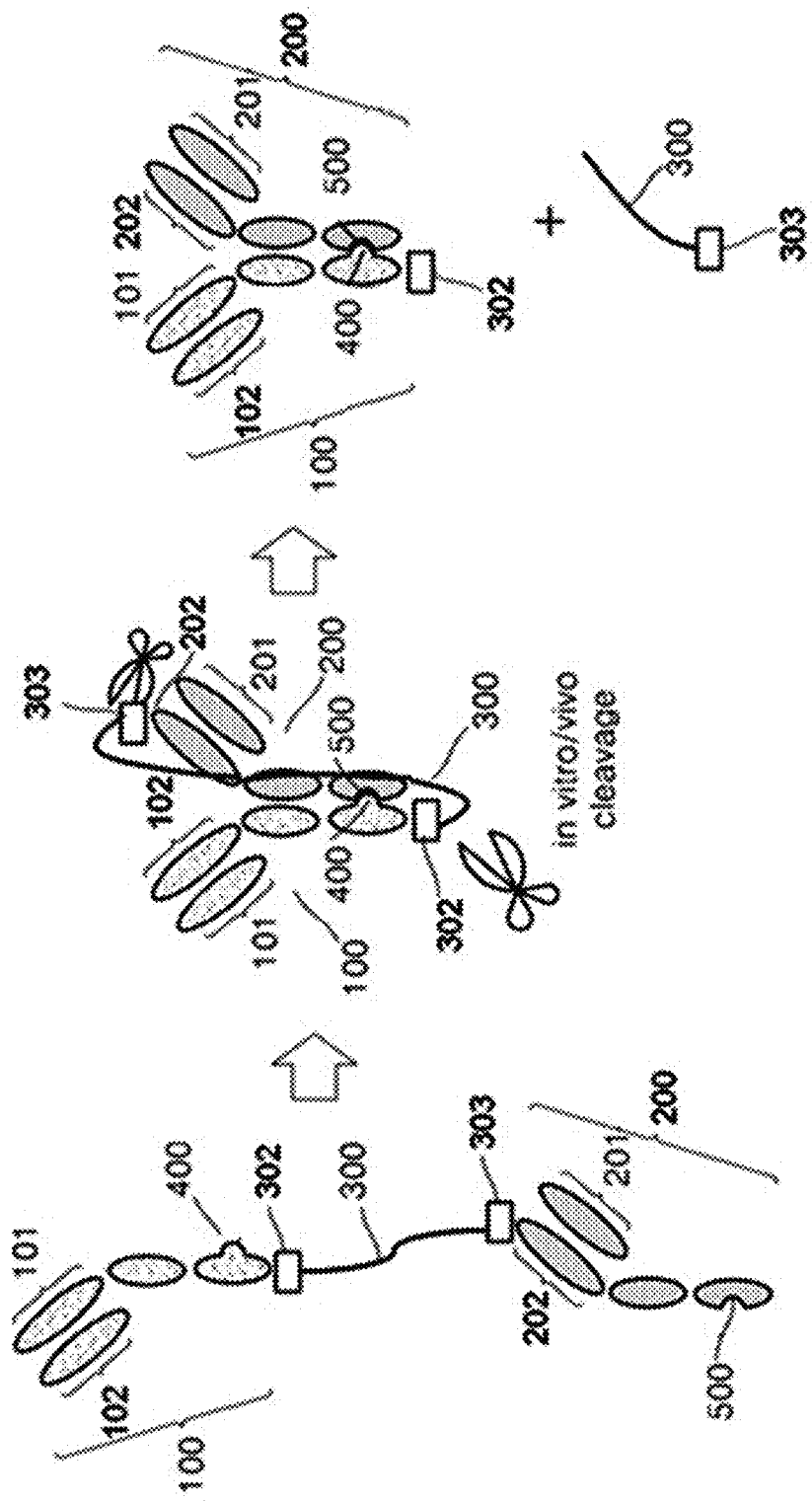
FIG. 2 illustrates preparation of a bispecific antibody using a first polypeptide, a second polypeptide, a linker, a first tag, a second tag, and a knob-hole formed in the CH3 domain of the first polypeptide and the second polypeptide.

For example, the protein complex may have a structure including a first polypeptide, a second polypeptide, and a first linker containing tags at both of its terminals, wherein the tags are each attached to the C-terminal of the first polypeptide and the N-terminal of the second polypeptide, one of the first polypeptide and the second polypeptide includes amino acid residues forming one or more knobs at its heavy chain constant region, for example, CH3 domain, and the other includes amino acid residues forming one or more holes at its heavy chain constant region, for example, CH3 domain region (see FIG. 2). Alternatively, the protein complex may have a structure including a first polypeptide, a second polypeptide, and a first linker containing a tag at its one terminal, wherein the tag is attached to the C-terminal of the first polypeptide or the N-terminal of the second polypeptide, one of the first polypeptide and the second polypeptide includes amino acid residues forming one or more knobs at its heavy chain constant region, for example, CH3 domain region, and the other includes amino acid residues forming one or more holes at its heavy chain constant region, for example, CH3 domain region (see FIG. 3).

According to one embodiment, the remainder region except the first antigen-binding region and the second antigen-binding region where the knobs and holes are located may be Fc portions of an antibody, for example, CH3 domain.

The protein complex according to one embodiment of the disclosure can increase binding ability between the first polypeptide and the second polypeptide by including one or more knobs and holes that can be mutually coupled to each other as described above, to thereby enhance the formation rate of a dimer.

The term "antigen-binding region" as used in the specification is interpreted, as a generic term, to encompass sites in an immunoglobulin molecule to which an antigen or an epitope binds, and the antigen-binding region may include CDR (complementarity determining region). The CDR refers to an amino acid sequence found in the hypervariable region of a heavy chain and a light chain of an immunoglobulin. The heavy and light chain may each include three CDRs (CDRH1, CDRH2, CDRH3, and CDRL1, CDRL2, CDRL3). The CDRs of an antibody can provide an essential contact residue for binding to an antigen or an epitope.

Throughout the specification, the term "antigen-binding region" includes a "heavy chain antigen-binding region" and a "light chain antigen-binding region" of an antibody. The "heavy chain antigen-binding region" may include one or more selected from the group consisting of three heavy chain CDRs (CDRH1, CDRH2, and CDRH3) and for example, it may be a heavy chain variable region of an antibody. The "light chain antigen-binding region" may include one or more selected from the group consisting of three light chain CDRs (CDRL1, CDRL2, and CDRL3) and for example, it may be a light chain variable region of an antibody.

The term "heavy chain" is taken to include a full-length heavy chain and fragments thereof, the full-length heavy chain including a variable region domain VH including an amino acid sequence including sufficient variable region sequences that determine specificity for antigens and three constant region domains, CH1, CH2 and CH3 domains. The term "light chain" is taken to include a full-length light chain and fragments thereof, the full-length light chain including a variable region domain VL including an amino acid sequence including sufficient variable region sequences that determine specificity for antigens and a constant region domain, CL.

According to one embodiment, the first polypeptide and the second polypeptide each may be a polypeptide including an antigen-binding region in a single stranded Fab, a single stranded Fab', or a single stranded Fv (scFv) form, and all or part of an Fc (fragment crystalline) domain (e.g., CH3, or CH2 domain). The Fab, which is a structure having the light chain and heavy chain variable regions, the light chain constant region, and the heavy chain first constant region (CH1), has one antigen-binding region. The Fab' differs from Fab in that Fab' has a hinge region including one or more cysteine residues at the C-terminal of the heavy chain CH1 domain. The scFv (single-chain Fv), in general, refers to a structure where the heavy chain variable region and the light chain variable region are linked via a peptide linker.

For example, the first polypeptide and the second polypeptide each may be a single stranded polypeptide including the single stranded antigen-binding region (scFv) where the light chain antigen-binding region and the heavy chain antigen-binding region are linked, and all or part of the Fc domain. The portions of the protein complex excluding (i.e., not including) the antigen-binding regions of the first polypeptide and the second polypeptide may be derived from all kinds of immunoglobulins, for example, IgG types (e.g., IgG1, IgG2, IgG3, IgG4, etc.), IgE type, IgD type, etc., but are not limited thereto.

In the first polypeptide and the second polypeptide, the antigen-binding region (scFv) and the Fc domain (all or part) may be linked via a hinge or without it. In particular embodiments, the hinge may have an amino acid sequence of SEQ ID NO: 100, SEQ ID NO: 101, SEQ ID NO: 102, SEQ ID NO: 103, SEQ ID NO: 104 or SEQ ID NO: 105.

According to one embodiment, the protein complex includes a first linker for connecting the first polypeptide and the second polypeptide. The first linker may link the C-terminal of the first polypeptide, and the N-terminal of the second light chain antigen-binding region or the N-terminal of the second heavy chain antigen-binding region of the second polypeptide. Further, the protein complex may include a second linker for connecting the first light chain antigen-binding region and the first heavy chain antigen-binding region inside the first polypeptide, and/or a third linker for connecting the second light chain antigen-binding region and the second heavy chain antigen-binding region inside the second polypeptide.

The first linker, the second linker, and the third linker may be peptide linkers identical to or different from one another. According to one embodiment, the peptide linker may be a polypeptide, for example, consisting of about 1 to about 100 or about 2 to about 50 arbitrary amino acids. The peptide linker, for example, may include Gly, Asn, and Ser residues, and further include neutral amino acids such as Thr and Ala. Amino acid sequences suitable for the peptide linker are known in the art. Furthermore, the length of the linker may be variably determined within such a limit that does not affect the functions of the fusion protein. In other words, the first, second, and third linkers each independently may include a total of about 1 to about 100, or about 2 to about 50 amino acids selected from the group consisting of Gly, Asn, Ser, Thr, and Ala.

In one embodiment, the first linker may include a tag attached to the C-terminal of the first polypeptide, and link the C-terminal of the tag attached to the C-terminal of the first polypeptide and the N-terminal of the second polypeptide (for example, the N-terminal of the second light chain antigen-binding region or the N-terminal of the second heavy chain antigen-binding region). In another embodiment, the first linker may include a tag attached to the N-terminal of the second polypeptide (for example, the N-terminal of the second light chain antigen-binding region or the N-terminal of the second heavy chain antigen-binding region), and link the C-terminal of the first polypeptide and the N-terminal of the tag attached to the N-terminal of the second polypeptide. In still another embodiment, the first linker may include a tag attached to the C-terminal of the first polypeptide and a tag attached to the N-terminal of the second polypeptide (for example, the N-terminal of the second light chain antigen-binding region or the N-terminal of the second heavy chain antigen-binding region), and link the C-terminal of the tag attached to the first polypeptide and the N-terminal of the tag attached to the second polypeptide.

The first linker separates space between the first polypeptide and the second polypeptide by a sufficient distance, thereby providing favorable distances so that each polypeptide can be folded into suitable two and three dimensional structures for its proper functioning and at the same time, preventing the first polypeptide and the second polypeptide from being spaced apart more than a certain distance to increase a binding possibility between them and lower the possibility of unwanted homodimers being formed and thus, it can serve to obtain the protein complex in a heterodimer form where the first polypeptide and the second polypeptide are coupled, in a high efficiency.

According to one embodiment, the first linker may include a tag inside it and/or at least one terminal of the both terminals. For example, the tag may be bound to the C-terminal of the first polypeptide, the N-terminal of the second polypeptide, or both of them, and it may include a cleavable amino acid sequence on at least one terminal or inside it. The tag to be bound to the N-terminal of the second polypeptide may be bound to the N-terminal of the second light chain antigen-binding region or the N-terminal of the second heavy chain antigen-binding region.

The term "tag" as used in the specification refers to a protein or polypeptide which is bound to the terminal of the first linker and is a mediator for connecting the polypeptides different from each other. According to one embodiment, the tag may have one terminal bound to the first linker and the other terminal linked to the N-terminal and/or C-terminal of the first polypeptide and/or the second polypeptide. For example, the tag may be bound to the C-terminal of the first polypeptide, and the first linker linked to the tag may link the C-terminal of the tag and the N-terminal of the second polypeptide (see FIG. 3). In another embodiment, the tag may be bound to the N-terminal of the second polypeptide and the first linker linked to the tag may link the N-terminal of the tag and the C-terminal of the first polypeptide. When the tag is a tag to be bound to the N-terminal of the second polypeptide, it may be bound to the N-terminal of the second light chain antigen-binding region or the N-terminal of the second heavy chain antigen-binding region. In another embodiment, the tag may be bound to the C-terminal of the first polypeptide and the N-terminal of the second polypeptide, respectively and the linker may link the C-terminal of the tag bound to the C-terminal of the first polypeptide and the N-terminal of the tag bound to the N-terminal of the second polypeptide (see FIG. 2).

According to one embodiment, the tag may include an in vitro or in vivo cleavable amino acid sequence. The in vitro or in vivo cleavage may be conducted by proteases. According to one embodiment, the tag may be one or more selected from the group consisting of ubiquitin, ubiquitin-like protein, TEV cleavage peptide (peptide including TEV protease cleavage site), and furin cleavage peptide (peptide including furin protease cleavage site), but is not limited thereto.

The TEV protease cleavage site included in the TEV cleavage peptide may be Glu-Asn-Leu-Tyr-Phe-Gln-(Gly/Ser), and the cleavage occurs between Gln-(Gly/Ser). The furin protease cleavage site included in the furin cleavage peptide may be Arg-X-(Arg/Lys)-Arg (X is any amino acid), and the cleavage occurs right after the target sequence.

Ubiquitin (Ub; Gene Accession No.: NP_001170884, NM_001177413), which is the most conservative protein that has been found in nature, consists of 76 amino acids and it is a water-soluble protein showing perfect homology among evolutionally various species such as insects, trout, and humans. Also, ubiquitin is stable against pH changes, is not readily degradable at a high temperature, and is known to be stable against proteases. In this regard, the ubiquitin can improve insolubility of the protein complex and can be cleaved in vitro or in vivo in a safe and easy way.

The ubiquitin-like protein is a protein having similar properties to the ubiquitin and for example, it may be selected from the group consisting of Nedd8 (NP_006147.1, NM_006156.1), SUMO-1 (NP_001005781.1, NM_001005781), SUMO-2 (NP_008868.3, NM_006937.3), NUB1 (NP_001230280.1, NM_001243351.1), PIC1 (AAB40388), UBL3 (NP_009037.1, NM_007106.3), UBL5 (NP_001041706.1, NM_001048241.2), ISG15 (NP_005092.1, NM_005101.3), etc., but is not limited thereto.

The ubiquitin or ubiquitin-like protein (Ubl) may be selected from the group consisting of a wild-type ubiquitin, a wild-type ubiquitin-like protein, a mutant ubiquitin, and a mutant ubiquitin-like protein.

The mutant ubiquitins refer to those where one or more amino acid sequences of the wild-type ubiquitin are replaced by other amino acid sequences and for example, it may include ubiquitin where Lys of the wild-type ubiquitin is substituted by Arg. According to one embodiment, in the mutant-type ubiquitin where Lys of the wild-type ubiquitin is substituted by Arg, the substitution may occur at one or more selected from the group consisting of Lys present at the $6^{th}$, $11^{th}$, $27^{th}$, $29^{th}$, $33^{rd}$, $48^{th}$ and $63^{rd}$ positions of the wild-type ubiquitin, and the substitution may occur independently or in combination at the above Lys locations. Accordingly, the mutant ubiquitin may be those where one or more selected from the group consisting of Lys present at the $6^{th}$, $11^{th}$, $27^{th}$, $29^{th}$, $33^{rd}$, $48^{th}$ and $63^{rd}$ positions of the wild-type ubiquitin (Gene Accession No.: NP_001170884, NM_001177413) are substituted by an amino acid other than Lys (e.g., an amino acid selected from the group consisting of Ala, Ile, Leu, Met, Phe, Pro, Trp, Val, Asn, Cys, Gln, Gly, Ser, Thr, Tyr, Asp, Glu, Arg and His, for example, Arg or Ala).

According to one embodiment, the ubiquitin or ubiquitin-like protein may include, at its C-terminal, amino acid sequences that are cleavable by proteases for in vitro or in vivo cleavage. The amino acid sequences cleavable by proteases can be identified through search database known in the pertinent art. For example, the proteases and the amino acid sequences cleavable thereby that are searchable in the PEPTIDECUTTER™ operated by the Swiss Institute of Bioinformatics (<<www.expasy.org/tools/peptidecutter/peptidecutter_enzymes.html>>) may be employed. In case that the cleavable amino acid sequences are included, the tag included in the protein complex is in vitro or in vivo cleaved from the protein complex, whereby two or more fusion proteins are able to perform their functions as a protein complex including a bispecific or multi-specific antigen binding sties.

The antigen-binding region of a specific antibody used in the specification refers to a site which, of the antibody structures, is involved in recognizing and binding to an antigen, and it may be selected from the group consisting of an antibody heavy chain and/or light chain complementarity determining region (CDR), a heavy chain variable region and/or light chain variable region including the CDR, scFv, (scFv)$_2$, Fab, Fab', and F(ab')$_2$.

According to one embodiment, the protein complex may have antigen-binding regions identical to or different from each other. That is, the first antigen-binding region and the second antigen-binding region which are the antigen-binding regions of the first polypeptide and the second polypeptide may consist of antigen-binding regions against antigens identical to or different from each other. Further, although the antigens used are the same, it is interpreted to include antigen-binding regions capable of binding to different epitopes.

Since the invention is directed to a complex protein including a heterodimer structure where two kinds of antigen-binding regions that bind to different antigens or different epitopes in case of the same antigen are coupled in a specific structure, it is not limited by such antigens or epitopes.

In an embodiment, the antigens capable of binding to the antigen-binding regions may include different regions of one selected from or two selected from the group consisting of DLL4, VEGFR2, Notch1, Notch2, Notch3, Notch4, Notch (pan), JAG1, JAG2, DLL(pan), JAG(pan), ERBB(pan), c-Met, IGF-1R, PDGFR, Patched, Hedgehog family polypeptides, Hedgehog(pan), WNT family polypeptides, WNT (pan), FZD1, FZD2, FZD3, FZD4, FZD5, FZD6, FZD7, FZD8, FZD9, FZD10, FZD(pan), LRP5, LRP6, CD20, IL-17, CD86, Muc16, PSCA, CD44, c-Kit, DDR1, DDR2, RSPO1, RSPO2, RSPO3, RSPO4, RSPO(pan), BMP family polypeptides, BMP(pan), BMPR1a, BMPR1b, EpCAM, tumor-associated glycoprotein-72 (TAG-72), tumor-associated antigen CA 125, Prostate specific membrane antigen (PSMA), High molecular weight melanoma-associated antigen (HMW-MAA), tumor-associated antigen expressing Lewis Y related carbohydrate, Carcinoembryonic antigen (CEA), CEACAM5, HMFG PEM, mucin MUC1, MUC18 and cytokeratin tumor-associated antigen, bacterial antigens, viral antigens, allergens, fluorescein, lysozyme, toll-like receptor 9, erythropoietin, CD2, CD3, CD3E, CD4, CD11, CD11a, CD14, CD18, CD19, CD20, CD22, CD23, CD25, CD28, CD29, CD30, CD33 (p67 protein), CD38, CD40, CD40L, CD52, CD54, CD56, CD80, CD147, GD3, IL-1, IL-1R, IL-2, IL-2R, IL-4, IL-5, IL-6, IL-6R, IL-8, IL-12, IL-15, IL-18, IL-23, interferon alpha, interferon beta, interferon gamma; TNF-alpha, TNF-beta2, TNF-alpha, TNF-alphabeta, TNF-R1, TNF-R11, FasL, CD27L, CD30L, 4-1BBL, TRAIL, RANKL, TWEAK, APRIL, BAFF, LIGHT, VEG1, OX40L, TRAIL Receptor-1, A1 Adenosine Receptor, Lymphotoxin Beta Receptor, TACI, BAFF-R, EPO; LFA-3, ICAM-1, ICAM-3, integrin beta1, integrin beta2, integrin alpha4/beta7, integrin alpha2, integrin alpha3, integrin alpha4, integrin alpha5, integrin alpha6, integrin alphav, alphaVbeta3 integrin, FGFR-3, Keratinocyte Growth Factor, VLA-1, VLA-4, L-selectin, anti-Id, E-selectin, HLA, HLADR, CTLA-4, T cell receptor, B7-1, B7-2, VNRintegrin, TGFbeta1, TGFbeta2, eotaxin1, BLyS (B-lymphocyte Stimulator), complement C5, IgE, factor VII, CD64, CBL, NCA 90, EGFR (ErbB-1), Her2/neu (ErbB-2), Her3 (ErbB-3), Her4 (ErbB4), Tissue Factor, VEGF, VEGFR, endothelin receptor, VLA-4, carbohydrate such as blood group antigen and carbohydrates associated therewith, Galili-Glycosylation, Gastrin, Gastrin receptors, tumor associated carbohydrate, Hapten NP-cap or NIP-cap, T cell receptor alpha/beta, E-selectin, digoxin, placental alkaline phosphatase (PLAP), testicular PLAP-like alkaline phosphatase, transferrin receptor, Heparanase I, human cardiac myosin, Glycoprotein IIb/IIIa (GPIIb/IIIa), human cytomegalovirus (HCMV) gH envelope glycoprotein, HIV gp120, HCMV, respiratory syncital virus RSV F, RSVF Fgp, VNR integrin, Hep B gp120, CMV, gpIIbIIIa, HIV IIIB gp120 V3 loop, respiratory syncytial virus (RSV) Fgp, Herpes simplex virus (HSV) gD glycoprotein, HSV gB glycoprotein, HCMV gB envelope glycoprotein, *Clostridium perfringens* toxin and fragments thereof, and the like, but may not be limited thereto.

In a particular embodiment, one of the first antigen-binding region of the first polypeptide and the second antigen-binding region of the second polypeptide may be an antigen-binding region of an antibody which specifically binds to c-Met.

"c-Met" or "c-Met protein" refers to a receptor tyrosine kinase (RTK) which binds hepatocyte growth factor (HGF). c-Met may be derived from any species, particularly a mammal, for instance, primates such as human c-Met (e.g., NP_000236), monkey c-Met (e.g., Macaca mulatta, NP_001162100), or rodents such as mouse c-Met (e.g., NP_032617.2), rat c-Met (e.g., NP_113705.1), and the like. The c-Met protein may include a polypeptide encoded by the nucleotide sequence identified as GenBank Accession Number NM_000245, a polypeptide including the amino acid sequence identified as GenBank Accession Number NP_000236 or extracellular domains thereof. The receptor tyrosine kinase c-Met participates in various mechanisms, such as cancer incidence, metastasis, migration of cancer cell, invasion of cancer cell, angiogenesis, and the like.

The anti-c-Met antibody providing an antigen-binding region that specifically recognizes and binds to c-Met, be any antibody capable of recognizing a specific region of c-Met, e.g., a specific region in the SEMA domain, as an epitope. The anti-c-Met antibody may be any antibody or antigen-binding fragment that acts on c-Met to induce c-Met intracellular internalization and degradation.

c-Met, a receptor for hepatocyte growth factor (HGF), may be divided into three portions: extracellular, transmembrane, and intracellular. The extracellular portion is composed of an α-subunit and a β-subunit which are linked to each other through a disulfide bond, and contains a SEMA domain responsible for binding HGF, a PSI domain (plexin-semaphorins-integrin identity/homology domain) and an IPT domain (immunoglobulin-like fold shared by plexins and transcriptional factors domain). The SEMA domain of c-Met protein may have the amino acid sequence of SEQ ID NO: 79, and is an extracellular domain that functions to bind HGF. A specific region of the SEMA domain, that is, a region including the amino acid sequence of SEQ ID NO: 71, which corresponds to a range from amino acid residues 106 to 124 of the amino acid sequence of the SEMA domain (SEQ ID NO: 79), is a loop region between the second and the third propellers within the epitopes of the SEMA domain. This region acts as an epitope for the anti-c-Met antibody provided in the present invention.

The term "epitope," as used herein, refers to an antigenic determinant, a part of an antigen recognized by an antibody. In one embodiment, the epitope may be a region comprising 5 or more contiguous (consecutive or non-consecutive) amino acid residues within the SEMA domain (SEQ ID NO: 79) of c-Met protein, for instance, 5 to 19 consecutive amino acid residues within the amino acid sequence of SEQ ID NO: 71. For example, the epitope may be a polypeptide including 5 to 19 contiguous amino acids selected from among partial combinations of the amino acid sequence of SEQ ID NO: 71, wherein the polypeptide includes the amino sequence of SEQ ID NO: 73 (EEPSQ) serving as an essential element for the epitope. For example, the epitope may be a polypeptide comprising, consisting essentially of, or consisting of the amino acid sequence of SEQ ID NO: 71, SEQ ID NO: 72, or SEQ ID NO: 73.

The epitope including the amino acid sequence of SEQ ID NO: 72 corresponds to the outermost part of the loop between the second and third propellers within the SEMA domain of a c-Met protein. The epitope including the amino acid sequence of SEQ ID NO: 73 is a site to which the antibody or antigen-binding fragment may bind. Thus, the anti-c-Met antibody may specifically bind to an epitope which has 5 to 19 consecutive or non-consecutive amino acids selected from among partial combinations of the amino acid sequence of SEQ ID NO: 71, including SEQ ID NO: 73 as an essential element. For example, the anti-c-Met antibody may specifically bind to an epitope including the amino acid sequence of SEQ ID NO: 71, SEQ ID NO: 72, or SEQ ID NO: 73. The epitope including the amino acid sequence of SEQ ID NO: 73 is a site to which the antibody or antigen-binding fragment according to one embodiment most specifically binds.

Thus, the anti-c-Met antibody may specifically bind to an epitope which has 5 to 19 consecutive or non-consecutive amino acids selected from among partial combinations of the amino acid sequence of SEQ ID NO: 71, including SEQ ID NO: 73 as an essential element. For example, the anti-c-Met antibody may specifically bind to an epitope including the amino acid sequence of SEQ ID NO: 71, SEQ ID NO: 72, or SEQ ID NO: 73.

In one embodiment, the antigen-binding region of the anti-c-Met antibody (an antigen-binding region specifically binding to a c-Met) may include:

at least one heavy chain complementarity determining region (CDR) selected from the group consisting of (a) a CDR-H1 including the amino acid sequence of SEQ ID NO: 4; (b) a CDR-H2 including the amino acid sequence of SEQ ID NO: 5, SEQ ID NO: 2, or an amino acid sequence including 8-19 consecutive amino acids within SEQ ID NO: 2 including amino acid residues from the $3^{rd}$ to $10^{th}$ positions of SEQ ID NO: 2; and (c) a CDR-H3 including the amino acid sequence of SEQ ID NO: 6, SEQ ID NO: 85, or an amino acid sequence including 6-13 consecutive amino acids within SEQ ID NO: 85 including amino acid residues from the $1^{st}$ to $6^{th}$ positions of SEQ ID NO: 85, or a heavy chain variable region including the at least one heavy chain complementarity determining region;

at least one light chain complementarity determining region (CDR) selected from the group consisting of (a) a CDR-L1 including the amino acid sequence of SEQ ID NO: 7, (b) a CDR-L2 including the amino acid sequence of SEQ ID NO: 8, and (c) a CDR-L3 including the amino acid sequence of SEQ ID NO: 9, SEQ ID NO: 86, or an amino acid sequence including 9-17 consecutive amino acids within SEQ ID NO: 89 including amino acid residues from the $1^{st}$ to $9^{th}$ positions of SEQ ID NO: 89, or a light chain variable region including the at least one light chain complementarity determining region;

a combination of the at least one heavy chain complementarity determining region and at least one light chain complementarity determining region; or a combination of the heavy chain variable region and the light chain variable region.

Herein, the amino acid sequences of SEQ ID NOS: 4 to 9 are respectively represented by following Formulas I to VI, below:

Formula I
(SEQ ID NO: 4)
Xaa₁-Xaa₂-Tyr-Tyr-Met-Ser,
wherein

Xaa₁ is absent or Pro or Ser,
and

Xaa₂ is Glu or Asp,

Formula II
(SEQ ID NO: 5)
Arg-Asn-Xaa₃-Xaa₄-Asn-Gly-Xaa₅-Thr,
wherein

Xaa₃ is Asn or Lys, Xaa₄ is Ala or Val,
and

Xaa₅ is Asn or Thr,

Formula III
(SEQ ID NO: 6)
Asp-Asn-Trp-Leu-Xaa₆-Tyr,
wherein

Xaa₆ is Ser or Thr,

-continued

Formula IV
(SEQ ID NO: 7)
Lys-Ser-Ser-Xaa₇-Ser-Leu-Leu-Ala-Xaa₈-

Gly-Asn-Xaa₉-Xaa₁₀-Asn-Tyr-Leu-Ala
wherein

Xaa₇ is His, Arg, Gln, or Lys, Xaa₈ is
Ser or Trp, Xaa₉ is His or Gln,
and

Xaa₁₀ is Lys or Asn,

Formula V
(SEQ ID NO: 8)
Trp-Xaa₁₁-Ser-Xaa₁₂-Arg-Val-Xaa₁₃
wherein

Xaa₁₁ is Ala or Gly, Xaa₁₂ is Thr or Lys,
and

Xaa₁₃ is Ser or Pro,
and

Formula VI
(SEQ ID NO: 9)
Xaa₁₄-Gln-Ser-Tyr-Ser-Xaa₁₅-Pro-Xaa₁₆-Thr
wherein

Xaa₁₄ is Gly, Ala, or Gln, Xaa₁₅ is Arg,
His, Ser, Ala, Gly, or Lys,
and

Xaa₁₆ is Leu, Tyr, Phe, or Met.

In one embodiment, the CDR-H1 may include an amino acid sequence selected from the group consisting of SEQ ID NOS: 1, 22, 23, and 24. The CDR-H2 may include an amino acid sequence selected from the group consisting of SEQ ID NOS: 2, 25, and 26. The CDR-H3 may include an amino acid sequence selected from the group consisting of SEQ ID NOS: 3, 27, 28, and 85.

The CDR-L1 may include an amino acid sequence selected from the group consisting of SEQ ID NOS: 10, 29, 30, 31, 32, 33, and 106. The CDR-L2 may include an amino acid sequence selected from the group consisting of SEQ ID NOS: 11, 34, 35, and 36. The CDR-L3 may include an amino acid sequence selected from the group consisting of SEQ ID NOS: 12, 13, 14, 15, 16, 37, 86, and 89.

In another embodiment, the antigen-binding region of the anti-c-Met antibody (the antigen-binding region specifically binding to c-Met) may include:

a heavy chain variable region including a polypeptide (CDR-H1) including an amino acid sequence selected from the group consisting of SEQ ID NOS: 1, 22, 23, and 24, a polypeptide (CDR-H2) including an amino acid sequence selected from the group consisting of SEQ ID NOS: 2, 25, and 26, and a polypeptide (CDR-H3) including an amino acid sequence selected from the group consisting of SEQ ID NOS: 3, 27, 28, and 85; and/or a light chain variable region including a polypeptide (CDR-L1) including an amino acid sequence selected from the group consisting of SEQ ID NOS: 10, 29, 30, 31, 32, 33 and 106, a polypeptide (CDR-L2) including an amino acid sequence selected from the group consisting of SEQ ID NOS: 11, 34, 35, and 36, and a polypeptide (CDR-L3) including an amino acid sequence selected from the group consisting of SEQ ID NOS 12, 13, 14, 15, 16, 37, 86, and 89.

In one particular embodiment, the antigen-binding region specifically binding to c-Met may include the variable domain of the heavy chain including the amino acid sequence of SEQ ID NO: 17, 74, 87, 90, 91, 92, 93, or 94 and the variable domain of the light chain including the amino acid sequence of SEQ ID NO: 18, 19, 20, 21, 75, 88, 95, 96, 97, 98, 99, or 107. According to one embodiment, the protein complex may be a single stranded polypeptide including an amino acid sequence of SEQ ID NO: 109, SEQ ID NO: 115, SEQ ID NO: 119, SEQ ID NO: 121, SEQ ID NO: 124, or SEQ ID NO: 126. The protein complex, which is a single stranded polypeptide including double-specific (specific to two antigens) properties linked by a tag and a linker, may serve as an antibody precursor protein capable of being manufactured into a bispecific antibody by the cleavage of the tag.

Another embodiment provides a bispecific antibody including the aforementioned protein complex. The bispecific antibody may be the protein complex itself or those having an intact antibody formed by the dimerization of the first polypeptide and the second polypeptide of the protein complex (e.g., through a general disulfide bond, knob/hole formation, etc.) and/or by the cleavage of the cleavage site of the tag included in the complex. For example, the bispecific antibody, in case that the protein complex includes one tag, may be those where the cleavage site of the tag is cleaved, and in case that the protein complex includes a total of two tags (first tag and second tag) at both terminals of the first linker, may be those where the cleavage sites of the two tags are cleaved whereby the first linker, or a form of the first tag, the second tag, or the first tag and the second tag being linked to the terminal of the first linker is eliminated.

Since the bispecific antibody has antigen-binding regions different from each other on each monomer, it may simultaneously recognize two different kinds of antigens selected from the group consisting of the aforementioned antigens as its targets, or simultaneously recognize different epitopes of one antigen as its targets.

According to one embodiment, the bispecific antibody may be a mouse-derived antibody, a human-derived antibody, a mouse-human chimeric antibody, or a humanized antibody. The bispecific antibody may be isolated from a living body or be non-naturally occurring. The bispecific antibody may be recombinant or synthetic.

The bispecific antibody may be F(ab')2, (scFv)2, Diabody, Di-scFv, nanobody, or IgG type.

When an animal-derived antibody goes through a chimerization process, an animal-derived IgG1 hinge is replaced by a human IgG1 hinge, but the animal-derived IgG1 hinge is shorter in length than the human IgG1 hinge, and disulfide bonds between the two heavy chains are reduced to 2 from 3. Thus, the rigidity of the hinges may have different effects. Therefore, modification of a hinge region can increase an antigen binding efficiency of a humanized antibody. Methods of deleting, inserting, or substituting an amino acid for modifying the amino acid sequences of the hinge region are well known to an ordinary person in the art.

Another embodiment provides a pharmaceutical composition including the protein complex and/or the bispecific antibody.

Another embodiment provides a polynucleotide encoding the aforementioned protein complex.

The term "polynucleotide" is a polymer of deoxyribonucleotides or ribonucleotides present in a single-stranded or double-stranded form. The polynucleotides encompass RNA genome sequences, DNA (gDNA and cDNA) and RNA sequences transcribed therefrom, and include analogues of natural polynucleotides unless particularly mentioned otherwise.

The polynucleotide includes not only nucleotide sequences encoding the amino acid sequences of the protein complex but also nucleotide sequences complementary thereto. The complementary sequences include not only completely complementary sequences but also substantially complementary sequences, which refer to sequences hybridizable with the nucleotide sequences encoding the amino acid sequences of the protein complex under stringent conditions known in the pertinent art.

The nucleotide sequences encoding the amino acid sequences of the protein complex may be mutated. The mutations include addition, deletion, or non-conservative or conservative substitution. A polynucleotide encoding the amino acid sequence of the protein complex is understood to include nucleotide sequences substantially identical to the nucleotide sequences described above. The substantially identical nucleotide sequences may be sequences with at least 80% homology, at least 90% homology, or at least 95% homology to the above described nucleotide sequences, when the sequences are aligned to correspond to each other as much as possible, and the aligned nucleotide sequences are analyzed using any algorithm commonly used in the art.

Another embodiment provides a recombinant vector (expression vector) including the polynucleotide encoding the protein complex and expression regulating factors (e.g., promoter, etc.) operatively linked to the polynucleotide.

The term "vector" used herein refers to a means for expressing a target gene in a host cell. For example, it includes a plasmid vector, a cosmid vector, and a virus vector such as a bacteriophage vector, an adenovirus vector, a retrovirus vector and an adeno-associated virus vector. Suitable recombinant vectors may be constructed by manipulating plasmids often used in the art (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19), a phage (for example, λgt4λB, λ-Charon, λΔz1, and M13), or a virus (for example, SV40).

The recombinant vector may include the polynucleotides encoding the protein complex and an expression regulating factor (sequence) such as promoter, which are operatively linked to each other. The term "operatively linked" used herein refers to a functional linkage between a nucleotide expression regulating sequence (for example, a promoter sequence) and other nucleotide sequences. Thus, the expression regulating sequence may regulate the transcription and/or translation of the other nucleotide sequences by being operatively linked.

The recombinant vector may be constructed typically for either cloning or expression. The expression vector may be any ordinary vectors known in the pertinent art for expressing an exogenous protein in plants, animals, or microorganisms. The recombinant vector may be constructed using various methods known in the art.

The recombinant vector may be constructed using a prokaryotic cell or a eukaryotic cell as a host. For example, when a prokaryotic cell is used as a host cell, the expression vector used generally includes a strong promoter capable of initiating transcription (for example, pL$^\lambda$ promoter, CMV promoter, trp promoter, lac promoter, tac promoter, T7 promoter, etc.), a ribosome binding site for initiating translation, and a transcription/translation termination sequence. When a eukaryotic cell is used as a host cell, the vector used generally includes the origin of replication acting in the eukaryotic cell, for example, a f1 replication origin, a SV40 replication origin, a pMB1 replication origin, an adeno replication origin, an AAV replication origin, or a BBV replication origin, but is not limited thereto. A promoter in an expression vector for a eukaryotic host cell may be a promoter derived from the genomes of mammalian cells (for example, a metallothionein promoter) or a promoter derived from mammalian viruses (for example, an adenovirus late promoter, a vaccinia virus 7.5K promoter, a SV40 promoter, a cytomegalovirus promoter, and a tk promoter of HSV). A transcription termination sequence in an expression vector for a eukaryotic host cell may be, in general, a polyadenylation sequence.

Another embodiment provides a recombinant cell including the recombinant vector.

The recombinant cell may be those obtained by transfecting the recombinant vector into a suitable host cell. Any host cells known in the pertinent art to enable stable and continuous cloning or expression of the recombinant vector may be used as the hose cell. Suitable prokaryotic host cells may include *E. coli* JM109, *E. coli* BL21, *E. coli* RR1, *E. coli* LE392, *E. coli* B, *E. coli* X 1776, *E. coli* W3110, *Bacillus* species strains such as *Bacillus subtillis* or *Bacillus thuringiensis*, intestinal bacteria and strains such as *Salmonella typhymurum, Serratia marcescens*, and various *Pseudomonas* species. Suitable eukaryotic host cells to be transformed may include yeasts, such as *Saccharomyce cerevisiae*, insect cells, plant cells, and animal cells, for example, Sp2/0, Chinese hamster ovary (CHO) K1, CHO, CHO-s, HEK293, HEK293f, DG44, PER.C6, W138, BHK, COS-7, 293, HepG2, Huh7, 3T3, RIN, and MDCK cell lines, but are not limited thereto.

The polynucleotide or the recombinant vector including the same may be transferred (transfected) into a host cell by using known transfer methods. Suitable transfer methods for prokaryotic host cells may include a method using $CaCl_2$ and electroporation. Suitable transfer methods for eukaryotic host cells may include microinjection, calcium phosphate precipitation, electroporation, liposome-mediated transfection, and gene bombardment, but are not limited thereto.

A transformed host cell may be selected using a phenotype expressed by a selected marker by any methods known in the art. For example, if the selected marker is a gene that is resistant to a specific antibiotic, a transformant may be easily selected by being cultured in a medium including the antibiotic.

Another embodiment provides a method of preparing a bispecific antibody including preparing the protein complex. As described above, since the protein complex improves the formation rate of a heterodimer having a right and left asymmetric structure in the process of forming an antibody, a bispecific antibody having a right and left asymmetric structure can be more efficiently prepared according to the above preparation method.

In one embodiment, the preparation of the protein complex can be carried out by expressing the above recombinant vector in a host cell or culturing the recombinant cell including the recombinant vector, thereby producing the protein complex. In another embodiment, the preparation of the protein complex may be carried out chemically by peptide synthesis for linking amino acids in accordance with the amino acid sequence of the protein complex.

The preparation of the bispecific antibody may be carried out in vivo or inside the cell, or in vitro or outside the cell.

When the bispecific antibody is prepared in vivo or inside the cell, the recombinant vector is expressed within a host cell, or the recombinant cell is cultured to produce a protein complex, which becomes an intact form of the bispecific antibody inside the cell, and then can be released outside the cell or outside the living body. Thus, the first polypeptide and the second polypeptide, after translated in endoplasmic reticulum, form a voluntary dimer by neighboring to each other via a linker and can form the protein complex. Thereafter, cleavable amino acid sequences present in the tag are cleaved from the protein complex by proteases present within the cell, whereby an intact form of the bispecific antibody can be generated. Due to one or more amino acid sequences being mutually coupled (knob or hole) in the region excluding the first antigen-binding region and the second antigen-binding region present in the first polypeptide and the second polypeptide, the formation rate of the bispecific antibody can be further increased. After that, the generated bispecific antibody may be purified using purification methods known in the art and then used.

When the bispecific antibody is prepared in vitro or outside the cell, for example, in case that the protein complex expressed from the recombinant vector is secreted, in a single stranded form, outside the cell or outside the living body, or in case that the protein complex is produced chemically by peptide synthesis, the preparation of the bispecific antibody may further include a step of cleaving the tag included in the protein complex, subsequent to the step of producing the protein complex by expressing the recombinant vector within the cell or producing the protein complex by peptide synthesis.

The protein complex is present in vitro or outside the cell in such a state that the first polypeptide and the second polypeptide are linked via a linker, and the first polypeptide and the second polypeptide are adjacent to each other so that they can voluntarily form a dimer. Due to one or more amino acid sequences to be mutually coupled (knob or hole) in the remainder region except the first antigen-binding region and the second antigen-binding region present in the first polypeptide and the second polypeptide, the formation rate of the bispecific antibody can be more increased.

According to one embodiment, the step of cleaving the tag may be carried out by adding a protease recognizing the cleavable amino acid sequences included in the tag. The tag may be selected from the group consisting of ubiquitin, ubiquitin-like protein, TEV cleavage peptide and furin cleavage peptide, but is not limited thereto. For example, the tag may be cleaved by adding a protease capable of cleaving ubiquitin, ubiquitin-like protein, TEV cleavage peptide or furin cleavage peptide to the protein complex, wherein the ubiquitin, ubiquitin-like protein, TEV cleavage peptide or furin cleavage peptide is cleaved by the protease and separated and thus, the bispecific antibody can be generated from the protein complex.

The step of cleaving the tag may be performed before or after the formation of the dimer.

Using the protein complex according to one embodiment, a bispecific antibody system having two antigens or two epitopes as its targets at the same time can be effectively constructed, and it can be thus favorably applied to develop antibody drugs due to the synergistic effects resultant from the double antibody functions.

One or more embodiments of the present invention will now be described in further detail with reference to the following Examples. However, these examples are for the illustrative purposes only and are not intended to limit the scope of the invention.

Figure 3:
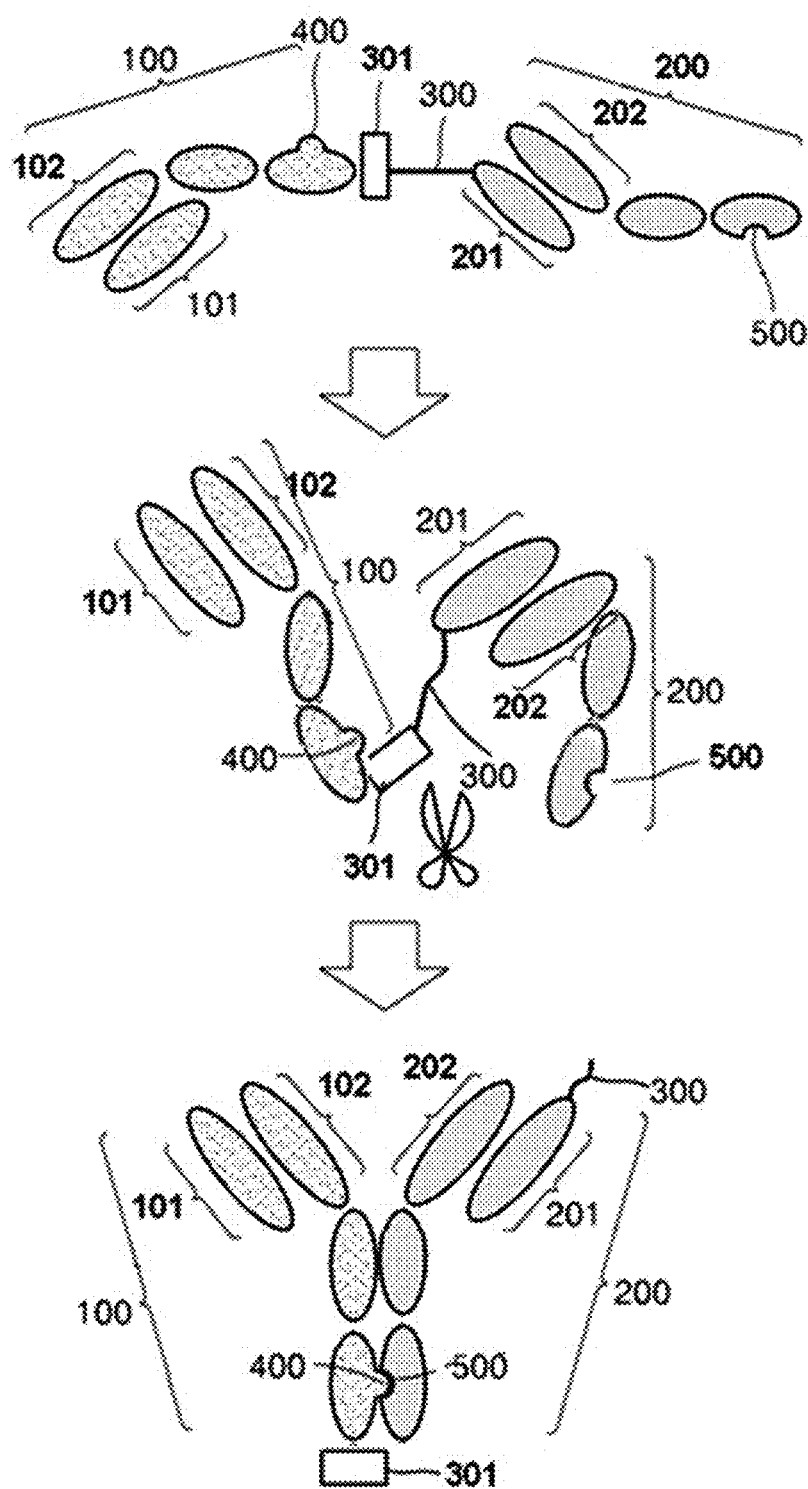
FIG. 3 illustrates preparation of a bispecific antibody using a first polypeptide, a second polypeptide, a linker, a tag, and a knob-hole formed in the CH3 domain of the first polypeptide and the second polypeptide.

FIG. 1 to FIG. 3 are the schematic diagrams of a protein complex including a first polypeptide containing a first antigen-binding region and a second polypeptide containing a second antigen-binding region.

FIG. 1 illustratively shows a protein complex (left and right) including a first polypeptide including a first antigen-binding region (red: including a first light chain antigen-binding region and a first heavy chain antigen-binding region), a second polypeptide including a second antigen-binding region (blue: including a second light chain antigen-binding region and a second heavy chain antigen-binding region), a tag bound to the C-terminal of the first polypeptide (yellow), and a linker for connecting the C-terminal of the tag and the N-terminal of the second polypeptide, and a bispecific antibody (right) in a complete form where the cleavable site of the tag is cleaved therefrom.

As illustrated in FIG. 2, a first polypeptide (100) including first antigen-binding regions (101 and 102) and a second polypeptide (200) including second antigen-binding regions (201 and 202) are each linked to a first tag (302) and a second tag (303) at their terminal, and the first tag (302) and the second tag (303) are linked to the terminals of a linker (300) consisting of a polypeptide. The first tag (302) and the second tag (303) include proteins such as ubiquitin or ubiquitin-like proteins and thus, they can be in vitro or in vivo cleaved. The first polypeptide (100) including the first antigen-binding regions (101 and 102) and the second polypeptide (200) including the second antigen binding sties (201 and 202) are in vitro or in vivo coupled through completely voluntary coupling by neighboring to each other, wherein a knob (400) formed on the CH3 domain of the first polypeptide (100) and a hole (500) formed on the CH3 domain of the second polypeptide (200) are mutually coupled to increase the formation rate of a bispecific protein complex having different antigen-binding regions from each other.

FIG. 3 shows an example where the second tag (301) is missing from the protein complex including the first polypeptide including the first antigen-binding regions and the second polypeptide including the second antigen-binding regions according to one embodiment disclosed in FIG. 2. As explained in the above, a bispecific protein complex having different antigen-binding regions from each other is formed through in vitro or in vivo cleavage of the protein complex, wherein the protein complex disclosed in FIG. 3 exists in such a form that a linker (300) is bound to the N-terminal of the second light chain antigen-binding region (201) or the second heavy chain binding site (202) of the second polypeptide (200) including the second antigen-binding regions (201 and 202) because it does not have the second tag (303), but the linker (300) does not affect the functions of the second polypeptide (200) including the second antigen-binding regions (201 and 202) as it only contains a short sequence of 2 to 50 amino acids.

Example 1: Preparation of Protein Complex Including Two Different Kinds of Antigen Binding Regions (Her2 and c-Met Double Specific Binding Protein Complex)

1.1. Preparation of Expression Vector

In order to prepare the precursor protein complex of a bispecific antibody including specific binding sites to Her2 and cMet, respectively, an expression vector for the protein complex was prepared by Genotech Co. Ltd. As a vector for protein overexpression, pCEP4 (Invitrogen) was used.

Figure 4:
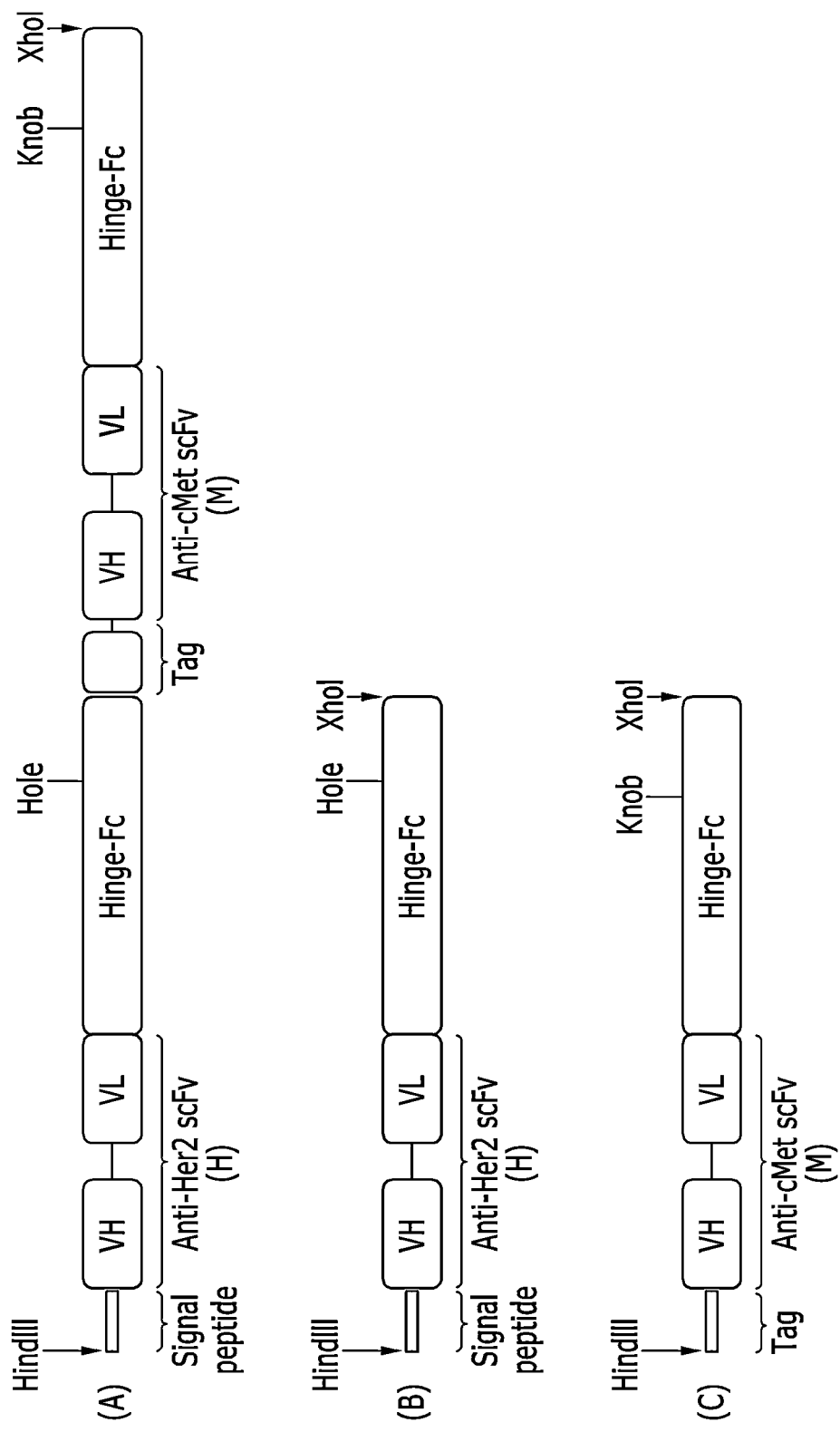
FIG. 4 is a schematic diagram showing DNA sequences (A)-(C) to be inserted into an expression vector for preparing a c-Met/Her2 double binding protein complex.

Specifically, as set forth in FIG. 4(A), a single sequence DNA (SEQ ID NO: 110) encoding the amino acid sequence (SEQ ID NO: 109) of the protein complex including a single chain polypeptide consisting of a secretion signal sequence (ss), a Her2 binding site H, and an Fc domain including a hinge and having an amino acid sequence forming a hole, a single chain polypeptide consisting of a cMet binding site M, and an Fc domain having an amino acid sequence forming a knob, a ubiquitin tag, and a linker was synthesized and inserted into pCEP4 (Invitrogen), thereby to prepare a protein complex expression vector.

The insert DNA fragment includes at its 5' end a nucleotide sequence to be cleavable by HindIII (SEQ ID NO: 113) and at its 3' end a nucleotide sequence to be cleavable by XhoI (SEQ ID NO: 114), and was inserted into the HindIII-XhoI restriction enzyme sequences of pCEP4 vector.

Further, for the comparison of a bispecific antibody induced from the protein complex and a bispecific antibody generated by each single chain polypeptide, the following two types of DNAs were synthesized.

As set forth in FIG. 4(B), DNA (SEQ ID NO: 111) corresponding to the amino acid sequence of a single chain polypeptide consisting of a secretion signal sequence, a Her2 binding site H, and an Fc domain including a hinge and having an amino acid sequence forming a hole was synthesized and inserted into pCEP4 vector via the HindIII-XhoI restriction enzyme sequences.

Likewise, as shown in FIG. 4(C), DNA (SEQ ID NO: 112) corresponding to the amino acid sequence of a single chain polypeptide consisting of a secretion signal sequence, a cMet binding site M, and an Fc domain having an amino acid sequence forming a knob was synthesized and inserted into pCEP4 vector via the HindIII-XhoI restriction enzyme sequences.

1.2. Expression of Protein Complex and Purification of Bispecific Antibody

In order to see the expression of the protein complex using the vector prepared in Example 1.1 above, the vector was introduced into human embryonic kidney cells (HEK293-F, Invitrogen) and after the transfection, the expression of the protein was evaluated. The HEK293-F cells were maintained in an orbital shaking incubator of 130 rpm, at 37° C., 8% $CO_2$ conditions. In order to introduce the vector into HEK293-F, after the cells were separated from the medium using centrifugation, they were suspended again with a fresh Freestyle 293 Expression medium (Invitrogen) at a cell concentration of $1\times10^6$/mL and then, 100 μg of the vector was introduced into the HEK293-F cells using a FreeStyle™ MAX reagent (Invitrogen) to transfect the cells.

On 7 to 8 days after the transfection, a cell culture solution including the protein complex was collected using centrifugation (4000×g, 10 min, 4° C.), and it was filtered using a filter having a pore size of 0.22 micron to eliminate the cell debris generated from the cell culture. A bispecific antibody was separated from the obtained filtrate, using Protein A affinity column (GE Healthcare).

First, Protein A affinity column was equilibrated with 1×PBS (Invitrogen) solution, then the filtrate was applied to Protein A affinity column equilibrated with the above solution, washed with a wash buffer (1×PBS) corresponding to 5 times the column volume, and then treated with an elution buffer including 10% glycerol (IgG elution buffer, Thermo Scientific) to elute the bispecific antibody. The eluted solution was neutralized immediately with 1 M Tris-HCl (pH 9.0) solution. The eluted solution was loaded onto HiLoad 16/60 Superdex 200 column equilibrated with 1×PBS to perform size exclusion chromatography. The purified protein concentration was measured using a gamma globulin antibody as a standard material. Thereafter, the concentrated bispecific antibody was verified finally through SDS-PAGE.

Figure 5:
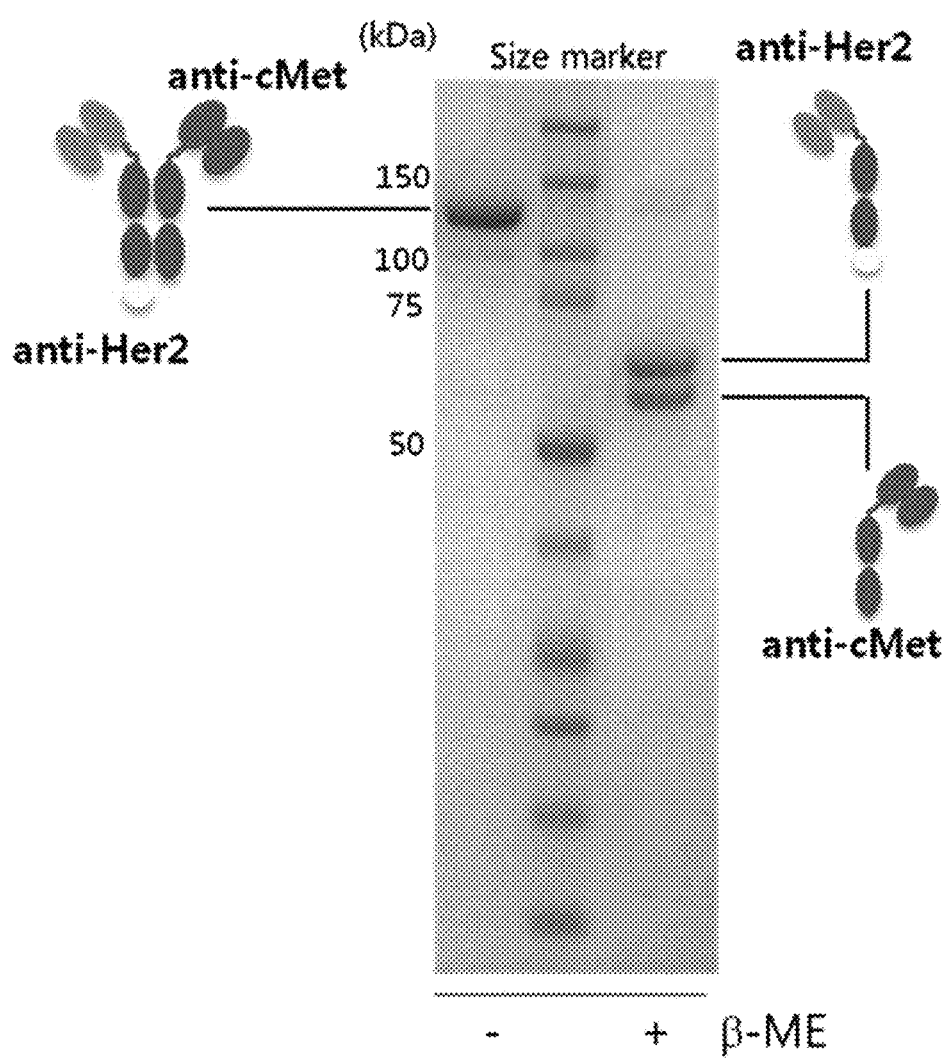
FIG. 5 is an electrophoresis gel showing the heterodimerization of a c-Met/Her2 double binding protein complex.

Prior to loading onto the gel, the bispecific antibody was divided into two samples, one was treated with 1 mM β-mercaptoethanol (reducing condition: R), and the other was loaded in a state of not being treated with β-mercaptoethanol (non-reducing condition: NR). The result is shown in FIG. 5. As shown in FIG. 5, the generation of disulfide bond which is the intrinsic property of an antibody was confirmed through the comparison in R/NR conditions, and homodimeric antibodies were not observed.

1.3. Ratio Analysis of Bispecific Antibody Prepared from Protein Complex

In order to analyze the ratio of the bispecific antibody (heterodimer) among the protein complex purified in Example 1.2, mass analysis was carried out. The mass analysis was conducted using high pressure liquid chromatography (HPLC) and LTQ Orbitrap MS system (Thermo scientific). Presto FF-C18 column (Imtakt) was connected to LC system, where the temperature and flow rate were set to 37° C. and 150 uL/min, respectively, and 20 ug of the protein complex was loaded onto the column. 0.1% trifluoroacetic acid solution in water solvent was used as buffer A, and 0.1% trifluoroacetic acid solution in acetonitrile solvent was used as buffer B. The protein was separated while the ratio of buffer B in the total solution (buffer A+buffer B) was being increased from 3% to 70% for 32 minutes, and it was introduced into the LTQ Orbitrap MS system to analyze the mass of the protein complex (LC-mass spectrometry). The result is shown in FIGS. 6A-6E.

Figure 6A:
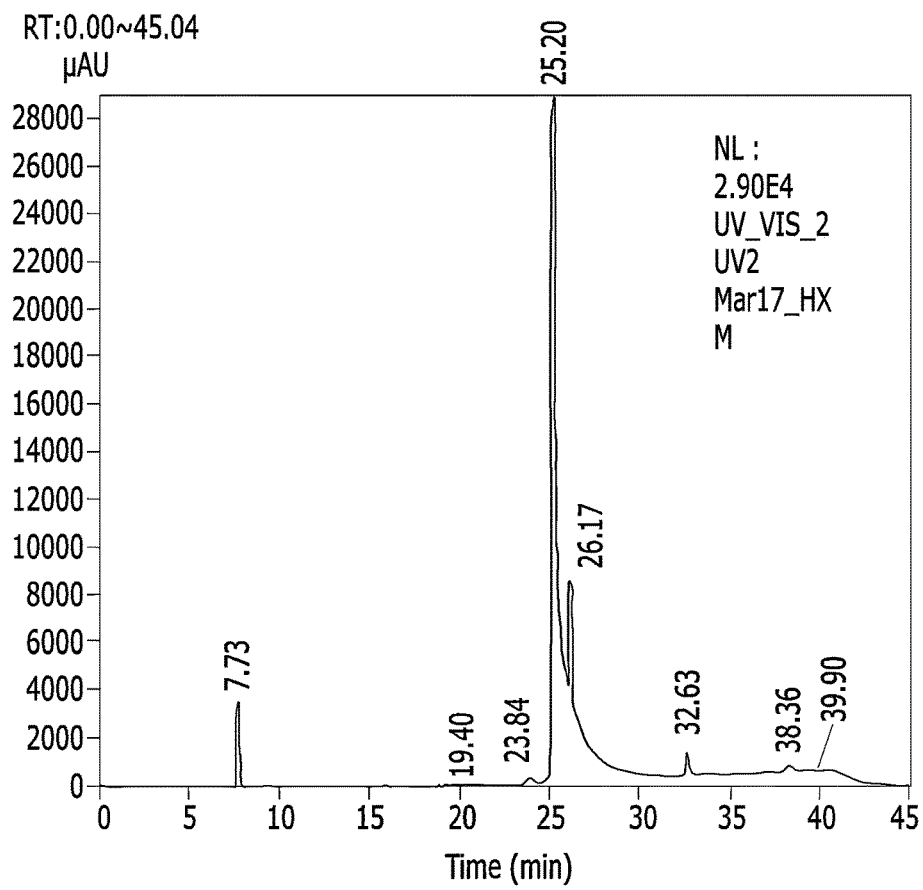
FIGS. 6A and 6B are graphs showing the mass analysis of a bispecific antibody prepared through heterodimerization from a c-Met/Her2 double binding protein complex.
Figure 6B:
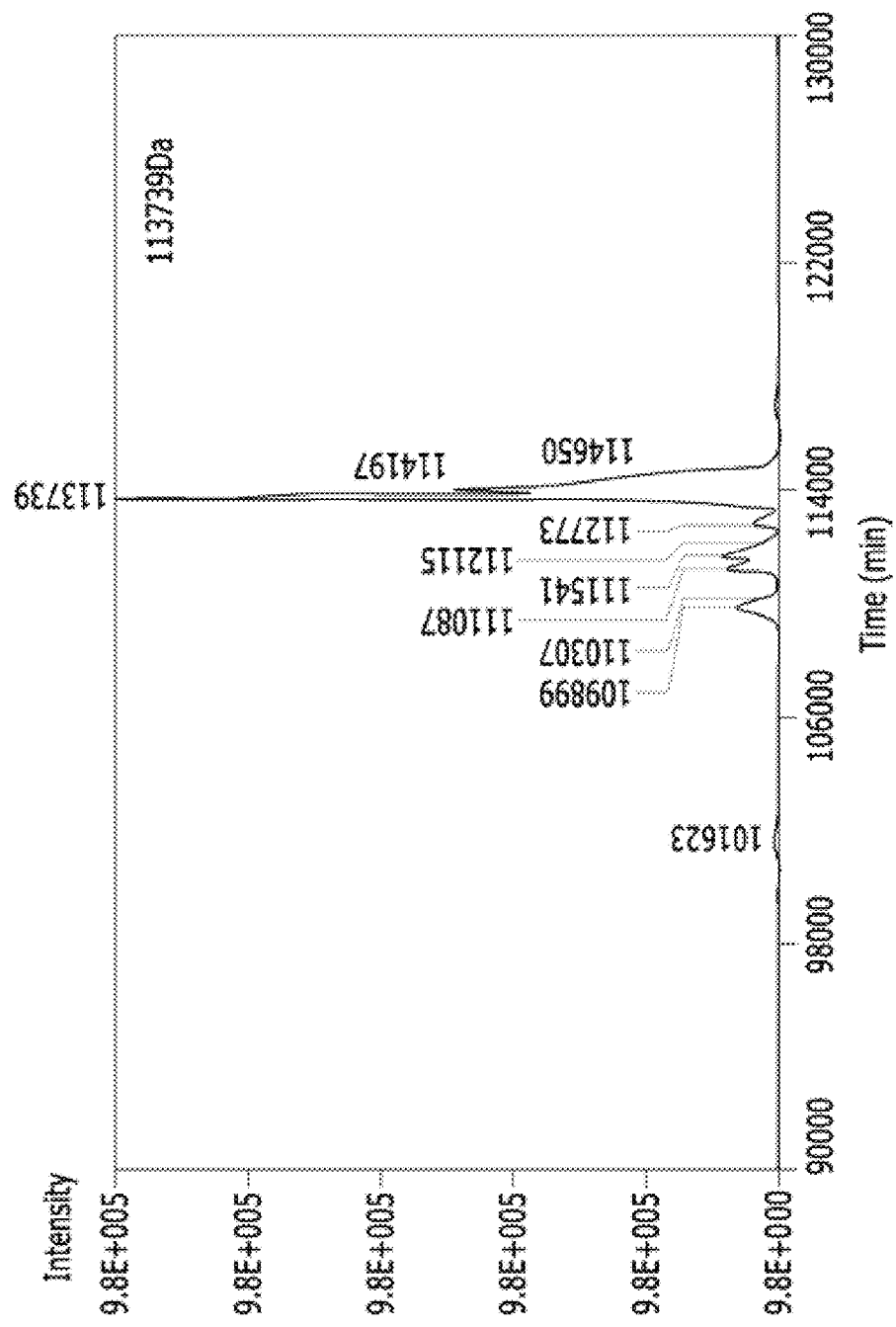
Figure 6C:
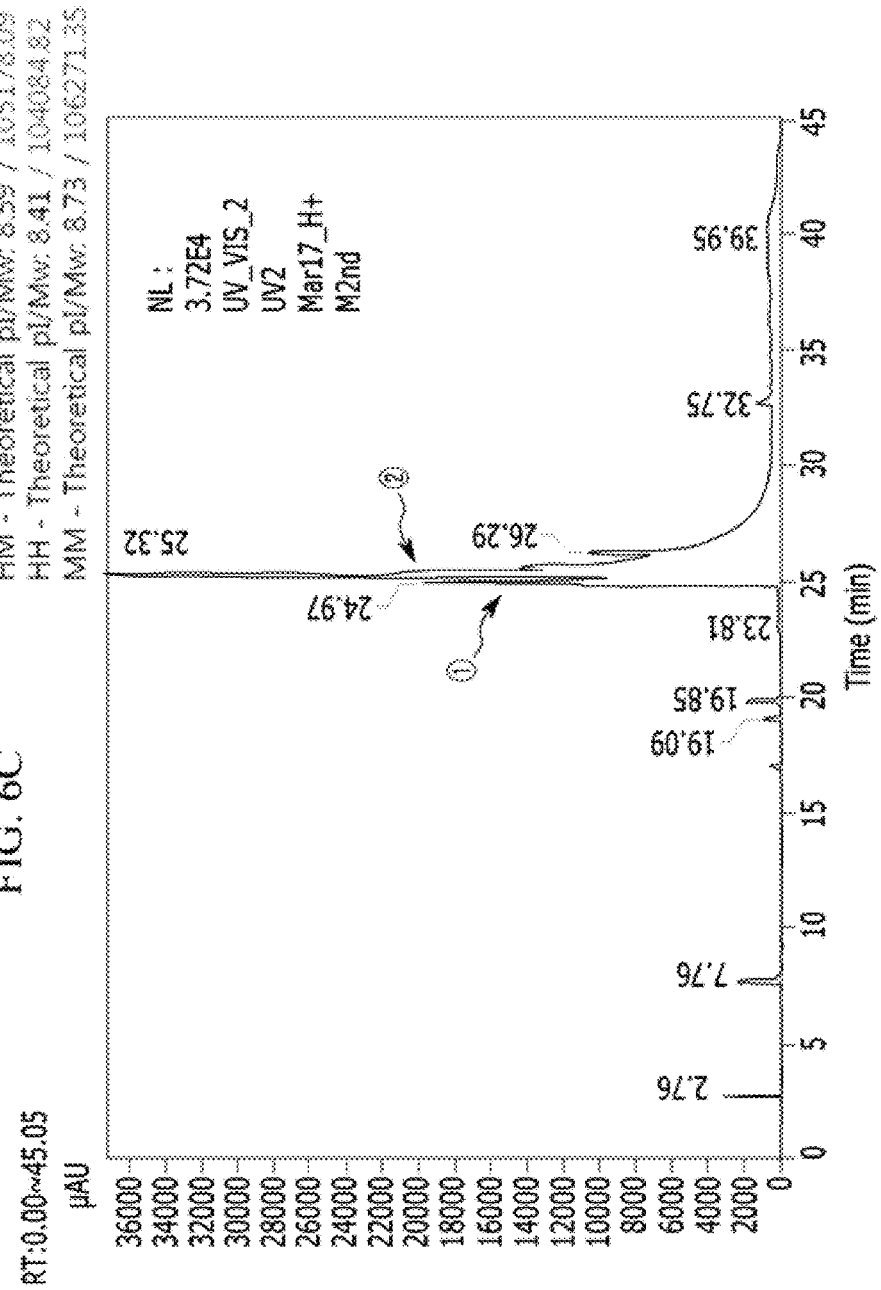
FIGS. 6C-6E are graphs showing the mass analysis of two antibodies co-expressed.
Figure 6D:
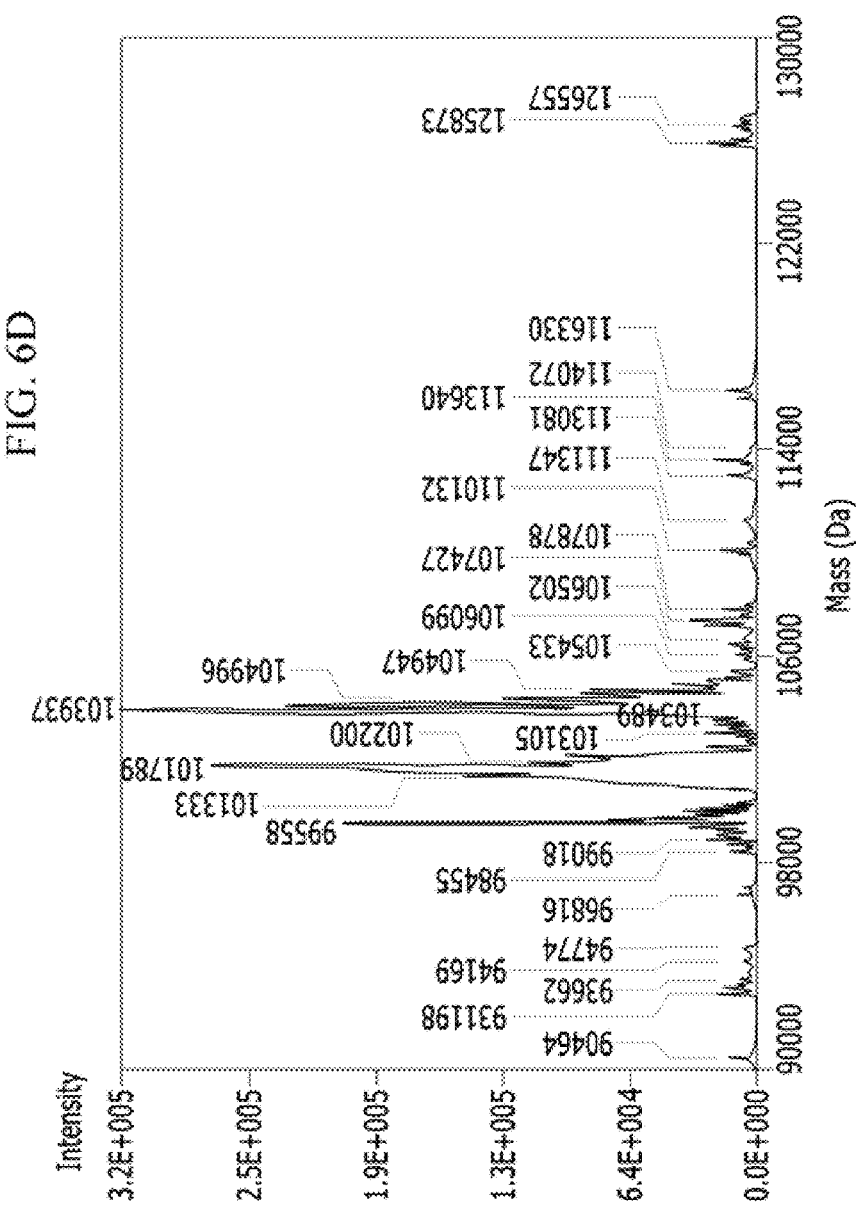
Figure 6E:
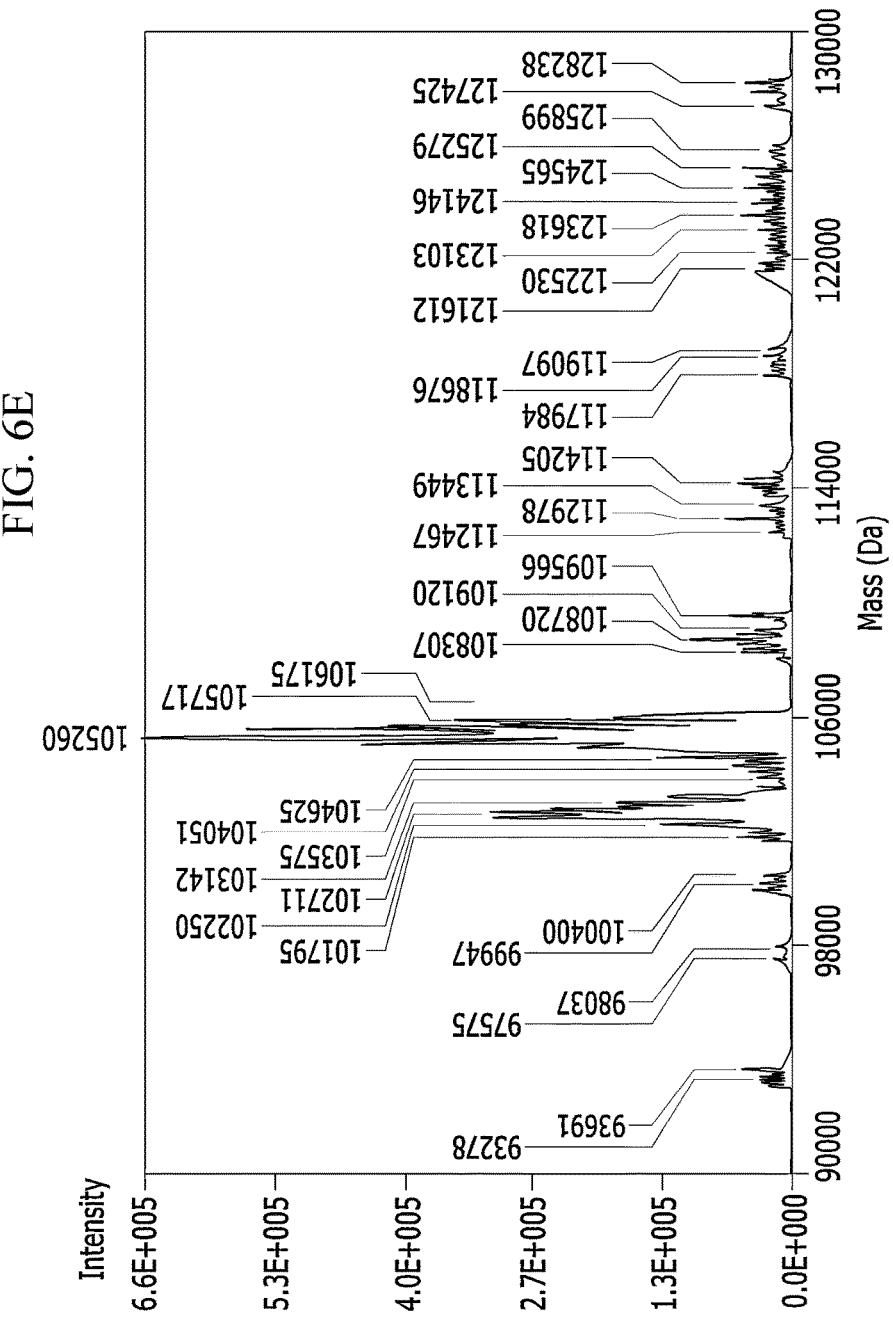

FIGS. 6A and 6B show the mass analysis results of the heterodimers formed from the protein complex purified in Example 1.2 above, and FIGS. 6C-6E show the mass analysis results obtained by co-expressing two antibody polypeptides (encoded by the DNA sequence of SEQ ID NO: 3 (see FIG. 4(B) and encoded by the DNA sequence of SEQ ID NO: 4 (see FIG. 4(C)) and purifying them according to the method set forth in Example 1.2. FIG. 6A is the liquid chromatography (LC) result, and FIG. 6B is the mass spectrometry result. As shown in the liquid chromatography and the mass spectrometry results in FIGS. 6A-6E, the products obtained from the protein complex expression consisted mostly of one substance, particularly, a substance having the heterodimer mass value, whereas the products obtained through the co-expression of the two polypeptides consisted of a mixture of substances having several mass values.

1.4. Bispecific Antigen-Antibody Reaction of Bispecific Antibody Prepared from Protein Complex In order to see the bispecific antigen-antibody reaction of the bispecific antibody prepared in Example 1.2, a surface plasmon resonance experiment was carried out using BiacoreT100 instrument (GE healthcare). As a running buffer and dilution buffer, 1×HBS-EP (GE healthcare) was used. Her2 molecules (RnD systems) with Fc fused thereto were immobilized on the surface of CM5 chip (GE healthcare) at about 2500 RU (response unit).

Figure 7:
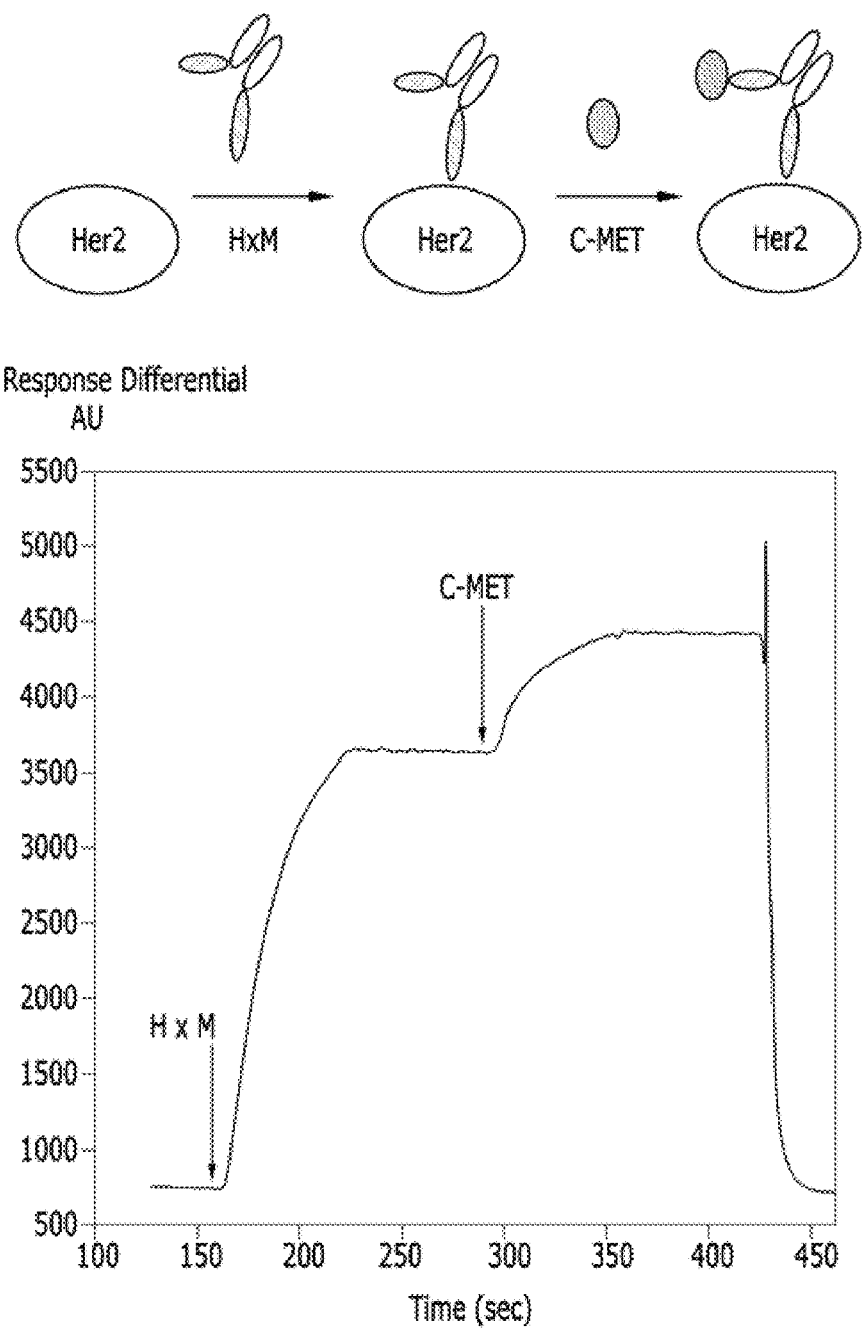
FIG. 7 is a sensorgram showing the bispecific antigen-antibody reaction of a bispecific antibody prepared from a c-Met/Her2 double binding protein complex.

About 500 nM bispecific antibody was flowed onto the surface and then cMet (RnD systems) with Fc fused thereto was flowed at a rate of 10 µL/min. Surface regeneration was carried out by flowing glycine-HCl (pH 2.0) (GE Healthcare) buffer for one minute at 10 µL/min. The generated sensorgram was fitted using BIA evaluation software and the result is shown in FIG. 7. As shown in FIG. 7, the bispecific antibody prepared in Example 1.2 exhibited bispecific antigen-antibody reaction by specifically recognizing its unique antigens c-Met and Her2.

Example 2: Preparation of Protein Complex Including Two Different Kinds of Antigen Binding Regions (c-Met and EGFR Double Specific Binding Protein Complex)

2.1. Preparation of Expression Vector

In order to prepare the precursor protein complex of a bispecific antibody including specific binding sites to c-Met and EGFR, respectively, an expression vector for the protein complex was prepared by Genotech Co. Ltd. As an animal cell expression vector for protein overexpression, pCEP4 (Invitrogen) was used.

Figure 8:
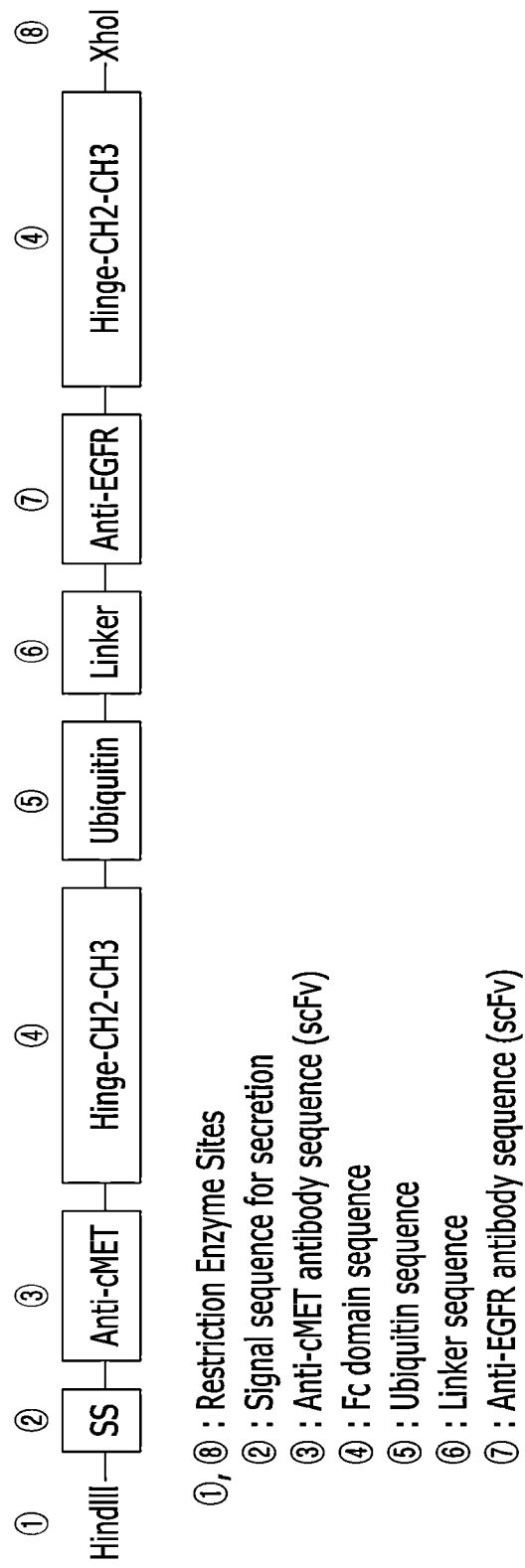
FIG. 8 is a diagram showing the structure of an anti c-Met/EGFR bispecific antibody produced by the cleavage of a c-Met/EGFR double binding protein complex.

Specifically, in order to express the precursor protein complex of the bispecific antibody, a single stranded DNA (SEQ ID NO: 116) encoding the amino acid sequence (SEQ ID NO: 115) of a single chain polypeptide having a structure as set forth in FIG. 8 (a secretion signal sequence, anti c-Met site (c-Met binding site), Fc (including a knob), tag (ubiquitin), GS linker, anti EGFR site (EGFR binding site), and Fc (including a hole)) was designed. The insert DNA fragment (SEQ ID NO: 116) includes at its 5' end a nucleotide sequence to be cleavable by HindIII (SEQ ID NO: 113) and at its 3' end a nucleotide sequence to be cleavable by XhoI (SEQ ID NO: 114), and was inserted into the HindIII-XhoI restriction enzyme sequences of pCEP4 vector.

Further, for the comparison of a bispecific antibody induced from the protein complex and a bispecific antibody generated by each single chain polypeptide, the following two types of DNAs were synthesized. Specifically, a single stranded DNA (SEQ ID NO: 115) encoding the amino acid sequence of a single chain polypeptide including a secretion signal sequence, an anti cMet site and a hinge, and an Fc domain was synthesized and inserted into pCEP4 vector via the HindIII-XhoI restriction enzyme sequences. Likewise, a single stranded DNA (SEQ ID NO: 116) encoding the amino acid sequence of a single chain polypeptide including a secretion signal sequence, an epidermal growth factor receptor (EGFR) binding site, and an Fc domain was synthesized and inserted into pCEP4 vector via the HindIII-XhoI restriction enzyme sequences.

2.2. Expression of Protein Complex and Purification of Bispecific Antibody

Figure 9:
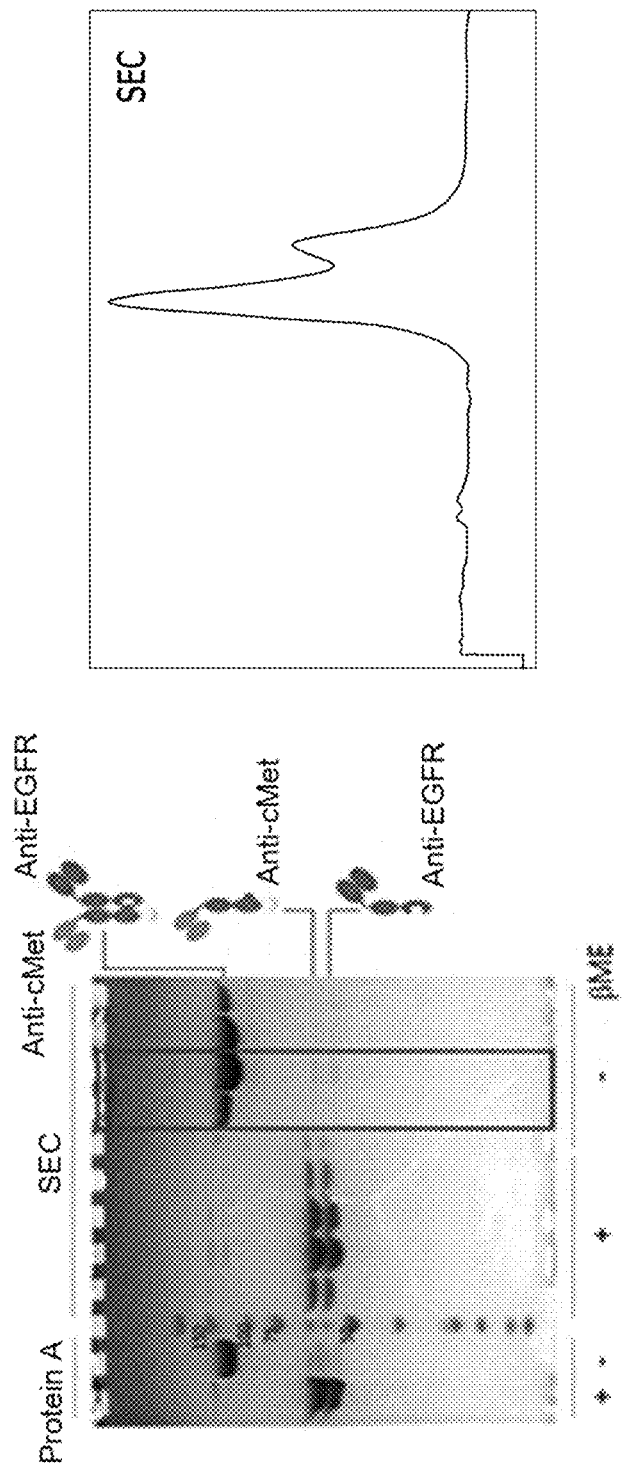
FIG. 9 is an electrophoresis photograph and SEC profile of a bispecific antibody produced by the cleavage of a c-Met/EGFR double binding protein complex.

In order to over-express the protein complex using the vector prepared in Example 2.1 above, human embryonic kidney cell (HEK293-F, Invitrogen) transformed with the vector was used. The HEK293-F cells were maintained in an orbital shaker of 130 rpm, at 37° C., 8% $CO_2$ conditions. For transfection, the cells were separated from the medium using centrifugation, they were then suspended again with a fresh Freestyle 293 Expression medium (Invitrogen) at a cell concentration of $1×10^6$/mL and then, the HEK293-F cells were transfected with 100 µg of the vector, using a FreeStyle™ MAX reagent (Invitrogen). On 7 to 8 days after the transfection, a cell culture solution including the protein complex was collected using centrifugation (4000×g, 10 min, 4° C.), and it was filtered using a filter having a pore size of 0.22 micron to eliminate the cell debris from the cell culture solution. The thus obtained supernatant (filtrate) was used for the purification of a bispecific antibody. The bispecific antibody was separated, using Protein A affinity column (GE Healthcare). First, Protein A affinity column was equilibrated with 1×PBS (Invitrogen) solution and then, the supernatant was applied to Protein A affinity column equilibrated with the above solution, washed with a wash buffer (1×PBS) corresponding to 5 times the column volume, and then treated with an elution buffer including 10% glycerol (IgG elution buffer, Thermo Scientific) to elute the bispecific antibody. The eluted solution was neutralized immediately with 1 M Tris-HCl (pH 9.0) solution. The eluted solution was loaded onto HiLoad 16/60 Superdex 200 column equilibrated with 1×PBS to perform size exclusion chromatography. The purified protein concentration was measured using a Herceptin antibody as a standard material. Thereafter, the concentrated bispecific antibody was verified finally through SDS-PAGE. Prior to loading onto the gel, the bispecific antibody was divided into two, one was treated with 1 mM β-mercaptoethanol (reducing condition: R), and the other was loaded in a state of not being treated with β-mercaptoethanol (non-reducing condition: NR). As a result, the generation of disulfide bond which is the intrinsic property of an antibody was confirmed through the comparison in R/NR conditions, and homodimeric antibodies were not observed, as shown in FIG. 9.

2.3. Bispecific Antigen-Antibody Reaction of Bispecific Antibody Prepared from Protein Complex In order to see the binding affinity of the bispecific antigen-antibody reaction of the bispecific antibody prepared in Example 2.2, the binding ability of the antibody to c-Met and EGFR was evaluated through surface plasmon resonance (SPR) experiment, using BiacoreT100 instrument (GE healthcare). As a running buffer and dilution buffer, 1×HBS-EP (GE healthcare) was used.

Human c-Met (Sino Biologicals) was immobilized on the surface of CM5 chip (GE healthcare) at about 2000 RU (response unit), using a standard amine-coupling reaction. The bispecific antibody prepared in Example 2.2 was flowed onto the surface at a rate of 10 µL/min for one minute and after their binding was confirmed, human EGFR extracellular domain (Prospec) was flowed at a flow rate of 10 µL/min for one minute. After each binding cycle was complete, surface regeneration was carried out by flowing the regeneration solution glycine-HCl (pH 2.0) (GE Healthcare) for one minute at a rate of 10 µL/min to eliminate the bound antigens and antibodies from the chip. As a result of analysis, the bispecific antigen binding protein complex was confirmed to have binding abilities to human c-Met and human EGFR at the same time (FIG. 10A).

The generated sensorgram was fitted in BIA evaluation software using 1:1 Langmuir binding model and the result is shown in FIG. 10B. As shown in FIG. 10B, when compared to monovalent antibodies (M×M or E×E), the bivalent antibody M×E maintained Kd values and thus, it was confirmed that there was no significant difference in binding ability to EGFR and c-Met, respectively.

Figure 11A:
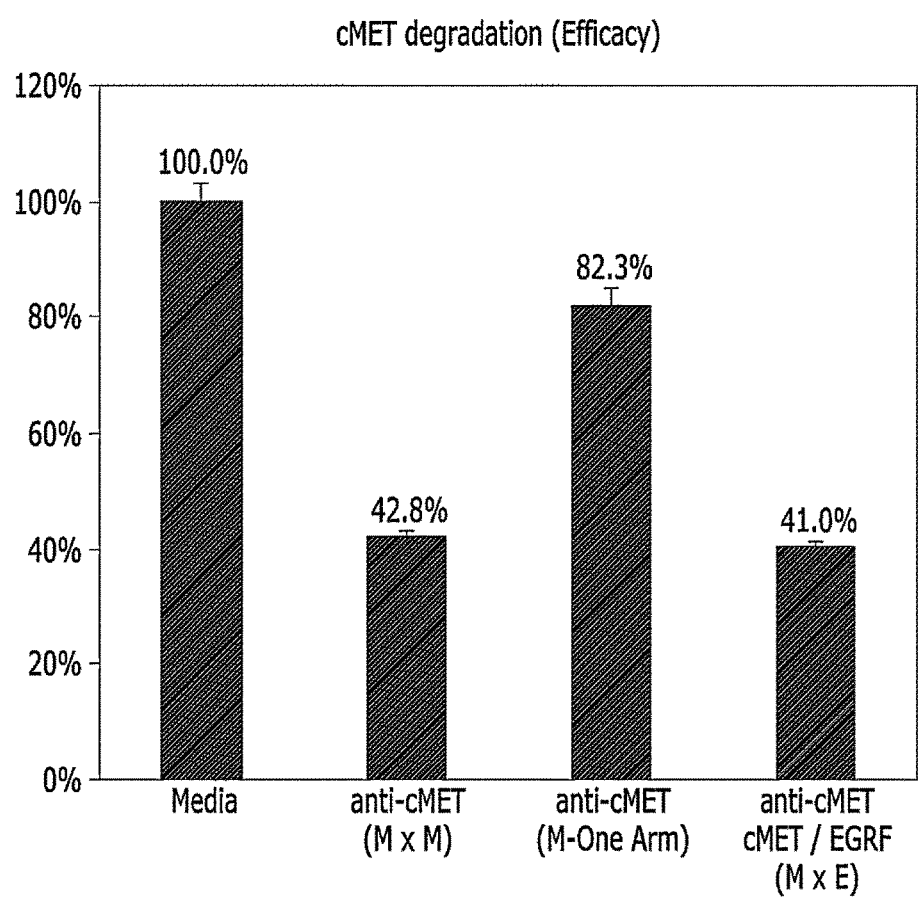
FIG. 11A is a graph showing the c-Met degradation level result of an anti c-Met/EGFR bispecific antibody (anti-cMET (M-One Arm): anti-cMET monospecific monovalent Ab)

2.4. c-Met Degradation by Bispecific Antibody Prepared from Protein Complex (MKN45): Efficacy To evaluate the efficacy of the bispecific antibody, the change of the total amount of c-Met was measured, using the fact that the antibody bound to c-Met degrades c-Met via internalization. It has already been known that the binding of c-Met and HGF accelerates the growth of cancer cells and therefore, the above evaluation is based on the idea that a reduction in the total amount of c-Met leads to the decrease of cancer cell growth. Human total HGF Receptor/c-Met ELISA kit (R&D system) was used and the experiment was carried out using the MKN45 stomach cancer cell line (ATCC). $2 \times 10^5$ cells/mL of the cells in DMEM medium (GIBCO) was mixed with 5 mg/mL of anti-c-Met antibody and cultured in 37° C., 5% $CO_2$ incubator for 24 hours, followed by ELISA experiment. The reaction was carried out ultimately using Super Aquablue (eBiosciences) and colorimetric signals were measured as OD values at 450 wavelengths. The value of a control group treated with no anti-c-Met antibody (group treated with media) was converted to 100% and the values obtained when anti-c-Met antibodies were treated were relatively calculated. The results are shown in a graph (FIG. 11A). As a result of measurement via quantitative ELISA methods, referring to FIG. 11A, the bispecific antibody (M×E) of Example 2.2 showed c-Met degradation level similar to single antibody (M×M).

Figure 11B:
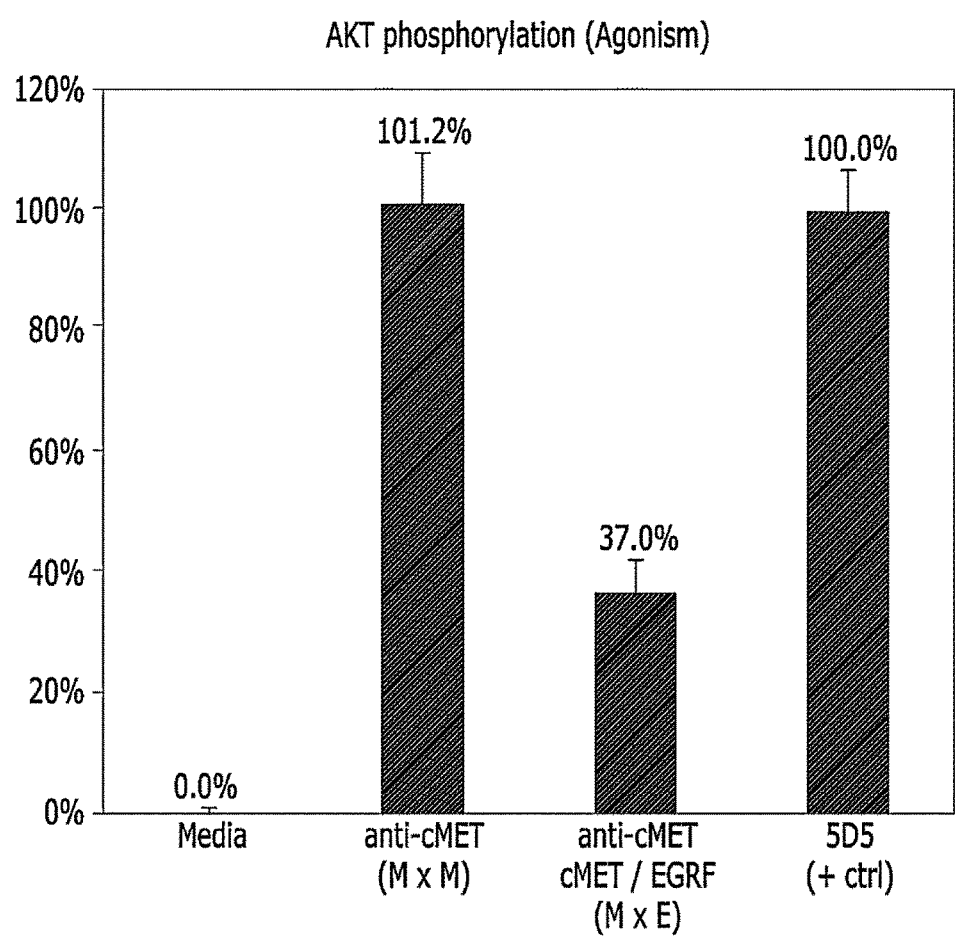
FIG. 11B is a graph showing the Akt phosphorylation (agonism) result of an anti c-Met/EGFR bispecific antibody.

2.5. Akt Phosphorylation of Bispecific Antibody Prepared from Protein Complex (Caki): Agonism Safety and efficacy for a therapeutic antibody were investigated by mechanism-based experiments. That is, agonism that might happen by the binding of the bispecific antibody and c-Met was evaluated through the measurement of a phosphorylation degree of AKT kinase using quantitative ELISA methods. A site within AKT to be phosphorylated is Ser 473, and PathScan phospho-AKT1 (Ser473) chemiluminescent Sandwich ELISA kit (Cell signaling) was employed. Caki-1 kidney cancer cell line (ATCC® HTB-46) which was cultured to $2 \times 10^5$ cells/ml one day prior was mixed with 5 ug/ml of antibody in serum-free DMEM media (Gibco) and treated for 30 minutes, followed by an experiment using ELISA kit. The result was obtained by measuring with a machine (2104 Envision® Multilabel Reader; Perkins Elmer). The phosphorylation degree of AKT was calculated in such a manner that phosphorylation by 5D5 (an anti-c-Met antibody, separated and purified from ATCC Cat. #HB-11895 hybridoma cells obtained from American Type Culture Collection (ATCC, Manassas, Va.)) was set as 100% and phosphorylation degrees by other anti-c-Met antibodies were calculated by comparison with that value. Cellular functions to be regulated by AKT include cell proliferation, cell survival, cell size regulation, response to available nutrients, intermediate metabolism, angiogenesis, tissue invasion, etc. All these processes represent the characteristics of cancer and many oncoproteins and tumor suppressors intersect in the AKT pathway, finely regulating cellular functions at the interface of signal transduction and classical metabolic regulation. Thus, as the degree of phosphorylated AKT that is an active form of AKT increases, the activity of cancer cells increases. In this regard, the degree of inhibiting AKT phosphorylation by the antibody was evaluated. As a result, it was confirmed that the bispecific antibody (M×E) of Example 2.2 inhibited AKT phosphorylation more highly than the single antibody (M×M), as shown in FIG. 11B.

Example 3: Preparation of Protein Complex Including Two Different Kinds of Antigen Binding Regions (c-Met and Her3 Double Specific Binding Protein Complex)

3.1. Preparation of Expression Vector

In order to prepare the precursor protein complex of a bispecific antibody including specific binding sites to c-Met and Her-3, respectively, an expression vector for the protein complex was prepared by Genotech Co. Ltd. As an animal cell expression vector for protein overexpression, pCEP4 (Invitrogen) was used.

Figure 12:
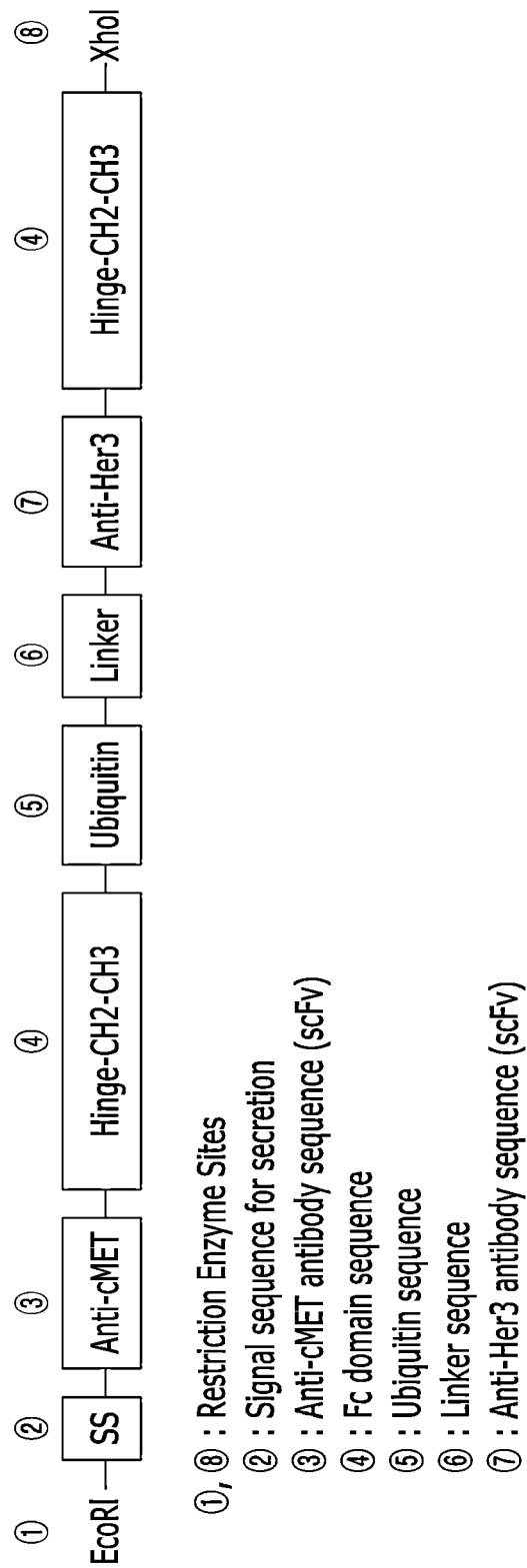
FIG. 12 is a diagram showing the structure of a bispecific antibody produced by the cleavage of a c-Met/Her3 double binding protein complex.

Specifically, in order to express the precursor protein complex of the bispecific antibody, a single stranded DNA (SEQ ID NO: 120) encoding the amino acid sequence (SEQ ID NO: 119) of a single chain polypeptide having a structure as set forth in FIG. 12 (a secretion signal sequence, anti c-Met site (c-Met binding site), Fc (including a knob), tag (ubiquitin), GS linker, anti Her3 site (Her3 binding site), and Fc (including a hole) was designed. The insert DNA fragment (SEQ ID NO: 120) includes at its 5' end a nucleotide sequence to be cleavable by HindIII (SEQ ID NO: 113) and at its 3' end a nucleotide sequence to be cleavable by XhoI (SEQ ID NO: 114), and was inserted into the HindIII-Xho1 restriction enzyme sequences of pCEP4 vector.

Further, a single stranded DNA (SEQ ID NO: 122) encoding the amino acid sequence (SEQ ID NO: 121) of a single chain polypeptide, except that the Fc does not include a knob or a hole in the structure shown in FIG. 12, having other portions identical to the structure as shown in FIG. 12 was designed. The insert DNA fragment (SEQ ID NO: 122) includes at its 5' end a nucleotide sequence to be cleavable by HindIII (SEQ ID NO: 113) and at its 3' end a nucleotide sequence to be cleavable by XhoI (SEQ ID NO: 114), and was inserted into the HindIII-Xho1 restriction enzyme sequences of pCEP4 vector.

Further, for the comparison of a bispecific antibody induced from the protein complex and a bispecific antibody generated by each single chain polypeptide, the following two types of DNAs were synthesized. Specifically, a single stranded DNA (SEQ ID NO: 117) encoding the amino acid sequence of a single chain polypeptide including a secretion signal sequence, an anti cMet site which is a hepatocyte growth factor receptor (c-Met) binding site and a hinge, and an Fc domain was synthesized and inserted into pCEP4 vector via the HindIII-Xho1 restriction enzyme sequences. Likewise, a single stranded DNA (SEQ ID NO: 123) encoding the amino acid sequence of a single chain polypeptide including a secretion signal sequence, a Her3 binding site, and an Fc domain was synthesized and inserted into pCEP4 vector via the HindIII-Xho1 restriction enzyme sequences.

3.2. Expression of Protein Complex and Purification of Bispecific Antibody

Figure 13A:
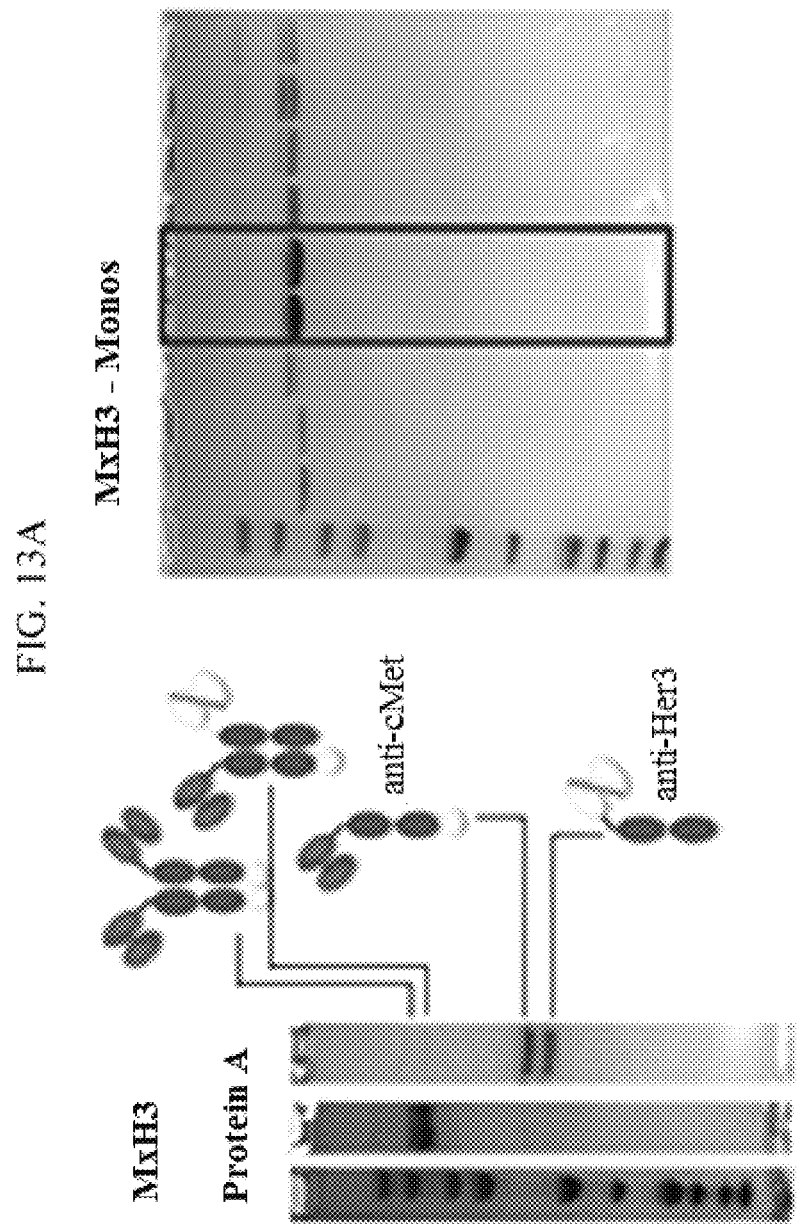
FIGS. 13A-13C depict an electrophoresis gel and SEC profile of an anti c-Met/Her3 bispecific antibody produced by the cleavage of a c-Met/Her3 double binding protein complex (not including a knob-hole)
Figure 13B:
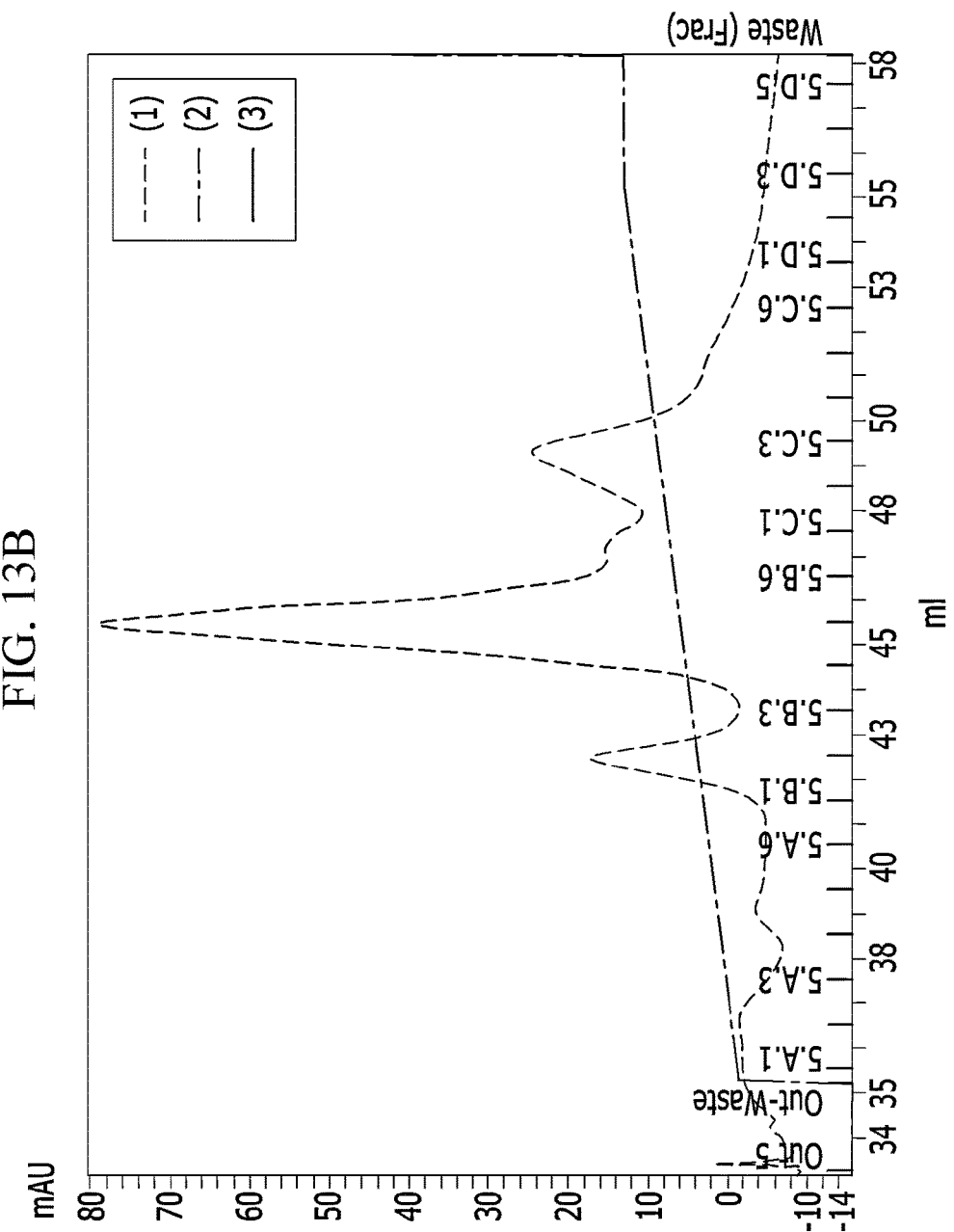
Figure 13C:
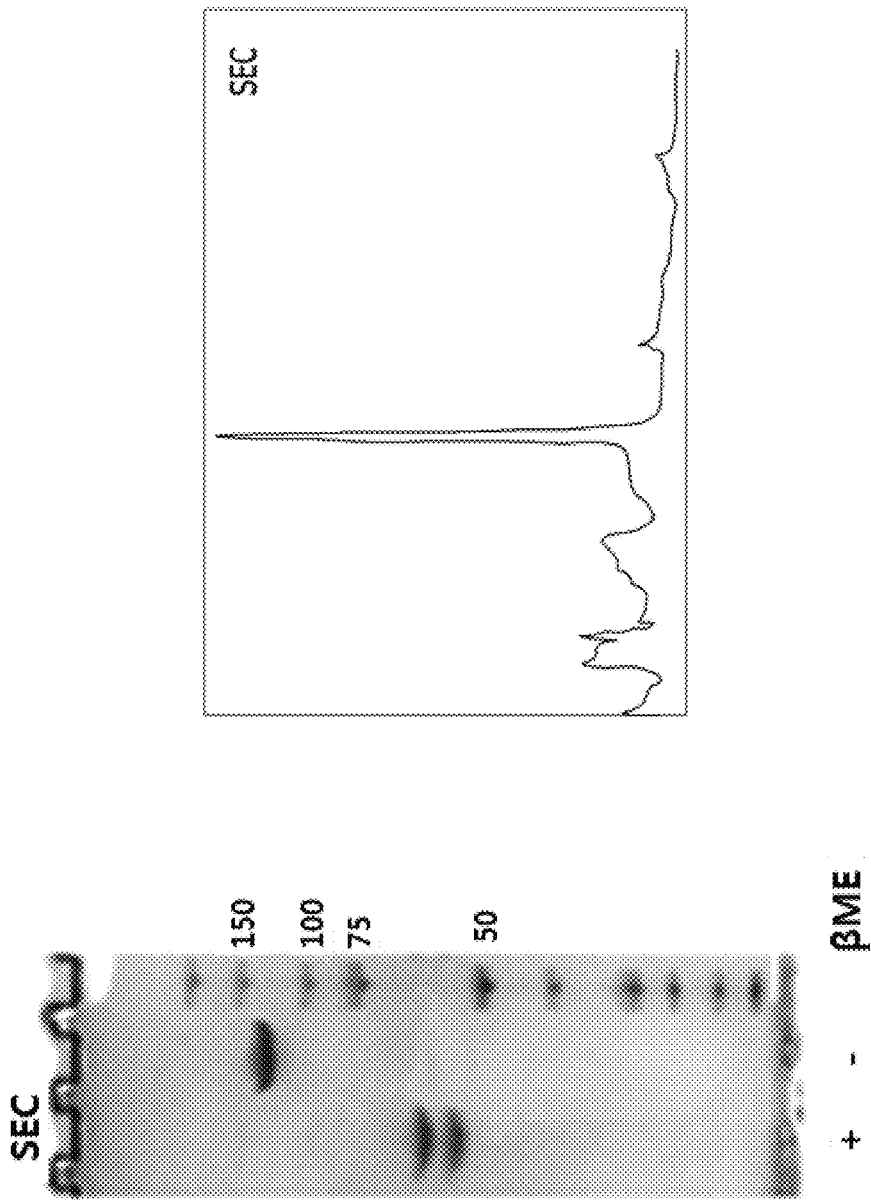
Figure 13D:
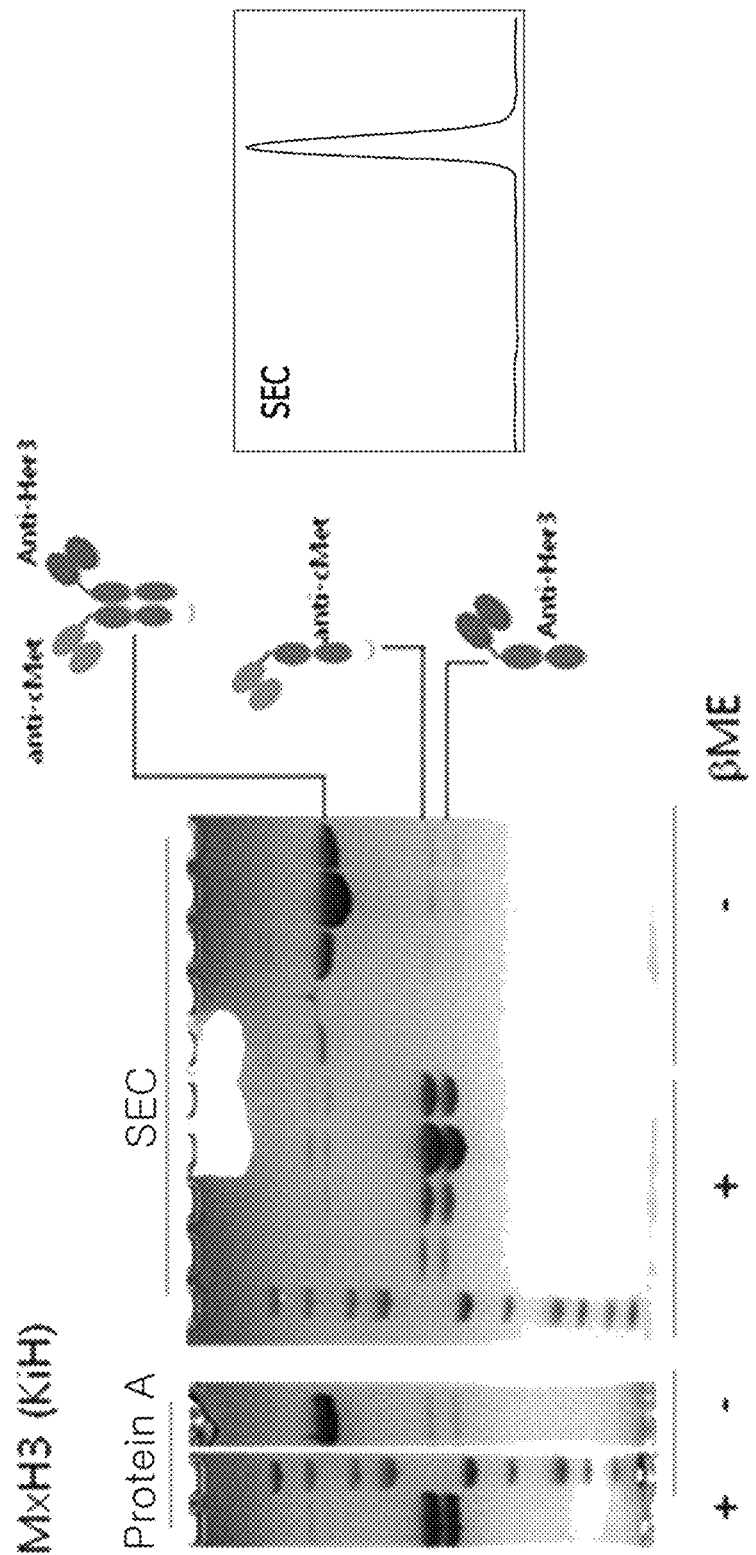
FIG. 13D is an electrophoresis gel and SEC profile of an anti c-Met/Her3 bispecific antibody produced by the cleavage of a c-Met/Her3 double binding protein complex (including a knob-hole) (in 13B, (1): UV 1 280 Chrom.1: MonoS M×HS scoBA 20120209 d4 001, (2): Conc B Chrom.1:MonoS N×H3 scoBA 20120209 d4 001; and (3): Fraction Chrom.1:MonoS M×H3 scoBA 20120209 d4 001)

In order to see the expression of the protein complex using the vector prepared in Example 3.1 above, the vector was introduced into a human embryonic kidney cell (HEK293-F, Invitrogen) and after the transfection, the expression of the protein was evaluated. The HEK293-F cells were maintained in an orbital shaker of 130 rpm, at 37° C., 8% $CO_2$ conditions. For transfection, the cells were separated from the medium using centrifugation, they were then suspended again with a fresh Freestyle 293 Expression medium (Invitrogen) at a cell concentration of $1 \times 10^6$/mL and then, the HEK293-F cells were transfected with 100 μg of the vector, using a FreeStyle™ MAX reagent (Invitrogen). On 7 to 8 days after the transfection, a cell culture solution including the protein complex was collected using centrifugation (4000×g, 10 min, 4° C.), and it was filtered using a filter having a pore size of 0.22 micron to eliminate the cell debris from the cell culture solution. The thus obtained supernatant (filtrate) was used for the purification of a bispecific antibody. The bispecific antibody was separated, using Protein A affinity column (GE Healthcare). First, Protein A affinity column was equilibrated with 1×PBS (Invitrogen) solution and then, the supernatant was applied to Protein A affinity column equilibrated with the above solution, washed with a wash buffer (1×PBS) corresponding to 5 times the column volume, and then treated with an elution buffer including 10% glycerol (IgG elution buffer, Thermo Scientific) to elute the bispecific antibody. The eluted solution was neutralized immediately with 1 M Tris-HCl (pH 9.0) solution. The eluted solution was loaded onto HiLoad 16/60 Superdex 200 column equilibrated with 1×PBS to perform size exclusion chromatography. The purified protein concentration was measured using a Herceptin antibody as a standard material. Thereafter, the concentrated bispecific antibody was verified finally through SDS-PAGE. Prior to loading onto the gel, the bispecific antibody was divided into two, one was treated with 1 mM β-mercaptoethanol (reducing condition: R), and the other was loaded in a state of not being treated with β-mercaptoethanol (non-reducing condition: NR). As a result, the generation of disulfide bond which is the intrinsic property of an antibody was confirmed through the comparison in R/NR conditions, and homodimeric antibodies were not observed, as shown in FIGS. 13A-13C (the result obtained from the double antibody vector of Example 3.1) and FIG. 13D (the result obtained from the control antibody vector of Example 3.1).

3.3. Bispecific Antigen-Antibody Reaction of Bispecific Antibody Prepared from Protein Complex In order to see the binding affinity of the bispecific antigen-antibody reaction of the bispecific antibody prepared in Example 3.2, surface plasmon resonance (SPR) experiment was carried out, using a BiacoreT100 instrument (GE healthcare). As a running buffer and dilution buffer, 1×HBS-EP (GE healthcare) was used.

Figure 14A:
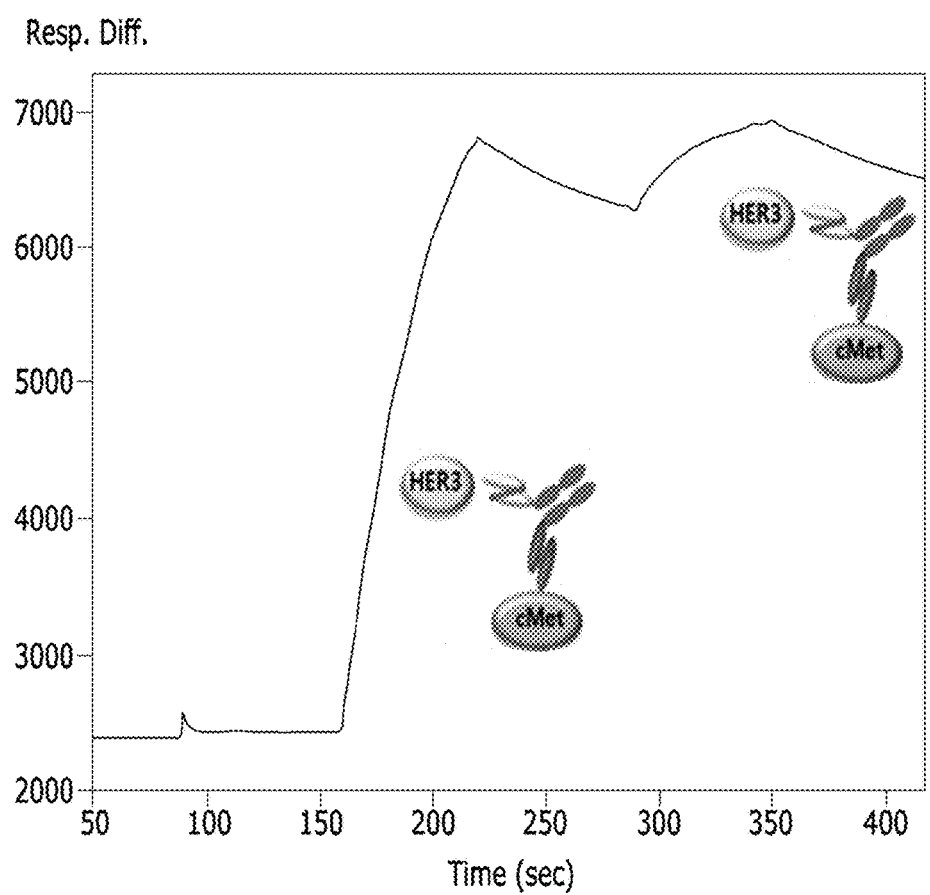
FIG. 14A is a graph and illustration showing the binding affinity result of the bispecific antigen-antibody reaction of an anti c-Met/Her3 bispecific antibody measured by Surface Plasmon Resonance (SPR) methods.

An extracellular domain protein of c-Met (RnD systems, Accession number: P08581) was immobilized on the surface of CM5 chip (GE healthcare) at about 5000 RU (response unit), using standard amine-coupling reaction. The bispecific antibody of about 500 RU was flowed to the surface and after their binding, human Her-3 (Sino Biologicals) was flowed at a flow rate of 50 μL/min. Association phase was 180 seconds, and separation phase (washed with a running buffer) was 600 seconds. After each binding cycle was complete, the regeneration solution glycine-HCl (pH 2.0) (GE Healthcare) was flowed for one minute at a rate of 10 μL/min to eliminate the bound antigens and antibodies from the chip. As a result of analysis, the bispecific antigen binding protein complex was confirmed to have binding abilities to human c-Met and human Her-3 at the same time (FIG. 14A).

Figure 14B:
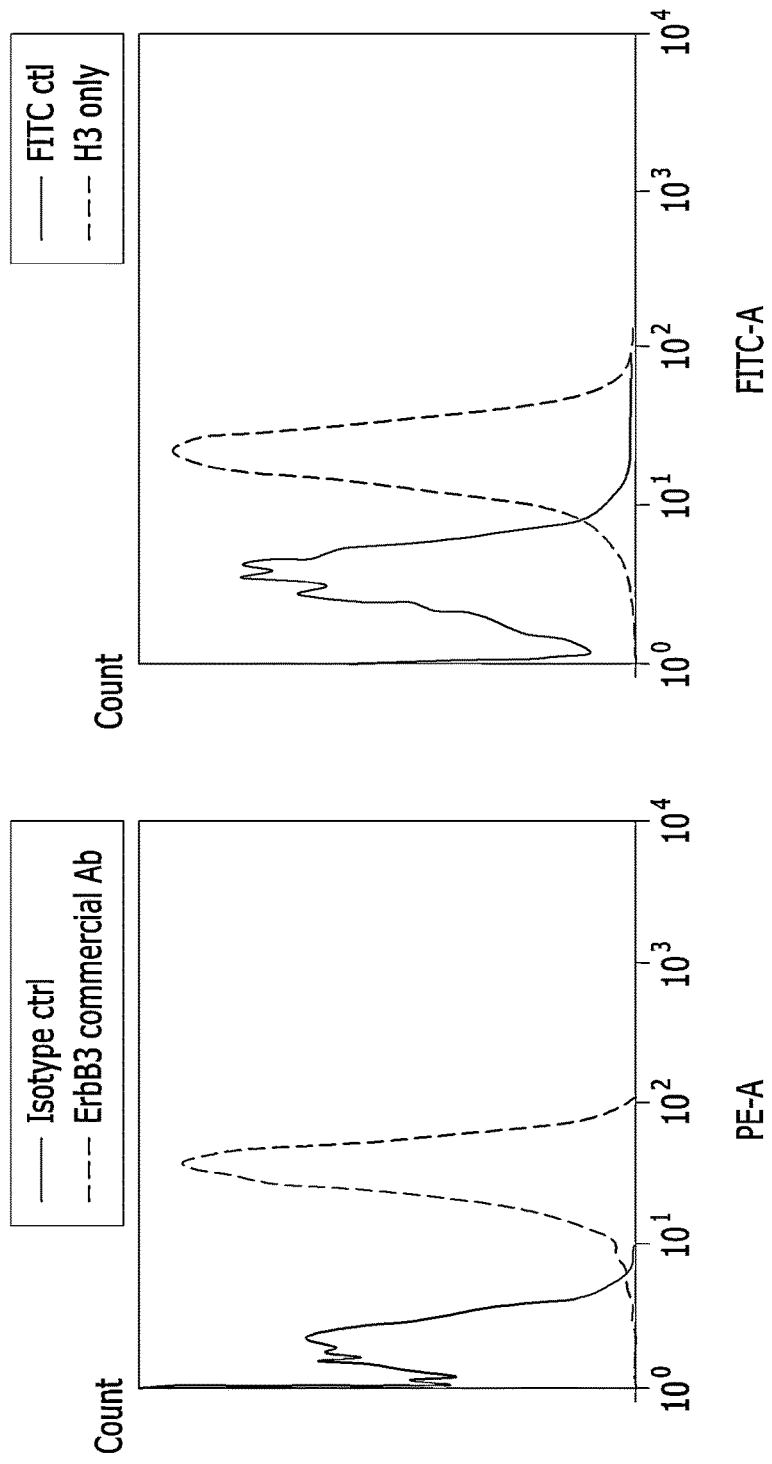
FIG. 14B are graphs showing the binding affinity results of Her-3 of an anti c-Met/Her3 bispecific antibody to ErbB3, compared to ErbB3 commercial Ab (left: ErbB3 commercial Ab, right: Her-3 of a bispecific antigen binding protein complex)

Further, in order to see the binding of the antigen-antibody reaction (ErbB3 and anti-Her-3) of the bispecific antibody, antigen-antibody reaction was carried out using MCF7 (breast cancer cell line) cells (ATCC) expressing ErbB3 and then measurement was performed using FACS (fluorescence activated cell sorter). ErbB3 commercial Ab (R&D) was used, as a control, in MCF7 (breast cancer cell line) expressing ErbB3 and the binding of Her-3 scFv of the bispecific antigen binding protein complex was evaluated. As a result, it was confirmed that the bispecific antigen binding protein complex showed no significant difference in binding, when compared to ErbB3 commercial Ab (FIG. 14B).

Figure 15A:
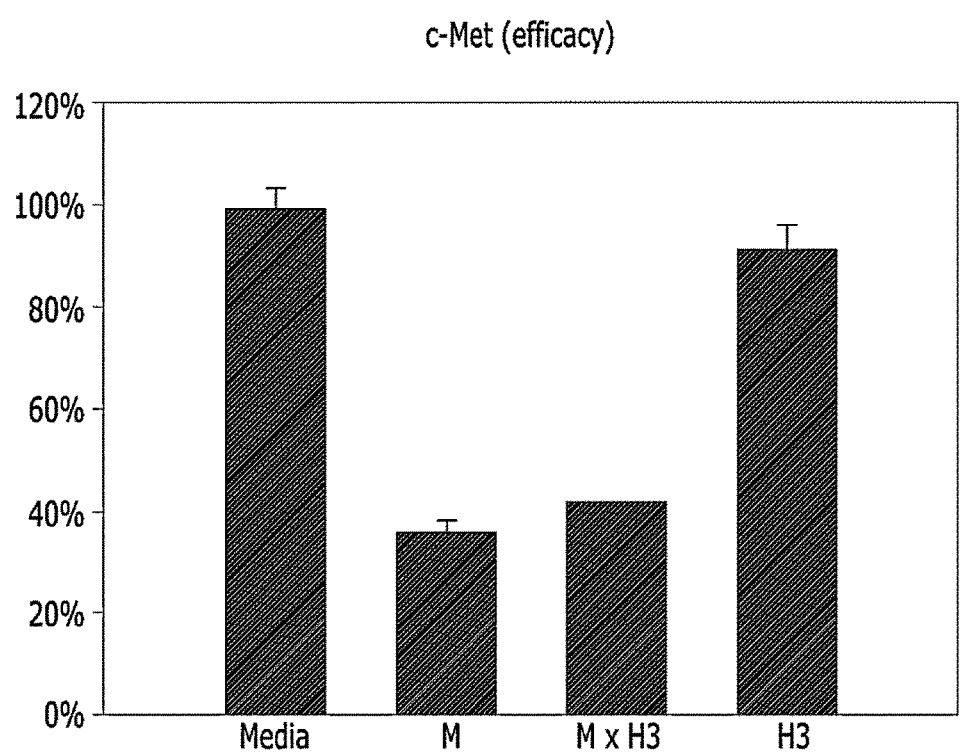
FIG. 15A is a graph showing the c-Met degradation level result of an anti c-Met/Her3 bispecific antibody.

3.4. c-Met Degradation by Bispecific Antibody Prepared from Protein Complex (MKN45): Efficacy A relative total amount of c-Met is to evaluate the efficacy of an antibody by measuring the change of the total amount of c-Met, using the fact that the antibody bound to c-Met degrades c-Met via internalization. It has already been known that the binding of c-met and HGF accelerates the growth of cancer cells and therefore, the above evaluation is based on the idea that a reduction in the total amount of c-Met leads to the decrease of cancer cell growth. Human total HGF R/c-Met ELISA kit (R&D system) was used and the experiment was carried out using MKN45 stomach cancer cell line (JCRB, JCRB1379). $2 \times 10^5$ cells/mL of the cells in 10% FBS-containing RPMI medium (Invitrogen, Gibco) was mixed with 5 mg/mL of anti-c-Met antibody and cultured in 37° C. incubator for 24 hours, followed by ELISA experiment. The reaction was carried out ultimately using Super Aquablue (eBiosciences) and colorimetric signals were measured as OD values at 450 wavelengths. The value of a control group treated with no anti-c-Met antibody (group treated with media) was converted to 100% and the values obtained when anti-c-Met antibodies were treated were relatively calculated. The results are shown in a graph (FIG. 15A). As a result of measurement via quantitative ELISA methods, referring to FIG. 15A, the bispecific antibody (M×H3) of Example 3.2 showed similar or a little increased c-Met degradation level, when compared to the single antibodies (M, H3).

Figure 15B:
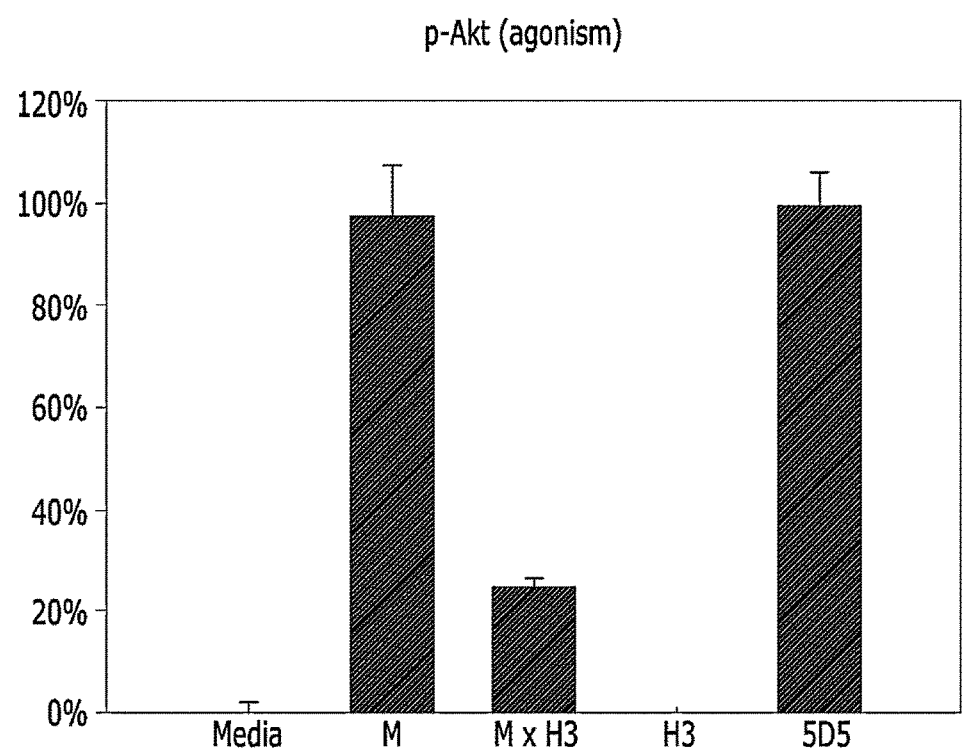
FIG. 15B is a graph showing the Akt phosphorylation (agonism) result of an anti c-Met/Her3 bispecific antibody.
Figure 16:
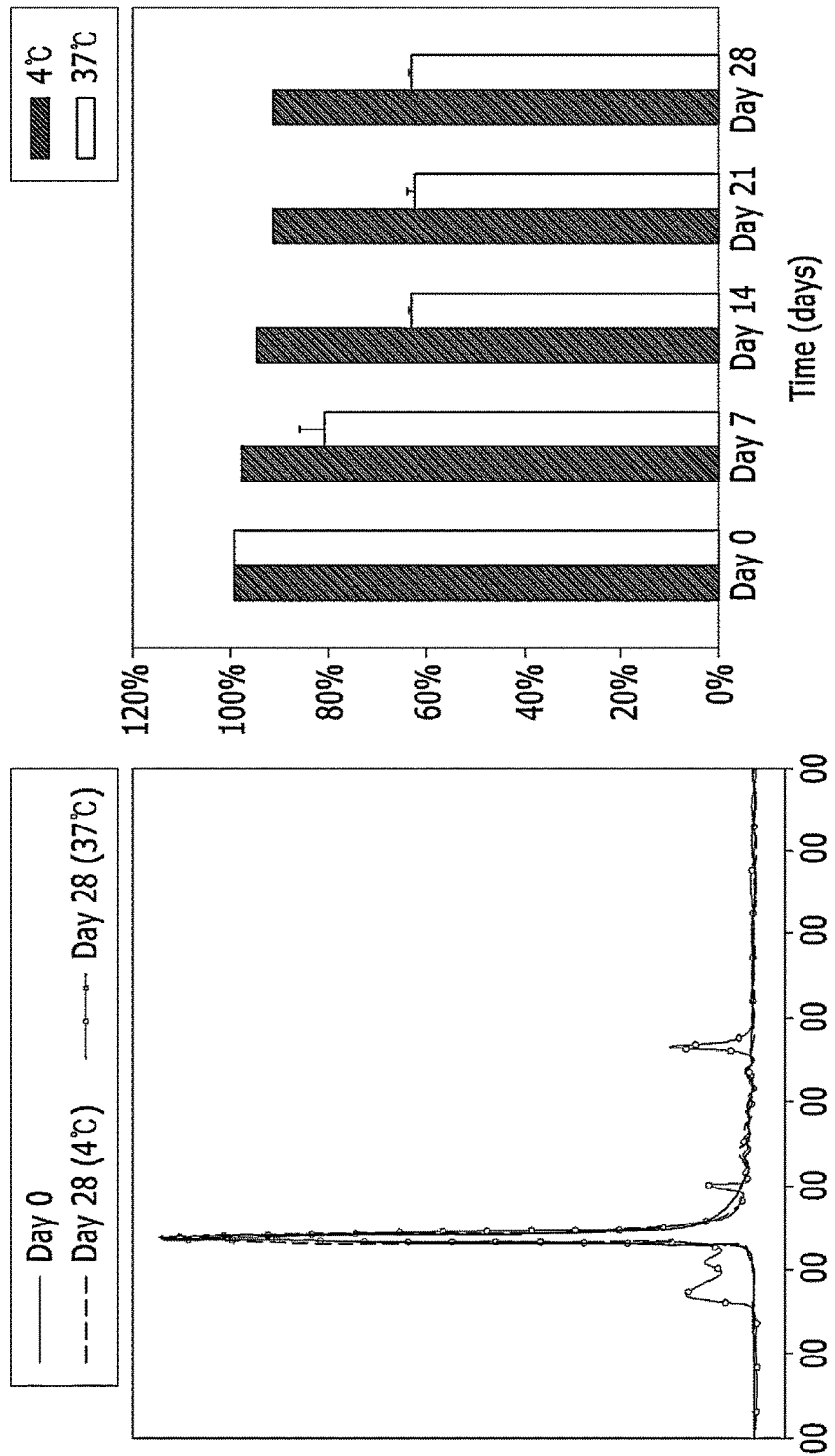
FIG. 16 are graphs showing the stability of an anti c-Met/Her3 bispecific antibody in a buffer.

3.5. Akt Phosphorylation of Bispecific Antibody Prepared from Protein Complex (Caki): Agonism Safety and efficacy for a therapeutic antibody were investigated by mechanism-based experiments. In order to see safety, the phosphorylation degree of AKT kinase was measured using quantitative ELISA methods. A site within AKT to be phosphorylated is Ser 473, and PathScan phospho-AKT1 (Ser473) chemiluminescent Sandwich ELISA kit (Cell signaling) was employed. Caki-1 kidney cancer cell line (ATCC® HTB-46™) which was cultured to $2\times10^5$ cells/ml one day before was mixed with 5 ug/ml of antibody in serum-free DMEM media (Invitrogen) and treated for 30 min, followed by an experiment using ELISA kit. The result was obtained by measuring with 2104 Envision® Multilabel Reader (Perkins Elmer). The phosphorylation degree of AKT was calculated in such a manner that phosphorylation by 5D5 was set 100% and phosphorylation degrees by other anti-c-Met antibodies were calculated by comparison with that value. Cellular functions to be regulated by AKT include cell proliferation, cell survival, cell size regulation, response to available nutrients, intermediate metabolism, angiogenesis, tissue invasion, etc. All these processes represent the characteristics of cancer and many oncoproteins and tumor suppressors intersect in the AKT pathway, finely regulating cellular functions at the interface of signal transduction and classical metabolic regulation. Thus, as the degree of phosphorylated AKT that is an active form of AKT increases, the activity of cancer cells increases. In this regard, the degree of inhibiting AKT phosphorylation by the antibody was evaluated. As a result, it was confirmed that the bispecific antibody of Example 3.2 unexpectedly inhibited AKT phosphorylation more highly than the single antibody, as shown in FIG. 15B.

Example 4: Preparation of Protein Complex Including Two Different Kinds of Antigen Binding Regions (c-Met and Ang2 Double Specific Binding Protein Complex)

4.1. Preparation of Expression Vector

In order to prepare the precursor protein complex of a bispecific antibody including specific binding sites to c-Met and Ang2, respectively, an expression vector for the protein complex was prepared by Genotech Co. Ltd. As an expression vector for protein overexpression, pCEP4 (Invitrogen) was used.

Figure 17:
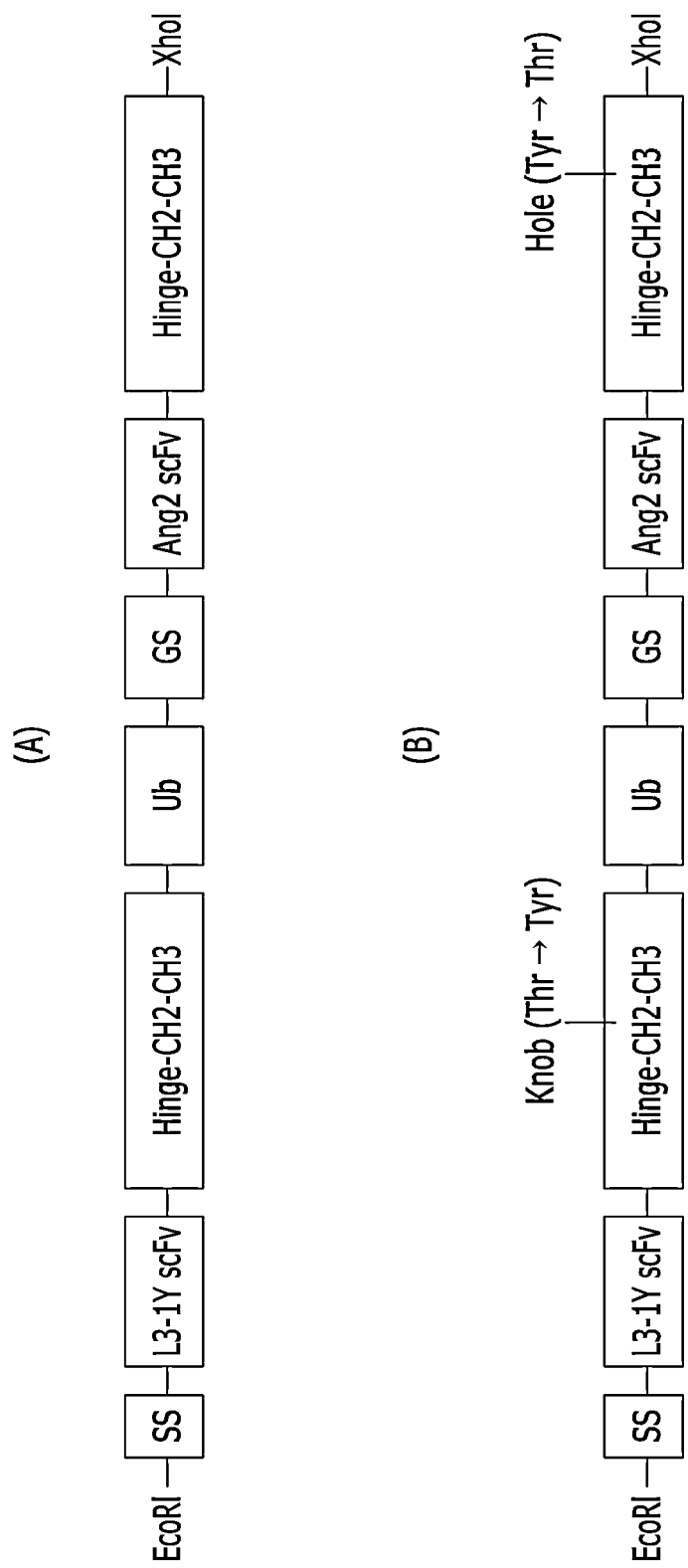
FIG. 17 is a schematic diagram showing DNA sequences (A) and (B) to be inserted into an expression vector for preparing a c-Met/Ang2 double binding protein complex.

Specifically, as set forth in FIG. 17(A), a single stranded DNA (SEQ ID NO: 125) encoding the amino acid sequence (SEQ ID NO: 124) of a protein complex including a single chain polypeptide consisting of a secretion signal sequence (ss), a cMet binding site, and an Fc domain including hinge, a single chain polypeptide consisting of an Ang2 binding site, and an Fc domain, a ubiquitin tag, and a linker was synthesized and inserted into pCEP4 (Invitrogen), thereby to prepare a protein complex expression vector.

Further, as set forth in FIG. 17(B), a single stranded DNA (SEQ ID NO: 127) encoding the amino acid sequence (SEQ ID NO: 126) of a protein complex including a secretion signal sequence (ss), a single chain polypeptide including a cMet binding site and a hinge, and an Fc domain including an amino acid sequence forming a knob, a single chain polypeptide including an Ang2 binding site, and an Fc domain including an amino acid sequence forming a hole, a ubiquitin tag, and a linker was synthesized and inserted into pCEP4 (Invitrogen), thereby to prepare a protein complex expression vector.

The insert DNA fragment includes at its 5' end a nucleotide sequence to be cleavable by HindIII (SEQ ID NO: 113) and at its 3' end a nucleotide sequence to be cleavable by XhoI (SEQ ID NO: 114), and was inserted into the HindIII-Xho 1 restriction enzyme sequences of pCEP4 vector.

4.2. Expression of Protein Complex and Purification of Bispecific Antibody

Figure 18A:
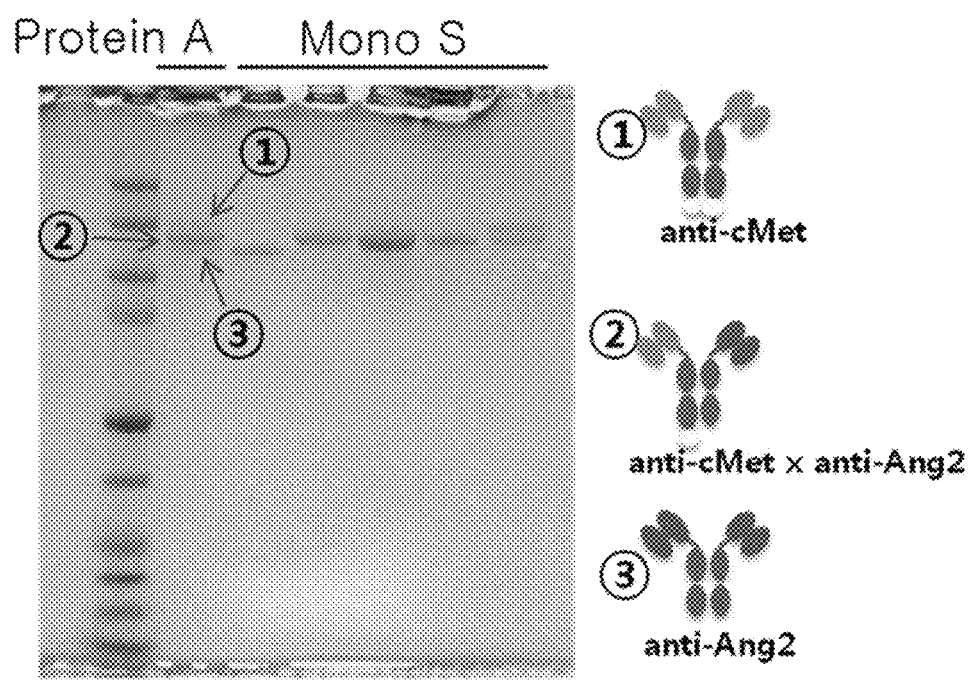
FIG. 18A is an electrophoresis photograph with accompanying illustration showing the SDS-PAGE result of a bispecific antibody produced from a c-Met/Ang2 double binding protein complex.
Figure 18B:
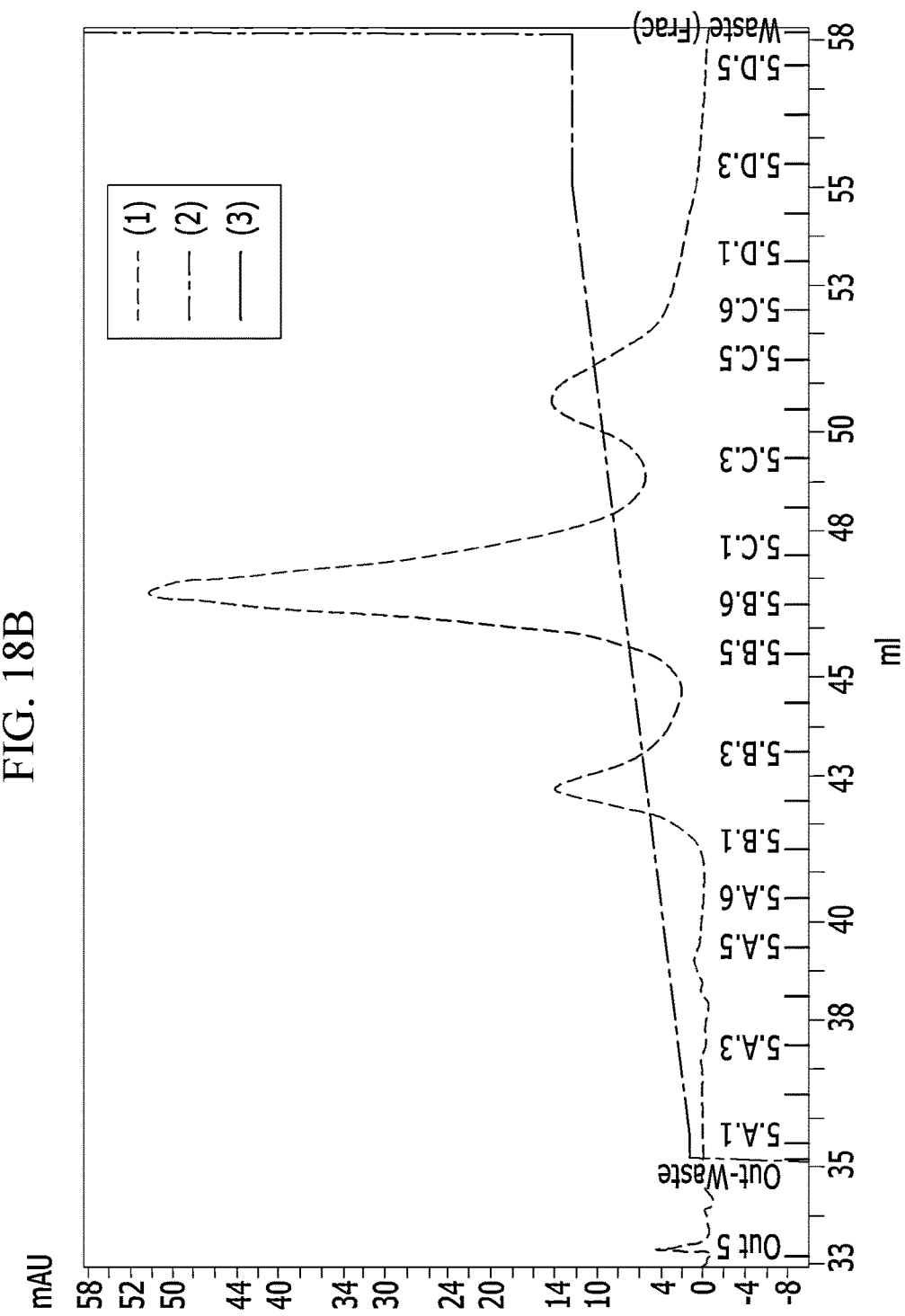
FIG. 18B is a graph showing the absorbance results of a bispecific antibody obtained through ion-exchange chromatography at 280 nm (wherein, (1): UV 1 280 Chrom.1: MonoS M×N scoBA 20120209 d8 001, (2): Conc B Chrom.1:MonoS N×N scoBA 20120209 d8 001; and (3): Fraction Chrom.1:MonoS M×N scoBA 20120208 d4 001)

In order to over-express the protein complex using the vector prepared in Example 4.1 above, human embryonic kidney cell (HEK293-F, Korean Cell Line Bank) transfected with the vector was used. The HEK293-F cells were maintained in an orbital shaker of 130 rpm, at 37° C., 8% $CO_2$ conditions. For transfection, $1\times10^6$ cells were separated from the medium using centrifugation, they were then suspended again with a fresh Freestyle 293 Expression medium (Invitrogen) and then, the HEK293-F cells were transfected with 100 µg of the vector, using a FreeStyle™ MAX reagent (Invitrogen). On 7 to 8 days after the transfection, a supernatant was collected using centrifugation (4000×g, 10 min, 4° C.), and it was filtered using a filter having a pore size of 0.22 micron. The thus obtained supernatant was used for the purification of a protein complex. The protein complex was separated, using Protein A affinity column (GE Healthcare). First, Protein A affinity column was equilibrated with 1×PBS (Invitrogen) solution and then, the supernatant was applied to Protein A affinity column equilibrated with the above solution, washed with a wash buffer (1×PBS) corresponding to 5 times the column volume, and then treated with an elution buffer including 10% glycerol (IgG elution buffer, Thermo Scientific) to elute the protein complex. The eluted solution was neutralized immediately with 1 M Tris-HCl (pH 9.0) solution. The eluted solution obtained via Protein A affinity column was applied again to Mono S column (GE Healthcare) column equilibrated with an equilibration solution (30 mM MES (pH 5.0)). The proteins that were not bound to the column were removed through the application of the equilibration solution, and the proteins bound to the column were eluted, using a wash solution including 25 mM MES and salt (NaCl), by gradually increasing the concentration of the salt from 150 mM to 300 mM. The fractions including the protein complex were evaluated via absorbance at 280 nm (FIG. 18B) and SDS-PAGE using a non-reducing gel (FIG. 18A). As a result, it was confirmed that a heterodimer was formed from the antibody having a cMet binding site and Hinge-Fc and ubiquitin and the antibody having an Ang2 binding site and Hinge-Fc, as shown in FIGS. 18A and 18B.

4.3. Antigen-Antibody Reaction

Figure 20:
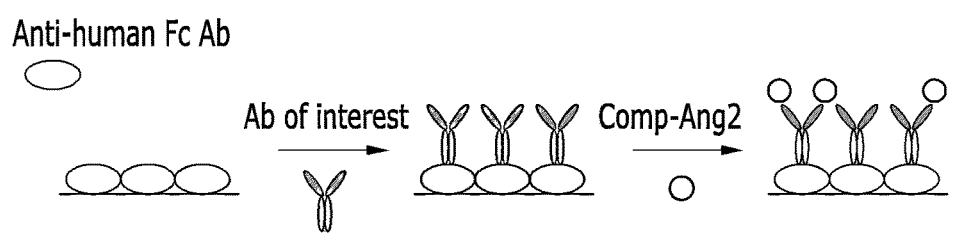
FIG. 20 is a table and illustration showing the affinity result of a c-Met/Ang2 bispecific antibody produced from a c-Met/Ang2 double binding protein complex toward Ang2 (N×N: anti-Ang2 monospecific bivalent Ab)

In order to see the binding affinity of the antibody prepared in Example 4.2 to their respective antigen, surface plasmon resonance (SPR) experiment was carried out, using BiacoreT100 instrument (GE healthcare). As a running buffer and dilution buffer, 1×HBS-EP (GE healthcare) was used. Each of the antibody was immobilized on the surface of CM5 chip (GE healthcare) at about 5000 RU (response unit), using a standard amine-coupling reaction. A single specific antibody or anti-human FC antibody (GE healthcare) was immobilized on the bottom of the chip, and the antigens (c-MET or Ang2; RnD systems) were flowed at several concentrations (6.25~100 nM) at a rate of 10 µL/min. Association phase was 180 seconds, and separation phase (washed with a running buffer) was 600 seconds. After each binding cycle was complete, the regeneration solution glycine-HCl (pH 2.0) (GE Healthcare) was flowed for one minute at a rate of 50 μL/min to eliminate the bound antigens and antibodies from the chip. The generated sensorgram was fitted in BIA evaluation software using 1:1 Langmuir binding model. It was confirmed from FIG. 19 and FIG. 20 that two monospecific antibodies, which are used for the construction of the bispecific antibody prepared in Example 4.2, specifically bound to their respective antigens.

4.4. Anti c-Met Efficacy and Agonistic Effect of Bispecific Antibody Prepared from Protein Complex Low side effects and efficacy of the bispecific antibody proposed in the invention to c-Met were investigated by mechanism-based experiments.

Whether the c-Met binding portion of the bispecific antibody has c-Met degradation activity was evaluated by measuring a total amount of c-Met. It has already been known that the binding of c-met and HGF accelerates the growth of cancer cells and therefore, if antibody treatment reduces the total amount of c-Met, it leads to the decrease of cancer cell growth and through this, the anticancer activity of the antibody can be supported.

Figure 21A:
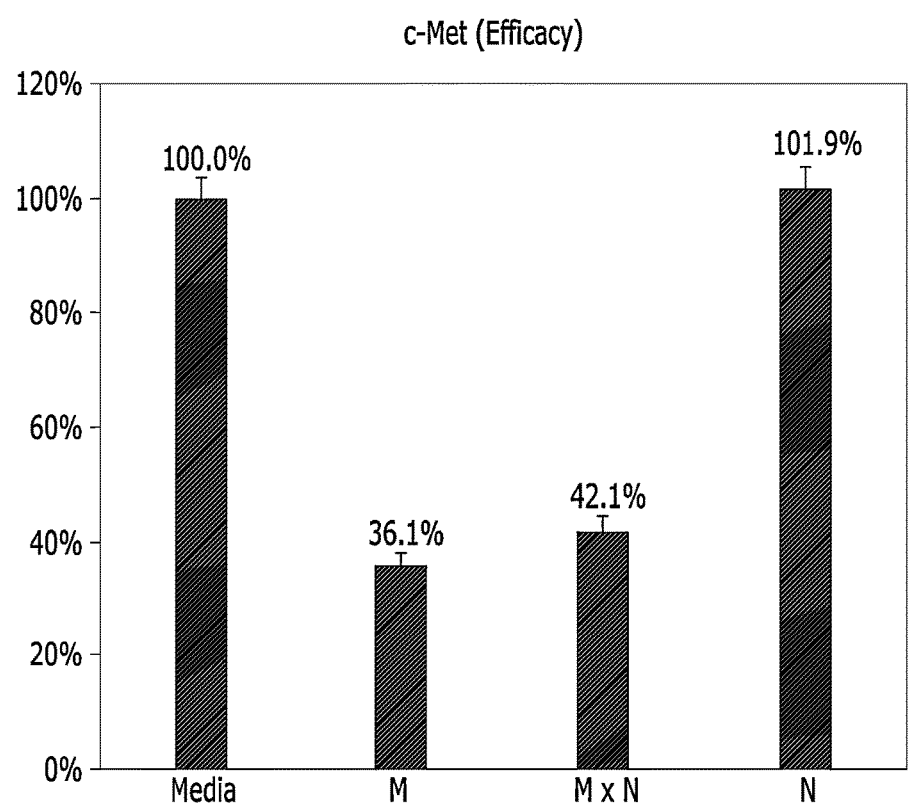
FIG. 21A is a graph showing the c-Met degradation activity of a bispecific antibody produced from a c-Met/Ang2 double binding protein complex.

$2 \times 10^5$ cells/mL of MKN45 stomach cancer cell line (JCRB0254, Shinjuku, Japan) were mixed with 5 ug/ml of each antibody and cultured (RPMI media, GIBCO) for 24 hours and then, ELISA experiment was carried out using Human total HGF R/c-Met ELISA kit (R&D system). The reaction was carried out ultimately by adding Super Aquablue (eBiosciences) and colorimetric signals were measured as OD values at 450 wavelengths. The values measured with regard to each antibody were converted into relative values against the control group treated with no antibody (media only, 100%) and shown in FIG. 21A. In FIG. 21A, M indicates an anti-c-Met antibody (anti c-Met scFv-Fc antibody including c-Met binding site (SEQ ID NO: 128) and Fc (SEQ ID NO: 129)), N indicates an anti Ang2 antibody (anti Ang2 scFv-Fc antibody having the amino acid sequence encoded by SEQ ID NO: 130), and M×N indicates the bispecific antibody prepared in Example 4.2 above.

As shown in FIG. 21A, the bispecific antibody showed excellent c-Met degradation efficacy, when compared to the untreated control group.

In order to see the safety of the antibody, the phosphorylation degree of AKT was quantitatively measured using ELISA methods. Cellular functions to be regulated by AKT include cell proliferation, cell survival, cell size regulation, response to available nutrients, intermediate metabolism, angiogenesis, tissue invasion, etc. All these processes represent the characteristics of cancer and many oncoproteins and tumor suppressors intersect in the AKT pathway, finely regulating cellular functions at the interface of signal transduction and classical metabolic regulation. Thus, as the degree of AKT activated by phosphorylation increases, a tumor formation potential increases. In this regard, the degree of inhibiting AKT phosphorylation by the antibody was evaluated to see anticancer effects of the antibody.

A site within AKT to be phosphorylated is Ser 473, and AKT phosphorylation was measured using PathScan phospho-AKT1 (Ser473) chemiluminescent Sandwich ELISA kit (Cell signaling).

Caki-1 kidney cancer cell line (HTB-46; American Type Culture Collection (ATCC), Manassas, Va.) which was cultured to $2 \times 10^5$ cells/ml one day before was mixed with 5 ug/ml of the antibody in serum-free DMEM media and treated for 30 minutes, followed by an experiment using an ELISA kit.

The obtained result was measured with a machine (Perkins Elmer). The phosphorylation degrees of AKT by the antibodies were obtained as relative values against the phosphorylation degree (100%) by the positive control 5D5.

Figure 21B:
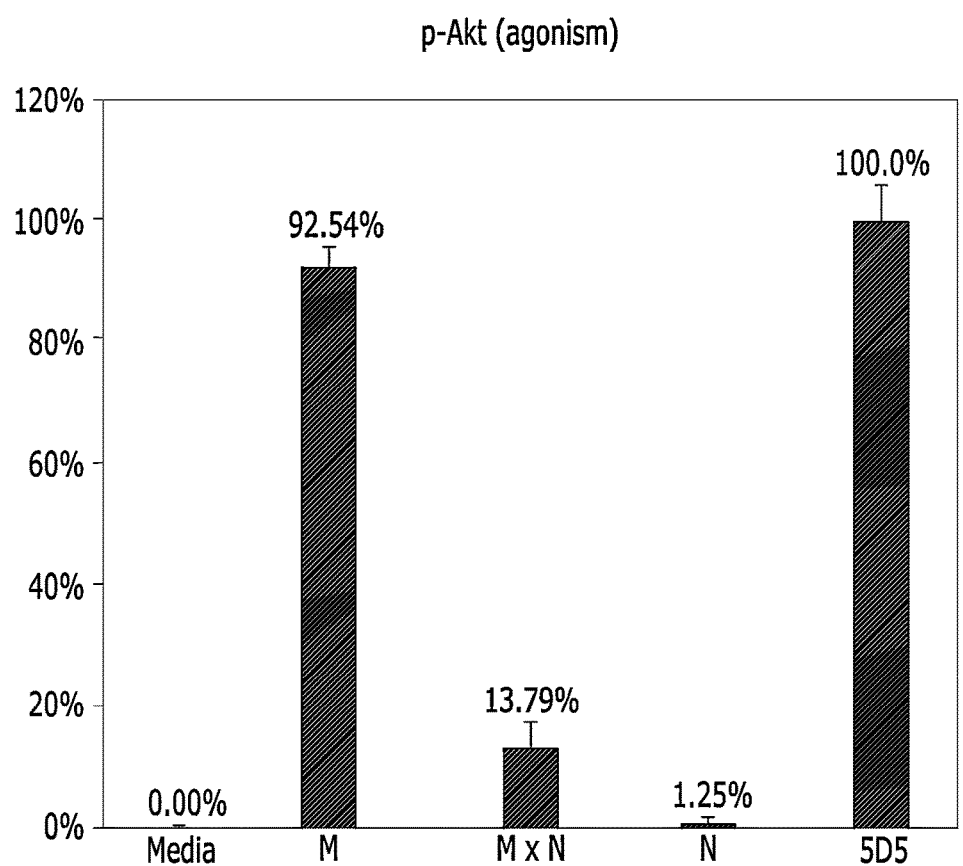
FIG. 21B is a graph showing the Akt phosphorylation level of a bispecific antibody produced from a protein complex.

The obtained result is shown in FIG. 21B. As shown in FIG. 21B, the bispecific antibody showed remarkably high AKT phosphorylation inhibitory effects, when compared to the positive control 5D5 (as an anti-c-Met antibody, separated and purified from ATCC Cat. #HB-11895 hybridoma cells obtained from American Type Culture Collection (ATCC, Manassas, Va.)).

Example 5: Preparation of Protein Complex Including Two Different Kinds of Antigen Binding Regions (c-Met and VEGF Double Specific Binding Protein Complex)

5.1: Preparation of Expression Vector for Protein Complex Including c-Met Antigen-Binding Region and VEGF Antigen-Binding Region In order to prepare the precursor protein complex of a bispecific antibody including specific binding sites to c-Met and VEGF, respectively, an expression vector for the protein complex was prepared by Genotech Co. Ltd, and as an animal cell expression vector for protein overexpression, pCEP4 (Invitrogen) was used.

Figure 27:
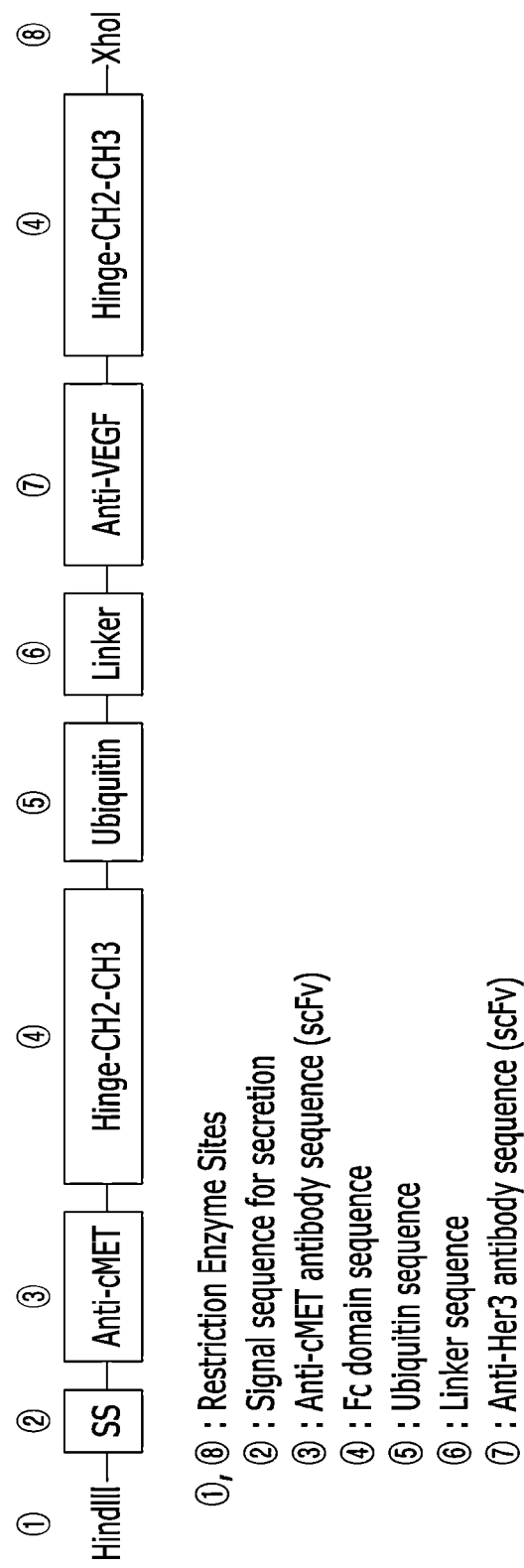
FIG. 27 is a schematic diagram illustrating the structure of an anti c-Met/VEGF bispecific antibody.

Specifically, as set forth in FIG. 27, a DNA insert (SEQ ID NO: 141) encoding a single chain polypeptide including a single chain polypeptide consisting of a secretion signal sequence (ss, amino acid sequence: SEQ ID NO: 131, coding base sequence: SEQ ID NO: 132), a c-Met binding site (anti-cMet, amino acid sequence: SEQ ID NO: 133, coding base sequence: SEQ ID NO: 134), and an Fc domain including a hinge and having a knob formed thereon (Hinge-C2-C3, amino acid sequence: SEQ ID NO: 135, knob; $151^{st}$ amino acid (Y)); a ubiquitin tag (amino acid sequence: SEQ ID NO: 137, coding base sequence: SEQ ID NO: 138); a GS linker (coding base sequence: ggatcc); a single chain polypeptide consisting of a VEGF binding site (anti-VEGF, amino acid sequence: SEQ ID NO: 139, coding base sequence: SEQ ID NO: 140), and an Fc domain including a hinge and having a hole formed thereon (Hinge-C2-C3, amino acid sequence: SEQ ID NO: 136, hole; $192^{nd}$ amino acid (T)); and a nucleotide sequence at 5' end to be cleavable with HindIII (SEQ ID NO: 113) and a nucleotide sequence at 3' end to be cleavable with XhoI (SEQ ID NO: 114) was synthesized.

The multicloning sites of pCEP4 vector (Invitrogen) were cleaved with HindIII and XhoI, and the above synthesized DNA insert was introduced thereto, thereby to prepare a vector for expressing a protein complex including specific binding sites to c-Met and VEGF, respectively.

Further, a protein complex (SEQ ID NO: 146) including an Fc domain where a knob and hole were not formed (SEQ ID NO: 144; base sequence: SEQ ID NO: 145), instead of the Fc domains where a knob or hole was formed of SEQ ID NO: 135 and SEQ ID NO: 136, was synthesized.

5.2: Expression of Protein Complex and Purification of Bispecific Antibody

In order to overexpress the protein complex using the vector prepared in Example 1 above, human embryonic kidney cell (HEK293-F, Invitrogen) transformed with the vector was used. The HEK293-F cells were maintained in an orbital shaker of 130 rpm, at 37° C., 8% $CO_2$ conditions. For transformation, the cells were separated from the medium using centrifugation, they were then suspended again with fresh Freestyle 293 Expression media (Invitrogen) at a cell concentration of $1 \times 10^6$/mL and then, the HEK293-F cells were transformed with 100 μg of the vector, using a Free- Style™ MAX reagent (Invitrogen). On 7 to 8 days after the transformation, a cell culture solution including the protein complex was collected using centrifugation (4000×g, 10 min, 4° C.), and it was filtered using a filter having a pore size of 0.22 micron to eliminate the cell debris from the cell culture solution. The thus obtained supernatant (filtrate) was used for the purification of a bispecific antibody. The bispecific antibody was separated, using Protein A affinity column (GE Healthcare). First, Protein A affinity column was equilibrated with 1×PBS (Invitrogen) solution and then, the supernatant was applied to Protein A affinity column equilibrated with the above solution, washed with a wash buffer (1×PBS) corresponding to 5 times the column volume, and then treated with an elution buffer including 10% glycerol (IgG elution buffer, Thermo Scientific) to elute the bispecific antibody. The eluted solution was neutralized immediately with 1 M Tris-HCl (pH 9.0) solution.

The buffer in the eluted solution was exchanged with 25 mM MES (pH 6.0) using HiTrap Desalting column (GE). The solution was loaded onto MonoS column (GE) equilibrated with 25 mM MES (pH 6.0) to perform cation exchange chromatography. The solution including the antibody was loaded onto MonoS column and then, the bispecific antibody (anti c-Met/anti VEGF double antibody) was eluted while the concentration of NaCl was being increased to 0~300 mM.

Figure 22A:
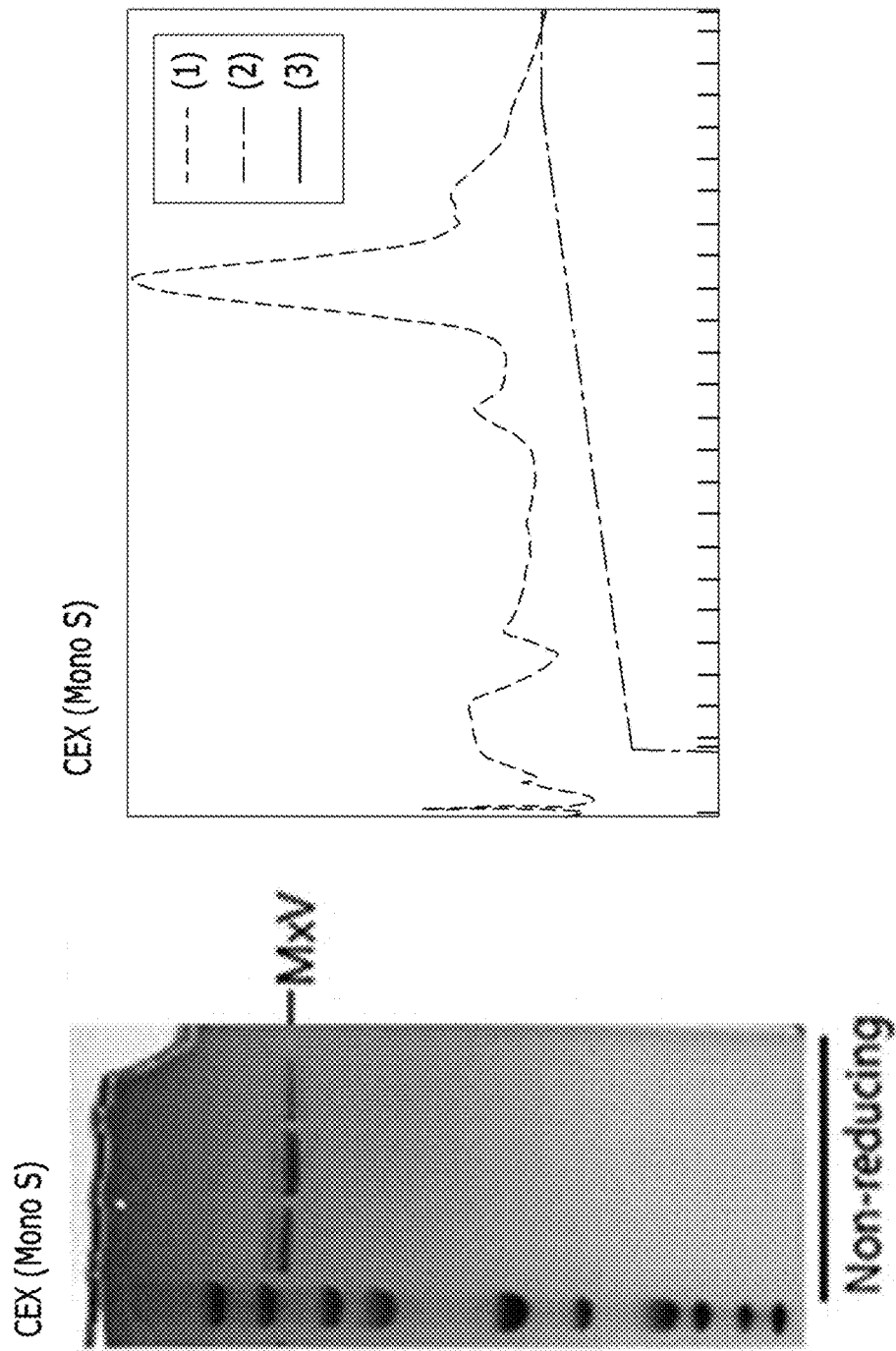
FIGS. 22A and 22B are the electrophoresis photograph and CEX profile, respectively, of an anti c-Met/VEGF bispecific antibody prepared via the cleavage of a single stranded polypeptide.
Figure 22B:
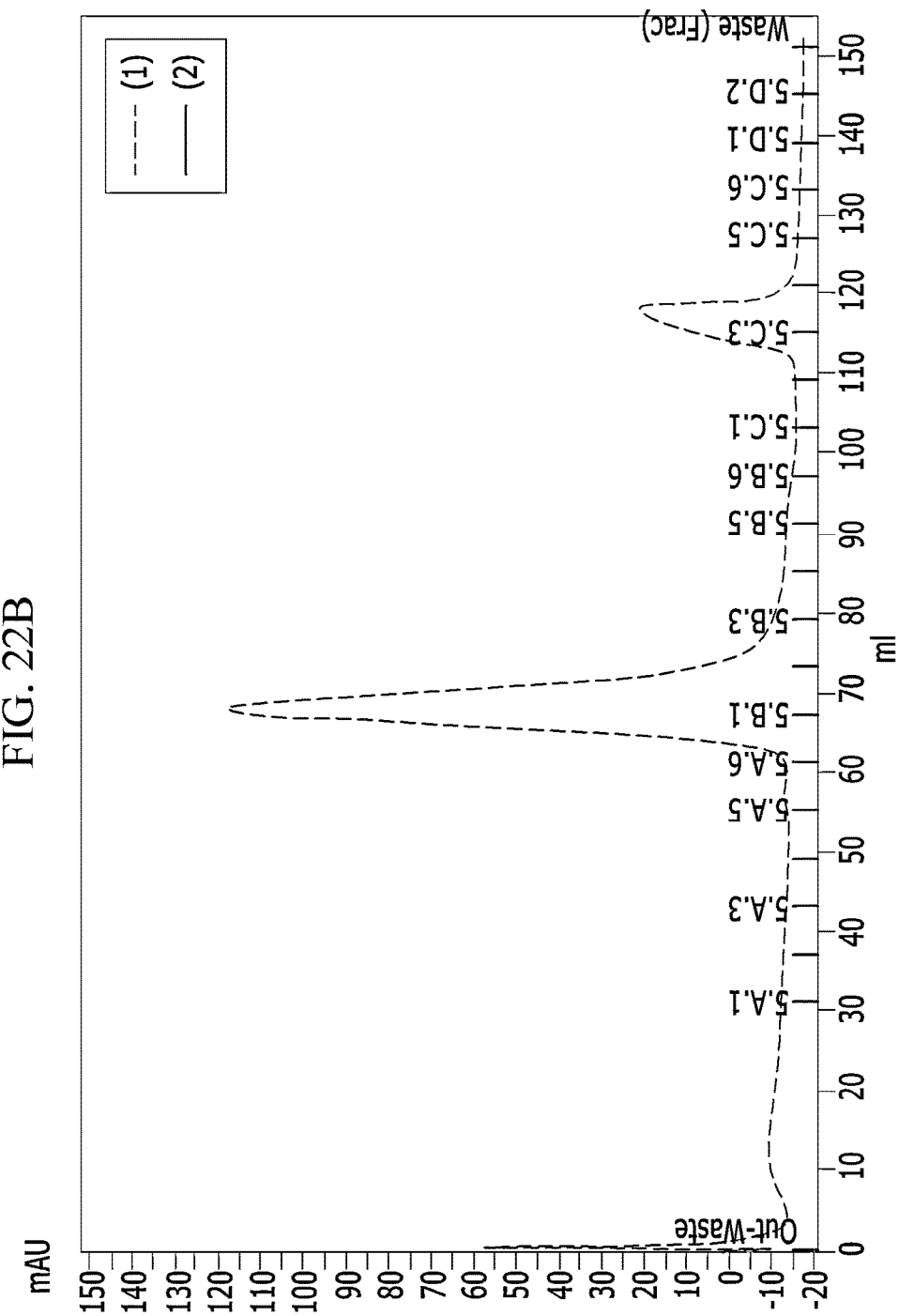

The purified protein concentration was measured using a Herceptin antibody as a standard material. Thereafter, the concentrated bispecific antibody was verified finally through SDS-PAGE. Prior to loading onto the gel, the bispecific antibody was divided into two, one was treated with 1 mM β-mercaptoethanol (reducing condition: R), and the other was loaded in a state of not being treated with β-mercaptoethanol (non-reducing condition: NR). As a result, the heterodimer formation of a peptide having the c-Met binding site, Hinge-Fc and ubiquitin, and a peptide having the VEGF binding site and Hinge-Fc was observed, as shown in FIGS. 22A and 22B.

5.3: Bispecific Antigen-Antibody Reaction of Bispecific Antibody Prepared from Protein Complex (Affinity Test)

Figure 23:
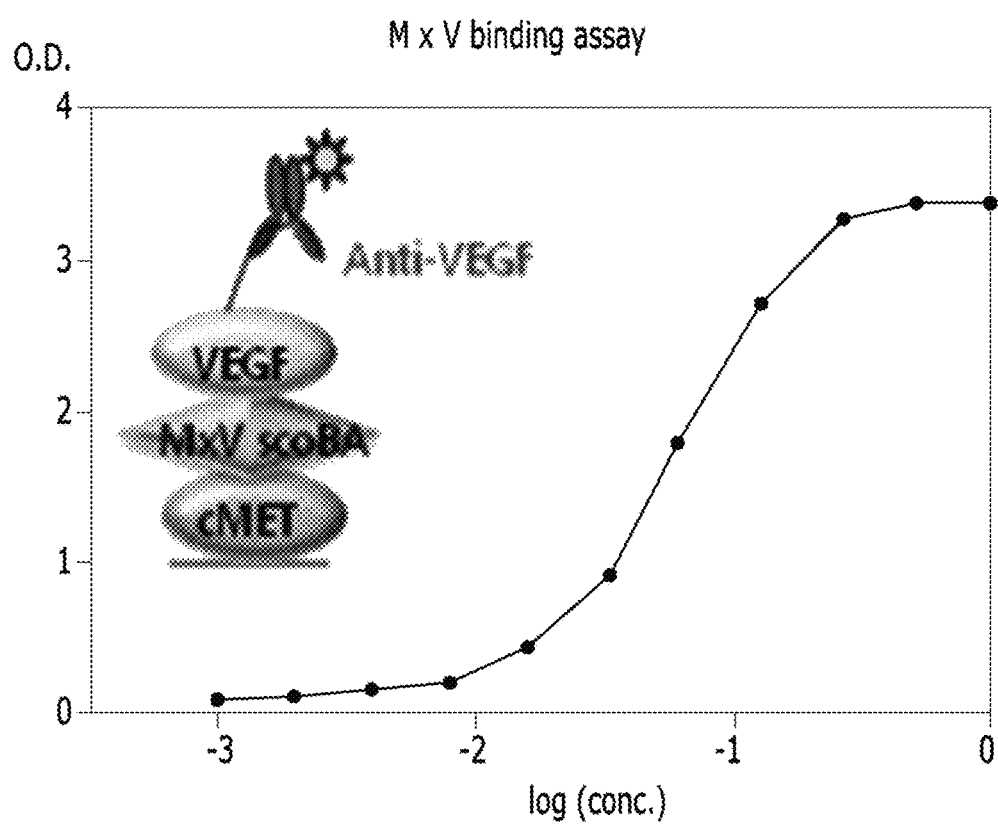
FIG. 23 is a graph showing the binding degree of an anti c-Met/VEGF bispecific antibody to c-Met and VEGF.

In order to see the bispecific antigen-antibody reaction of the bispecific antibody prepared in Example 2, a binding assay using ELISA methods was carried out. c-Met antigen (R&D systems) diluted in PBS (Invitrogen) was seeded onto a 96-well immunoplate (Nunc) at 200 ng per well and reacted overnight at 4° C. The immnuoplate with the antigen attached thereto was blocked with 2% BSA solution at a room temperature for one hour and the, the bispecific antibody was seeded onto each well by 2-fold serial dilution starting from 1 ug/ml concentration and reacted at a room temperature for one hour. The plate was washed three times with PBS containing 0.5% Tween-20 and then, VEGF antigen (R&D systems) with 6×His tag bound thereto was seeded at 100 ng per well and reacted for one hour. For detection, anti-His-HRP antibody (abcam) diluted in 1:5000 was seeded and reacted for one hour and after the reaction was complete, 100 ul of TMB substrate (eBioscience) was seeded and then, absorbance was measured at 405 nm. The results are shown in FIG. 23. As in FIG. 23, the bispecific antibody prepared in Example 2 showed bispecific antigen-antibody reaction by specifically recognizing its unique antigens c-Met and VEGF.

5.4: c-Met Degradation ELISA (MKN45)

The efficacy of the antibody was evaluated by measuring the change of the total amount of c-Met, using the fact that an antibody bound to c-Met degrades c-Met via internalization. It has already been known that the binding of c-met and HGF accelerates the growth of cancer cells and therefore, the above evaluation is based on the idea that a reduction in the total amount of c-Met leads to the decrease of cancer cell growth.

The amount of c-Met was measured using quantitative ELISA methods, and the experiment was performed in MKN45 stomach cancer cell line (JCRB0254; Health Science Research Resource Bank (HSRRB, Shinjuku, Japan)), using human total HGF R/c-Met ELISA kit(R&D systems). 200,000 cells/ml of MKN45 cells were mixed with 5 ug/ml of the bispecific antibody prepared in the above and cultured for 24 hours (media: RPMI with 10% Fetal Bovine Serum), followed by the ELISA experiment. The reaction was carried out ultimately using Super Aquablue (eBiosciences) and colorimetric signals were measured as OD values at 450 wavelengths. The value of a control group treated with no anti-c-Met antibody (media) was set 100%, and the values obtained when the anti-c-Met antibodies were treated were converted into relative values to the control group.

Figure 24:
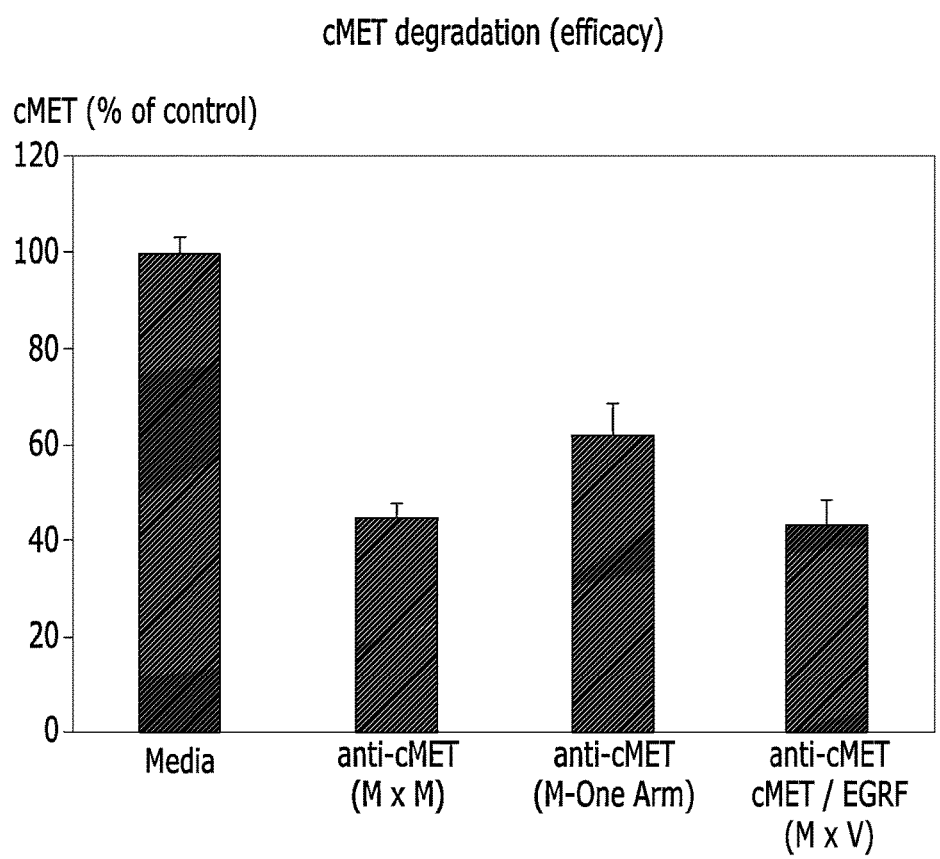
FIG. 24 is a graph showing the c-Met degradation degree of an anti c-Met/VEGF bispecific antibody.

The obtained results are shown in FIG. 24. As seen in FIG. 24, the bispecific antibody (M×V) of Example 2 showed c-Met degradation potentials equivalent to or above the single antibody (M×M). The single antibody (M×M) is a single antibody prepared to include only Anti-cMET scFv of SEQ ID NO: 133 as its antigen-binding region, referring to the preparation method of the bispecific antibody (M×V) of Examples 1 and 2.

5.5: Akt Phosphorylation (Caki) (Agonism Test of Antibody)

Safety and efficacy for a therapeutic antibody were investigated by mechanism-based experiments. In order to see the safety, the phosphorylation degree of AKT kinase was measured using quantitative ELISA methods. Cellular functions to be regulated by AKT include cell proliferation, cell survival, cell size regulation, response to available nutrients, intermediate metabolism, angiogenesis, tissue invasion, etc. All these processes represent the characteristics of cancer and many oncoproteins and tumor suppressors intersect in the AKT pathway, finely regulating cellular functions at the interface of signal transduction and classical metabolic regulation. Thus, as the degree of phosphorylated AKT that is an active form of AKT increases, the activity of cancer cells increases. In this regard, this Example evaluates how much the above prepared bispecific antibody can inhibit the phosphorylation of AKT, compared to the treatment with the positive control antibody 5D5.

A site within AKT to be phosphorylated is Ser 473, and AKT phosphorylation was measured using PathScan phospho-AKT1 (Ser473) chemiluminescent Sandwich ELISA kit (Cell signaling). Caki-1 kidney cancer cell line (HTB-46; American Type Culture Collection (ATCC), Manassas, Va.) which was cultured to 200,000 cells/ml one day before was mixed with 5 ug/ml of the above prepared bispecific antibody in serum-free DMEM media (GIBCO, Invitrogen) and treated for 30 min, followed by an experiment using ELISA kit. The result was obtained by measuring with a machine (Perkins Elmer). The phosphorylation degree of AKT was calculated in such a manner that phosphorylation degree by the positive control 5D5 (American Type Culture Collection; ATCC, Manassas, Va.) was set 100% and phosphorylation degrees by other anti-c-Met antibodies and the dual targeting antibody were calculated by comparison with that value.

Figure 25:
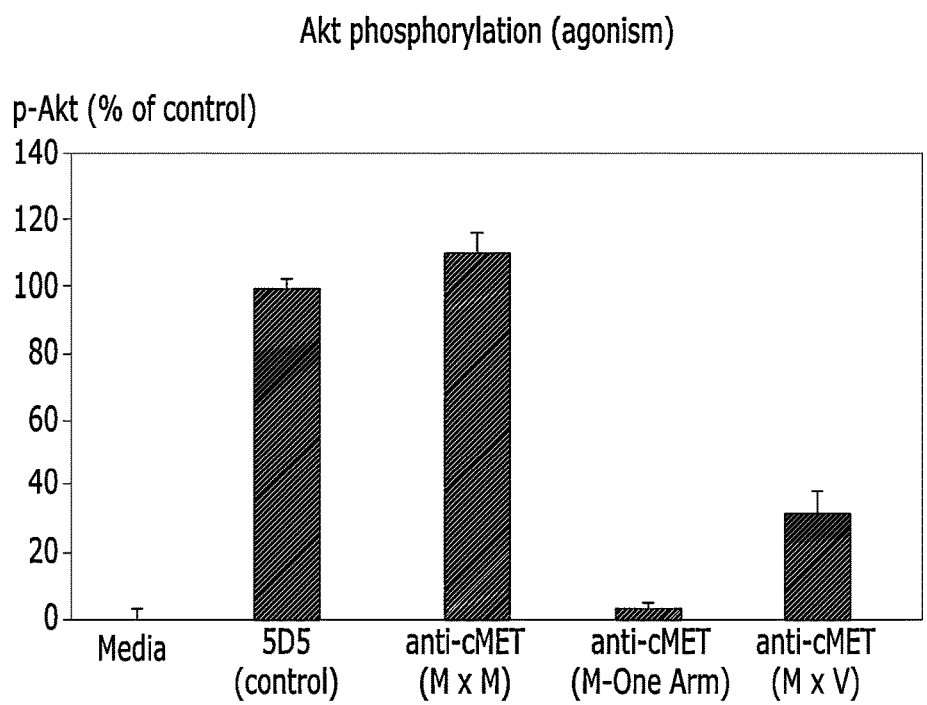
FIG. 25 is a graph showing the Akt phosphorylation degree of an anti c-Met/VEGF bispecific antibody.

The obtained result is shown in FIG. 25. As seen in FIG. 25, the bispecific antibody (M×V) inhibited AKT phosphorylation more significantly strongly than the single antibody (M×M).

5.6: HUVEC Growth Inhibitory Test (Antibody Efficacy Test)

Human cancer cell line HUVEC cells were obtained from Health Science Research Resource Bank (HSRRB, Shinjuku, Japan). The cell line was cultured in RPMI1640 media (GIBCO, Cat. #11875-119) containing 10% (v/v) fetal bovine serum (FBS, GIBCO Cat. #16000-044) and 1% (v/v) penicillin/streptomycin (GIBCO, Cat. #15410-122). The cell line was cultured under a humid atmosphere containing 5% $CO_2$ at 37° C., and they were subcultured before confluence. The number of the cells was measured using a CEDEX Analyzer (Roche Diagnostics). In order to see tumor cell proliferation according to in vitro antibody treatment, Celltiter Glo (CTG: Promega Co.) luminescent assay was employed.

This analysis was carried out according to the manufacturer's manual. In brief, the HUVEC cells in the FBS 10% (v/v) containing RPMI1640 media were seeded at a concentration of $1 \times 10^4$ cells per well onto a black 96-well plate (Corning Incorporated, Cat. #Costar 3603), which was then treated with the antibody that was diluted using 10% FBS containing RPMI 1640 media to final concentrations 0.008 ug/mL, 0.04 ug/mL, 0.2 ug/mL, and 1 ug/mL. After 72-hour incubation, 100 ul of CTG solution (Promega) was added to each well, which was then incubated at a room temperature for 30 min. The obtained luminescent signals were recorded using Envision 2104 Multi-label Reader (Perkin Elmer, Waltham, Mass., USA).

Figure 26:
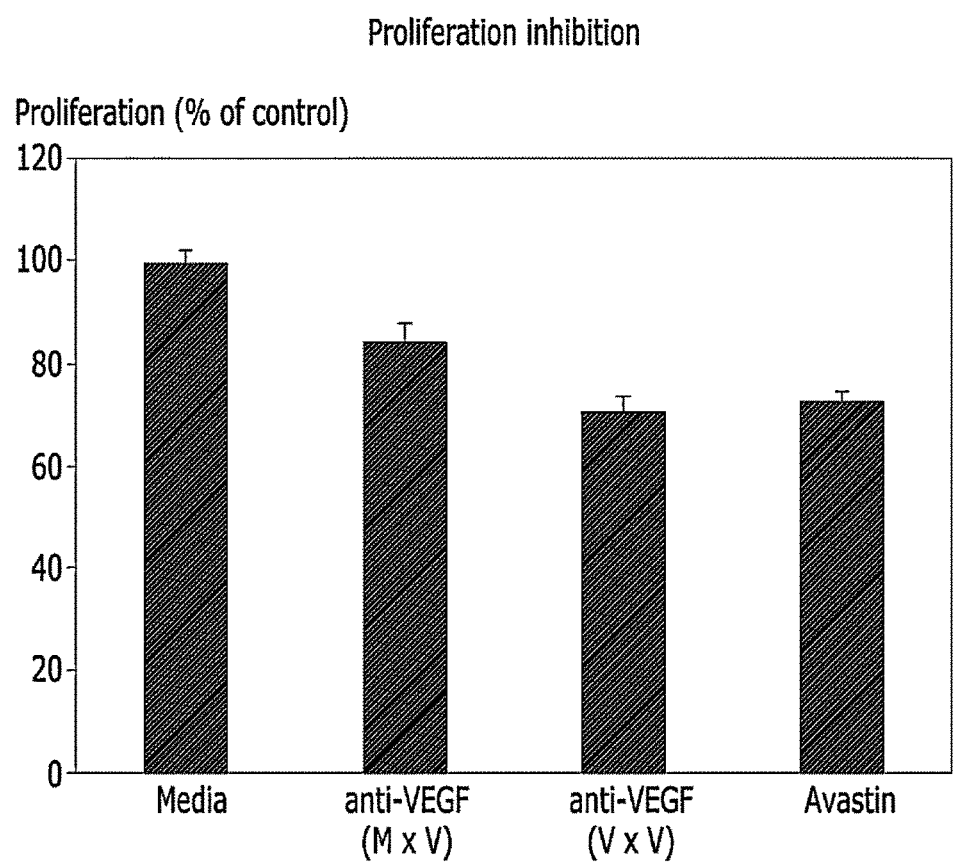
FIG. 26 is a graph showing the growth inhibitory degree of human cancer cell line (HUVEC cells) by an anti c-Met/VEGF bispecific antibody.

The result corresponding to 1 ug/ml of the obtained results is shown in FIG. 26. The anti-VEGF (V×V) is a single antibody prepared to include only anti-VEGF scFv of SEQ ID NO: 139 as its antigen-binding region, referring to the preparation method of the bispecific antibody (M×V) of Examples 1 and 2, and avastin was obtained from Samsung Medical Center. As seen in FIG. 26, the bispecific antibody (M×V) had HUVEC cancer cell line growth inhibitory effects, using only one antigen-binding region.

REFERENCE NUMERALS

100: first polypeptide
101: first light chain antigen-binding region
102: first heavy chain antigen-binding region
200: second polypeptide
201: second light chain antigen-binding region
202: second heavy chain antigen-binding region
300: first linker
301: tag
302: first tag
303: second tag
400: knob
500: hole All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A fusion protein comprising:
   a first polypeptide;
   a second polypeptide; and
   a linker connecting the first polypeptide and the second polypeptide,
   wherein the first polypeptide comprises (a) a first antigen-binding region comprising a single stranded Fab, a single stranded Fab', or a single stranded Fv (scFv), and (b) an Fc domain comprising a CH3 domain, a CH2 domain, or a combination thereof,
   the second polypeptide comprises (a) a second antigen-binding region comprising a single stranded Fab, a single stranded Fab', or a single stranded Fv (scFv), and (b) an Fc domain comprising a CH3 domain, a CH2 domain, or a combination thereof, and
   the linker connects the C-terminal of the first polypeptide and the N-terminal of the second polypeptide, and comprises a tag including a cleavable amino acid sequence at one terminal or both terminals of the linker, and
   wherein one of the first polypeptide and the second polypeptide comprises at least one amino acid residue forming at least one knob on a site not located within the antigen-binding region, and the other of the first or second polypeptide comprises at least one amino acid residue forming at least one hole on a site not located within the antigen-binding region, and wherein the knob and hole are located such that the knob of one polypeptide couples to the hole of the other polypeptide.

2. The fusion protein according to claim 1, wherein the knob is formed on a CH3 domain of one polypeptide of the first polypeptide or the second polypeptide, and the hole is formed on a CH3 domain of the other polypeptide.

3. The fusion protein according to claim 1, wherein
   the amino acid residue forming a knob is at least one selected from the group consisting of Arg, Phe, Tyr, and Trp, and
   the amino acid residue forming a hole is at least one selected from the group consisting of Ala, Ser, Thr, Gly, and Val.

4. The fusion protein according to claim 1, wherein the first antigen-binding
   region and the second antigen-binding region bind to different antigens or recognize different epitopes.

5. The fusion protein according to claim 1, wherein the tag is one or more selected from the group consisting of ubiquitin, an ubiquitin-like protein, a peptide comprising TEV protease cleavage site, and a peptide comprising a furin protease cleavage site.

6. The fusion protein according to claim 1, wherein the linker is a polypeptide linker comprising about 2 to about 50 amino acids.

7. A bispecific antibody comprising the fusion protein of claim 1.

8. A bispecific antibody comprising
   a first polypeptide;
   a second polypeptide; and
   a linker connecting the first polypeptide and the second polypeptide,
   wherein the first polypeptide comprises (a) a first antigen-binding region comprising a single stranded Fab, a single stranded Fab', or a single stranded Fv (scFv), and (b) an Fc domain comprising a CH3 domain, a CH2 domain, or a combination thereof; and
   the second polypeptide comprises (a) a second antigen-binding region comprising a single stranded Fab, a single stranded Fab', or a single stranded Fv (scFv), and (b) an Fc domain comprising a CH3 domain, a CH2 domain, or a combination thereof, and
   the linker connects the C-terminal of the first polypeptide and the N-terminal of the second polypeptide, and comprises a tag including a cleavable amino acid sequence at one terminal or both terminals of the linker, wherein in case that the linker comprises one tag at one terminal, the cleavable amino acid sequence of the tag is cleaved, and in case the linker comprises tags at both terminals, the cleavable amino acid sequences of both tags are cleaved whereby the linker is eliminated, and
   wherein one of the first polypeptide and the second polypeptide comprises at least one amino acid residue forming at least one knob on a site not located within the antigen-binding region, and the other of the first or second polypeptide comprises at least one amino acid residue forming at least one hole on a site not located within the antigen-binding region, and wherein the knob and hole are located such that the knob of one polypeptide couples to the hole of the other polypeptide.

9. A polynucleotide encoding the fusion protein of claim 1.

10. A recombinant vector comprising the polynucleotide of claim 9 and an expression regulating sequence which is operatively linked to the polynucleotide.

11. A cultured recombinant cell comprising the recombinant vector of claim 10.

12. A method of preparing a the fusion protein of claim 1 comprising expressing a recombinant vector comprising the polynucleotide encoding the fusion protein of claim 1 and an expression regulating sequence which is operatively linked to the polynucleotide.

13. A method of preparing a bispecific antibody comprising preparing a fusion protein of claim 1 and cleaving the tag of the fusion protein to provide the bispecific antibody.

14. The method according to claim 13, wherein the step of cleaving the tag is performed by adding a protease that recognizes the cleavable amino acid sequence in the tag.

15. A pharmaceutical composition comprising the fusion protein of claim 1.

16. A pharmaceutical composition comprising the bispecific antibody of claim 8.

17. The fusion protein according to claim 1, wherein one of the first antigen-binding region and the second antigen-binding region specifically binds c-Met and comprises a heavy chain variable region comprising (a) a CDR-H1 comprising the amino acid sequence of SEQ ID NO: 1, (b) a CDR-H2 comprising the amino acid sequence of SEQ ID NO: 2, (c) a CDR-H3 comprising the amino acid sequence of SEQ ID NO: 3, and a light chain variable region comprising (d) a CDR-L1 comprising the amino acid sequence of SEQ ID NO: 10 or SEQ ID NO: 106, (e) a CDR-L2 comprising the amino acid sequence of SEQ ID NO: 11, and (f) a CDR-L3 comprising the amino acid sequence of SEQ ID NO: 12, SEQ ID NO: 13, SEQ ID NO: 14, SEQ ID NO: 15, or SEQ ID NO: 16.

18. The bispecific antibody according to claim 8, wherein one of the first antigen-binding region and the second antigen-binding region specifically binds c-Met and comprises a heavy chain variable region comprising (a) a CDR-H1 comprising the amino acid sequence of SEQ ID NO: 1, (b) a CDR-H2 comprising the amino acid sequence of SEQ ID NO: 2, (c) a CDR-H3 comprising the amino acid sequence of SEQ ID NO: 3, and a light chain variable region comprising (d) a CDR-L1 comprising the amino acid sequence of SEQ ID NO: 10 or SEQ ID NO: 106, (e) a CDR-L2 comprising the amino acid sequence of SEQ ID NO: 11, and (f) a CDR-L3 comprising the amino acid sequence of SEQ ID NO: 12, SEQ ID NO: 13, SEQ ID NO: 14, SEQ ID NO: 15, or SEQ ID NO: 16.

* * * * *

SEQUENCE LISTING

```
<160> NUMBER OF SEQ ID NOS: 151

<210> SEQ ID NO 1
<211> LENGTH: 5
<212> TYPE: PRT
<213> ORGANISM: Artificial Sequence
<220> FEATURE:
<223> OTHER INFORMATION: Synthetic (heavy chain CDR1 of AbF46)

<400> SEQUENCE: 1

Asp Tyr Tyr Met Ser
1               5
```

-continued

```
<210> SEQ ID NO 2
<211> LENGTH: 19
<212> TYPE: PRT
<213> ORGANISM: Artificial Sequence
<220> FEATURE:
<223> OTHER INFORMATION: Synthetic (heavy chain CDR2 of AbF46)

<400> SEQUENCE: 2

Phe Ile Arg Asn Lys Ala Asn Gly Tyr Thr Thr Glu Tyr Ser Ala Ser
1               5                   10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic (heavy chain CDR3 of AbF46)

<400> SEQUENCE: 3

Asp Asn Trp Phe Ala Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic (heavy chain CDR1 of c-Met antibody)
<220> FEATURE:
<221> NAME/KEY: MOD_RES
<222> LOCATION: (1)..(1)
<223> OTHER INFORMATION: Xaa is Pro or Ser or absent
<220> FEATURE:
<221> NAME/KEY: MOD_RES
<222> LOCATION: (2)..(2)
<223> OTHER INFORMATION: Xaa is Glu or Asp

<400> SEQUENCE: 4

Xaa Xaa Tyr Tyr Met Ser
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic (heavy chain CDR2 of c-Met antibody)
<220> FEATURE:
<221> NAME/KEY: MOD_RES
<222> LOCATION: (3)..(3)
<223> OTHER INFORMATION: Xaa is Asn or Lys
<220> FEATURE:
<221> NAME/KEY: MOD_RES
<222> LOCATION: (4)..(4)
<223> OTHER INFORMATION: Xaa is Ala or Val
<220> FEATURE:
<221> NAME/KEY: MOD_RES
<222> LOCATION: (7)..(7)
<223> OTHER INFORMATION: Xaa is Asn or Thr

<400> SEQUENCE: 5

Arg Asn Xaa Xaa Asn Gly Xaa Thr
1               5

<210> SEQ ID NO 6
<211> LENGTH: 6
<212> TYPE: PRT
<213> ORGANISM: Artificial Sequence
<220> FEATURE:
```

```
<223> OTHER INFORMATION: Synthetic (heavy chain CDR3 of c-Met antibody)
<220> FEATURE:
<221> NAME/KEY: MOD_RES
<222> LOCATION: (5)..(5)
<223> OTHER INFORMATION: Xaa is Ser or Thr

<400> SEQUENCE: 6

Asp Asn Trp Leu Xaa Tyr
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic (light chain CDR1 of c-Met antibody)
<220> FEATURE:
<221> NAME/KEY: MOD_RES
<222> LOCATION: (4)..(4)
<223> OTHER INFORMATION: Xaa is His, Arg, Gln or Lys
<220> FEATURE:
<221> NAME/KEY: MOD_RES
<222> LOCATION: (9)..(9)
<223> OTHER INFORMATION: Xaa is Ser or Trp
<220> FEATURE:
<221> NAME/KEY: MOD_RES
<222> LOCATION: (12)..(12)
<223> OTHER INFORMATION: Xaa is His or Gln
<220> FEATURE:
<221> NAME/KEY: MOD_RES
<222> LOCATION: (13)..(13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
1               5                   10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic (light chain CDR2 of c-Met antibody)
<220> FEATURE:
<221> NAME/KEY: MOD_RES
<222> LOCATION: (2)..(2)
<223> OTHER INFORMATION: Xaa is Ala or Gly
<220> FEATURE:
<221> NAME/KEY: MOD_RES
<222> LOCATION: (4)..(4)
<223> OTHER INFORMATION: Xaa is Thr or Lys
<220> FEATURE:
<221> NAME/KEY: MOD_RES
<222> LOCATION: (7)..(7)
<223> OTHER INFORMATION: Xaa is Ser or Pro

<400> SEQUENCE: 8

Trp Xaa Ser Xaa Arg Val Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic (light chain CDR3 of c-Met antibody)
<220> FEATURE:
<221> NAME/KEY: MOD_RES
<222> LOCATION: (1)..(1)
<223> OTHER INFORMATION: Xaa is Gly, Ala or Gln
<220> FEATURE:
```

```
<221> NAME/KEY: MOD_RES
<222> LOCATION: (6)..(6)
<223> OTHER INFORMATION: Xaa is Arg, His, Ser, Ala, Gly or Lys
<220> FEATURE:
<221> NAME/KEY: MOD_RES
<222> LOCATION: (8)..(8)
<223> OTHER INFORMATION: Xaa is Leu, Tyr, Phe or Met

<400> SEQUENCE: 9

Xaa Gln Ser Tyr Ser Xaa Pro Xaa Thr
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic (light chain CDR1 of AbF46)

<400> SEQUENCE: 10

Lys Ser Ser Gln Ser Leu Leu Ala Ser Gly Asn Gln Asn Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic (light chain CDR2 of AbF46)

<400> SEQUENCE: 11

Trp Ala Ser Thr Arg Val Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic (light chain CDR3 of AbF46)

<400> SEQUENCE: 12

Gln Gln Ser Tyr Ser Ala Pro Leu Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic (CDR-L3 derived from L3-1 clone)

<400> SEQUENCE: 13

Gln Gln Ser Tyr Ser Arg Pro Tyr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic (CDR-L3 derived from L3-2 clone)

<400> SEQUENCE: 14

Gly Gln Ser Tyr Ser Arg Pro Leu Thr
1               5
```

<210> SEQ ID NO 15
<211> LENGTH: 9
<212> TYPE: PRT
<213> ORGANISM: Artificial Sequence
<220> FEATURE:
<223> OTHER INFORMATION: Synthetic (CDR-L3 derived from L3-3 clone)

<400> SEQUENCE: 15

Ala Gln Ser Tyr Ser His Pro Phe Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic (CDR-L3 derived from L3-5 clone)

<400> SEQUENCE: 16

Gln Gln Ser Tyr Ser Arg Pro Phe Thr
1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic (heavy chain variable region of anti
      c-Met humanized antibody(huAbF46-H4)

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4)

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

```
Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
                100                 105                 110

Lys Arg
```

<210> SEQ ID NO 19
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 19

```
Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gly Gln
                 85                  90                  95

Ser Tyr Ser Arg Pro Leu Thr Phe Gly Gln Gly Thr Lys Val Glu Ile
                100                 105                 110

Lys Arg
```

<210> SEQ ID NO 20
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 20

```
Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Ala Gln
                 85                  90                  95
```

```
Ser Tyr Ser His Pro Phe Ser Phe Gly Gln Gly Thr Lys Val Glu Ile
            100                 105                 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Phe Thr Phe Gly Gln Gly Thr Lys Val Glu Ile
            100                 105                 110

Lys Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic (CDR-H1 derived from H11-4 clone)

<400> SEQUENCE: 22

Pro Glu Tyr Tyr Met Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic (CDR-H1 derived from YC151 clone)

<400> SEQUENCE: 23

Pro Asp Tyr Tyr Met Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic (CDR-H1 derived from YC193 clone)

<400> SEQUENCE: 24

Ser Asp Tyr Tyr Met Ser
1               5
```

<210> SEQ ID NO 25
<211> LENGTH: 8
<212> TYPE: PRT
<213> ORGANISM: Artificial Sequence
<220> FEATURE:
<223> OTHER INFORMATION: Synthetic (CDR-H2 derived from YC244 clone)

<400> SEQUENCE: 25

Arg Asn Asn Ala Asn Gly Asn Thr
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic (CDR-H2 derived from YC321 clone)

<400> SEQUENCE: 26

Arg Asn Lys Val Asn Gly Tyr Thr
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic (CDR-H3 derived from YC354 clone)

<400> SEQUENCE: 27

Asp Asn Trp Leu Ser Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic (CDR-H3 derived from YC374 clone)

<400> SEQUENCE: 28

Asp Asn Trp Leu Thr Tyr
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic (CDR-L1 derived from L1-1 clone)

<400> SEQUENCE: 29

Lys Ser Ser His Ser Leu Leu Ala Ser Gly Asn Gln Asn Asn Tyr Leu
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic (CDR-L1 derived from L1-3 clone)

<400> SEQUENCE: 30

Lys Ser Ser Arg Ser Leu Leu Ser Ser Gly Asn His Lys Asn Tyr Leu
1               5                   10                  15

Ala

```
<210> SEQ ID NO 31
<211> LENGTH: 17
<212> TYPE: PRT
<213> ORGANISM: Artificial Sequence
<220> FEATURE:
<223> OTHER INFORMATION: Synthetic (CDR-L1 derived from L1-4 clone)

<400> SEQUENCE: 31

Lys Ser Ser Lys Ser Leu Leu Ala Ser Gly Asn Gln Asn Asn Tyr Leu
1               5                   10                  15

Ala

<210> SEQ ID NO 32
<211> LENGTH: 17
<212> TYPE: PRT
<213> ORGANISM: Artificial Sequence
<220> FEATURE:
<223> OTHER INFORMATION: Synthetic (CDR-L1 derived from L1-12 clone)

<400> SEQUENCE: 32

Lys Ser Ser Arg Ser Leu Leu Ala Ser Gly Asn Gln Asn Asn Tyr Leu
1               5                   10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic (CDR-L1 derived from L1-22 clone)

<400> SEQUENCE: 33

Lys Ser Ser His Ser Leu Leu Ala Ser Gly Asn Gln Asn Asn Tyr Leu
1               5                   10                  15

Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic (CDR-L2 derived from L2-9 clone)

<400> SEQUENCE: 34

Trp Ala Ser Lys Arg Val Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic (CDR-L2 derived from L2-16 clone)

<400> SEQUENCE: 35

Trp Gly Ser Thr Arg Val Ser
1               5

<210> SEQ ID NO 36
<211> LENGTH: 7
<212> TYPE: PRT
<213> ORGANISM: Artificial Sequence
```

```
<220> FEATURE:
<223> OTHER INFORMATION: Synthetic (CDR-L2 derived from L2-16 clone)

<400> SEQUENCE: 36

Trp Gly Ser Thr Arg Val Pro
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic (CDR-L3 derived from L3-32 clone)

<400> SEQUENCE: 37

Gln Gln Ser Tyr Ser Lys Pro Phe Thr
1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic (nucleotide sequence of heavy chain
      of chAbF46)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 38
gaattcgccg ccaccatgga atggagctgg gttttctcg taacactttt aaatggtatc      60
cagtgtgagg tgaagctggt ggagtctgga ggaggcttgg tacagcctgg gggttctctg    120
agactctcct gtgcaacttc tgggttcacc ttcactgatt actacatgag ctgggtccgc    180
cagcctccag gaaaggcact tgagtggttg gttttatta gaaacaaagc taatggttac     240
acaacagagt acagtgcatc tgtgaagggt cggttcacca tctccagaga taattcccaa    300
agcatcctct atcttcaaat ggacaccctg agagctgagg acagtgccac ttattactgt    360
gcaagagata actggtttgc ttactgggc caagggactc tggtcactgt ctctgcagct    420
agcaccaagg gcccatcggt cttcccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
```

```
ctctactccc tcagcagcgt ggtgaccgtg ccctccagca gcttgggcac ccagacctac      660
atctgcaacg tgaatcacaa gcccagcaac accaaggtgg acaagaaagt tgagcccaaa      720
tcttgtgaca aaactcacac atgcccaccg tgcccagcac ctgaactcct ggggggaccg      780
tcagtcttcc tcttcccccc aaaacccaag gacaccctca tgatctcccg gacccctgag      840
gtcacatgcg tggtggtgga cgtgagccac gaagaccctg aggtcaagtt caactggtac      900
gtggacggcg tggaggtgca taatgccaag acaaagccgc gggaggagca gtacaacagc      960
acgtaccgtg tggtcagcgt cctcaccgtc ctgcaccagg actggctgaa tggcaaggag     1020
tacaagtgca aggtctccaa caaagccctc ccagccccca tcgagaaaac catctccaaa     1080
gccaaagggc agccccgaga accacaggtg tacaccctgc ccccatcccg ggaggagatg     1140
accaagaacc aggtcagcct gacctgcctg gtcaaaggct tctatcccag cgacatcgcc     1200
gtggagtggg agagcaatgg gcagccggag aacaactaca agaccacgcc tcccgtgctg     1260
gactccgacg gctccttctt cctctacagc aagctcaccg tggacaagag caggtggcag     1320
caggggaacg tcttctcatg ctccgtgatg catgaggctc tgcacaacca ctacacgcag     1380
aagagcctct ccctgtctcc gggtaaatga ctcgag                              1416

<210> SEQ ID NO 39
<211> LENGTH: 759
<212> TYPE: DNA
<213> ORGANISM: Artificial Sequence
<220> FEATURE:
<223> OTHER INFORMATION: Synthetic (nucleotide sequence of light chain
      of chAbF46)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39
gaattcacta gtgattaatt cgccgccacc atggattcac aggcccaggt cctcatgttg       60
ctgctgctat cggtatctgg tacctgtgga cattttgatg acccagtc tccatcctcc       120 ctgactgtgt cagcaggaga aaggtcact atgagctgca agtccagtca gagtctttta       180
gctagtggca accaaaataa ctacttggcc tggcaccagc agaaaccagg acgatctcct       240
aaaatgctga taattgggc atccactagg gtatctggag tccctgatcg cttcatagc       300 agtggatctg ggacggattt cactctgacc atcaacagtg tgcaggctga agatctggct       360
```

```
gtttattact gtcagcagtc ctacagcgct ccgctcacgt tcggtgctgg gaccaagctg    420
gagctgaaac gtacggtggc tgcaccatct gtcttcatct ccccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                          759
```

```
<210> SEQ ID NO 40
<211> LENGTH: 447
<212> TYPE: PRT
<213> ORGANISM: Artificial Sequence
<220> FEATURE:
<223> OTHER INFORMATION: Synthetic (amino acid sequence of H1-heavy)

<400> SEQUENCE: 40
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic (amino acid sequence of H3-heavy)

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

```
Thr Lys Val Asp Lys Lys Val Glu Pro Lys Ser Cys Asp Lys Thr His
            210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
                260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
            435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic (amino acid sequence of H4-heavy)

<400> SEQUENCE: 42

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Thr Asp Tyr
            20                  25                  30
Tyr Met Ser Trp Val Arg Gln Ala Pro Gly Lys Gly Leu Glu Trp Leu
        35                  40                  45
Gly Phe Ile Arg Asn Lys Ala Asn Gly Tyr Thr Thr Glu Tyr Ser Ala
    50                  55                  60
Ser Val Lys Gly Arg Phe Thr Ile Ser Arg Asp Asn Ser Lys Asn Thr
65                  70                  75                  80
Leu Tyr Leu Gln Met Asn Ser Leu Arg Ala Glu Asp Thr Ala Val Tyr
                85                  90                  95
Tyr Cys Ala Arg Asp Asn Trp Phe Ala Tyr Trp Gly Gln Gly Thr Leu
            100                 105                 110
Val Thr Val Ser Ser Ala Ser Thr Lys Gly Pro Ser Val Phe Pro Leu
        115                 120                 125
```

-continued

```
Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic (amino acid sequence of H1-light)

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45
```

```
Pro Pro Lys Met Leu Ile Ile Trp Ala Ser Thr Arg Val Ser Gly Val
 50                  55                  60

Pro Asp Arg Phe Ser Gly Ser Gly Ser Gly Thr Asp Phe Thr Leu Thr
 65              70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gly Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic (amino acid sequence of H2-light)

<400> SEQUENCE: 44

Asp Ile Val Met Thr Gln Thr Pro Leu Ser Leu Pro Val Thr Pro Gly
 1               5                  10                  15

Glu Pro Ala Ser Ile Ser Cys Lys Ser Ser Gln Ser Leu Leu Ala Ser
             20                  25                  30

Gly Asn Gln Asn Asn Tyr Leu Ala Trp His Leu Gln Lys Pro Gly Gln
         35                  40                  45

Ser Pro Gln Met Leu Ile Ile Trp Ala Ser Thr Arg Val Ser Gly Val
 50                  55                  60

Pro Asp Arg Phe Ser Gly Ser Gly Ser Gly Thr Asp Phe Thr Leu Lys
 65              70                  75                  80

Ile Ser Arg Val Glu Ala Glu Asp Val Gly Val Tyr Tyr Cys Gln Gln
                 85                  90                  95

Ser Tyr Ser Ala Pro Leu Thr Phe Gly Gln Gly Thr Lys Leu Glu Leu
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190
```

```
Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic (amino acid sequence of H3-light)

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 46
<211> LENGTH: 219
<212> TYPE: PRT
<213> ORGANISM: Artificial Sequence
<220> FEATURE:
<223> OTHER INFORMATION: Synthetic (amino acid sequence of H4-light)

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60
```

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
            85                  90                  95

Ser Tyr Ser Ala Pro Leu Thr Phe Gly Gln Gly Thr Lys Val Glu Ile
        100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215

<210> SEQ ID NO 47
<211> LENGTH: 1350
<212> TYPE: DNA
<213> ORGANISM: Artificial Sequence
<220> FEATURE:
<223> OTHER INFORMATION: Synthetic (nucleotide sequence of H1-heavy)

<400> SEQUENCE: 47
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca agctaacgg ttacaccaca      180 gaatacagtg cgtctgtgaa aggcagattc accatctcaa gagataattc aaagaactca     240
ctgtatctgc aaatgaacag cctgaaaacc gaggacacgg ccgtgtatta ctgtgctaga     300
gataactggt ttgcttactg gggtcaagga accctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660 gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga gatgaccaag    1080
aaccaggtca gcctgacctg cctggtcaaa ggcttctatc ccagcgacat cgccgtggag    1140

| | |
|---|---|
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 48
<211> LENGTH: 1350
<212> TYPE: DNA
<213> ORGANISM: Artificial Sequence
<220> FEATURE:
<223> OTHER INFORMATION: Synthetic (nucleotide sequence of H3-heavy)

<400> SEQUENCE: 48

| | |
|---|---|
| gaggtgcagc tggtggagtc tgggggaggc ttggtccagc ctggagggtc cctgagactc | 60 |
| tcctgtgcag cctctggatt caccttcact gactactaca tgagctgggt ccgccaggct | 120 |
| ccagggaagg gctggagtg gttgggcttt attagaaaca aagctaacgg ttacaccaca | 180 |
| gaatacagtg cgtctgtgaa aggcagattc accatctcaa gagataattc aaagaactca | 240 |
| ctgtatctgc aaatgaacag cctgcgtgct gaggacacgg ccgtgtatta ctgtgctaga | 300 |
| gataactggt ttgcttactg gggtcaagga accctggtca ccgtctcctc ggctagcacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| gacaaaactc acacatgccc accgtgccca gcacctgaac tcctgggggg accgtcagtc | 720 |
| ttcctcttcc cccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga gatgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 49
<211> LENGTH: 1350
<212> TYPE: DNA
<213> ORGANISM: Artificial Sequence
<220> FEATURE:
<223> OTHER INFORMATION: Synthetic (nucleotide sequence of H4-heavy)

<400> SEQUENCE: 49

| | |
|---|---|
| gaggttcagc tggtggagtc tggcggtggc ctggtgcagc cggggggctc actccgtttg | 60 |
| tcctgtgcag cttctggctt caccttcact gattactaca tgagctgggt gcgtcaggcc | 120 |
| ccgggtaagg gcctggaatg gttgggtttt attagaaaca agctaatgg ttacacaaca | 180 |

| | |
|---|---|
| gagtacagtg catctgtgaa gggtcgtttc actataagca gagataattc caaaaacaca | 240 |
| ctgtacctgc agatgaacag cctgcgtgct gaggacactg ccgtctatta ttgtgctaga | 300 |
| gataactggt ttgcttactg gggccaaggg actctggtca ccgtctcctc ggctagcacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| gacaaaactc acacatgccc accgtgccca gcacctgaac tcctgggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga gatgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 50
<211> LENGTH: 669
<212> TYPE: DNA
<213> ORGANISM: Artificial Sequence
<220> FEATURE:
<223> OTHER INFORMATION: Synthetic (nucleotide sequence of H1-light)

<400> SEQUENCE: 50

| | |
|---|---|
| gacatcgtga tgacccagtc tccagactcc ctggctgtgt ctctgggcga gagggccacc | 60 |
| atcaactgca gtccagcca gagtctttta gctagcggca ccaaaataa ctacttagct | 120 |
| tggcaccagc agaaaccagg acagcctcct aagatgctca tatttgggc atctacccgg | 180 |
| gtatccgggg tccctgaccg attcagtggc agcgggtctg gacagattt cactctcacc | 240 |
| atcagcagcc tgcaggctga agatgtggca gtttattact gtcagcaatc ctatagtgct | 300 |
| cctctcacgt tcggaggcgg taccaaggtg gagatcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga aacacaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 51
<211> LENGTH: 669
<212> TYPE: DNA

<213> ORGANISM: Artificial Sequence
<220> FEATURE:
<223> OTHER INFORMATION: Synthetic (nucleotide sequence of H2-light)

<400> SEQUENCE: 51

| | |
|---|---|
| gatattgtga tgacccagac tccactctcc ctgcccgtca cccctggaga gccggcctcc | 60 |
| atctcctgca agtccagtca gagtctttta gctagtggca accaaaataa ctacttggcc | 120 |
| tggcacctgc agaagccagg gcagtctcca cagatgctga tcatttgggc atccactagg | 180 |
| gtatctggag tcccagacag gttcagtggc agtgggtcag gcactgattt cacactgaaa | 240 |
| atcagcaggg tggaggctga ggatgttgga gtttattact gccagcagtc ctacagcgct | 300 |
| ccgctcacgt tcggacaggg taccaagctg gagctcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga aacacaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 52
<211> LENGTH: 669
<212> TYPE: DNA
<213> ORGANISM: Artificial Sequence
<220> FEATURE:
<223> OTHER INFORMATION: Synthetic (nucleotide sequence of H3-light)

<400> SEQUENCE: 52

| | |
|---|---|
| gacatcgtga tgacccagtc tccagactcc ctggctgtgt ctctgggcga gagggccacc | 60 |
| atcaactgca agtccagcca gagtctttta gctagcggca accaaaataa ctacttagct | 120 |
| tggtaccagc agaaaccagg acagcctcct aagctgctca ttatttgggc atctacccgg | 180 |
| gtatccgggg tccctgaccg attcagtggc agcgggtctg ggacagattt cactctcacc | 240 |
| atcagcagcc tgcaggctga agatgtggca gtttattact gtcagcaatc ctatagtgct | 300 |
| cctctcacgt tcggaggcgg taccaaggtg gagatcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga aacacaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 53
<211> LENGTH: 669
<212> TYPE: DNA
<213> ORGANISM: Artificial Sequence
<220> FEATURE:
<223> OTHER INFORMATION: Synthetic (nucleotide sequence of H4-light)

<400> SEQUENCE: 53

| | |
|---|---|
| gatatccaga tgacccagtc cccgagctcc ctgtccgcct ctgtgggcga tagggtcacc | 60 |
| atcacctgca agtccagtca gagtctttta gctagtggca accaaaataa ctacttggcc | 120 |
| tggcaccaac agaaaccagg aaaagctccg aaaatgctga ttatttgggc atccactagg | 180 |

```
gtatctggag tcccttctcg cttctctgga tccgggtctg ggacggattt cactctgacc      240
atcagcagtc tgcagccgga agacttcgca acttattact gtcagcagtc ctacagcgct      300
ccgctcacgt tcggacaggg taccaaggtg gagatcaaac gtacggtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga acacaaagt ctacgcctgc       600 gaagtcaccc atcagggcct gagctcgccc gtcacaaaga gcttcaacag gggagagtgt      660
tgactcgag                                                              669
```

<210> SEQ ID NO 54
<211> LENGTH: 23
<212> TYPE: PRT
<213> ORGANISM: Artificial Sequence
<220> FEATURE:
<223> OTHER INFORMATION: Synthetic (linker between VH and VL)

<400> SEQUENCE: 54

Gly Leu Gly Gly Leu Gly Gly Gly Ser Gly Gly Gly Gly Ser Gly
1               5                   10                  15

Gly Ser Ser Gly Val Gly Ser
            20

<210> SEQ ID NO 55
<211> LENGTH: 1088
<212> TYPE: DNA
<213> ORGANISM: Artificial Sequence
<220> FEATURE:
<223> OTHER INFORMATION: Synthetic (polynucleotide encoding scFv of
      huAbF46 antibody)

<400> SEQUENCE: 55

```
gctagcgttt tagcagaagt tcaattggtt gaatctggtg gtggtttggt tcaaccaggt       60
ggttctttga gattgtcttg tgctgcttct ggttttactt tcaccgatta ttacatgtcc      120
tgggttagac aagctccagg taaaggtttg gaatggttgg gtttcattag aaacaaggct      180
aacggttaca ctaccgaata ttctgcttct gttaagggta gattcaccat ttctagagac      240
aactctaaga acaccttgta cttgcaaatg aactccttga gagctgaaga tactgctgtt      300
tattactgcg ctagagataa ttggtttgct tattggggtc aaggtacttt ggttactgtt      360
tcttctggcc tcggggggcct cggaggagga ggtagtggcg gaggaggctc cggtggatcc      420
agcggtgtgg gttccgatat tcaaatgacc caatctccat cttcttttgtc tgcttcagtt      480 ggtgatagag ttaccattac ttgtaagtcc tcccaatctt tgttggcttc tggtaatcag      540 acaattact tggcttggca tcaacaaaaa ccaggtaaag ctccaaagat gttgattatt      600
tgggcttcta ccagagtttc tggtgttcca tctagatttt ctggttctgg ttccggtact      660 gatttactt tgaccatttc atccttgcaa ccagaagatt tcgctactta ctactgtcaa      720
caatcttact ctgctccatt gacttttggt caagtacaa aggtcgaaat caagagagaa      780
ttcggtaagc ctatccctaa ccctctcctc ggtctcgatt ctacgggtgg tggtggatct      840
ggtggtggtg gttctggtgg tggtggttct caggaactga caactatatg cgagcaaatc      900
ccctcaccaa cttagaatc gacgccgtac tctttgtcaa cgactactat tttgccaac        960 gggaaggcaa tgcaaggagt ttttgaatat tacaaatcag taacgtttgt cagtaattgc     1020
```
ggttctcacc cctcaacaac tagcaaaggc agccccataa acacacagta tgttttttga    1080
gtttaaac                                                              1088

<210> SEQ ID NO 56
<211> LENGTH: 5597
<212> TYPE: DNA
<213> ORGANISM: Artificial Sequence
<220> FEATURE:
<223> OTHER INFORMATION: Synthetic (expression vector including
      polynucleotide encoding scFv of huAbF46 antibody)
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56
acggattaga agccgccgag cgggtgacag ccctccgaag gaagactctc ctccgtgcgt     60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaaatac   480 gactcactat agggaatatt aagctaattc tacttcatac attttcaatt aagatgcagt    540
tacttcgctg ttttttcaata tttttctgtta ttgctagcgt tttagcagaa gttcaattgg   600
ttgaatctgg tggtggtttg gttcaaccag gtggttcttt gagattgtct tgtgctgctt    660
ctggttttac tttcaccgat tattacatgt cctgggttag acaagctcca ggtaaaggtt    720

```
tggaatggtt gggtttcatt agaaacaagg ctaacggtta cactaccgaa tattctgctt      780
ctgttaaggg tagattcacc atttctagag acaactctaa gaacaccttg tacttgcaaa      840
tgaactcctt gagagctgaa gatactgctg tttattactg cgctagagat aattggtttg      900
cttattgggg tcaaggtact ttggttactg tttcttctgg cctcggggc ctcggaggag       960 gaggtagtgg cggaggaggc tccggtggat ccagcgtgt gggttccgat attcaaatga       1020
cccaatctcc atcttctttg tctgcttcag ttggtgatag agttaccatt acttgtaagt     1080
cctcccaatc tttgttggct tctggtaatc agaacaatta cttggcttgg catcaacaaa     1140
aaccaggtaa agctccaaag atgttgatta tttgggcttc taccagagtt tctggtgttc     1200
catctagatt ttctggttct ggttccggta ctgattttac tttgaccatt tcatccttgc     1260
aaccagaaga tttcgctact tactactgtc aacaatctta ctctgctcca ttgacttttg     1320
gtcaaggtac aaaggtcgaa atcaagagag aattcggtaa gcctatccct aaccctctcc     1380
tcggtctcga ttctacgggt ggtggtggat ctggtggtgg tggttctggt ggtggtggtt     1440
ctcaggaact gacaactata tgcgagcaaa tcccctcacc aactttagaa tcgacgccgt     1500
actctttgtc aacgactact attttggcca acgggaaggc aatgcaagga gttttttgaat    1560 attacaaatc agtaacgttt gtcagtaatt gcggttctca cccctcaaca actagcaaag    1620
gcagccccat aaacacacag tatgtttttt gagtttaaac ccgctgatct gataacaaca    1680
gtgtagatgt aacaaaatcg actttgttcc cactgtactt ttagctcgta caaaatacaa    1740 tatactttc atttctccgt aaacaacatg ttttcccatg taatatcctt ttctatttt      1800 cgttccgtta ccaactttac acatacttta tatagctatt cacttctata cactaaaaaa    1860
ctaagacaat tttaattttg ctgcctgcca tatttcaatt tgttataaat tcctataatt    1920
tatcctatta gtagctaaaa aaagatgaat gtgaatcgaa tcctaagaga attgggcaag    1980
tgcacaaaca atacttaaat aaatactact cagtaataac ctatttctta gcatttttga    2040
cgaaatttgc tattttgtta gagtcttta caccatttgt ctccacacct ccgcttacat    2100
caacaccaat aacgccattt aatctaagcg catcaccaac attttctggc gtcagtccac   2160
cagctaacat aaaatgtaag ctctcggggc tctcttgcct tccaacccag tcagaaatcg   2220
agttccaatc aaaagttca cctgtcccac ctgcttctga atcaaacaag ggaataaacg    2280
aatgaggttt ctgtgaagct gcactgagta gtatgttgca gtcttttgga aatacgagtc    2340
ttttaataac tggcaaaccg aggaactctt ggtattcttg ccacgactca tctccgtgca    2400
gttggacgat atcaatgccg taatcattga ccagagccaa aacatcctcc ttaggttgat    2460
tacgaaacac gccaaccaag tatttcggag tgcctgaact attttttatat gcttttacaa   2520 gacttgaaat tttccttgca ataaccgggt caattgttct ctttctattg ggcacacata    2580
taatacccag caagtcagca tcggaatcta gagcacattc tgcggcctct gtgctctgca   2640
agccgcaaac tttcaccaat ggaccagaac tacctgtgaa attaataaca gacatactcc    2700
aagctgcctt tgtgtgctta atcacgtata ctcacgtgct caatagtcac caatgccctc   2760
cctcttggcc ctctccttt cttttttcga ccgaatttct tgaagacgaa agggcctcgt    2820
gatacgccta ttttttatagg ttaatgtcat gataataatg gtttcttagg acggatcgct   2880
tgcctgtaac ttacacgcgc ctcgtatctt ttaatgatgg aataatttgg gaatttactc    2940
tgtgtttatt tattttatg ttttgtattt ggatttaga aagtaaataa agaaggtaga     3000
agagttacgg aatgaagaaa aaaaaataaa caaaggttta aaaaatttca acaaaaagcg    3060
```

```
tactttacat atatatttat tagacaagaa aagcagatta aatagatata cattcgatta    3120
acgataagta aaatgtaaaa tcacaggatt ttcgtgtgtg gtcttctaca cagacaagat    3180
gaaacaattc ggcattaata cctgagagca ggaagagcaa gataaaaggt agtatttgtt    3240
ggcgatcccc ctagagtctt ttacatcttc ggaaaacaaa aactattttt tctttaattt    3300 cttttttac tttctatttt taatttatat atttatatta aaaaatttaa attataatta     3360
tttttatagc acgtgatgaa aaggacccag gtggcacttt tcggggaaat gtgcgcggaa    3420
cccctatttg tttattttc taaatacatt caaatatgta tccgctcatg agacaataac     3480
cctgataaat gcttcaataa tattgaaaaa ggaagagtat gagtattcaa catttccgtg    3540
tcgcccttat tccctttttt gcggcatttt gccttcctgt ttttgctcac ccagaaacgc    3600
tggtgaaagt aaaagatgct gaagatcagt tgggtgcacg agtgggttac atcgaactgg    3660
atctcaacag cggtaagatc cttgagagtt ttcgccccga agaacgtttt ccaatgatga    3720 gcactttaa agttctgcta tgtggcgcgg tattatcccg tgttgacgcc gggcaagagc      3780
aactcggtcg ccgcatacac tattctcaga atgacttggt tgagtactca ccagtcacag    3840
aaaagcatct tacggatggc atgacagtaa gagaattatg cagtgctgcc ataaccatga    3900
gtgataacac tgcggccaac ttacttctga caacgatcgg aggaccgaag gagctaaccg    3960
cttttttgca caacatgggg gatcatgtaa ctcgccttga tcgttgggaa ccggagctga    4020
atgaagccat accaaacgac gagcgtgaca ccacgatgcc tgtagcaatg gcaacaacgt    4080
tgcgcaaact attaactggc gaactactta ctctagcttc ccggcaacaa ttaatagact    4140
ggatggaggc ggataaagtt gcaggaccac ttctgcgctc ggcccttccg gctggctggt    4200
ttattgctga taaatctgga gccggtgagc gtgggtctcg cggtatcatt gcagcactgg    4260
ggccagatgg taagccctcc cgtatcgtag ttatctacac gacgggcagt caggcaacta    4320
tggatgaacg aaatagacag atcgctgaga taggtgcctc actgattaag cattggtaac    4380
tgtcagacca agtttactca tatatacttt agattgattt aaaacttcat ttttaattta    4440
aaaggatcta ggtgaagatc ctttttgata atctcatgac caaaatccct taacgtgagt    4500
tttcgttcca ctgagcgtca gaccccgtag aaaagatcaa aggatcttct tgagatcctt    4560 ttttttctgcg cgtaatctgc tgcttgcaaa caaaaaaacc accgctacca gcggtggttt    4620
gtttgccgga tcaagagcta ccaactcttt ttccgaaggt aactggcttc agcagagcgc    4680
agataccaaa tactgtcctt ctagtgtagc cgtagttagg ccaccacttc aagaactctg    4740
tagcaccgcc tacatacctc gctctgctaa tcctgttacc agtggctgct gccagtggcg    4800
ataagtcgtg tcttaccggg ttggactcaa gacgatagtt accggataag gcgcagcggt    4860
cgggctgaac ggggggttcg tgcacacagc ccagcttgga gcgaacgacc tacaccgaac    4920
tgagatacct acagcgtgag cattgagaaa gcgccacgct tcccgaaggg agaaaggcgg    4980
acaggtatcc ggtaagcggc agggtcggaa caggagagcg cacgagggag cttccagggg    5040
ggaacgcctg gtatctttat agtcctgtcg ggtttcgcca cctctgactt gagcgtcgat    5100
ttttgtgatg ctcgtcaggg gggcggagcc tatggaaaaa cgccagcaac gcggcctttt    5160
tacggttcct ggccttttgc tggccttttg ctcacatgtt ctttcctgcg ttatcccctg    5220
attctgtgga taaccgtatt accgcctttg agtgagctga taccgctcgc cgcagccgaa    5280
cgaccgagcg cagcgagtca gtgagcgagg aagcggaaga gcgcccaata cgcaaaccgc    5340
ctctccccgc gcgttggccg attcattaat gcagctggca cgacaggttt cccgactgga    5400
aagcgggcag tgagcgcaac gcaattaatg tgagttacct cactcattag gcaccccagg    5460
```

```
ctttacactt tatgcttccg gctcctatgt tgtgtggaat tgtgagcgga taacaatttc    5520
acacaggaaa cagctatgac catgattacg ccaagctcgg aattaaccct cactaaaggg    5580
aacaaaagct ggctagt                                                  5597
```

<210> SEQ ID NO 57
<211> LENGTH: 13
<212> TYPE: PRT
<213> ORGANISM: Artificial Sequence
<220> FEATURE:
<223> OTHER INFORMATION: Synthetic (U6-HC7 hinge)

<400> SEQUENCE: 57

Glu Pro Lys Ser Cys Asp Cys His Cys Pro Pro Cys Pro
1               5                   10

<210> SEQ ID NO 58
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-1 clone)

<400> SEQUENCE: 58

```
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca agtccagtca gagtctttta    180
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtcagcagtc ctacagccgc ccgtacacgt tcggacaggg taccaaggtg    420
gagatcaaac gtacg                                                    435
```

<210> SEQ ID NO 59
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-2 clone)

<400> SEQUENCE: 59

```
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca agtccagtca gagtctttta    180
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtgggcagtc ctacagccgt ccgctcacgt tcggacaggg taccaaggtg    420
gagatcaaac gtacg                                                    435
```

<210> SEQ ID NO 60
<211> LENGTH: 435
<212> TYPE: DNA
<213> ORGANISM: Artificial Sequence

```
<220> FEATURE:
<223> OTHER INFORMATION: Synthetic (polynucleotide encoding CDR-L3
      derived from L3-3 clone)

<400> SEQUENCE: 60
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca agtccagtca gagtcttta     180 gctagtggca accaaaataa ctacttggcc tggcaccaac agaaaccagg aaaagctccg     240
aaaatgctga ttatttgggc atccactagg gtatctggag tcccttctcg cttctctgga     300
tccgggtctg ggacggattt cactctgacc atcagcagtc tgcagccgga agacttcgca     360
acttattact gtgcacagtc ctacagccat ccgttctctt tcggacaggg taccaaggtg     420
gagatcaaac gtacg                                                      435

<210> SEQ ID NO 61
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-5 clone)

<400> SEQUENCE: 61
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca agtccagtca gagtcttta     180 gctagtggca accaaaataa ctacttggcc tggcaccaac agaaaccagg aaaagctccg     240
aaaatgctga ttatttgggc atccactagg gtatctggag tcccttctcg cttctctgga     300
tccgggtctg ggacggattt cactctgacc atcagcagtc tgcagccgga agacttcgca     360
acttattact gtcagcagtc ctacagccgc cgtttacgt tcggacaggg taccaaggtg      420
gagatcaaac gtacg                                                      435

<210> SEQ ID NO 62
<211> LENGTH: 462
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, U6-HC7 hinge and constant region of
      human IgG1)

<400> SEQUENCE: 62

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95
```

```
Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 63
<211> LENGTH: 1410
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, U6-HC7 hinge and
      constant region of human IgG1)
```

<400> SEQUENCE: 63

```
gaattcgccg ccaccatgga atggagctgg gttttctcg taacactttt aaatggtatc    60
cagtgtgagg ttcagctggt ggagtctggc ggtggcctgg tgcagccagg gggctcactc   120
cgtttgtcct gtgcagcttc tggcttcacc ttcactgatt actacatgag ctgggtgcgt   180
caggccccgg gtaagggcct ggaatggttg ggttttatta gaaacaaagc taatggttac   240
acaacagagt acagtgcatc tgtgaagggt cgtttcacta agcagaga taattccaaa    300
aacacactgt acctgcagat gaacagcctg cgtgctgagg acactgccgt ctattattgt   360
gctagagata actggtttgc ttactgggc caagggactc tggtcaccgt ctcctcggct   420
agcaccaagg gcccatcggt cttccccctg gcaccctcct ccaagagcac ctctggggc   480
acagcggccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac   660
atctgcaacg tgaatcacaa gcccagcaac accaaggtgg acaagaaagt tgagcccaaa   720
agctgcgatt gccactgtcc tccatgtcca gcacctgaac tcctgggggg accgtcagtc   780
ttcctcttcc cccaaaacc caaggacacc ctcatgatct cccggacccc tgaggtcaca   840
tgcgtggtgg tggacgtgag ccacgaagac cctgaggtca agttcaactg gtacgtggac   900
ggcgtggagg tgcataatgc caagacaaag ccgcgggagg agcagtacaa cagcacgtac   960
cgtgtggtca gcgtcctcac cgtcctgcac caggactggc tgaatggcaa ggagtacaag  1020
tgcaaggtct ccaacaaagc cctcccagcc cccatcgaga aaaccatctc caaagccaaa  1080
gggcagcccc gagaaccaca ggtgtacacc ctgcccccat cccgggagga gatgaccaag  1140
aaccaggtca gcctgacctg cctggtcaaa ggcttctatc ccagcgacat cgccgtggag  1200
tgggagagca atgggcagcc ggagaacaac tacaagacca cgcctcccgt gctggactcc  1260
gacggctcct tcttcctcta cagcaagctc accgtggaca agagcaggtg gcagcagggg  1320
aacgtcttct catgctccgt gatgcatgag gctctgcaca accactacac gcagaagagc  1380
ctctcccctgt ctccgggtaa atgactcgag                                   1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, human IgG2 hinge and constant region of
      human IgG1)

<400> SEQUENCE: 64

```
Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95
```

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
            115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
            165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
            195                 200                 205

Ser Leu Gly Thr Gln Thr Tyr Ile Cys Asn Val Asn His Lys Pro Ser
            210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
            245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
            325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
            355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
            405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
            450                 455                 460

<210> SEQ ID NO 65
<211> LENGTH: 1407
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, human IgG2 hinge and
      constant region of human IgG1)

<400> SEQUENCE: 65

```
gaattcgccg ccaccatgga atggagctgg gttttctcg taacactttt aaatggtatc      60
cagtgtgagg ttcagctggt ggagtctggc ggtggcctgg tgcagccagg gggctcactc    120
cgtttgtcct gtgcagcttc tggcttcacc ttcactgatt actacatgag ctgggtgcgt    180
caggccccgg gtaagggcct ggaatggttg ggttttatta gaaacaaagc taatggttac    240
acaacagagt acagtgcatc tgtgaagggt cgtttcacta agcagaga taattccaaa      300
aacacactgt acctgcagat gaacagcctg cgtgctgagg acactgccgt ctattattgt    360
gctagagata actggtttgc ttactggggc caagggactc tggtcaccgt ctcctcggct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagaggaag    720
tgctgtgtgg agtgccccc ctgcccagca cctgaactcc tggggggacc gtcagtcttc      780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaagggg   1080
cagccccgag aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
ggctccttct tcctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaatg actcgag                                         1407
```

<210> SEQ ID NO 66
<211> LENGTH: 460
<212> TYPE: PRT
<213> ORGANISM: Artificial Sequence
<220> FEATURE:
<223> OTHER INFORMATION: Synthetic (polypeptide consisting of heavy chain of huAbF46-H4-A1, human IgG2 hinge and constant region of human IgG2)

<400> SEQUENCE: 66

```
Met Glu Trp Ser Trp Val Phe Leu Val Thr Leu Leu Asn Gly Ile Gln
  1               5                  10                  15

Cys Glu Val Gln Leu Val Glu Ser Gly Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
```

```
                    85                  90                  95
Thr Leu Tyr Leu Gln Met Asn Ser Leu Arg Ala Glu Asp Thr Ala Val
                100                 105                 110

Tyr Tyr Cys Ala Arg Asp Asn Trp Phe Ala Tyr Trp Gly Gln Gly Thr
            115                 120                 125

Leu Val Thr Val Ser Ser Ala Ser Thr Lys Gly Pro Ser Val Phe Pro
        130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 67
<211> LENGTH: 1404
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, human IgG2 hinge and
```

-continued constant region of human IgG2)

<400> SEQUENCE: 67

```
gaattcgccg ccaccatgga atggagctgg gttttctcg taacactttt aaatggtatc      60
cagtgtgagg ttcagctggt ggagtctggc ggtggcctgg tgcagccagg ggctcactc     120
cgtttgtcct gtgcagcttc tggcttcacc ttcactgatt actacatgag ctgggtgcgt    180
caggccccgg gtaagggcct ggaatggttg ggttttatta gaaacaaagc taatggttac    240
acaacagagt acagtgcatc tgtgaagggt cgtttcacta agcagaga taattccaaa      300
aacacactgt acctgcagat gaacagcctg cgtgctgagg acactgccgt ctattattgt    360
gctagagata actggtttgc ttactgggc caagggactc tggtcaccgt ctcctcggct     420
agcaccaagg gcccatcggt cttcccctg gcgccctgct ccaggagcac ctccgagagc     480
acagcggccc tgggctgcct ggtcaaggac tacttccccg aaccggtgac ggtgtcgtgg    540
aactcaggcg ctctgaccag cggcgtgcac accttcccag ctgtcctaca gtcctcagga    600
ctctactccc tcagcagcgt ggtgaccgtg ccctccagca cttcggcac ccagacctac     660
acctgcaacg tagatcacaa gcccagcaac accaaggtgg acaagacagt tgagcgcaaa    720
tgttgtgtcg agtgcccacc gtgcccagca ccacctgtgg caggaccgtc agtcttcctc    780
ttcccccaa acccaagga caccctcatg atctcccgga cccctgaggt cacgtgcgtg     840
gtggtggacg tgagccacga agaccccgag gtccagttca actggtacgt ggacggcgtg    900
gaggtgcata atgccaagac aaagccacgg gaggagcagt tcaacagcac gttccgtgtg    960
gtcagcgtcc tcaccgttgt gcaccaggac tggctgaacg gcaaggagta caagtgcaag   1020
gtctccaaca aaggcctccc agccccatc gagaaaacca tctccaaaac caaagggcag    1080
ccccgagaac acaggtgta caccctgccc ccatcccggg aggagatgac caagaaccag    1140
gtcagcctga cctgcctggt caaaggcttc taccccagcg acatcgccgt ggagtgggag   1200
agcaatgggc agccggagaa caactacaag accacgcctc ccatgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatgact cgag                                          1404
```

<210> SEQ ID NO 68
<211> LENGTH: 240
<212> TYPE: PRT
<213> ORGANISM: Artificial Sequence
<220> FEATURE:
<223> OTHER INFORMATION: Synthetic (polypeptide consisting of light
      chain of huAbF46-H4-A1(H36Y) and human kappa constant region)

<400> SEQUENCE: 68

```
Met Asp Ser Gln Ala Gln Val Leu Met Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp Tyr Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
```

```
                    85                  90                  95
Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 69
<211> LENGTH: 758
<212> TYPE: DNA
<213> ORGANISM: Artificial Sequence
<220> FEATURE:
<223> OTHER INFORMATION: Synthetic (polynucleotide encoding polypeptide
      consisting of light chain of huAbF46-H4-A1(H36Y) and
      human kappa constant region)

<400> SEQUENCE: 69
aattcactag tgattaattc gccgccacca tggattcaca ggcccaggtc ctcatgttgc      60
tgctgctatc ggtatctggt acctgtggag atatccagat gacccagtcc ccgagctccc     120
tgtccgcctc tgtgggcgat agggtcacca tcacctgcaa gtccagtcag agtcttttag     180
ctagtggcaa ccaaaataac tacttggcct ggtaccaaca gaaaccagga aaagctccga     240
aaatgctgat tatttgggca tccactaggg tatctggagt cccttctcgc ttctctggat     300
ccgggtctgg gacggatttc actctgacca tcagcagtct gcagccggaa gacttcgcaa     360
cttattactg tcagcagtcc tacagccgcc cgtacacgtt cggacagggt accaaggtgg     420
agatcaaacg tacggtggct gcaccatctg tcttcatctt cccgccatct gatgagcagt     480
tgaaatctgg aactgcctct gttgtgtgcc tgctgaataa cttctatccc agagaggcca     540
aagtacagtg gaaggtggat aacgccctcc aatcgggtaa ctcccaggag agtgtcacag     600
agcaggacag caaggacagc acctacagcc tcagcagcac cctgacgctg agcaaagcag     660
actacgagaa acacaaagtc tacgcctgcg aagtcaccca tcagggcctg agctcgcccg     720
tcacaaagag cttcaacagg ggagagtgtt gactcgag                             758

<210> SEQ ID NO 70
<211> LENGTH: 240
<212> TYPE: PRT
<213> ORGANISM: Artificial Sequence
<220> FEATURE:
<223> OTHER INFORMATION: Synthetic (polypeptide consisting of light
      chain of huAbF46-H4-A1 and human kappa constant region)

<400> SEQUENCE: 70

Met Asp Ser Gln Ala Gln Val Leu Met Leu Leu Leu Leu Ser Val Ser
```

```
                1               5                  10                 15
            Gly Thr Cys Gly Asp Ile Gln Met Thr Gln Ser Pro Ser Ser Leu Ser
                             20                 25                 30

Ala Ser Val Gly Asp Arg Val Thr Ile Thr Cys Lys Ser Gln Ser
                             35                 40                 45

Leu Leu Ala Ser Gly Asn Gln Asn Asn His Leu Ala Trp Tyr Gln Gln
                             50                 55                 60

Lys Pro Gly Lys Ala Pro Lys Met Leu Ile Ile Trp Ala Ser Thr Arg
             65                 70                 75                 80

Val Ser Gly Val Pro Ser Arg Phe Ser Gly Ser Gly Ser Gly Thr Asp
                             85                 90                 95

Phe Thr Leu Thr Ile Ser Ser Leu Gln Pro Glu Asp Phe Ala Thr Tyr
                            100                105                110

Tyr Cys Gln Gln Ser Tyr Ser Arg Pro Tyr Thr Phe Gly Gln Gly Thr
                            115                120                125

Lys Val Glu Ile Lys Arg Thr Val Ala Ala Pro Ser Val Phe Ile Phe
             130                135                140

Pro Pro Ser Asp Glu Gln Leu Lys Ser Gly Thr Ala Ser Val Val Cys
             145                150                155                160

Leu Leu Asn Asn Phe Tyr Pro Arg Glu Ala Lys Val Gln Trp Lys Val
                            165                170                175

Asp Asn Ala Leu Gln Ser Gly Asn Ser Gln Glu Ser Val Thr Glu Gln
                            180                185                190

Asp Ser Lys Asp Ser Thr Tyr Ser Leu Ser Ser Thr Leu Thr Leu Ser
                            195                200                205

Lys Ala Asp Tyr Glu Lys His Lys Val Tyr Ala Cys Glu Val Thr His
             210                215                220

Gln Gly Leu Ser Ser Pro Val Thr Lys Ser Phe Asn Arg Gly Glu Cys
             225                230                235                240

<210> SEQ ID NO 71
            <211> LENGTH: 19
            <212> TYPE: PRT
            <213> ORGANISM: Artificial Sequence
            <220> FEATURE:
            <223> OTHER INFORMATION: Synthetic (epitope in SEMA domain of c-Met)

<400> SEQUENCE: 71

Phe Ser Pro Gln Ile Glu Glu Pro Ser Gln Cys Pro Asp Cys Val Val
             1               5                  10                 15

Ser Ala Leu

<210> SEQ ID NO 72
            <211> LENGTH: 10
            <212> TYPE: PRT
            <213> ORGANISM: Artificial Sequence
            <220> FEATURE:
            <223> OTHER INFORMATION: Synthetic (epitope in SEMA domain of c-Met)

<400> SEQUENCE: 72

Pro Gln Ile Glu Glu Pro Ser Gln Cys Pro
             1               5                  10

<210> SEQ ID NO 73
            <211> LENGTH: 5
            <212> TYPE: PRT
            <213> ORGANISM: Artificial Sequence
            <220> FEATURE:
            <223> OTHER INFORMATION: Synthetic (epitope in SEMA domain of c-Met)
```

<400> SEQUENCE: 73

Glu Glu Pro Ser Gln
1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic (heavy chain variable region of
      anti-c-Met antibody (AbF46 or huAbF46-H1))

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 75
<211> LENGTH: 114
<212> TYPE: PRT
<213> ORGANISM: Artificial Sequence
<220> FEATURE:
<223> OTHER INFORMATION: Synthetic (light chain variable region of
      anti-c-Met antibody (AbF46 or huAbF46-H1)

<400> SEQUENCE: 75

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg

<210> SEQ ID NO 76
<211> LENGTH: 1416
<212> TYPE: DNA

```
<213> ORGANISM: Artificial Sequence
<220> FEATURE:
<223> OTHER INFORMATION: Synthetic (nucleotide sequence of heavy chain
      of anti-c-Met antibody (AbF46 or huAbF46-H1))
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 76
gaattcgccg ccaccatgga atggagctgg gttttctcg taacactttt aaatggtatc     60
cagtgtgagg tgaagctggt ggagtctgga ggaggcttgg tacagcctgg gggttctctg    120
agactctcct gtgcaactt ctgggttcacc ttcactgatt actacatgag ctgggtccgc    180
cagcctccag gaaaggcact tgagtggttg ggttttatta gaaacaaagc taatggttac    240
acaacagagt acagtgcatc tgtgaagggt cggttcacca tctccagaga taattcccaa    300
agcatcctct atcttcaaat ggacaccctg agagctgagg acagtgccac ttattactgt    360
gcaagagata ctggtttgc ttactgggc aagggactc tggtcactgt ctctgcagct      420
agcaccaagg gcccatcggt cttcccctg caccctcct ccaagagcac ctctgggggc     480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggaggagatg   1140
accaagaacc aggtcagcct gacctgcctg gtcaaaggct tctatccag cgacatcgcc    1200 gtggagtggg agagcaatgg gcagccggag aacaactaca agaccacgcc tcccgtgctg   1260
gactccgacg gctccttctt cctctacagc aagctcaccg tggacaagag caggtggcag   1320
```

```
caggggaacg tcttctcatg ctccgtgatg catgaggctc tgcacaacca ctacacgcag    1380
aagagcctct ccctgtctcc gggtaaatga ctcgag                              1416
```

<210> SEQ ID NO 77
<211> LENGTH: 759
<212> TYPE: DNA
<213> ORGANISM: Artificial Sequence
<220> FEATURE:
<223> OTHER INFORMATION: Synthetic (nucleotide sequence of light chain
      of anti-c-Met antibody (AbF46 or huAbF46-H1))
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77

```
gaattcacta gtgattaatt cgccgccacc atggattcac aggcccaggt cctcatgttg     60
ctgctgctat cggtatctgg tacctgtgga gacattttga tgacccagtc tccatcctcc    120
ctgactgtgt cagcaggaga gaaggtcact atgagctgca agtccagtca gagtctttta    180
gctagtggca accaaaataa ctacttggcc tggcaccagc agaaaccagg acgatctcct    240
aaaatgctga taatttgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                           759
```

<210> SEQ ID NO 78
<211> LENGTH: 4170
<212> TYPE: DNA
<213> ORGANISM: Artificial Sequence
<220> FEATURE:
<223> OTHER INFORMATION: Synthetic (polynucleotide encoding c-Met
      protein)

<400> SEQUENCE: 78

```
atgaaggccc ccgctgtgct tgcacctggc atcctcgtgc tcctgtttac cttggtgcag    60
aggagcaatg gggagtgtaa agaggcacta gcaaagtccg agatgaatgt gaatatgaag   120
tatcagcttc ccaacttcac cgcggaaaca cccatccaga atgtcattct acatgagcat   180
cacattttcc ttggtgccac taactacatt tatgttttaa atgaggaaga ccttcagaag   240
gttgctgagt acaagactgg gcctgtgctg aacacccag attgtttccc atgtcaggac    300
tgcagcagca aagccaattt atcaggaggt gtttggaaag ataacatcaa catggctcta   360
gttgtcgaca cctactatga tgatcaactc attagctgtg gcagcgtcaa cagagggacc   420
tgccagcgac atgtctttcc ccacaatcat actgctgaca tacagtcgga ggttcactgc   480
atattctccc cacagataga agagcccagc cagtgtcctg actgtgtggt gagcgccctg   540
ggagccaaag tcctttcatc tgtaaaggac cggttcatca acttctttgt aggcaatacc   600
ataaattctt cttatttccc agatcatcca ttgcattcga tatcagtgag aaggctaaag   660
gaaacgaaag atggttttat gtttttgacg gaccagtcct acattgatgt tttacctgag   720
ttcagagatt cttaccccat taagtatgtc catgcctttg aaagcaacaa ttttatttac   780
ttcttgacgg tccaaaggga aactctagat gctcagactt tcacacaag aataatcagg    840 ttctgttcca taaactctgg attgcattcc tacatggaaa tgcctctgga gtgtattctc   900
acagaaaaga gaaaaagag atccacaaag aaggaagtgt ttaatatact tcaggctgcg    960
tatgtcagca agcctggggc ccagcttgct agacaaatag gagccagcct gaatgatgac  1020
attcttttcg gggtgttcgc acaaagcaag ccagattctg ccgaaccaat ggatcgatct  1080
gccatgtgtg cattccctat caaatatgtc aacgacttct caacaagat cgtcaacaaa   1140 acaatgtga atgtctcca gcattttac ggacccaatc atgagcactg ctttaatagg     1200
acacttctga gaaattcatc aggctgtgaa gcgcgccgtg atgaatatcg aacagagttt  1260
accacagctt tgcagcgcgt tgacttattc atgggtcaat tcagcgaagt cctcttaaca  1320
tctatatcca ccttcattaa aggagacctc accatagcta atcttgggac atcagagggt  1380
cgcttcatgc aggttgtggt ttctcgatca ggaccatcaa cccctcatgt gaattttctc  1440
ctggactccc atccagtgtc tccagaagtg attgtggagc atacattaaa ccaaaatggc  1500
tacacactgg ttatcactgg gaagaagatc acgaagatcc cattgaatgg cttgggctgc  1560
agacatttcc agtcctgcag tcaatgcctc tctgccccac cctttgttca gtgtggctgg  1620
tgccacgaca atgtgtgcg atcggaggaa tgcctgagcg ggacatggac tcaacagatc  1680
tgtctgcctg caatctacaa ggttttccca aatagtgcac cccttgaagg agggacaagg  1740
ctgaccatat gtggctggga ctttggattt cggaggaata taaatttga tttaaagaaa  1800 actagagttc ccttggaaa tgagagctgc accttgactt aagtgagag cacgatgaat   1860 acattgaaat gcacagttgg tcctgccatg aataagcatt tcaatatgtc cataattatt  1920
tcaaatggcc acgggacaac acaatacagt acattctcct atgtggatcc tgtaataaca  1980
agtatttcgc cgaaatacgg tcctatggct ggtggcactt tacttacttt aactggaaat  2040
tacctaaaca gtgggaattc tagacacatt tcaattggtg aaaaacatg tactttaaaa   2100 agtgtgtcaa acagtattct tgaatgttat accccagccc aaaccatttc aactgagttt  2160
gctgttaaat tgaaaattga cttagccaac cgagagacaa gcatcttcag ttaccgtgaa  2220
gatcccattg tctatgaaat tcatccaacc aaatctttta ttagtggtgg gagcacaata  2280
acaggtgttg ggaaaaacct gaattcagtt agtgtcccga gaatggtcat aaatgtgcat  2340
```

-continued

```
gaagcaggaa ggaactttac agtggcatgt caacatcgct ctaattcaga gataatctgt    2400
tgtaccactc cttccctgca acagctgaat ctgcaactcc ccctgaaaac caaagccttt    2460
ttcatgttag atgggatcct ttccaaatac tttgatctca tttatgtaca taatcctgtg    2520
tttaagcctt ttgaaaagcc agtgatgatc tcaatgggca atgaaaatgt actggaaatt    2580
aagggaaatg atattgaccc tgaagcagtt aaaggtgaag tgttaaaagt tggaaataag    2640
agctgtgaga atatacactt acattctgaa gccgttttat gcacggtccc caatgacctg    2700
ctgaaattga acagcgagct aaatatagag tggaagcaag caatttcttc aaccgtcctt    2760
ggaaaagtaa tagttcaacc agatcagaat ttcacaggat tgattgctgg tgttgtctca    2820
atatcaacag cactgttatt actacttggg ttttttcctgt ggctgaaaaa gagaaagcaa    2880
attaaagatc tgggcagtga attagttcgc tacgatgcaa gagtacacac tcctcatttg    2940
gataggcttg taagtgcccg aagtgtaagc ccaactacag aaatggtttc aaatgaatct    3000
gtagactacc gagctacttt tccagaagat cagtttccta attcatctca gaacggttca    3060
tgccgacaag tgcagtatcc tctgacagac atgtccccca tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat tgtgcatttc    3240
aatgaagtca taggaagagg gcattttggt tgtgtatatc atgggacttt gttggacaat    3300
gatggcaaga aaattcactg tgctgtgaaa tccttgaaca gaatcactga cataggagaa    3360
gtttcccaat ttctgaccga gggaatcatc atgaaagatt ttagtcatcc caatgtcctc    3420
tcgctcctgg gaatctgcct gcgaagtgaa gggtctccgc tggtggtcct accatacatg    3480
aaacatggag atcttcgaaa tttcattcga aatgagactc ataatccaac tgtaaaagat    3540
cttattggct ttggtcttca agtagccaaa ggcatgaaat atcttgcaag caaaagcttt    3600
gtccacagag acttggctgc aagaaactgt atgctggatg aaaaattcac agtcaaggtt    3660
gctgattttg tcttgccagg agacatgtat gataaagaat actatagtgt acacaacaaa    3720
acaggtgcaa agctgccagt gaagtggatg gctttggaaa gtctgcaaac tcaaaagttt    3780
accaccaagt cagatgtgtg gtcctttggc gtgctcctct gggagctgat gacaagagga    3840
gccccacctt atcctgacgt aaacaccttt gatataactg tttacttgtt gcaagggaga    3900
agactcctac aacccgaata ctgcccagac cccttatatg aagtaatgct aaaatgctgg    3960
caccctaaag ccgaaatgcg cccatccttt tctgaactgg tgtcccggat atcagcgatc    4020
ttctctactt tcattgggga gcactatgtc catgtgaacg ctacttatgt gaacgtaaaa    4080
tgtgtcgctc cgtatccttc tctgttgtca tcagaagata cgctgatga tgaggtggac    4140 acacgaccag cctccttctg ggagacatca                                     4170
```

<210> SEQ ID NO 79
<211> LENGTH: 444
<212> TYPE: PRT
<213> ORGANISM: Artificial Sequence
<220> FEATURE:
<223> OTHER INFORMATION: Synthetic (SEMA domain of c-Met)

<400> SEQUENCE: 79

Leu His Glu His His Ile Phe Leu Gly Ala Thr Asn Tyr Ile Tyr Val
1               5                   10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys

```
                35                  40                  45
Ala Asn Leu Ser Gly Gly Val Trp Lys Asp Asn Ile Asn Met Ala Leu
 50                  55                  60

Val Val Asp Thr Tyr Tyr Asp Asp Gln Leu Ile Ser Cys Gly Ser Val
 65                  70                  75                  80

Asn Arg Gly Thr Cys Gln Arg His Val Phe Pro His Asn His Thr Ala
                 85                  90                  95

Asp Ile Gln Ser Glu Val His Cys Ile Phe Ser Pro Gln Ile Glu Glu
                100                 105                 110

Pro Ser Gln Cys Pro Asp Cys Val Val Ser Ala Leu Gly Ala Lys Val
            115                 120                 125

Leu Ser Val Lys Asp Arg Phe Ile Asn Phe Val Gly Asn Thr
            130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
                180                 185                 190

Tyr Val His Ala Phe Glu Ser Asn Asn Phe Ile Tyr Phe Leu Thr Val
            195                 200                 205

Gln Arg Glu Thr Leu Asp Ala Gln Thr Phe His Thr Arg Ile Ile Arg
210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
                260                 265                 270

Leu Ala Arg Gln Ile Gly Ala Ser Leu Asn Asp Asp Ile Leu Phe Gly
            275                 280                 285

Val Phe Ala Gln Ser Lys Pro Asp Ser Ala Glu Pro Met Asp Arg Ser
290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
            355                 360                 365

Gln Arg Val Asp Leu Phe Met Gly Gln Phe Ser Glu Val Leu Leu Thr
            370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Val Ser Arg Ser Gly Pro
                405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
            435                 440

<210> SEQ ID NO 80
```

```
<211> LENGTH: 451
<212> TYPE: PRT
<213> ORGANISM: Artificial Sequence
<220> FEATURE:
<223> OTHER INFORMATION: Synthetic (PSI-IPT domain of c-Met)

<400> SEQUENCE: 80

Tyr Thr Leu Val Ile Thr Gly Lys Lys Ile Thr Lys Ile Pro Leu Asn
1               5                   10                  15

Gly Leu Gly Cys Arg His Phe Gln Ser Cys Ser Gln Cys Leu Ser Ala
            20                  25                  30

Pro Pro Phe Val Gln Cys Gly Trp Cys His Asp Lys Cys Val Arg Ser
        35                  40                  45

Glu Glu Cys Leu Ser Gly Thr Trp Thr Gln Gln Ile Cys Leu Pro Ala
50                  55                  60

Ile Tyr Lys Val Phe Pro Asn Ser Ala Pro Leu Glu Gly Gly Thr Arg
65                  70                  75                  80

Leu Thr Ile Cys Gly Trp Asp Phe Gly Phe Arg Arg Asn Asn Lys Phe
                85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
        115                 120                 125

Ala Met Asn Lys His Phe Asn Met Ser Ile Ile Ser Asn Gly His
130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
            180                 185                 190

Gly Gly Lys Thr Cys Thr Leu Lys Ser Val Ser Asn Ser Ile Leu Glu
        195                 200                 205

Cys Tyr Thr Pro Ala Gln Thr Ile Ser Thr Glu Phe Ala Val Lys Leu
210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
        275                 280                 285

Ser Val Pro Arg Met Val Ile Asn Val His Glu Ala Gly Arg Asn Phe
290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335

Ala Phe Phe Met Leu Asp Gly Ile Leu Ser Lys Tyr Phe Asp Leu Ile
            340                 345                 350

Tyr Val His Asn Pro Val Phe Lys Pro Phe Glu Lys Pro Val Met Ile
        355                 360                 365

Ser Met Gly Asn Glu Asn Val Leu Glu Ile Lys Gly Asn Asp Ile Asp
370                 375                 380
```

```
Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Glu Leu Asn Ile Glu Trp Lys Gln Ala
            420                 425                 430

Ile Ser Ser Thr Val Leu Gly Lys Val Ile Val Gln Pro Asp Gln Asn
        435                 440                 445

Phe Thr Gly
    450

<210> SEQ ID NO 81
<211> LENGTH: 313
<212> TYPE: PRT
<213> ORGANISM: Artificial Sequence
<220> FEATURE:
<223> OTHER INFORMATION: Synthetic (TyrKc domain of c-Met)

<400> SEQUENCE: 81

Val His Phe Asn Glu Val Ile Gly Arg Gly His Phe Gly Cys Val Tyr
1               5                   10                  15

His Gly Thr Leu Leu Asp Asn Asp Gly Lys Lys Ile His Cys Ala Val
            20                  25                  30

Lys Ser Leu Asn Arg Ile Thr Asp Ile Gly Glu Val Ser Gln Phe Leu
        35                  40                  45

Thr Glu Gly Ile Ile Met Lys Asp Phe Ser His Pro Asn Val Leu Ser
    50                  55                  60

Leu Leu Gly Ile Cys Leu Arg Ser Glu Gly Ser Pro Leu Val Val Leu
65                  70                  75                  80

Pro Tyr Met Lys His Gly Asp Leu Arg Asn Phe Ile Arg Asn Glu Thr
                85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
    130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
    210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285
```

```
Pro Ser Leu Leu Ser Ser Glu Asp Asn Ala Asp Asp Glu Val Asp Thr
    290                 295                 300

Arg Pro Ala Ser Phe Trp Glu Thr Ser
305                 310
```

<210> SEQ ID NO 82
<211> LENGTH: 1332
<212> TYPE: DNA
<213> ORGANISM: Artificial Sequence
<220> FEATURE:
<223> OTHER INFORMATION: Synthetic (polynucleotide encoding SEMA domain
      of c-Met)

<400> SEQUENCE: 82

```
ctacatgagc atcacatttt ccttggtgcc actaactaca tttatgtttt aaatgaggaa      60
gaccttcaga aggttgctga gtacaagact gggcctgtgc tggaacaccc agattgtttc     120
ccatgtcagg actgcagcag caaagccaat ttatcaggag gtgtttggaa agataacatc     180
aacatggctc tagttgtcga cacctactat gatgatcaac tcattagctg tggcagcgtc     240
aacagaggga cctgccagcg acatgtcttt ccccacaatc atactgctga catacagtcg     300
gaggttcact gcatattctc cccacagata aagagcccca gccagtgtcc tgactgtgtg     360
gtgagcgccc tgggagccaa agtcctttca tctgtaaagg accggttcat caacttcttt     420
gtaggcaata ccataaattc ttcttatttc ccagatcatc cattgcattc gatatcagtg     480
agaaggctaa aggaaacgaa agatggtttt atgttttga cggaccagtc ctacattgat     540
gttttacctg agtcagaga ttcttacccc attaagtatg tccatgcctt tgaaagcaac     600
aattttattt acttcttgac ggtccaaagg gaaactctag atgctcagac ttttcacaca     660
agaataatca ggttctgttc cataaactct ggattgcatt cctacatgga aatgcctctg     720
gagtgtattc tcacagaaaa gagaaaaaag agatccacaa gaaggaagt gtttaatata     780 cttcaggctg cgtatgtcag caagcctggg gcccagcttg ctagacaaat aggagccagc     840
ctgaatgatg acattctttt cggggtgttc gcacaaagca agccagattc tgccgaacca     900
atggatcgat ctgccatgtg tgcattccct atcaaatatg tcaacgactt cttcaacaag     960
atcgtcaaca aaaacaatgt gagatgtctc cagcattttt acggacccaa tcatgagcac    1020
tgctttaata ggacacttct gagaaattca tcaggctgtg aagcgcgccg tgatgaatat    1080
cgaacagagt ttaccacagc tttgcagcgc gttgacttat tcatgggtca attcagcgaa    1140
gtcctcttaa catctatatc caccttcatt aaaggagacc tcaccatagc taatcttggg    1200
acatcagagg gtcgcttcat gcaggttgtg gtttctcgat caggaccatc aacccctcat    1260
gtgaattttc cctggactc ccatccagtg tctccagaag tgattgtgga gcatacatta    1320
aaccaaaatg gc                                                         1332
```

<210> SEQ ID NO 83
<211> LENGTH: 1299
<212> TYPE: DNA
<213> ORGANISM: Artificial Sequence
<220> FEATURE:
<223> OTHER INFORMATION: Synthetic (polynucleotide encoding PSI-IPT
      domain of c-Met)

<400> SEQUENCE: 83

```
tacacactgg ttatcactgg gaagaagatc acgaagatcc cattgaatgg cttgggctgc     60
agacatttcc agtcctgcag tcaatgcctc tctgccccac cctttgttca gtgtggctgg    120
```

```
tgccacgaca aatgtgtgcg atcggaggaa tgcctgagcg ggacatggac tcaacagatc      180
tgtctgcctg caatctacaa ggttttccca aatagtgcac cccttgaagg agggacaagg      240
ctgaccatat gtggctggga ctttggattt cggaggaata ataaatttga tttaaagaaa      300
actagagttc tccttggaaa tgagagctgc accttgactt taagtgagag cacgatgaat      360
acattgaaat gcacagttgg tcctgccatg aataagcatt tcaatatgtc cataattatt      420
tcaaatggcc acgggacaac acaatacagt acattctcct atgtggatcc tgtaataaca      480
agtatttcgc cgaaatacgg tcctatggct ggtggcactt tacttacttt aactggaaat      540
tacctaaaca gtgggaattc tagacacatt tcaattggtg aaaaacatg tacttaaaa       600 agtgtgtcaa acagtattct tgaatgttat accccagccc aaaccatttc aactgagttt      660
gctgttaaat tgaaaattga cttagccaac cgagagacaa gcatcttcag ttaccgtgaa      720
gatcccattg tctatgaaat tcatccaacc aaatctttta ttagtggtgg gagcacaata      780
acaggtgttg ggaaaaacct gaattcagtt agtgtcccga gaatggtcat aaatgtgcat      840
gaagcaggaa ggaactttac agtggcatgt caacatcgct ctaattcaga gataatctgt      900
tgtaccactc cttccctgca acagctgaat ctgcaactcc ccctgaaaac caaagccttt      960
ttcatgttag atgggatcct ttccaaatac tttgatctca tttatgtaca taatcctgtg     1020
tttaagcctt tgaaaagcc agtgatgatc tcaatgggca atgaaaatgt actggaaatt     1080
aagggaaatg atattgaccc tgaagcagtt aaaggtgaag tgttaaaagt tggaaataag     1140
agctgtgaga atatacactt acattctgaa gccgttttat gcacggtccc caatgacctg     1200
ctgaaattga acagcgagct aaatatagag tggaagcaag caatttcttc aaccgtcctt     1260
ggaaaagtaa tagttcaacc agatcagaat ttcacagga                            1299
```

<210> SEQ ID NO 84
<211> LENGTH: 939
<212> TYPE: DNA
<213> ORGANISM: Artificial Sequence
<220> FEATURE:
<223> OTHER INFORMATION: Synthetic (polynucleotide encoding TyrKc domain of c-Met)

<400> SEQUENCE: 84

```
gtgcatttca atgaagtcat aggaagaggg cattttggtt gtgtatatca tgggactttg       60
ttggacaatg atggcaagaa aattcactgt gctgtgaaat ccttgaacag aatcactgac      120
ataggagaag tttcccaatt tctgaccgag ggaatcatca tgaaagattt tagtcatccc      180
aatgtcctct cgctcctggg aatctgcctg cgaagtgaag ggtctccgct ggtggtccta      240
ccatacatga acatggagat tcttgaaat tcattcgaa atgagactca taatccaact       300
gtaaaagatc ttattggctt tggtcttcaa gtagccaaag gcatgaaata tcttgcaagc      360
aaaaagtttg tccacagaga cttggctgca agaaactgta tgctggatga aaaattcaca      420
gtcaaggttg ctgattttgg tcttgccaga gacatgtatg ataaagaata ctatagtgta      480
cacaacaaaa caggtgcaaa gctgccagtg aagtggatgg ctttggaaag tctgcaaact      540
caaaagttta ccaccaagtc agatgtgtgg tccttggcg tgctcctctg ggagctgatg      600
acaagaggag cccaccttta tcctgacgta aacaccttg atataactgt ttacttgttg      660
caagggagaa gactcctaca acccgaatac tgcccagacc ccttatatga agtaatgcta      720
aaatgctggc accctaaagc cgaaatgcgc ccatcctttt ctgaactggt gtcccggata      780
tcagcgatct tctctacttt cattggggag cactatgtcc atgtgaacgc tacttatgtg      840
```

```
aacgtaaaat gtgtcgctcc gtatccttct ctgttgtcat cagaagataa cgctgatgat    900
gaggtggaca cacgaccagc ctccttctgg gagacatca                            939
```

<210> SEQ ID NO 85
<211> LENGTH: 13
<212> TYPE: PRT
<213> ORGANISM: Artificial Sequence
<220> FEATURE:
<223> OTHER INFORMATION: Synthetic (heavy chain CDR3 of anti-c-Met
      antibody)

<400> SEQUENCE: 85

Asp Asn Trp Phe Ala Tyr Trp Gly Gln Gly Thr Leu Val
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic (light chain CDR3 of anti-c-Met
      antibody)

<400> SEQUENCE: 86

Leu Thr Phe Gly Ala Gly Thr Lys Leu Glu
1               5                   10

<210> SEQ ID NO 87
<211> LENGTH: 117
<212> TYPE: PRT
<213> ORGANISM: Artificial Sequence
<220> FEATURE:
<223> OTHER INFORMATION: Synthetic (heavy chain variable region of
      monoclonal antibody AbF46)

<400> SEQUENCE: 87

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

<210> SEQ ID NO 88
<211> LENGTH: 114
<212> TYPE: PRT
<213> ORGANISM: Artificial Sequence
<220> FEATURE:
<223> OTHER INFORMATION: Synthetic (light chain variable region of
      anti-c-Met antibody)

<400> SEQUENCE: 88

Asp Ile Leu Met Thr Gln Ser Pro Ser Ser Leu Thr Val Ser Ala Gly

```
                1               5                  10                  15
        Glu Lys Val Thr Met Ser Cys Lys Ser Ser Gln Ser Leu Leu Ala Ser
                        20                  25                  30

Gly Asn Gln Asn Asn Tyr Leu Ala Trp His Gln Gln Lys Pro Gly Arg
                        35                  40                  45

Ser Pro Lys Met Leu Ile Ile Trp Ala Ser Thr Arg Val Ser Gly Val
                    50                  55                  60

Pro Asp Arg Phe Ile Gly Ser Gly Ser Gly Thr Asp Phe Thr Leu Thr
        65                  70                  75                  80

Ile Asn Ser Val Gln Ala Glu Asp Leu Ala Val Tyr Tyr Cys Gln Gln
                        85                  90                  95

Ser Tyr Ser Ala Pro Leu Thr Phe Gly Ala Gly Thr Lys Leu Glu Leu
                    100                 105                 110

Lys Arg
```

<210> SEQ ID NO 89
<211> LENGTH: 17
<212> TYPE: PRT
<213> ORGANISM: Artificial Sequence
<220> FEATURE:
<223> OTHER INFORMATION: Synthetic (light chain CDR3 of anti-c-Met antibody)

<400> SEQUENCE: 89

```
        Gln Gln Ser Tyr Ser Ala Pro Leu Thr Phe Gly Ala Gly Thr Lys Leu
        1               5                   10                  15

Glu
```

<210> SEQ ID NO 90
<211> LENGTH: 117
<212> TYPE: PRT
<213> ORGANISM: Artificial Sequence
<220> FEATURE:
<223> OTHER INFORMATION: Synthetic (heavy chain variable region of AT-VH1)

<400> SEQUENCE: 90

```
        Glu Val Lys Leu Val Glu Ser Gly Gly Gly Leu Val Gln Pro Gly Gly
        1               5                   10                  15

Ser Leu Arg Leu Ser Cys Ala Thr Ser Gly Phe Thr Phe Thr Asp Tyr
                        20                  25                  30

Tyr Met Ser Trp Val Arg Gln Pro Pro Gly Lys Gly Leu Glu Trp Leu
                        35                  40                  45

Gly Phe Ile Arg Asn Lys Ala Asn Gly Tyr Thr Thr Glu Tyr Ser Ala
                    50                  55                  60

Ser Val Lys Gly Arg Phe Thr Ile Ser Arg Asp Asn Ser Lys Ser Thr
        65                  70                  75                  80

Leu Tyr Leu Gln Met Asn Ser Leu Arg Ala Glu Asp Ser Ala Thr Tyr
                        85                  90                  95

Tyr Cys Ala Arg Asp Asn Trp Phe Ala Tyr Trp Gly Gln Gly Thr Leu
                    100                 105                 110

Val Thr Val Ser Ser
                115
```

<210> SEQ ID NO 91
<211> LENGTH: 117
<212> TYPE: PRT
<213> ORGANISM: Artificial Sequence
<220> FEATURE:

<223> OTHER INFORMATION: Synthetic (heavy chain variable region of AT-VH2)

<400> SEQUENCE: 91

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic (heavy chain variable region of AT-VH3)

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic (heavy chain variable region of AT-VH4)

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr

```
                    20                  25                  30

Tyr Met Ser Trp Val Arg Gln Pro Pro Gly Lys Gly Leu Glu Trp Leu
                35                  40                  45

Gly Phe Ile Arg Asn Lys Ala Asn Gly Tyr Thr Thr Glu Tyr Ser Ala
            50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 94
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH5)

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Gly Leu Glu Trp Leu
                35                  40                  45

Gly Phe Ile Arg Asn Lys Ala Asn Gly Tyr Thr Thr Glu Tyr Ser Ala
            50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 95
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
                35                  40                  45

Ala Pro Lys Met Leu Ile Ile Trp Ala Ser Thr Arg Val Ser Gly Val
            50                  55                  60

Pro Ser Arg Phe Ser Gly Ser Gly Ser Gly Thr Asp Phe Thr Leu Thr
```

```
                65                  70                  75                  80
Ile Ser Ser Leu Gln Pro Glu Asp Phe Ala Thr Tyr Tyr Cys Gln Gln
                    85                  90                  95

Ser Tyr Ser Ala Pro Leu Thr Phe Gly Gln Gly Thr Lys Val Glu Ile
                100                 105                 110

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic (light chain variable region of
      AT-Vk1)

<400> SEQUENCE: 96

Asp Ile Leu Met Thr Gln Ser Pro Ser Ser Leu Thr Ala Ser Val Gly
1               5                   10                  15

Asp Arg Val Thr Met Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                    85                  90                  95

Ser Tyr Ser Ala Pro Leu Thr Phe Gly Gln Gly Thr Lys Leu Glu Ile
                100                 105                 110

Lys

<210> SEQ ID NO 97
<211> LENGTH: 113
<212> TYPE: PRT
<213> ORGANISM: Artificial Sequence
<220> FEATURE:
<223> OTHER INFORMATION: Synthetic (light chain variable region of
      AT-Vk2)

<400> SEQUENCE: 97

Asp Ile Leu Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                    85                  90                  95

Ser Tyr Ser Ala Pro Leu Thr Phe Gly Gln Gly Thr Lys Leu Glu Ile
                100                 105                 110

Lys
```

```
<210> SEQ ID NO 98
<211> LENGTH: 113
<212> TYPE: PRT
<213> ORGANISM: Artificial Sequence
<220> FEATURE:
<223> OTHER INFORMATION: Synthetic (light chain variable region of
      AT-Vk3)

<400> SEQUENCE: 98

Asp Ile Gln Met Thr Gln Ser Pro Ser Leu Ser Ala Ser Val Gly
1               5                   10                  15

Asp Arg Val Thr Ile Thr Cys Lys Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic (light chain variable region of
      AT-Vk4)

<400> SEQUENCE: 99

Asp Ile Gln Met Thr Gln Ser Pro Ser Leu Ser Ala Ser Val Gly
1               5                   10                  15

Asp Arg Val Thr Ile Thr Cys Lys Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic (modified hinge region(U7-HC6))

<400> SEQUENCE: 100

Glu Pro Ser Cys Asp Lys His Cys Cys Pro Pro Cys Pro
1               5                   10
```

<210> SEQ ID NO 101
<211> LENGTH: 13
<212> TYPE: PRT
<213> ORGANISM: Artificial Sequence
<220> FEATURE:
<223> OTHER INFORMATION: Synthetic (modified hinge region(U6-HC7))

<400> SEQUENCE: 101

Glu Pro Lys Ser Cys Asp Cys His Cys Pro Pro Cys Pro
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic (modified hinge region(U3-HC9))

<400> SEQUENCE: 102

Glu Arg Lys Cys Cys Val Glu Cys Pro Pro Cys Pro
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Synthetic (modified hinge region(U6-HC8))

<400> SEQUENCE: 103

Glu Pro Arg Asp Cys Gly Cys Lys Pro Cys Pro Pro Cys Pro
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Synthetic (modified hinge region(U8-HC5))

<400> SEQUENCE: 104

Glu Lys Cys Asp Lys Thr His Thr Cys Pro Pro Cys Pro
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic (human hinge region)

<400> SEQUENCE: 105

Glu Pro Lys Ser Cys Asp Lys Thr His Thr Cys Pro Pro Cys Pro
1               5                   10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic (CDR-L1 of antibody L3-11Y)

<400> SEQUENCE: 106

Lys Ser Ser Gln Ser Leu Leu Ala Trp Gly Asn Gln Asn Asn Tyr Leu
1               5                   10                  15

Ala

```
<210> SEQ ID NO 107
<211> LENGTH: 114
<212> TYPE: PRT
<213> ORGANISM: Artificial Sequence
<220> FEATURE:
<223> OTHER INFORMATION: Synthetic (amino acid sequence of light chain
      variable region of antibody L3-11Y)

<400> SEQUENCE: 107
```

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

```
<210> SEQ ID NO 108
<211> LENGTH: 220
<212> TYPE: PRT
<213> ORGANISM: Artificial Sequence
<220> FEATURE:
<223> OTHER INFORMATION: Synthetic (amino acid sequence of light chain
      of antibody L3-11Y)

<400> SEQUENCE: 108
```

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

```
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 109
<211> LENGTH: 1058
<212> TYPE: PRT
<213> ORGANISM: Artificial Sequence
<220> FEATURE:
<223> OTHER INFORMATION: Synthetic (anti-c-Met/anti-Her2 bispecific
      antibody)

<400> SEQUENCE: 109

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Asp Val Asn Thr Ala Val Ala Trp Tyr Gln Gln
            180                 185                 190

Lys Pro Gly Lys Ala Pro Lys Leu Leu Ile Tyr Ser Ala Ser Phe Leu
        195                 200                 205

Tyr Ser Gly Val Pro Ser Arg Phe Ser Gly Ser Arg Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln His Tyr Thr Thr Pro Pro Thr Phe Gly Gln Gly Thr
                245                 250                 255

Lys Val Glu Ile Lys Arg Glu Pro Lys Ser Cys Asp Lys Thr His Thr
            260                 265                 270

Cys Pro Pro Cys Pro Ala Pro Glu Leu Leu Gly Gly Pro Ser Val Phe
        275                 280                 285

Leu Phe Pro Pro Lys Pro Lys Asp Thr Leu Met Ile Ser Arg Thr Pro
    290                 295                 300

Glu Val Thr Cys Val Val Val Asp Val Ser His Glu Asp Pro Glu Val
```

```
                305                 310                 315                 320
            Lys Phe Asn Trp Tyr Val Asp Gly Val Glu Val His Asn Ala Lys Thr
                            325                 330                 335
            Lys Pro Arg Glu Glu Gln Tyr Asn Ser Thr Tyr Arg Val Val Ser Val
                            340                 345                 350
            Leu Thr Val Leu His Gln Asp Trp Leu Asn Gly Lys Glu Tyr Lys Cys
                            355                 360                 365
            Lys Val Ser Asn Lys Ala Leu Pro Ala Pro Ile Glu Lys Thr Ile Ser
                    370                 375                 380
            Lys Ala Lys Gly Gln Pro Arg Glu Pro Gln Val Tyr Thr Leu Pro Pro
            385                 390                 395                 400
            Ser Arg Glu Glu Met Thr Lys Asn Gln Val Ser Leu Thr Cys Leu Val
                                405                 410                 415
            Lys Gly Phe Tyr Pro Ser Asp Ile Ala Val Glu Trp Glu Ser Asn Gly
                            420                 425                 430
            Gln Pro Glu Asn Asn Tyr Lys Thr Thr Pro Pro Val Leu Asp Ser Asp
                            435                 440                 445
            Gly Ser Phe Phe Leu Thr Ser Lys Leu Thr Val Asp Lys Ser Arg Trp
                    450                 455                 460
            Gln Gln Gly Asn Val Phe Ser Cys Ser Val Met His Glu Ala Leu His
            465                 470                 475                 480
            Asn His Tyr Thr Gln Lys Ser Leu Ser Leu Ser Pro Gly Lys Met Gln
                                485                 490                 495
            Ile Phe Val Lys Thr Leu Thr Gly Lys Thr Ile Thr Leu Glu Val Glu
                            500                 505                 510
            Pro Ser Asp Thr Ile Glu Asn Val Lys Ala Lys Ile Gln Asp Lys Glu
                    515                 520                 525
            Gly Ile Pro Pro Asp Gln Gln Arg Leu Ile Phe Ala Gly Lys Gln Leu
                    530                 535                 540
            Glu Asp Gly Arg Thr Leu Ser Asp Tyr Asn Ile Gln Lys Glu Ser Thr
            545                 550                 555                 560
            Leu His Leu Val Leu Arg Leu Arg Gly Gly Ser Glu Val Gln Leu
                                565                 570                 575
            Val Glu Ser Gly Gly Gly Leu Val Gln Pro Gly Gly Ser Leu Arg Leu
                            580                 585                 590
            Ser Cys Ala Ala Ser Gly Phe Thr Phe Thr Asp Tyr Tyr Met Ser Trp
                            595                 600                 605
            Val Arg Gln Ala Pro Gly Lys Gly Leu Glu Trp Leu Gly Phe Ile Arg
                    610                 615                 620
            Asn Lys Ala Asn Gly Tyr Thr Thr Glu Tyr Ser Ala Ser Val Lys Gly
            625                 630                 635                 640
            Arg Phe Thr Ile Ser Arg Asp Asn Ser Lys Asn Thr Leu Tyr Leu Gln
                            645                 650                 655
            Met Asn Ser Leu Arg Ala Glu Asp Thr Ala Val Tyr Tyr Cys Ala Arg
                            660                 665                 670
            Asp Asn Trp Phe Ala Tyr Trp Gly Gln Gly Thr Leu Val Thr Val Ser
                    675                 680                 685
            Ser Gly Leu Gly Gly Leu Gly Gly Gly Ser Gly Gly Gly Ser
                    690                 695                 700
            Gly Gly Ser Ser Gly Val Gly Ser Asp Ile Gln Met Thr Gln Ser Pro
            705                 710                 715                 720
            Ser Ser Leu Ser Ala Ser Val Gly Asp Arg Val Thr Ile Thr Cys Lys
                            725                 730                 735
```

Ser Ser Gln Ser Leu Ala Ser Gly Asn Gln Asn Tyr Leu Ala
        740             745             750

Trp His Gln Gln Lys Pro Gly Lys Ala Pro Lys Met Leu Ile Ile Trp
        755             760             765

Ala Ser Thr Arg Val Ser Gly Val Pro Ser Arg Phe Ser Gly Ser Gly
        770             775             780

Ser Gly Thr Asp Phe Thr Leu Thr Ile Ser Ser Leu Gln Pro Glu Asp
785             790             795             800

Phe Ala Thr Tyr Tyr Cys Gln Gln Ser Tyr Ser Arg Pro Tyr Thr Phe
                805             810             815

Gly Gln Gly Thr Lys Val Glu Ile Lys Arg Glu Pro Lys Ser Cys Asp
                820             825             830

Lys Thr His Thr Cys Pro Pro Cys Pro Ala Pro Glu Leu Leu Gly Gly
                835             840             845

Pro Ser Val Phe Leu Phe Pro Pro Lys Pro Lys Asp Thr Leu Met Ile
850             855             860

Ser Arg Thr Pro Glu Val Thr Cys Val Val Val Asp Val Ser His Glu
865             870             875             880

Asp Pro Glu Val Lys Phe Asn Trp Tyr Val Asp Gly Val Glu Val His
                885             890             895

Asn Ala Lys Thr Lys Pro Arg Glu Glu Gln Tyr Asn Ser Thr Tyr Arg
                900             905             910

Val Val Ser Val Leu Thr Val Leu His Gln Asp Trp Leu Asn Gly Lys
                915             920             925

Glu Tyr Lys Cys Lys Val Ser Asn Lys Ala Leu Pro Ala Pro Ile Glu
                930             935             940

Lys Thr Ile Ser Lys Ala Lys Gly Gln Pro Arg Glu Pro Gln Val Tyr
945             950             955             960

Thr Leu Pro Pro Ser Arg Glu Glu Met Thr Lys Asn Gln Val Ser Leu
                965             970             975

Tyr Cys Leu Val Lys Gly Phe Tyr Pro Ser Asp Ile Ala Val Glu Trp
                980             985             990

Glu Ser Asn Gly Gln Pro Glu Asn Asn Tyr Lys Thr Thr Pro Pro Val
                995             1000            1005

Leu Asp Ser Asp Gly Ser Phe Phe Leu Tyr Ser Lys Leu Thr Val
        1010            1015            1020

Asp Lys Ser Arg Trp Gln Gln Gly Asn Val Phe Ser Cys Ser Val
        1025            1030            1035

Met His Glu Ala Leu His Asn His Tyr Thr Gln Lys Ser Leu Ser
        1040            1045            1050

Leu Ser Pro Gly Lys
        1055

<210> SEQ ID NO 110
<211> LENGTH: 3195
<212> TYPE: DNA
<213> ORGANISM: Artificial Sequence
<220> FEATURE:
<223> OTHER INFORMATION: Synthetic (DNA encoding anti-c-Met/anti-Her2
      bispecific antibody)

<400> SEQUENCE: 110
aagcttgcca ccatgggatg gtcatgtatc atcctttttc tagtagcaac tgcaactgga    60
gtacattcag aagttcagct ggtggagtct ggcggtggcc tggtgcagcc agggggctca   120

```
ctccgtttgt cctgtgcagc ttctggcttc aacattaaag acacctatat acactgggtg    180
cgtcaggccc cgggtaaggg cctggaatgg gttgcaagga tttatcctac gaatggttat    240
actagatatg ccgatagcgt caagggccgt tcactataa gcgcagacac atccaaaaac    300
acagcctacc tgcagatgaa cagcctgcgt gctgaggaca ctgccgtcta ttattgttct    360
agatggggag gggacggctt ctatgctatg gactactggg gtcaaggaac cctggtcacc    420
gtctcctcgg gtggtggcgg ttcaggcgga ggtggctctg gcggtggcgg atcggatatc    480
cagatgaccc agtccccgag ctccctgtcc gcctctgtgg gcgatagggt caccatcacc    540
tgccgtgcca gtcaggatgt gaatactgct gtagcctggt atcaacagaa accaggaaaa    600
gctccgaaac tactgattta ctcggcatcc ttcctctatt ctggagtccc ttctcgcttc    660
tctggctcca gatctgggac ggatttcact ctgaccatca gcagtctgca gccggaagac    720
ttcgcaactt attactgtca gcaacattat actactcctc ccacgttcgg acagggtacc    780
aaggtggaga tcaaacgaga gcccaagagc tgcgacaaga cccacacctg ccccccctgc    840
cccgcccccg agctgctggg cggccccagc gtgttcctgt tccccccaaa gcccaaggac    900
accctgatga tcagccgcac ccccgaggtg acctgcgtgg tggtggacgt gagccacgag    960
gaccccgagg tgaagttcaa ctggtacgtg gacggcgtgg aggtgcacaa cgccaagacc   1020
aagccccgcg aggagcagta caacagcacc taccgcgtgg tgagcgtgct gaccgtgctg   1080
caccaggact ggctgaacgg caaggagtac aagtgcaagg tgagcaacaa ggccctgccc   1140
gcccccatcg agaagaccat cagcaaggcc aagggccagc ccgcgagcc caggtgtac   1200 accctgcccc cagccgcga ggagatgacc aagaaccagg tgagcctgac ctgcctggtg   1260
aagggcttct accccagcga catcgccgtg gagtgggaga gcaacggcca gcccgagaac   1320
aactacaaga ccaccccccc cgtgctggac agcgacggca gcttcttcct gaccagcaag   1380
ctgaccgtgg acaagagccg ctggcagcag ggcaacgtgt tcagctgcag cgtgatgcac   1440
gaggccctgc acaaccacta cacccagaag agcctgagcc tgagcccggg caagatgcag   1500
atcttcgtga agaccctgac cggcaagacc atcaccctgg aggtggagcc agcgacacc   1560 atcgagaacg tgaaggccaa gatccaggac aaggagggca tccccccga ccagcagcgc   1620 ctgatcttcg ccggcaagca gctggaggac ggccgcaccc tgagcgacta caacatccag   1680
aaggagagca ccctgcacct ggtgctgcgc ctgcgcggcg gcggatccga ggttcagctg   1740
gtggagtctg gcggtggcct ggtgcagcca gggggctcac tccgtttgtc ctgtgcagct   1800
tctggcttca ccttcactga ttactacatg agctgggtgc gtcaggcccc gggtaagggc   1860
ctggaatggt tgggttttat tagaaacaaa gctaatggtt acacaacaga gtacagtgca   1920
tctgtgaagg gtcgtttcac tataagcaga gataattcca aaaacacact gtacctgcag   1980
atgaacagcc tgcgtgctga ggacactgcc gtctattatt gtgctagaga taactggttt   2040
gcttactggg gccaagggac tctggtcacc gtctcctcgg gcctgggcgg cctgggcgga   2100
ggaggctctg gaggcggcgg aagcggcggc agcagcggcg tgggcagcga tatccagatg   2160
acccagtccc cgagctccct gtccgcctct gtgggcgata gggtcaccat cacctgcaag   2220
tccagtcaga gtctttttagc tagtggcaac caaaataact acttggcctg caccaacag   2280 aaaccaggaa aagctccgaa aatgctgatt atttgggcat ccactaggt atctggagtc   2340 ccttctcgct ctctgggtc cgggtctggg acggatttca ctctgaccat cagcagtctg   2400
cagccggaag acttcgcaac ttattactgt cagcagtcct acagccgccc gtacacgttc   2460
ggacagggta ccaaggtgga gatcaaacgt gagcccaaga gctgcgacaa gacccacacc   2520
```

```
tgcccccct gccccgcccc cgagctgctg ggcggcccca gcgtgttcct gttccccccc    2580
aagcccaagg acaccctgat gatcagccgc accccgagg tgacctgcgt ggtggtggac    2640
gtgagccacg aggaccccga ggtgaagttc aactggtacg tggacggcgt ggaggtgcac    2700
aacgccaaga ccaagcccg cgaggagcag tacaacagca cctaccgcgt ggtgagcgtg    2760
ctgaccgtgc tgcaccagga ctggctgaac ggcaaggagt acaagtgcaa ggtgagcaac    2820
aagggcctgc cgcccccat cgagaagacc atcagcaagg ccaagggcca gccccgcgag    2880
ccccaggtgt acaccctgcc cccagccgc gaggagatga ccaagaacca ggtgagcctg    2940
tactgcctgg tgaagggctt ctaccccagc gacatcgccg tggagtggga gagcaacggc    3000
cagcccgaga caactacaa gaccaccccc cccgtgctgg acagcgacgg cagcttcttc    3060
ctgtacagca agctgaccgt ggacaagagc cgctggcagc agggcaacgt gttcagctgc    3120
agcgtgatgc acgaggccct gcacaaccac tacacccaga gagcctgag cctgagcccc    3180 ggcaagtgac tcgag                                                     3195

<210> SEQ ID NO 111
<211> LENGTH: 1500
<212> TYPE: DNA
<213> ORGANISM: Artificial Sequence
<220> FEATURE:
<223> OTHER INFORMATION: Synthetic (DNA encoding control antibody (Her2
      binding region and hole)

<400> SEQUENCE: 111
aagcttgcca ccatgggatg gtcatgtatc atccttttc tagtagcaac tgcaactgga      60
gtacattcag aagttcagct ggtggagtct ggcggtggcc tggtgcagcc agggggctca    120
ctccgtttgt cctgtgcagc ttctggcttc aacattaaag acacctatat acactgggtg    180
cgtcaggccc cgggtaaggg cctggaatgg gttgcaagga tttatcctac gaatggttat    240
actagatatg ccgatagcgt caagggccgt tcactataa gcgcagacac atccaaaaac    300
acagcctacc tgcagatgaa cagcctgcgt gctgaggaca ctgccgtcta ttattgttct    360
agatggggag gggacggctt ctatgctatg gactactggg gtcaaggaac cctggtcacc    420
gtctcctcgg gtggtggcgg ttcaggcgga ggtggctctg gcggtggcgg atcggatatc    480
cagatgaccc agtccccgag ctccctgtcc gcctctgtgg gcgataggt caccatcacc    540 tgccgtgcca gtcaggatgt gaatactgct gtagcctggt atcaacagaa accaggaaaa    600
gctccgaaac tactgattta tcggcatcc ttcctctatt ctggagtccc ttctcgcttc    660
tctggctcca gatctgggac ggatttcact ctgaccatca gcagtctgca gccggaagac    720
ttcgcaactt attactgtca gcaacattat actactcctc ccacgttcgg acagggtacc    780
aaggtggaga tcaaacgaga gcccaagagc tgcgacaaga cccacacctg ccccccctgc    840
cccgcccccg agctgctggg cggcccagc gtgttcctgt tccccccaa gcccaaggac    900 accctgatga tcagccgcac ccccgaggtg acctgcgtgg tggtggacgt gagccacgag    960
gaccccgagg tgaagttcaa ctggtacgtg gacggcgtgg aggtgcacaa cgccaagacc    1020 aagcccgcg aggagcagta caacagcacc taccgcgtgg tgagcgtgct gaccgtgctg    1080
caccaggact ggctgaacgg caaggagtac aagtgcaagg tgagcaacaa ggccctgccc    1140
gcccccatcg agaagaccat cagcaaggcc aagggccagc cccgcgagcc ccaggtgtac    1200
accctgcccc cagccgcga ggagatgacc aagaaccagg tgagcctgac ctgcctggtg    1260
aagggcttct accccagcga catcgccgtg gagtgggaga gcaacggcca gcccgagaac    1320
```

```
aactacaaga ccacccccc cgtgctggac agcgacggca gcttcttcct gaccagcaag    1380
ctgaccgtgg acaagagccg ctggcagcag ggcaacgtgt tcagctgcag cgtgatgcac    1440
gaggccctgc acaaccacta cacccagaag agcctgagcc tgagcccgg caagctcgag     1500
```

<210> SEQ ID NO 112
<211> LENGTH: 1536
<212> TYPE: DNA
<213> ORGANISM: Artificial Sequence
<220> FEATURE:
<223> OTHER INFORMATION: Synthetic (DNA encoding control antibody (c-Met binding region and knob))

<400> SEQUENCE: 112

```
aagcttgcca ccatgggatg gtcatgtatc atcctttttc tagtagcaac tgcaactgga     60
gtacattcag aggttcagct ggtggagtct ggcggtggcc tggtgcagcc aggggggctca    120 ctccgtttgt cctgtgcagc ttctggcttc accttcactg attactacat gagctgggtg    180
cgtcaggccc cgggtaaggg cctggaatgg ttgggtttta ttagaaacaa agctaatggt    240
tacacaacag agtacagtgc atctgtgaag ggtcgtttca ctataagcag agataattcc    300
aaaaacacac tgtacctgca gatgaacagc ctgcgtgctg aggacactgc cgtctattat    360
tgtgctagag ataactggtt tgcttactgg ggccaaggga ctctggtcac cgtctcctcg    420
ggcctgggcg gcctgggcgg aggaggctct ggaggcggcg gaagcggcgg cagcagcggc    480
gtgggcagcg atatccagat gacccagtcc ccgagctccc tgtccgcctc tgtgggcgat    540
agggtcacca tcacctgcaa gtccagtcag agtcttttag ctagtggcaa ccaaaataac    600
tacttggcct ggcaccaaca gaaaccagga aaagctccga aaatgctgat tatttgggca    660
tccactaggt atctggagt ccttctcgc ttctctgggt ccgggtctgg gacggatttc    720
actctgacca tcagcagtct gcagccggaa gacttcgcaa cttattactg tcagcagtcc    780
tacagccgcc cgtacacgtt cggacagggt accaaggtgg agatcaaacg tgagcccaag    840
agctgcgaca gacccacac ctgccccccc tgccccgccc cgagctgct gggcggcccc    900 agcgtgttcc tgttcccccc caagcccaag gacaccctga tgatcagccg cacccccgag    960
gtgacctgcg tggtggtgga cgtgagccac gaggacccg aggtgaagtt caactggtac   1020
gtggacggcg tggaggtgca caacgccaag accaagcccc gcgaggagca gtacaacagc   1080
acctaccgcg tggtgagcgt gctgaccgtg ctgcaccagg actggctgaa cggcaaggag   1140
tacaagtgca aggtgagcaa caaggccctg cccgccccca tcgagaagac catcagcaag   1200 gccaagggc agccccgcga gccccaggtg tacaccctgc ccccagccg cgaggagatg   1260 accaagaacc aggtgagcct gtactgcctg gtgaagggct tctacccag cgacatcgcc   1320 gtggagtggg agagcaacgg ccagcccgag aacaactaca agaccacccc ccccgtgctg   1380
gacagcgacg gcagcttctt cctgtacagc aagctgaccg tggacaagag ccgctggcag   1440
cagggcaacg tgttcagctg cagcgtgatg cacgaggccc tgcacaacca ctacacccag   1500
aagagcctga gcctgagccc cggcaagtga ctcgag                              1536
```

<210> SEQ ID NO 113
<211> LENGTH: 6
<212> TYPE: DNA
<213> ORGANISM: Artificial Sequence
<220> FEATURE:
<223> OTHER INFORMATION: Synthetic (Hind III site)

<400> SEQUENCE: 113

```
<210> SEQ ID NO 114
<211> LENGTH: 6
<212> TYPE: DNA
<213> ORGANISM: Artificial Sequence
<220> FEATURE:
<223> OTHER INFORMATION: Synthetic (XhoI site)

<400> SEQUENCE: 114 ctcgag                                                                    6

<210> SEQ ID NO 115
<211> LENGTH: 1058
<212> TYPE: PRT
<213> ORGANISM: Artificial Sequence
<220> FEATURE:
<223> OTHER INFORMATION: Synthetic (anti-c-Met/anti-EGFR bispecific
      antibody)

<400> SEQUENCE: 115
```

```
Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Tyr Met Ser Trp Val Arg Gln Ala Pro Gly Lys Gly Leu
    50                  55                  60

Glu Trp Leu Gly Phe Ile Arg Asn Lys Ala Asn Gly Tyr Thr Thr Glu
65                  70                  75                  80

Tyr Ser Ala Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Asn Trp Phe Ala Tyr Trp Gly Gln
        115                 120                 125

Gly Thr Leu Val Thr Val Ser Ser Gly Leu Gly Gly Leu Gly Gly Gly
    130                 135                 140

Gly Ser Gly Gly Gly Ser Gly Gly Ser Ser Gly Val Gly Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ser Ser Gln Ser Leu Leu Ala Ser Gly
            180                 185                 190

Asn Gln Asn Asn Tyr Leu Ala Trp His Gln Gln Lys Pro Gly Lys Ala
        195                 200                 205

Pro Lys Met Leu Ile Ile Trp Ala Ser Thr Arg Val Ser Gly Val Pro
    210                 215                 220

Ser Arg Phe Ser Gly Ser Gly Ser Gly Thr Asp Phe Thr Leu Thr Ile
225                 230                 235                 240

Ser Ser Leu Gln Pro Glu Asp Phe Ala Thr Tyr Tyr Cys Gln Gln Ser
                245                 250                 255

Tyr Ser Arg Pro Tyr Thr Phe Gly Gln Gly Thr Lys Val Glu Ile Lys
            260                 265                 270

Arg Glu Pro Lys Ser Cys Asp Lys Thr His Thr Cys Pro Pro Cys Pro
        275                 280                 285
```

```
Ala Pro Glu Leu Leu Gly Gly Pro Ser Val Phe Leu Phe Pro Lys
    290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Glu Glu Met
                405                 410                 415

Thr Lys Asn Gln Val Ser Leu Tyr Cys Leu Val Lys Gly Phe Tyr Pro
            420                 425                 430

Ser Asp Ile Ala Val Glu Trp Glu Ser Asn Gly Gln Pro Glu Asn Asn
        435                 440                 445

Tyr Lys Thr Thr Pro Pro Val Leu Asp Ser Asp Gly Ser Phe Phe Leu
    450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly Lys Met Gln Ile Phe Val Lys Thr
            500                 505                 510

Leu Thr Gly Lys Thr Ile Thr Leu Glu Val Glu Pro Ser Asp Thr Ile
        515                 520                 525

Glu Asn Val Lys Ala Lys Ile Gln Asp Lys Glu Gly Ile Pro Pro Asp
530                 535                 540

Gln Gln Arg Leu Ile Phe Ala Gly Lys Gln Leu Glu Asp Gly Arg Thr
545                 550                 555                 560

Leu Ser Asp Tyr Asn Ile Gln Lys Glu Ser Thr Leu His Leu Val Leu
                565                 570                 575

Arg Leu Arg Gly Gly Ser Gln Val Gln Leu Val Gln Ser Gly Ala
            580                 585                 590

Glu Val Lys Lys Pro Gly Ser Ser Val Lys Val Ser Cys Lys Ala Ser
        595                 600                 605

Gly Phe Thr Phe Thr Asp Tyr Lys Ile His Trp Val Arg Gln Ala Pro
    610                 615                 620

Gly Gln Gly Leu Glu Trp Met Gly Tyr Phe Asn Pro Asn Ser Gly Tyr
625                 630                 635                 640

Ser Thr Tyr Ala Gln Lys Phe Gln Gly Arg Val Thr Ile Thr Ala Asp
                645                 650                 655

Lys Ser Thr Ser Thr Ala Tyr Met Glu Leu Ser Ser Leu Arg Ser Glu
            660                 665                 670

Asp Thr Ala Val Tyr Tyr Cys Ala Arg Leu Ser Pro Gly Gly Tyr Tyr
        675                 680                 685

Val Met Asp Ala Trp Gly Gln Gly Thr Thr Val Thr Val Ser Ser Gly
    690                 695                 700
```

```
Gly Gly Gly Ser Ser Gly Gly Ser Gly Gly Gly Ser Asp Ile
705                 710                 715                 720

Gln Met Thr Gln Ser Pro Ser Ser Leu Ser Ala Ser Val Gly Asp Arg
            725                 730                 735

Val Thr Ile Thr Cys Arg Ala Ser Gln Gly Ile Asn Asn Tyr Leu Asn
            740                 745                 750

Trp Tyr Gln Gln Lys Pro Gly Lys Ala Pro Lys Arg Leu Ile Tyr Asn
        755                 760                 765

Thr Asn Asn Leu Gln Thr Gly Val Pro Ser Arg Phe Ser Gly Ser Gly
    770                 775                 780

Ser Gly Thr Glu Phe Thr Leu Thr Ile Ser Ser Leu Gln Pro Glu Asp
785                 790                 795                 800

Phe Ala Thr Tyr Tyr Cys Leu Gln His Asn Ser Phe Pro Thr Phe Gly
            805                 810                 815

Gln Gly Thr Lys Leu Glu Ile Lys Arg Thr Glu Pro Lys Ser Cys Asp
        820                 825                 830

Lys Thr His Thr Cys Pro Pro Cys Pro Ala Pro Glu Leu Leu Gly Gly
    835                 840                 845

Pro Ser Val Phe Leu Phe Pro Pro Lys Pro Lys Asp Thr Leu Met Ile
850                 855                 860

Ser Arg Thr Pro Glu Val Thr Cys Val Val Val Asp Val Ser His Glu
865                 870                 875                 880

Asp Pro Glu Val Lys Phe Asn Trp Tyr Val Asp Gly Val Glu Val His
            885                 890                 895

Asn Ala Lys Thr Lys Pro Arg Glu Glu Gln Tyr Asn Ser Thr Tyr Arg
        900                 905                 910

Val Val Ser Val Leu Thr Val Leu His Gln Asp Trp Leu Asn Gly Lys
    915                 920                 925

Glu Tyr Lys Cys Lys Val Ser Asn Lys Ala Leu Pro Ala Pro Ile Glu
930                 935                 940

Lys Thr Ile Ser Lys Ala Lys Gly Gln Pro Arg Glu Pro Gln Val Tyr
945                 950                 955                 960

Thr Leu Pro Pro Ser Arg Glu Glu Met Thr Lys Asn Gln Val Ser Leu
            965                 970                 975

Thr Cys Leu Val Lys Gly Phe Tyr Pro Ser Asp Ile Ala Val Glu Trp
        980                 985                 990

Glu Ser Asn Gly Gln Pro Glu Asn  Asn Tyr Lys Thr Thr  Pro Pro Val
    995                 1000                1005

Leu Asp  Ser Asp Gly Ser Phe  Phe Leu Thr Ser Lys  Leu Thr Val
    1010                1015                1020

Asp Lys  Ser Arg Trp Gln Gln  Gly Asn Val Phe Ser  Cys Ser Val
    1025                1030                1035

Met His  Glu Ala Leu His Asn  His Tyr Thr Gln Lys  Ser Leu Ser
    1040                1045                1050

Leu Ser  Pro Gly Lys
    1055

<210> SEQ ID NO 116
<211> LENGTH: 3195
<212> TYPE: PRT
<213> ORGANISM: Artificial Sequence
<220> FEATURE:
<223> OTHER INFORMATION: Synthetic (DNA encoding the bispecific antibody
      of SEQ ID NO: 115)

<400> SEQUENCE: 116
```

```
Ala Ala Gly Cys Thr Thr Gly Cys Cys Ala Cys Cys Ala Thr Gly Gly
1               5                   10                  15

Gly Ala Thr Gly Gly Thr Cys Ala Thr Gly Thr Ala Thr Cys Ala Thr
            20                  25                  30

Cys Cys Thr Thr Thr Thr Thr Cys Thr Ala Gly Thr Ala Gly Cys Ala
        35                  40                  45

Ala Cys Thr Gly Cys Ala Ala Cys Thr Gly Gly Ala Gly Thr Ala Cys
    50                  55                  60

Ala Thr Thr Cys Ala Gly Ala Gly Gly Thr Thr Cys Ala Gly Cys Thr
65                  70                  75                  80

Gly Gly Thr Gly Gly Ala Gly Thr Cys Thr Gly Gly Cys Gly Gly Thr
                85                  90                  95

Gly Gly Cys Cys Thr Gly Gly Thr Gly Cys Ala Gly Cys Cys Ala Gly
            100                 105                 110

Gly Gly Gly Gly Cys Thr Cys Ala Cys Thr Cys Cys Gly Thr Thr Thr
        115                 120                 125

Gly Thr Cys Cys Thr Gly Thr Gly Cys Ala Gly Cys Thr Thr Cys Thr
    130                 135                 140

Gly Gly Cys Thr Thr Cys Ala Cys Cys Thr Thr Cys Ala Cys Thr Gly
145                 150                 155                 160

Ala Thr Thr Ala Cys Thr Ala Cys Ala Thr Gly Ala Gly Cys Thr Gly
                165                 170                 175

Gly Gly Thr Gly Cys Gly Thr Cys Ala Gly Gly Cys Cys Cys Cys Gly
            180                 185                 190

Gly Gly Thr Ala Ala Gly Gly Gly Cys Cys Thr Gly Gly Ala Ala Thr
        195                 200                 205

Gly Gly Thr Thr Gly Gly Gly Thr Thr Thr Thr Ala Thr Thr Ala Gly
    210                 215                 220

Ala Ala Ala Cys Ala Ala Ala Gly Cys Thr Ala Ala Thr Gly Gly Thr
225                 230                 235                 240

Thr Ala Cys Ala Cys Ala Ala Cys Ala Gly Ala Gly Thr Ala Cys Ala
                245                 250                 255

Gly Thr Gly Cys Ala Thr Cys Thr Gly Thr Gly Ala Ala Gly Gly Gly
            260                 265                 270

Thr Cys Gly Thr Thr Thr Cys Ala Cys Thr Ala Thr Ala Ala Gly Cys
        275                 280                 285

Ala Gly Ala Gly Ala Thr Ala Ala Thr Thr Cys Cys Ala Ala Ala Ala
    290                 295                 300

Ala Cys Ala Cys Ala Cys Thr Gly Thr Ala Cys Cys Thr Gly Cys Ala
305                 310                 315                 320

Gly Ala Thr Gly Ala Ala Cys Ala Gly Cys Cys Thr Gly Cys Gly Thr
                325                 330                 335

Gly Cys Thr Gly Ala Gly Gly Ala Cys Ala Cys Thr Gly Cys Cys Gly
            340                 345                 350

Thr Cys Thr Ala Thr Thr Ala Thr Thr Gly Thr Gly Cys Thr Ala Gly
        355                 360                 365

Ala Gly Ala Thr Ala Ala Cys Thr Gly Gly Thr Thr Thr Gly Cys Thr
    370                 375                 380

Thr Ala Cys Thr Gly Gly Gly Gly Cys Cys Ala Ala Gly Gly Gly Ala
385                 390                 395                 400

Cys Thr Cys Thr Gly Gly Thr Cys Ala Cys Cys Gly Thr Cys Thr Cys
                405                 410                 415
```

-continued

```
Cys Thr Cys Gly Gly Cys Cys Thr Gly Gly Cys Gly Cys
            420                 425             430

Cys Thr Gly Gly Gly Cys Gly Gly Ala Gly Gly Ala Gly Gly Cys Thr
            435                 440             445

Cys Thr Gly Gly Ala Gly Gly Cys Gly Gly Cys Gly Gly Ala Ala Gly
            450                 455             460

Cys Gly Gly Cys Gly Gly Cys Ala Cys Ala Gly Cys Gly Gly Cys
465             470                 475             480

Gly Thr Gly Gly Gly Cys Ala Gly Cys Gly Ala Thr Ala Thr Cys Cys
                485                 490             495

Ala Gly Ala Thr Gly Ala Cys Cys Ala Gly Thr Cys Cys Cys Cys
            500                 505             510

Gly Ala Gly Cys Thr Cys Cys Thr Gly Thr Cys Cys Gly Cys Cys
            515                 520             525

Thr Cys Thr Gly Thr Gly Gly Cys Gly Ala Thr Ala Gly Gly Gly
            530                 535             540

Thr Cys Ala Cys Cys Ala Thr Cys Ala Cys Thr Gly Cys Ala Ala
545                 550                 555             560

Gly Thr Cys Cys Ala Gly Thr Cys Ala Gly Ala Gly Thr Cys Thr Thr
                565                 570             575

Thr Thr Ala Gly Cys Thr Ala Gly Thr Gly Gly Cys Ala Ala Cys Cys
            580                 585             590

Ala Ala Ala Ala Thr Ala Ala Cys Thr Ala Cys Thr Thr Gly Gly Cys
            595                 600             605

Cys Thr Gly Gly Cys Ala Cys Cys Ala Ala Cys Ala Gly Ala Ala Ala
            610                 615             620

Cys Cys Ala Gly Gly Ala Ala Ala Gly Cys Thr Cys Cys Gly Ala
625             630                 635             640

Ala Ala Ala Thr Gly Cys Thr Gly Ala Thr Thr Ala Thr Thr Thr Gly
            645                 650             655

Gly Gly Cys Ala Thr Cys Cys Ala Cys Thr Ala Gly Gly Thr Ala
                660                 665             670

Thr Cys Thr Gly Gly Ala Gly Thr Cys Cys Thr Thr Cys Thr Cys
            675                 680             685

Gly Cys Thr Thr Cys Thr Cys Thr Gly Gly Gly Thr Cys Cys Gly Gly
            690                 695             700

Gly Thr Cys Thr Gly Gly Gly Ala Cys Gly Gly Ala Thr Thr Thr Cys
705                 710                 715             720

Ala Cys Thr Cys Thr Gly Ala Cys Cys Ala Thr Cys Ala Gly Cys Ala
                725                 730             735

Gly Thr Cys Thr Gly Cys Ala Gly Cys Cys Gly Gly Ala Ala Gly Ala
            740                 745             750

Cys Thr Thr Cys Gly Cys Ala Ala Cys Thr Thr Ala Thr Thr Ala Cys
            755                 760             765

Thr Gly Thr Cys Ala Gly Cys Ala Gly Thr Cys Cys Thr Ala Cys Ala
            770                 775             780

Gly Cys Cys Gly Cys Cys Cys Gly Thr Ala Cys Ala Cys Gly Thr Thr
785                 790                 795             800

Cys Gly Gly Ala Cys Ala Gly Gly Gly Thr Ala Cys Cys Ala Ala Gly
                805                 810             815

Gly Thr Gly Gly Ala Gly Ala Thr Cys Ala Ala Ala Cys Gly Thr Gly
            820                 825             830

Ala Gly Cys Cys Cys Ala Ala Gly Ala Gly Cys Thr Gly Cys Gly Ala
```

```
            835                 840                 845
Cys Ala Ala Gly Ala Cys Cys Ala Cys Ala Cys Cys Thr Gly Cys
            850                 855                 860
Cys Cys Cys Cys Cys Cys Thr Gly Cys Cys Cys Gly Cys Cys Cys
            865                 870                 875             880
Cys Cys Gly Ala Gly Cys Thr Gly Cys Thr Gly Gly Cys Gly Gly
                                885                 890                 895
Cys Cys Cys Cys Ala Gly Cys Gly Thr Gly Thr Thr Cys Cys Thr Gly
                900                 905                 910
Thr Thr Cys Cys Cys Cys Cys Cys Ala Ala Gly Cys Cys Ala
                    915                 920                 925
Ala Gly Gly Ala Cys Ala Cys Cys Thr Gly Ala Thr Gly Ala Thr
        930                 935                 940
Cys Ala Gly Cys Cys Gly Cys Ala Cys Cys Cys Gly Ala Gly
945                 950                 955                 960
Gly Thr Gly Ala Cys Cys Thr Gly Cys Gly Thr Gly Gly Thr Gly
                        965                 970                 975
Thr Gly Gly Ala Cys Gly Thr Gly Ala Gly Cys Cys Ala Cys Gly Ala
                    980                 985                 990
Gly Gly Ala Cys Cys Cys Cys Gly Ala Gly Gly Thr Gly Ala Ala Gly
            995                 1000                1005
Thr Thr Cys Ala Ala Cys Thr Gly Gly Thr Ala Cys Gly Thr Gly
    1010                1015                1020
Gly Ala Cys Gly Gly Cys Gly Thr Gly Gly Ala Gly Gly Thr Gly
    1025                1030                1035
Cys Ala Cys Ala Ala Cys Gly Cys Cys Ala Ala Gly Ala Cys Cys
    1040                1045                1050
Ala Ala Gly Cys Cys Cys Cys Gly Cys Gly Ala Gly Gly Ala Gly
    1055                1060                1065
Cys Ala Gly Thr Ala Cys Ala Ala Cys Ala Gly Cys Ala Cys Cys
    1070                1075                1080
Thr Ala Cys Cys Gly Cys Gly Thr Gly Gly Thr Gly Ala Gly Cys
    1085                1090                1095
Gly Thr Gly Cys Thr Gly Ala Cys Cys Gly Thr Gly Cys Thr Gly
    1100                1105                1110
Cys Ala Cys Cys Ala Gly Gly Ala Cys Thr Gly Gly Cys Thr Gly
    1115                1120                1125
Ala Ala Cys Gly Gly Cys Ala Ala Gly Gly Ala Gly Thr Ala Cys
    1130                1135                1140
Ala Ala Gly Thr Gly Cys Ala Ala Gly Gly Thr Gly Ala Gly Cys
    1145                1150                1155
Ala Ala Cys Ala Ala Gly Gly Cys Cys Cys Thr Gly Cys Cys Cys
    1160                1165                1170
Gly Cys Cys Cys Cys Ala Thr Cys Gly Ala Gly Ala Ala Gly
    1175                1180                1185
Ala Cys Cys Ala Thr Cys Ala Gly Cys Ala Ala Gly Gly Cys Cys
    1190                1195                1200
Ala Ala Gly Gly Gly Cys Cys Ala Gly Cys Cys Cys Cys Gly Cys
    1205                1210                1215
Gly Ala Gly Cys Cys Cys Ala Gly Gly Thr Gly Thr Ala Cys
    1220                1225                1230
Ala Cys Cys Cys Thr Gly Cys Cys Cys Cys Cys Ala Gly Cys
    1235                1240                1245
```

```
Cys Gly Cys Gly Ala Gly Gly Ala Gly Ala Thr Gly Ala Cys Cys
    1250                1255                1260

Ala Ala Gly Ala Ala Cys Cys Ala Gly Gly Thr Gly Ala Gly Cys
    1265                1270                1275

Cys Thr Gly Thr Ala Cys Thr Gly Cys Cys Thr Gly Gly Thr Gly
    1280                1285                1290

Ala Ala Gly Gly Gly Cys Thr Thr Cys Thr Ala Cys Cys Cys Cys
    1295                1300                1305

Ala Gly Cys Gly Ala Cys Ala Thr Cys Gly Cys Cys Gly Thr Gly
    1310                1315                1320

Gly Ala Gly Thr Gly Gly Gly Ala Gly Ala Gly Cys Ala Ala Cys
    1325                1330                1335

Gly Gly Cys Cys Ala Gly Cys Cys Cys Gly Ala Gly Ala Ala Cys
    1340                1345                1350

Ala Ala Cys Thr Ala Cys Ala Ala Gly Ala Cys Cys Ala Cys Cys
    1355                1360                1365

Cys Cys Cys Cys Cys Cys Gly Thr Gly Cys Thr Gly Gly Ala Cys
    1370                1375                1380

Ala Gly Cys Gly Ala Cys Gly Gly Cys Ala Gly Cys Thr Thr Cys
    1385                1390                1395

Thr Thr Cys Cys Thr Gly Thr Ala Cys Ala Gly Cys Ala Ala Gly
    1400                1405                1410

Cys Thr Gly Ala Cys Cys Gly Thr Gly Gly Ala Cys Ala Ala Gly
    1415                1420                1425

Ala Gly Cys Cys Gly Cys Thr Gly Gly Cys Ala Gly Cys Ala Gly
    1430                1435                1440

Gly Gly Cys Ala Ala Cys Gly Thr Gly Thr Thr Cys Ala Gly Cys
    1445                1450                1455

Thr Gly Cys Ala Gly Cys Gly Thr Gly Ala Thr Gly Cys Ala Cys
    1460                1465                1470

Gly Ala Gly Gly Cys Cys Cys Thr Gly Cys Ala Cys Ala Ala Cys
    1475                1480                1485

Cys Ala Cys Thr Ala Cys Ala Cys Cys Cys Ala Gly Ala Ala Gly
    1490                1495                1500

Ala Gly Cys Cys Thr Gly Ala Gly Cys Cys Thr Gly Ala Gly Cys
    1505                1510                1515

Cys Cys Cys Gly Gly Cys Ala Ala Gly Ala Thr Gly Cys Ala Gly
    1520                1525                1530

Ala Thr Cys Thr Thr Cys Gly Thr Gly Cys Ala Gly Thr Gly Thr
    1535                1540                1545

Gly Thr Thr Gly Thr Gly Thr Gly Cys Gly Ala Cys Ala Thr Thr
    1550                1555                1560

Gly Cys Ala Cys Ala Thr Gly Cys Gly Gly Cys Cys Gly Cys Gly
    1565                1570                1575

Ala Cys Thr Gly Thr Gly Ala Gly Cys Thr Gly Ala Gly Ala Thr
    1580                1585                1590

Cys Thr Cys Gly Gly Cys Ala Gly Gly Cys Gly Cys Cys Thr Cys
    1595                1600                1605

Cys Ala Gly Cys Gly Gly Cys Cys Gly Ala Gly Ala Ala Gly Gly
    1610                1615                1620

Gly Cys Ala Gly Gly Cys Cys Cys Cys Gly Thr Gly Gly Cys Cys
    1625                1630                1635
```

```
Cys Cys Cys Gly Ala Cys Cys Ala Gly Cys Ala Gly Cys Gly Cys
    1640            1645                1650

Cys Thr Gly Ala Thr Cys Thr Cys Gly Cys Cys Gly Gly Cys
    1655            1660                1665

Ala Ala Gly Cys Ala Gly Cys Thr Gly Gly Ala Gly Gly Ala Cys
    1670            1675                1680

Gly Gly Cys Cys Gly Cys Ala Cys Cys Cys Thr Gly Ala Gly Cys
    1685            1690                1695

Gly Ala Cys Thr Ala Cys Ala Ala Cys Ala Thr Cys Cys Ala Gly
    1700            1705                1710

Ala Ala Gly Gly Ala Gly Ala Gly Cys Ala Cys Cys Cys Thr Gly
    1715            1720                1725

Cys Ala Cys Cys Thr Gly Gly Thr Gly Cys Thr Gly Cys Gly Cys
    1730            1735                1740

Cys Thr Gly Cys Gly Cys Gly Gly Cys Gly Gly Cys Gly Gly Ala
    1745            1750                1755

Thr Cys Cys Cys Ala Gly Gly Thr Gly Cys Ala Gly Cys Thr Gly
    1760            1765                1770

Gly Thr Gly Cys Ala Gly Ala Gly Cys Gly Gly Cys Gly Cys Cys
    1775            1780                1785

Gly Ala Gly Gly Thr Gly Ala Ala Gly Ala Ala Gly Cys Cys Cys
    1790            1795                1800

Gly Gly Cys Ala Gly Cys Ala Gly Cys Gly Thr Gly Ala Ala Gly
    1805            1810                1815

Gly Thr Gly Ala Gly Cys Thr Gly Cys Ala Ala Gly Gly Cys Cys
    1820            1825                1830

Ala Gly Cys Gly Gly Cys Thr Thr Cys Ala Cys Cys Thr Thr Cys
    1835            1840                1845

Ala Cys Cys Gly Ala Cys Thr Ala Cys Ala Ala Gly Ala Thr Cys
    1850            1855                1860

Cys Ala Cys Thr Gly Gly Gly Thr Gly Cys Gly Cys Cys Ala Gly
    1865            1870                1875

Gly Cys Cys Cys Cys Cys Gly Gly Cys Cys Ala Gly Gly Gly Cys
    1880            1885                1890

Cys Thr Gly Gly Ala Gly Thr Gly Gly Ala Thr Gly Gly Gly Cys
    1895            1900                1905

Thr Ala Cys Thr Thr Cys Ala Ala Cys Cys Cys Cys Ala Ala Cys
    1910            1915                1920

Ala Gly Cys Gly Gly Cys Thr Ala Cys Ala Gly Cys Ala Cys Cys
    1925            1930                1935

Thr Ala Cys Gly Cys Cys Cys Ala Gly Ala Ala Gly Thr Thr Cys
    1940            1945                1950

Cys Ala Gly Gly Gly Cys Cys Gly Cys Gly Thr Gly Ala Cys Cys
    1955            1960                1965

Ala Thr Cys Ala Cys Cys Gly Cys Cys Gly Ala Cys Ala Ala Gly
    1970            1975                1980

Ala Gly Cys Ala Cys Cys Ala Gly Cys Ala Cys Cys Gly Cys Cys
    1985            1990                1995

Thr Ala Cys Ala Thr Gly Gly Ala Gly Cys Thr Gly Ala Gly Cys
    2000            2005                2010

Ala Gly Cys Cys Thr Gly Cys Gly Cys Ala Gly Cys Gly Ala Gly
    2015            2020                2025

Gly Ala Cys Ala Cys Cys Gly Cys Cys Gly Thr Gly Thr Ala Cys
```

```
                    2030                2035                2040

Thr Ala Cys Thr Gly Cys Gly Cys Cys Cys Gly Cys Cys Thr Gly
   2045                2050                2055

Ala Gly Cys Cys Cys Cys Gly Gly Cys Gly Gly Cys Thr Ala Cys
   2060                2065                2070

Thr Ala Cys Gly Thr Gly Ala Thr Gly Gly Ala Cys Gly Cys Cys
   2075                2080                2085

Thr Gly Gly Gly Gly Cys Cys Ala Gly Gly Cys Ala Cys Cys
   2090                2095                2100

Ala Cys Cys Gly Thr Gly Ala Cys Cys Gly Thr Gly Ala Gly Cys
   2105                2110                2115

Ala Gly Cys Gly Gly Ala Gly Gly Cys Gly Gly Ala Gly Gly Cys
   2120                2125                2130

Ala Gly Cys Ala Gly Cys Gly Gly Cys Gly Gly Ala Gly Gly Cys
   2135                2140                2145

Ala Gly Cys Gly Gly Ala Gly Gly Cys Gly Gly Cys Gly Gly Ala
   2150                2155                2160

Ala Gly Cys Gly Ala Cys Ala Thr Cys Cys Ala Gly Ala Thr Gly
   2165                2170                2175

Ala Cys Cys Cys Ala Gly Ala Gly Cys Cys Cys Cys Ala Gly Cys
   2180                2185                2190

Ala Gly Cys Cys Thr Gly Ala Gly Cys Gly Cys Cys Ala Gly Cys
   2195                2200                2205

Gly Thr Gly Gly Gly Cys Gly Ala Cys Cys Gly Cys Gly Thr Gly
   2210                2215                2220

Ala Cys Cys Ala Thr Cys Ala Cys Cys Thr Gly Cys Cys Gly Cys
   2225                2230                2235

Gly Cys Cys Ala Gly Cys Cys Ala Gly Gly Gly Cys Ala Thr Cys
   2240                2245                2250

Ala Ala Cys Ala Ala Cys Thr Ala Cys Cys Thr Gly Ala Ala Cys
   2255                2260                2265

Thr Gly Gly Thr Ala Cys Cys Ala Gly Cys Ala Gly Ala Ala Gly
   2270                2275                2280

Cys Cys Cys Gly Gly Cys Ala Ala Gly Gly Cys Cys Cys Cys Cys
   2285                2290                2295

Ala Ala Gly Cys Gly Cys Cys Thr Gly Ala Thr Cys Thr Ala Cys
   2300                2305                2310

Ala Ala Cys Ala Cys Cys Ala Ala Cys Ala Ala Cys Cys Thr Gly
   2315                2320                2325

Cys Ala Gly Ala Cys Cys Gly Gly Cys Gly Thr Gly Cys Cys Cys
   2330                2335                2340

Ala Gly Cys Cys Gly Cys Thr Thr Cys Ala Gly Cys Gly Gly Cys
   2345                2350                2355

Ala Gly Cys Gly Gly Cys Ala Gly Cys Gly Gly Cys Ala Cys Cys
   2360                2365                2370

Gly Ala Gly Thr Thr Cys Ala Cys Cys Cys Thr Gly Ala Cys Cys
   2375                2380                2385

Ala Thr Cys Ala Gly Cys Ala Gly Cys Cys Thr Gly Cys Ala Gly
   2390                2395                2400

Cys Cys Cys Gly Ala Gly Gly Ala Cys Thr Thr Cys Gly Cys Cys
   2405                2410                2415

Ala Cys Cys Thr Ala Cys Thr Ala Cys Thr Gly Cys Cys Thr Gly
   2420                2425                2430
```

```
Cys Ala Gly Cys Ala Cys Ala Ala Cys Ala Gly Cys Thr Thr Cys
2435                 2440                2445

Cys Cys Cys Ala Cys Cys Thr Thr Cys Gly Gly Cys Cys Ala Gly
2450                 2455                2460

Gly Gly Cys Ala Cys Ala Ala Gly Cys Thr Gly Gly Ala Gly
2465                 2470                2475

Ala Thr Cys Ala Ala Gly Cys Gly Cys Ala Cys Cys Gly Ala Gly
2480                 2485                2490

Cys Cys Cys Ala Ala Gly Ala Gly Cys Thr Gly Cys Gly Ala Cys
2495                 2500                2505

Ala Ala Gly Ala Cys Cys Ala Cys Ala Cys Cys Thr Gly Cys
2510                 2515                2520

Cys Cys Cys Cys Cys Cys Thr Gly Cys Cys Cys Gly Cys Cys
2525                 2530                2535

Cys Cys Cys Gly Ala Gly Cys Thr Gly Cys Thr Gly Gly Gly Cys
2540                 2545                2550

Gly Gly Cys Cys Cys Cys Ala Gly Cys Gly Thr Gly Thr Thr Cys
2555                 2560                2565

Cys Thr Gly Thr Thr Cys Cys Cys Cys Cys Cys Ala Ala Gly
2570                 2575                2580

Cys Cys Cys Ala Ala Gly Gly Ala Cys Ala Cys Cys Cys Thr Gly
2585                 2590                2595

Ala Thr Gly Ala Thr Cys Ala Gly Cys Cys Gly Cys Ala Cys Cys
2600                 2605                2610

Cys Cys Cys Gly Ala Gly Gly Thr Gly Ala Cys Cys Thr Gly Cys
2615                 2620                2625

Gly Thr Gly Gly Thr Gly Gly Thr Gly Gly Ala Cys Gly Thr Gly
2630                 2635                2640

Ala Gly Cys Cys Ala Cys Gly Ala Gly Gly Ala Cys Cys Cys Cys
2645                 2650                2655

Gly Ala Gly Gly Thr Gly Ala Ala Gly Thr Thr Cys Ala Ala Cys
2660                 2665                2670

Thr Gly Gly Thr Ala Cys Gly Thr Gly Gly Ala Cys Gly Gly Cys
2675                 2680                2685

Gly Thr Gly Gly Ala Gly Gly Thr Gly Cys Ala Cys Ala Ala Cys
2690                 2695                2700

Gly Cys Cys Ala Ala Gly Ala Cys Cys Ala Ala Gly Cys Cys Cys
2705                 2710                2715

Cys Gly Cys Gly Ala Gly Gly Ala Gly Cys Ala Gly Thr Ala Cys
2720                 2725                2730

Ala Ala Cys Ala Gly Cys Ala Cys Cys Thr Ala Cys Cys Gly Cys
2735                 2740                2745

Gly Thr Gly Gly Thr Gly Ala Gly Cys Gly Thr Gly Cys Thr Gly
2750                 2755                2760

Ala Cys Cys Gly Thr Gly Cys Thr Gly Cys Ala Cys Cys Ala Gly
2765                 2770                2775

Gly Ala Cys Thr Gly Gly Cys Thr Gly Ala Ala Cys Gly Gly Cys
2780                 2785                2790

Ala Ala Gly Gly Ala Gly Thr Ala Cys Ala Ala Gly Thr Gly Cys
2795                 2800                2805

Ala Ala Gly Gly Thr Gly Ala Gly Cys Ala Ala Cys Ala Ala Gly
2810                 2815                2820
```

Gly Cys Cys Cys Thr Gly Cys Cys Gly Cys Cys Cys Cys Cys
2825                2830                2835

Ala Thr Cys Gly Ala Gly Ala Ala Gly Ala Cys Ala Thr Cys
2840                2845                2850

Ala Gly Cys Ala Ala Gly Gly Cys Cys Ala Ala Gly Gly Gly Cys
2855                2860                2865

Cys Ala Gly Cys Cys Cys Gly Cys Gly Ala Gly Cys Cys Cys
2870                2875                2880

Cys Ala Gly Gly Thr Gly Thr Ala Cys Ala Cys Cys Thr Gly
2885                2890                2895

Cys Cys Cys Cys Cys Ala Gly Cys Cys Gly Cys Gly Ala Gly
2900                2905                2910

Gly Ala Gly Ala Thr Gly Ala Cys Cys Ala Ala Gly Ala Ala Cys
2915                2920                2925

Cys Ala Gly Gly Thr Gly Ala Gly Cys Cys Thr Gly Ala Cys Cys
2930                2935                2940

Thr Gly Cys Cys Thr Gly Gly Thr Gly Ala Ala Gly Gly Gly Cys
2945                2950                2955

Thr Thr Cys Thr Ala Cys Cys Cys Ala Gly Cys Gly Ala Cys
2960                2965                2970

Ala Thr Cys Gly Cys Cys Gly Thr Gly Gly Ala Gly Thr Gly Gly
2975                2980                2985

Gly Ala Gly Ala Gly Cys Ala Ala Cys Gly Gly Cys Cys Ala Gly
2990                2995                3000

Cys Cys Cys Gly Ala Gly Ala Ala Cys Ala Ala Cys Thr Ala Cys
3005                3010                3015

Ala Ala Gly Ala Cys Cys Ala Cys Cys Cys Cys Cys Cys Cys
3020                3025                3030

Gly Thr Gly Cys Thr Gly Gly Ala Cys Ala Gly Cys Gly Ala Cys
3035                3040                3045

Gly Gly Cys Ala Gly Cys Thr Thr Cys Thr Thr Cys Cys Thr Gly
3050                3055                3060

Ala Cys Cys Ala Gly Cys Ala Ala Gly Cys Thr Gly Ala Cys Cys
3065                3070                3075

Gly Thr Gly Gly Ala Cys Ala Ala Gly Ala Gly Cys Cys Gly Cys
3080                3085                3090

Thr Gly Gly Cys Ala Gly Cys Ala Gly Gly Gly Cys Ala Ala Cys
3095                3100                3105

Gly Thr Gly Thr Thr Cys Ala Gly Cys Thr Gly Cys Ala Gly Cys
3110                3115                3120

Gly Thr Gly Ala Thr Gly Cys Ala Cys Gly Ala Gly Gly Cys Cys
3125                3130                3135

Cys Thr Gly Cys Ala Cys Ala Ala Cys Cys Ala Cys Thr Ala Cys
3140                3145                3150

Ala Cys Cys Cys Ala Gly Ala Ala Gly Ala Gly Cys Cys Thr Gly
3155                3160                3165

Ala Gly Cys Cys Thr Gly Ala Gly Cys Cys Cys Cys Gly Gly Cys
3170                3175                3180

Ala Ala Gly Thr Gly Ala Cys Thr Cys Gly Ala Gly
3185                3190                3195

<210> SEQ ID NO 117
<211> LENGTH: 1536
<212> TYPE: DNA

<213> ORGANISM: Artificial Sequence
<220> FEATURE:
<223> OTHER INFORMATION: Synthetic (DNA encoding control anti-c-Met antibody)

<400> SEQUENCE: 117

| | |
|---|---|
| aagcttgcca ccatgggatg gtcatgtatc atccttttc tagtagcaac tgcaactgga | 60 |
| gtacattcag aggttcagct ggtggagtct ggcggtggcc tggtgcagcc agggggctca | 120 |
| ctccgtttgt cctgtgcagc ttctggcttc accttcactg attactacat gagctgggtg | 180 |
| cgtcaggccc cgggtaaggg cctggaatgg ttgggtttta ttagaaacaa agctaatggt | 240 |
| tacacaacag agtacagtgc atctgtgaag ggtcgtttca ctataagcag agataattcc | 300 |
| aaaaacacac tgtacctgca gatgaacagc ctgcgtgctg aggacactgc cgtctattat | 360 |
| tgtgctagag ataactggtt tgcttactgg ggccaaggga ctctggtcac cgtctcctcg | 420 |
| ggcctgggcg gcctgggcgg aggaggctct ggaggcggcg gaagcggcgg cagcagcggc | 480 |
| gtgggcagca tatccagat gacccagtcc ccgagctccc tgtccgcctc tgtgggcgat | 540 |
| agggtcacca tcacctgcaa gtccagtcag agtcttttag ctagtggcaa ccaaaataac | 600 |
| tacttggcct ggcaccaaca gaaaccagga aaagctccga aaatgctgat tatttgggca | 660 |
| tccactaggg tatctggagt ccccttctcgc ttctctgggt ccgggtctgg gacggatttc | 720 |
| actctgacca tcagcagtct gcagccggaa gacttcgcaa cttattactg tcagcagtcc | 780 |
| tacagccgcc cgtacacgtt cggacagggt accaaggtgg agatcaaacg tgagcccaag | 840 |
| agctgcgaca gacccacac ctgccccccc tgccccgccc ccgagctgct gggcggcccc | 900 |
| agcgtgttcc tgttcccccc caagcccaag gacaccctga tgatcagccg cacccccgag | 960 |
| gtgacctgcg tggtggtgga cgtgagccac gaggacccg aggtgaagtt caactggtac | 1020 |
| gtggacggcg tggaggtgca caacgccaag accaagcccc gcgaggagca gtacaacagc | 1080 |
| acctaccgcg tggtgagcgt gctgaccgtg ctgcaccagg actggctgaa cggcaaggag | 1140 |
| tacaagtgca aggtgagcaa caaggccctg cccgccccca tcgagaagac catcagcaag | 1200 |
| gccaagggcc agccccgcga gccccaggtg tacaccctgc cccccagccg cgaggagatg | 1260 |
| accaagaacc aggtgagcct gacctgcctg gtgaagggct tctaccccag cgacatcgcc | 1320 |
| gtggagtggg agagcaacgg ccagcccgag aacaactaca agaccacccc ccccgtgctg | 1380 |
| gacagcgacg gcagcttctt cctgtacagc aagctgaccg tggacaagag ccgctggcag | 1440 |
| cagggcaacg tgttcagctg cagcgtgatg cacgaggccc tgcacaacca ctacacccag | 1500 |
| aagagcctga gcctgagccc cggcaagtga ctcgag | 1536 |

<210> SEQ ID NO 118
<211> LENGTH: 1503
<212> TYPE: DNA
<213> ORGANISM: Artificial Sequence
<220> FEATURE:
<223> OTHER INFORMATION: Synthetic (DNA encoding control anti-EGFR antibody)

<400> SEQUENCE: 118

| | |
|---|---|
| aagcttgcca ccatgggatg gtcatgtatc atccttttc tagtagcaac tgcaactgga | 60 |
| gtacattcac aggtgcagct ggtgcagagc ggcgccgagg tgaagaagcc cggcagcagc | 120 |
| gtgaaggtga gctgcaaggc cagcggcttc accttcaccg actacaagat ccactgggtg | 180 |
| cgccaggccc ccggccaggg cctggagtgg atgggctact caacccccaa cagcggctac | 240 |
| agcacctacg cccagaagtt ccagggccgc gtgaccatca ccgccgacaa gagcaccagc | 300 |

```
accgcctaca tggagctgag cagcctgcgc agcgaggaca ccgccgtgta ctactgcgcc    360
cgcctgagcc ccggcggcta ctacgtgatg acgcctggg gccagggcac caccgtgacc    420
gtgagcagcg gaggcggagg cagcagcggc ggaggcagcg gaggcggcgg aagcgacatc    480
cagatgaccc agagccccag cagcctgagc gccagcgtgg gcgaccgcgt gaccatcacc    540
tgccgcgcca gccagggcat caacaactac ctgaactggt accagcagaa gcccggcaag    600
gcccccaagc gcctgatcta caacaccaac aacctgcaga ccggcgtgcc cagccgcttc    660
agcggcagcg gcagcggcac cgagttcacc ctgaccatca gcagcctgca gcccgaggac    720
ttcgccacct actactgcct gcagcacaac agcttcccca ccttcggcca gggcaccaag    780
ctggagatca gcgcaccga gcccaagagc tgcgacaaga cccacacctg ccccccctgc    840 cccgccccg agctgctggg cggccccagc gtgttcctgt tccccccaa gcccaaggac    900 accctgatga tcagccgcac ccccgaggtg acctgcgtgg tggtggacgt gagccacgag    960
gaccccgagg tgaagttcaa ctggtacgtg acggcgtgg aggtgcacaa cgccaagacc    1020
aagccccgcg aggagcagta caacagcacc taccgcgtgg tgagcgtgct gaccgtgctg    1080
caccaggact ggctgaacgg caaggagtac aagtgcaagg tgagcaacaa ggccctgccc    1140
gcccccatcg agaagaccat cagcaaggcc aagggccagc cccgcgagcc ccaggtgtac    1200
accctgcccc ccagccgcga ggagatgacc aagaaccagg tgagcctgac ctgcctggtg    1260
aagggcttct accccagcga catcgccgtg gagtgggaga gcaacggcca gcccgagaac    1320
aactacaaga ccaccccccc cgtgctggac agcgacggca gcttcttcct gtacagcaag    1380
ctgaccgtgg acaagagccg ctggcagcag ggcaacgtgt tcagctgcag cgtgatgcac    1440
gaggccctgc acaaccacta cacccagaag agcctgagcc tgagccccgg caagtgactc    1500
gag                                                                    1503
```

<210> SEQ ID NO 119
<211> LENGTH: 1063
<212> TYPE: PRT
<213> ORGANISM: Artificial Sequence
<220> FEATURE:
<223> OTHER INFORMATION: Synthetic (anti-c-Met/anti-Her3 bispecific
      antibody with knobe and hole)

<400> SEQUENCE: 119

```
Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Tyr Met Ser Trp Val Arg Gln Ala Pro Gly Lys Gly Leu
    50                  55                  60

Glu Trp Leu Gly Phe Ile Arg Asn Lys Ala Asn Gly Tyr Thr Thr Glu
65                  70                  75                  80

Tyr Ser Ala Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Asn Trp Phe Ala Tyr Trp Gly Gln
        115                 120                 125

Gly Thr Leu Val Thr Val Ser Ser Gly Leu Gly Gly Leu Gly Gly Gly
```

```
                130             135             140
Gly Ser Gly Gly Gly Ser Gly Gly Ser Ser Gly Val Gly Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ser Ser Gln Ser Leu Leu Ala Ser Gly
            180                 185                 190

Asn Gln Asn Asn Tyr Leu Ala Trp His Gln Gln Lys Pro Gly Lys Ala
        195                 200                 205

Pro Lys Met Leu Ile Ile Trp Ala Ser Thr Arg Val Ser Gly Val Pro
    210                 215                 220

Ser Arg Phe Ser Gly Ser Gly Ser Gly Thr Asp Phe Thr Leu Thr Ile
225                 230                 235                 240

Ser Ser Leu Gln Pro Glu Asp Phe Ala Thr Tyr Tyr Cys Gln Gln Ser
                245                 250                 255

Tyr Ser Arg Pro Tyr Thr Phe Gly Gln Gly Thr Lys Val Glu Ile Lys
            260                 265                 270

Arg Glu Pro Lys Ser Cys Asp Lys Thr His Thr Cys Pro Pro Cys Pro
        275                 280                 285

Ala Pro Glu Leu Leu Gly Gly Pro Ser Val Phe Leu Phe Pro Pro Lys
    290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
    370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Glu Glu Met
                405                 410                 415

Thr Lys Asn Gln Val Ser Leu Tyr Cys Leu Val Lys Gly Phe Tyr Pro
            420                 425                 430

Ser Asp Ile Ala Val Glu Trp Glu Ser Asn Gly Gln Pro Glu Asn Asn
        435                 440                 445

Tyr Lys Thr Thr Pro Pro Val Leu Asp Ser Asp Gly Ser Phe Phe Leu
    450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly Lys Met Gln Ile Phe Val Lys Thr
            500                 505                 510

Leu Thr Gly Lys Thr Ile Thr Leu Glu Val Glu Pro Ser Asp Thr Ile
        515                 520                 525

Glu Asn Val Lys Ala Lys Ile Gln Asp Lys Glu Gly Ile Pro Pro Asp
    530                 535                 540

Gln Gln Arg Leu Ile Phe Ala Gly Lys Gln Leu Glu Asp Gly Arg Thr
545                 550                 555                 560
```

```
Leu Ser Asp Tyr Asn Ile Gln Lys Glu Ser Thr Leu His Leu Val Leu
                565                 570                 575

Arg Leu Arg Gly Gly Ser Gln Val Gln Leu Gln Glu Ser Gly Gly
            580                 585                 590

Gly Leu Val Lys Pro Gly Gly Ser Leu Arg Leu Ser Cys Ala Ala Ser
            595                 600                 605

Gly Phe Thr Phe Ser Ser Tyr Trp Met Ser Trp Val Arg Gln Ala Pro
            610                 615                 620

Gly Lys Gly Leu Glu Trp Val Ala Asn Ile Asn Arg Asp Gly Ser Ala
625                 630                 635                 640

Ser Tyr Tyr Val Asp Ser Val Lys Gly Arg Phe Thr Ile Ser Arg Asp
                645                 650                 655

Asp Ala Lys Asn Ser Leu Tyr Leu Gln Met Asn Ser Leu Arg Ala Glu
                660                 665                 670

Asp Thr Ala Val Tyr Tyr Cys Ala Arg Asp Arg Gly Val Gly Tyr Phe
                675                 680                 685

Asp Leu Trp Gly Arg Gly Thr Leu Val Thr Val Ser Ser Ala Ser Thr
            690                 695                 700

Gly Gly Gly Gly Ser Gly Gly Gly Ser Gly Gly Gly Gly Ser Gln
705                 710                 715                 720

Ser Ala Leu Thr Gln Pro Ala Ser Val Ser Gly Ser Pro Gly Gln Ser
                725                 730                 735

Ile Thr Ile Ser Cys Thr Gly Thr Ser Ser Asp Val Gly Gly Tyr Asn
                740                 745                 750

Phe Val Ser Trp Tyr Gln Gln His Pro Gly Lys Ala Pro Lys Leu Met
                755                 760                 765

Ile Tyr Asp Val Ser Asp Arg Pro Ser Gly Val Ser Asp Arg Phe Ser
770                 775                 780

Gly Ser Lys Ser Gly Asn Thr Ala Ser Leu Ile Ile Ser Gly Leu Gln
785                 790                 795                 800

Ala Asp Asp Glu Ala Asp Tyr Tyr Cys Ser Ser Tyr Gly Ser Ser Ser
                805                 810                 815

Thr His Val Ile Phe Gly Gly Gly Thr Lys Val Thr Val Leu Gly Glu
                820                 825                 830

Pro Lys Ser Cys Asp Lys Thr His Thr Cys Pro Pro Cys Pro Ala Pro
                835                 840                 845

Glu Leu Leu Gly Gly Pro Ser Val Phe Leu Phe Pro Pro Lys Pro Lys
850                 855                 860

Asp Thr Leu Met Ile Ser Arg Thr Pro Glu Val Thr Cys Val Val Val
865                 870                 875                 880

Asp Val Ser His Glu Asp Pro Glu Val Lys Phe Asn Trp Tyr Val Asp
                885                 890                 895

Gly Val Glu Val His Asn Ala Lys Thr Lys Pro Arg Glu Glu Gln Tyr
                900                 905                 910

Asn Ser Thr Tyr Arg Val Val Ser Val Leu Thr Val Leu His Gln Asp
                915                 920                 925

Trp Leu Asn Gly Lys Glu Tyr Lys Cys Lys Val Ser Asn Lys Ala Leu
            930                 935                 940

Pro Ala Pro Ile Glu Lys Thr Ile Ser Lys Ala Lys Gly Gln Pro Arg
945                 950                 955                 960

Glu Pro Gln Val Tyr Thr Leu Pro Pro Ser Arg Glu Glu Met Thr Lys
                965                 970                 975
```

```
Asn Gln Val Ser Leu Thr Cys Leu Val Lys Gly Phe Tyr Pro Ser Asp
            980                 985                 990

Ile Ala Val Glu Trp Glu Ser Asn  Gly Gln Pro Glu Asn  Asn Tyr Lys
        995                 1000                1005

Thr Thr  Pro Pro Val Leu Asp  Ser Asp Gly Ser Phe  Phe Leu Thr
    1010             1015                 1020

Ser Lys  Leu Thr Val Asp Lys  Ser Arg Trp Gln Gln  Gly Asn Val
    1025             1030                 1035

Phe Ser  Cys Ser Val Met His  Glu Ala Leu His Asn  His Tyr Thr
    1040             1045                 1050

Gln Lys  Ser Leu Ser Leu Ser  Pro Gly Lys
    1055             1060
```

<210> SEQ ID NO 120
<211> LENGTH: 3210
<212> TYPE: DNA
<213> ORGANISM: Artificial Sequence
<220> FEATURE:
<223> OTHER INFORMATION: Synthetic (DNA encoding the bispecific antibody of SEQ ID NO 119)

<400> SEQUENCE: 120

```
aagcttgcca ccatgggatg gtcatgtatc atccttttc tagtagcaac tgcaactgga      60
gtacattcag aggttcagct ggtggagtct ggcggtggcc tggtgcagcc aggggggctca     120
ctccgtttgt cctgtgcagc ttctggcttc accttcactg attactacat gagctgggtg     180
cgtcaggccc cgggtaaggg cctggaatgg ttgggtttta ttagaaacaa agctaatggt     240
tacacaacag agtacagtgc atctgtgaag ggtcgtttca ctataagcag agataattcc     300
aaaaacacac tgtacctgca gatgaacagc ctgcgtgctg aggacactgc cgtctattat     360
tgtgctagag ataactggtt tgcttactgg ggccaaggga ctctggtcac cgtctcctcg     420
ggcctgggcg gcctgggcgg aggaggctct ggaggcggcg gaagcggcgg cagcagcggc     480
gtgggcagcg atatccagat gacccagtcc ccgagctccc tgtccgcctc tgtgggcgat     540
aggtcaccca tcacctgcaa gtccagtcag agtctttag ctagtggcaa ccaaaataac     600
tacttggcct ggcaccaaca gaaaccagga aaagctccga aatgctgat tatttgggca     660
tccactaggg tatctggagt ccccttctcgc ttctctgggt ccgggtctgg acggatttc     720
actctgacca tcagcagtct gcagccggaa gacttcgcaa cttattactg tcagcagtcc     780
tacagccgcc cgtacacgtt cggacagggt accaaggtgg agatcaaacg tgagcccaag     840
agctgcgaca gacccacac ctgccccccc tgccccgccc cgagctgct gggcggcccc     900
agcgtgttcc tgttcccccc caagcccaag gacaccctga tgatcagccg cacccccgag     960
gtgacctgcg tggtggtgga cgtgagccac gaggaccccg aggtgaagtt caactggtac    1020
gtggacggcg tggaggtgca caacgccaag accaagcccc gcgaggagca gtacaacagc    1080
acctaccgcg tggtgagcgt gctgaccgtg ctgcaccagg actggctgaa cggcaaggag    1140
tacaagtgca aggtgagcaa caaggccctg ccgcccccca tcgagaagac catcagcaag    1200
gccaagggcc agccccgcga gccccaggtg tacaccctgc ccccagccg cgaggagatg    1260
accaagaacc aggtgagcct gtactgcctg gtgaagggct ctacccag cgacatcgcc    1320
gtggagtggg agagcaacgg ccagcccgag aacaactaca agaccacccc ccccgtgctg    1380
gacagcgacg gcagcttctt cctgtacagc aagctgaccg tggacaagag ccgctggcag    1440
cagggcaacg tgttcagctg cagcgtgatg cacgaggccc tgcacaacca ctacacccag    1500
```

```
aagagcctga gcctgagccc cggcaagatg cagatcttcg tgaagaccct gaccggcaag    1560
accatcaccc tggaggtgga gcccagcgac accatcgaga cgtgaaggc caagatccag     1620
gacaaggagg gcatcccccc cgaccagcag cgcctgatct tcgccggcaa gcagctggag    1680
gacgccgca ccctgagcga ctacaacatc cagaaggaga gcaccctgca cctggtgctg     1740
cgcctgcgcg gcggcggatc ccaggtgcag ctgcaggaga gcggcggcgg cctggtgaag    1800
cccggcggca gcctgcgcct gagctgcgcc gccagcggct tcaccttcag cagctactgg    1860
atgagctggg tgcgccaggc ccccggcaag ggcctggagt gggtggccaa catcaaccgc    1920
gacggcagcg ccagctacta cgtggacagc gtgaagggcc gcttcaccat cagccgcgac    1980
gacgccaaga acagcctgta cctgcagatg aacagcctgc gcgccgagga caccgccgtg    2040
tactactgcg cccgcgaccg cggcgtgggc tacttcgacc tgtggggccg cggcaccctg    2100
gtgaccgtga gcagcgccag caccggcggc ggcggcagcg gcggcggcgg cagcggcggc    2160
ggcggcagcc agagcgccct gacccagccc gccagcgtga gcggcagccc cggccagagc    2220
atcaccatca gctgcaccgg caccagcagc gacgtgggcg gctacaactt cgtgagctgg    2280
taccagcagc accccggcaa ggccccaag ctgatgatct acgacgtgag cgaccgcccc    2340
agcggcgtga gcgaccgctt cagcggcagc aagagcggca caccgccag cctgatcatc    2400
agcggcctgc aggccgacga cgaggccgac tactactgca gcagctacgg cagcagcagc    2460
acccacgtga tcttcggcgg cggcaccaag gtgaccgtgc tgggcgagcc caagagctgc    2520
gacaagaccc acacctgccc ccctgccccc gccccgagc tgctgggcgg cccagcgtg     2580
ttcctgttcc cccccaagcc caaggacacc ctgatgatca gccgcacccc cgaggtgacc    2640
tgcgtggtgg tggacgtgag ccacgaggac cccgaggtga agttcaactg gtacgtggac    2700
ggcgtggagg tgcacaacgc caagaccaag ccccgcgagg agcagtacaa cagcacctac    2760
cgcgtggtga gcgtgctgac cgtgctgcac caggactggc tgaacggcaa ggagtacaag    2820
tgcaaggtga gcaacaaggc cctgcccgcc cccatcgaga gaccatcag caaggccaag    2880
ggccagcccc gcgagcccca ggtgtacacc ctgcccccca gccgcgagga tgaccaag     2940
aaccaggtga gcctgacctg cctggtgaag ggcttctacc ccagcgacat cgccgtggag    3000
tgggagagca acggccagcc cgagaacaac tacaagacca ccccccccgt gctggacagc    3060
gacggcagct tcttcctgac cagcaagctg accgtggaca gagccgctg gcagcaggc     3120
aacgtgttca gctgcagcgt gatgcacgag gccctgcaca ccactacac ccagaagagc    3180
ctgagcctga gccccggcaa gtgactcgag                                     3210
```

<210> SEQ ID NO 121
<211> LENGTH: 1063
<212> TYPE: PRT
<213> ORGANISM: Artificial Sequence
<220> FEATURE:
<223> OTHER INFORMATION: Synthetic (anti-c-Met/anti-Her3 bispecific
      antibody without knob and hole)

<400> SEQUENCE: 121

```
Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Tyr Met Ser Trp Val Arg Gln Ala Pro Gly Lys Gly Leu
```

```
            50                  55                  60
Glu Trp Leu Gly Phe Ile Arg Asn Lys Ala Asn Gly Tyr Thr Thr Glu
 65                  70                  75                  80

Tyr Ser Ala Ser Val Lys Gly Arg Phe Thr Ile Ser Arg Asp Asn Ser
                 85                  90                  95

Lys Asn Thr Leu Tyr Leu Gln Met Asn Ser Leu Arg Ala Glu Asp Thr
                100                 105                 110

Ala Val Tyr Tyr Cys Ala Arg Asp Asn Trp Phe Ala Tyr Trp Gly Gln
                115                 120                 125

Gly Thr Leu Val Thr Val Ser Ser Gly Leu Gly Gly Leu Gly Gly Gly
            130                 135                 140

Gly Ser Gly Gly Gly Ser Gly Gly Ser Ser Gly Val Gly Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ser Ser Gln Ser Leu Leu Ala Ser Gly
                180                 185                 190

Asn Gln Asn Asn Tyr Leu Ala Trp His Gln Gln Lys Pro Gly Lys Ala
                195                 200                 205

Pro Lys Met Leu Ile Ile Trp Ala Ser Thr Arg Val Ser Gly Val Pro
210                 215                 220

Ser Arg Phe Ser Gly Ser Gly Ser Gly Thr Asp Phe Thr Leu Thr Ile
225                 230                 235                 240

Ser Ser Leu Gln Pro Glu Asp Phe Ala Thr Tyr Tyr Cys Gln Gln Ser
                245                 250                 255

Tyr Ser Arg Pro Tyr Thr Phe Gly Gln Gly Thr Lys Val Glu Ile Lys
                260                 265                 270

Arg Glu Pro Lys Ser Cys Asp Lys Thr His Thr Cys Pro Pro Cys Pro
                275                 280                 285

Ala Pro Glu Leu Leu Gly Gly Pro Ser Val Phe Leu Phe Pro Pro Lys
                290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
                340                 345                 350

Gln Tyr Asn Ser Thr Tyr Arg Val Val Ser Val Leu Thr Val Leu His
                355                 360                 365

Gln Asp Trp Leu Asn Gly Lys Glu Tyr Lys Cys Lys Val Ser Asn Lys
                370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Glu Glu Met
                405                 410                 415

Thr Lys Asn Gln Val Ser Leu Thr Cys Leu Val Lys Gly Phe Tyr Pro
                420                 425                 430

Ser Asp Ile Ala Val Glu Trp Glu Ser Asn Gly Gln Pro Glu Asn Asn
                435                 440                 445

Tyr Lys Thr Thr Pro Pro Val Leu Asp Ser Asp Gly Ser Phe Phe Leu
                450                 455                 460

Tyr Ser Lys Leu Thr Val Asp Lys Ser Arg Trp Gln Gln Gly Asn Val
465                 470                 475                 480
```

```
Phe Ser Cys Ser Val Met His Glu Ala Leu His Asn His Tyr Thr Gln
            485                 490                 495

Lys Ser Leu Ser Leu Ser Pro Gly Lys Met Gln Ile Phe Val Lys Thr
            500                 505                 510

Leu Thr Gly Lys Thr Ile Thr Leu Glu Val Glu Pro Ser Asp Thr Ile
            515                 520                 525

Glu Asn Val Lys Ala Lys Ile Gln Asp Lys Glu Gly Ile Pro Pro Asp
            530                 535                 540

Gln Gln Arg Leu Ile Phe Ala Gly Lys Gln Leu Glu Asp Gly Arg Thr
545                 550                 555                 560

Leu Ser Asp Tyr Asn Ile Gln Lys Glu Ser Thr Leu His Leu Val Leu
            565                 570                 575

Arg Leu Arg Gly Gly Ser Gln Val Gln Leu Gln Glu Ser Gly Gly
            580                 585                 590

Gly Leu Val Lys Pro Gly Gly Ser Leu Arg Leu Ser Cys Ala Ala Ser
            595                 600                 605

Gly Phe Thr Phe Ser Ser Tyr Trp Met Ser Trp Val Arg Gln Ala Pro
            610                 615                 620

Gly Lys Gly Leu Glu Trp Val Ala Asn Ile Asn Arg Asp Gly Ser Ala
625                 630                 635                 640

Ser Tyr Tyr Val Asp Ser Val Lys Gly Arg Phe Thr Ile Ser Arg Asp
            645                 650                 655

Asp Ala Lys Asn Ser Leu Tyr Leu Gln Met Asn Ser Leu Arg Ala Glu
            660                 665                 670

Asp Thr Ala Val Tyr Tyr Cys Ala Arg Asp Arg Gly Val Gly Tyr Phe
            675                 680                 685

Asp Leu Trp Gly Arg Gly Thr Leu Val Thr Val Ser Ser Ala Ser Thr
            690                 695                 700

Gly Gly Gly Gly Ser Gly Gly Gly Ser Gly Gly Gly Gly Ser Gln
705                 710                 715                 720

Ser Ala Leu Thr Gln Pro Ala Ser Val Ser Gly Ser Pro Gly Gln Ser
            725                 730                 735

Ile Thr Ile Ser Cys Thr Gly Thr Ser Ser Asp Val Gly Gly Tyr Asn
            740                 745                 750

Phe Val Ser Trp Tyr Gln Gln His Pro Gly Lys Ala Pro Lys Leu Met
            755                 760                 765

Ile Tyr Asp Val Ser Asp Arg Pro Ser Gly Val Ser Asp Arg Phe Ser
            770                 775                 780

Gly Ser Lys Ser Gly Asn Thr Ala Ser Leu Ile Ile Ser Gly Leu Gln
785                 790                 795                 800

Ala Asp Asp Glu Ala Asp Tyr Tyr Cys Ser Ser Tyr Gly Ser Ser Ser
            805                 810                 815

Thr His Val Ile Phe Gly Gly Gly Thr Lys Val Thr Val Leu Gly Glu
            820                 825                 830

Pro Lys Ser Cys Asp Lys Thr His Thr Cys Pro Pro Cys Pro Ala Pro
            835                 840                 845

Glu Leu Leu Gly Gly Pro Ser Val Phe Leu Phe Pro Pro Lys Pro Lys
            850                 855                 860

Asp Thr Leu Met Ile Ser Arg Thr Pro Glu Val Thr Cys Val Val Val
865                 870                 875                 880

Asp Val Ser His Glu Asp Pro Glu Val Lys Phe Asn Trp Tyr Val Asp
            885                 890                 895
```

```
Gly Val Glu Val His Asn Ala Lys Thr Lys Pro Arg Glu Glu Gln Tyr
                900                 905                 910

Asn Ser Thr Tyr Arg Val Val Ser Val Leu Thr Val Leu His Gln Asp
            915                 920                 925

Trp Leu Asn Gly Lys Glu Tyr Lys Cys Lys Val Ser Asn Lys Ala Leu
        930                 935                 940

Pro Ala Pro Ile Glu Lys Thr Ile Ser Lys Ala Lys Gly Gln Pro Arg
945                 950                 955                 960

Glu Pro Gln Val Tyr Thr Leu Pro Pro Ser Arg Glu Glu Met Thr Lys
                965                 970                 975

Asn Gln Val Ser Leu Thr Cys Leu Val Lys Gly Phe Tyr Pro Ser Asp
            980                 985                 990

Ile Ala Val Glu Trp Glu Ser Asn  Gly Gln Pro Glu Asn  Asn Tyr Lys
        995                 1000                1005

Thr Thr  Pro Pro Val Leu Asp  Ser Asp Gly Ser Phe  Phe Leu Tyr
    1010                1015                1020

Ser Lys  Leu Thr Val Asp Lys  Ser Arg Trp Gln Gln  Gly Asn Val
    1025                1030                1035

Phe Ser  Cys Ser Val Met His  Glu Ala Leu His Asn  His Tyr Thr
    1040                1045                1050

Gln Lys  Ser Leu Ser Leu Ser  Pro Gly Lys
    1055                1060

<210> SEQ ID NO 122
<211> LENGTH: 3192
<212> TYPE: DNA
<213> ORGANISM: Artificial Sequence
<220> FEATURE:
<223> OTHER INFORMATION: Synthetic (DNA encoding the bispecific antibody
      of SEQ ID NO 121)

<400> SEQUENCE: 122
atgggatggt catgtatcat ccttttttcta gtagcaactg caactggagt acattcagag       60
gttcagctgg tggagtctgg cggtggcctg gtgcagccag ggggctcact ccgtttgtcc      120
tgtgcagctt ctggcttcac cttcactgat tactacatga ctgggtgcg tcaggccccg       180 ggtaagggcc tggaatggtt gggttttatt agaaacaaag ctaatggtta cacaacagag      240
tacagtgcat ctgtgaaggg tcgtttcact ataagcagag ataattccaa aaacacactg      300
tacctgcaga tgaacagcct gcgtgctgag acactgccg tcattattg cctagagat         360 aactggtttg cttactgggg ccaagggact ctggtcaccg tctcctcggg cctgggcggc      420
ctgggcggcg gcggcagcgg cggcggcggc agcggcggca gcggcgt gggcagcgat         480 atccagatga cccagtcccc gagctccctg tccgcctctg tgggcgatag ggtcaccatc      540
acctgcaagt ccagtcagag tcttttagct agtggcaacc aaaataacta cttggcctgg      600
caccaacaga aaccaggaaa agctccgaaa atgctgatta tttgggcatc cactagggta      660
tctggagtcc cttctcgctt ctctggctcc gggtctggga cggatttcac tctgaccatc      720
agcagtctgc agccggaaga cttcgcaact tattactgtc agcagtccta cagccgcccg      780
tacacgttcg gacagggtac caaggtggag atcaaacgtg agcccaaatc ttgtgacaaa      840
actcacacat gcccaccgtg cccagcacct gaactcctgg ggggcccgtc agtcttcctc      900
ttccccccaa aacccaagga caccctcatg atctcccgga cccctgaggt cacatgcgtg      960
gtggtggacg tgagccacga agaccctgag gtcaagttca actggtacgt ggacggcgtg     1020
gaggtgcata atgccaagac aaagccgcgg gaggagcagt acaacagcac gtaccgtgtg     1080
```

```
gtcagcgtcc tcaccgtcct gcaccaggac tggctgaatg gcaaggagta caagtgcaag    1140
gtctccaaca aagccctccc agcccccatc gagaaaacca tctccaaagc caagggcag     1200 ccccgagaac cacaggtgta caccctgccc ccatcccggg aagagatgac caagaaccag    1260
gtcagcctga cctgcctggt caaaggcttc tatcccagcg acatcgccgt ggagtgggag    1320
agcaatgggc agccggagaa caactacaag accacgcctc ccgtgctgga ctccgacggc    1380
tccttcttcc tctacagcaa gctcaccgtg gacaagagca ggtggcagca ggggaacgtc    1440
ttctcatgct ccgtgatgca tgaggctctg cacaaccact acacgcagaa gagcctctcc    1500
ctgtctccgg gtaaaatgca gatcttcgtg aaaaccctga ccggcaagac catcaccctg    1560
gaagtggaac cagcgacac catcgagaac gtgaaggcca agatccagga caaagagggc     1620
atcccccccg accagcagag actgatcttc gccggcaagc agctggaaga tggcagaacc    1680
ctgagcgact acaacatcca gaaagagtcc accctgcacc tggtgctgcg gctgagaggc    1740
ggaggatccc aggtgcagct gcaggagagc ggcggcggcc tggtgaagcc cggcggcagc    1800
ctgcgcctga gctgcgccgc cagcggcttc accttcagca gctactggat gagctgggtg    1860
cgccaggccc ccggcaaggg cctggagtgg gtggccaaca tcaaccgcga cggcagcgcc    1920
agctactacg tggacagcgt gaagggccgc ttcaccatca gccgcgacga cgccaagaac    1980
agcctgtacc tgcagatgaa cagcctgcgc gccgaggaca ccgccgtgta ctactgcgcc    2040
cgcgaccgcg gcgtgggcta cttcgacctg tggggccgcg gcaccctggt gaccgtgagc    2100
agcgccagca ccggaggcgg cggaagcggc ggaggaggct ctggcggcgg cggaagccag    2160
agcgccctga cccagccccg cagcgtgagc ggcagccccg gcagagcat caccatcagc     2220 tgcaccggca ccagcagcga cgtgggcggc tacaacttcg tgagctggta ccagcagcac    2280
cccggcaagg cccccaagct gatgatctac gacgtgagcg accgccccag cggcgtgagc    2340
gaccgcttca gcggcagcaa gagcggcaac accgccagcc tgatcatcag cggcctgcag    2400
gccgacgacg aggccgacta ctactgcagc agctacggca gcagcacc ccacgtgatc      2460 ttcggcggcg gcaccaaggt gaccgtgctg ggcgagccca atcttgtga caaaactcac     2520 acatgcccac cgtgcccagc acctgaactc ctggggggac cgtcagtctt cctcttcccc    2580
ccaaaaccca aggacaccct catgatctcc cggacccctg aggtcacatg cgtggtggtc    2640
gacgtgagcc acgaagaccc tgaggtcaag ttcaactggt acgtggacgg cgtggaggtg    2700
cataatgcca agacaaagcc gcgggaggag cagtacaaca gcacgtaccg tgtggtcagc    2760
gtcctcaccg tcctgcacca ggactggctg aatggcaagg agtacaagtg caaggtctcc    2820
aacaaagccc tcccagcccc catcgagaaa accatctcca aagccaaagg gcagccccga    2880
gaaccacagg tgtacacccct gcccccatcc cgggaagaga tgaccaagaa ccaggtcagc    2940
ctgacctgcc tggtcaaagg cttctatccc agcgacatcg ccgtggagtg ggagagcaat    3000
gggcagccgg agaacaacta caagaccacg cctcccgtgc tggactccga cggctccttc    3060
ttcctctaca gcaagctcac cgtggacaag agcaggtggc agcaggggaa cgtcttctca    3120
tgctccgtga tgcatgaggc tctgcacaac cactacacgc agaagagcct ctccctgtct    3180
ccgggtaaat ga                                                       3192
```

<210> SEQ ID NO 123
<211> LENGTH: 1500
<212> TYPE: DNA
<213> ORGANISM: Artificial Sequence
<220> FEATURE:

<223> OTHER INFORMATION: Synthetic (DNA encoding control anti-Her3 antibody)

<400> SEQUENCE: 123

```
atgggctgga gctgcatcat cctgttcctg gtggccaccg ccaccggcgt gcacagccag      60
gtgcagctgc aggagagcgg cggcggcctg gtgaagcccg gcggcagcct gcgcctgagc     120
tgcgccgcca gcggcttcac cttcagcagc tactggatga gctgggtgcg ccaggccccc     180
ggcaagggcc tggagtgggt ggccaacatc aaccgcgacg gcagcgccag ctactacgtg     240
gacagcgtga agggccgctt caccatcagc cgcgacgacg ccaagaacag cctgtacctg     300
cagatgaaca gcctgcgcgc cgaggacacc gccgtgtact actgcgcccg caccgcggc      360
gtgggctact cgacctgtg gggccgcggc accctggtga ccgtgagcag cgccagcacc     420
ggcggcggcg cagcggcgg cggcggcagc ggcggcggcg cagccagag cgccctgacc     480
cagccccgcca gcgtgagcgg cagccccggc cagagcatca ccatcagctg caccggcacc     540
agcagcgacg tgggcggcta caacttcgtg agctggtacc agcagcaccc cggcaaggcc     600
cccaagctga tgatctacga cgtgagcgac cgccccagcg gcgtgagcga ccgcttcagc     660
ggcagcaaga gcggcaacac cgccagcctg atcatcagcg gcctgcaggc cgacgacgag     720
gccgactact actgcagcag ctacggcagc agcagcaccc acgtgatctt cggcggcggc     780
accaaggtga ccgtgctggg cgagcccaaa tcttgtgaca aaactcacac atgcccaccg     840
tgcccagcac ctgaactcct ggggggcccg tcagtcttcc tcttccccc aaaacccaag     900
gacaccctca tgatctcccg gacccctgag gtcacatgcg tggtggtgga cgtgagccac     960
gaagaccctg aggtcaagtt caactggtac gtggacggcg tggaggtgca taatgccaag    1020
acaaagccgc gggaggagca gtacaacagc acgtaccgtg tggtcagcgt cctcaccgtc    1080
ctgcaccagg actggctgaa tggcaaggag tacaagtgca aggtctccaa caaagccctc    1140
ccagccccca tcgagaaaac catctccaaa gccaaagggc agccccgaga accacaggtg    1200
tacaccctgc ccccatcccg ggaagagatg accaagaacc aggtcagcct gacctgcctg    1260
gtcaaaggct tctatcccag cgacatcgcc gtggagtggg agagcaatgg gcagccggag    1320
aacaactaca agaccacgcc tcccgtgctg gactccgacg gctccttctt cctctacagc    1380
aagctcaccg tggacaagag caggtggcag caggggaacg tcttctcatg ctccgtgatg    1440
catgaggctc tgcacaacca ctacacgcag aagagcctct ccctgtctcc gggtaaatga    1500
```

<210> SEQ ID NO 124
<211> LENGTH: 1066
<212> TYPE: PRT
<213> ORGANISM: Artificial Sequence
<220> FEATURE:
<223> OTHER INFORMATION: Synthetic (anti-c-Met/anti-Ang2 bispecific antibody without knob and hole)

<400> SEQUENCE: 124

```
Met Gly Trp Ser Cys Ile Ile Leu Phe Leu Val Ala Thr Ala Thr Gly
  1               5                  10                  15

Val His Ser Glu Val Gln Leu Val Glu Ser Gly Gly Gly Leu Val Gln
             20                  25                  30

Pro Gly Gly Ser Leu Arg Leu Ser Cys Ala Ala Ser Gly Phe Thr Phe
         35                  40                  45

Thr Asp Tyr Tyr Met Ser Trp Val Arg Gln Ala Pro Gly Lys Gly Leu
     50                  55                  60

Glu Trp Leu Gly Phe Ile Arg Asn Lys Ala Asn Gly Tyr Thr Thr Glu
```

```
                65                  70                  75                  80
Tyr Ser Ala Ser Val Lys Gly Arg Phe Thr Ile Ser Arg Asp Asn Ser
                    85                  90                  95
Lys Asn Thr Leu Tyr Leu Gln Met Asn Ser Leu Arg Ala Glu Asp Thr
                    100                 105                 110
Ala Val Tyr Tyr Cys Ala Arg Asp Asn Trp Phe Ala Tyr Trp Gly Gln
                    115                 120                 125
Gly Thr Leu Val Thr Val Ser Ser Gly Leu Gly Gly Leu Gly Gly Gly
                    130                 135                 140
Gly Ser Gly Gly Gly Ser Gly Gly Ser Ser Gly Val Gly Ser Asp
145                 150                 155                 160
Ile Gln Met Thr Gln Ser Pro Ser Ser Leu Ser Ala Ser Val Gly Asp
                    165                 170                 175
Arg Val Thr Ile Thr Cys Lys Ser Ser Gln Ser Leu Leu Ala Ser Gly
                    180                 185                 190
Asn Gln Asn Asn Tyr Leu Ala Trp His Gln Gln Lys Pro Gly Lys Ala
                    195                 200                 205
Pro Lys Met Leu Ile Ile Trp Ala Ser Thr Arg Val Ser Gly Val Pro
                    210                 215                 220
Ser Arg Phe Ser Gly Ser Gly Ser Gly Thr Asp Phe Thr Leu Thr Ile
225                 230                 235                 240
Ser Ser Leu Gln Pro Glu Asp Phe Ala Thr Tyr Tyr Cys Gln Gln Ser
                    245                 250                 255
Tyr Ser Arg Pro Tyr Thr Phe Gly Gln Gly Thr Lys Val Glu Ile Lys
                    260                 265                 270
Arg Glu Pro Lys Ser Cys Asp Lys Thr His Thr Cys Pro Pro Cys Pro
                    275                 280                 285
Ala Pro Glu Leu Leu Gly Gly Pro Ser Val Phe Leu Phe Pro Pro Lys
                    290                 295                 300
Pro Lys Asp Thr Leu Met Ile Ser Arg Thr Pro Glu Val Thr Cys Val
305                 310                 315                 320
Val Val Asp Val Ser His Glu Asp Pro Glu Val Lys Phe Asn Trp Tyr
                    325                 330                 335
Val Asp Gly Val Glu Val His Asn Ala Lys Thr Lys Pro Arg Glu Glu
                    340                 345                 350
Gln Tyr Asn Ser Thr Tyr Arg Val Val Ser Val Leu Thr Val Leu His
                    355                 360                 365
Gln Asp Trp Leu Asn Gly Lys Glu Tyr Lys Cys Lys Val Ser Asn Lys
                    370                 375                 380
Ala Leu Pro Ala Pro Ile Glu Lys Thr Ile Ser Lys Ala Lys Gly Gln
385                 390                 395                 400
Pro Arg Glu Pro Gln Val Tyr Thr Leu Pro Pro Ser Arg Glu Glu Met
                    405                 410                 415
Thr Lys Asn Gln Val Ser Leu Thr Cys Leu Val Lys Gly Phe Tyr Pro
                    420                 425                 430
Ser Asp Ile Ala Val Glu Trp Glu Ser Asn Gly Gln Pro Glu Asn Asn
                    435                 440                 445
Tyr Lys Thr Thr Pro Pro Val Leu Asp Ser Asp Gly Ser Phe Phe Leu
                    450                 455                 460
Tyr Ser Lys Leu Thr Val Asp Lys Ser Arg Trp Gln Gln Gly Asn Val
465                 470                 475                 480
Phe Ser Cys Ser Val Met His Glu Ala Leu His Asn His Tyr Thr Gln
                    485                 490                 495
```

```
Lys Ser Leu Ser Leu Ser Pro Gly Lys Met Gln Ile Phe Val Lys Thr
            500                 505                 510
Leu Thr Gly Lys Thr Ile Thr Leu Glu Val Glu Pro Ser Asp Thr Ile
        515                 520                 525
Glu Asn Val Lys Ala Lys Ile Gln Asp Lys Glu Gly Ile Pro Pro Asp
    530                 535                 540
Gln Gln Arg Leu Ile Phe Ala Gly Lys Gln Leu Glu Asp Gly Arg Thr
545                 550                 555                 560
Leu Ser Asp Tyr Asn Ile Gln Lys Glu Ser Thr Leu His Leu Val Leu
                565                 570                 575
Arg Leu Arg Gly Gly Ser Gln Val Gln Leu Val Gln Ser Gly Ala
            580                 585                 590
Glu Val Lys Lys Pro Gly Ala Ser Val Lys Val Ser Cys Lys Ala Ser
            595                 600                 605
Gly Tyr Thr Phe Thr Gly Tyr Tyr Met His Trp Val Arg Gln Ala Pro
        610                 615                 620
Gly Gln Gly Leu Glu Trp Met Gly Trp Ile Asn Pro Asn Ser Gly Gly
625                 630                 635                 640
Thr Asn Tyr Ala Gln Lys Phe Gln Gly Arg Val Thr Met Thr Arg Asp
                645                 650                 655
Thr Ser Ile Ser Thr Ala Tyr Met Glu Leu Ser Arg Leu Arg Ser Asp
            660                 665                 670
Asp Thr Ala Val Tyr Tyr Cys Ala Arg Ser Pro Asn Pro Tyr Tyr Tyr
        675                 680                 685
Asp Ser Ser Gly Tyr Tyr Pro Gly Ala Phe Asp Ile Trp Gly Gln
        690                 695                 700
Gly Thr Met Val Thr Val Ser Gly Gly Gly Ser Gly Gly Gly Gly
705                 710                 715                 720
Ser Gly Gly Gly Ser Gln Pro Gly Leu Thr Gln Pro Pro Ser Val
                725                 730                 735
Ser Val Ala Pro Gly Gln Thr Ala Arg Ile Thr Cys Gly Gly Asn Asn
            740                 745                 750
Ile Gly Ser Lys Ser Val His Trp Tyr Gln Gln Lys Pro Gly Gln Ala
            755                 760                 765
Pro Val Leu Val Val Tyr Asp Asp Ser Asp Arg Pro Ser Gly Ile Pro
        770                 775                 780
Glu Arg Phe Ser Gly Ser Asn Ser Gly Asn Thr Ala Thr Leu Thr Ile
785                 790                 795                 800
Ser Arg Val Glu Ala Gly Asp Glu Ala Asp Tyr Tyr Cys Gln Val Trp
                805                 810                 815
Asp Ser Ser Asp His Tyr Val Phe Gly Thr Gly Thr Lys Val Thr
            820                 825                 830
Val Leu Glu Pro Lys Ser Cys Asp Lys Thr His Thr Cys Pro Pro Cys
        835                 840                 845
Pro Ala Pro Glu Leu Leu Gly Gly Pro Ser Val Phe Leu Phe Pro Pro
        850                 855                 860
Lys Pro Lys Asp Thr Leu Met Ile Ser Arg Thr Pro Glu Val Thr Cys
865                 870                 875                 880
Val Val Val Asp Val Ser His Glu Asp Pro Glu Val Lys Phe Asn Trp
                885                 890                 895
Tyr Val Asp Gly Val Glu Val His Asn Ala Lys Thr Lys Pro Arg Glu
            900                 905                 910
```

```
Glu Gln Tyr Asn Ser Thr Tyr Arg Val Val Ser Val Leu Thr Val Leu
        915                 920                 925

His Gln Asp Trp Leu Asn Gly Lys Glu Tyr Lys Cys Lys Val Ser Asn
        930                 935                 940

Lys Ala Leu Pro Ala Pro Ile Glu Lys Thr Ile Ser Lys Ala Lys Gly
945                 950                 955                 960

Gln Pro Arg Glu Pro Gln Val Tyr Thr Leu Pro Pro Ser Arg Glu Glu
            965                 970                 975

Met Thr Lys Asn Gln Val Ser Leu Thr Cys Leu Val Lys Gly Phe Tyr
        980                 985                 990

Pro Ser Asp Ile Ala Val Glu Trp  Glu Ser Asn Gly Gln  Pro Glu Asn
        995                 1000                 1005

Asn Tyr  Lys Thr Thr Pro Pro  Val Leu Asp Ser Asp  Gly Ser Phe
    1010                 1015                 1020

Phe Leu  Tyr Ser Lys Leu Thr  Val Asp Lys Ser Arg  Trp Gln Gln
    1025                 1030                 1035

Gly Asn  Val Phe Ser Cys Ser  Val Met His Glu Ala  Leu His Asn
    1040                 1045                 1050

His Tyr  Thr Gln Lys Ser Leu  Ser Leu Ser Pro Gly  Lys
    1055                 1060                 1065

<210> SEQ ID NO 125
<211> LENGTH: 3201
<212> TYPE: DNA
<213> ORGANISM: Artificial Sequence
<220> FEATURE:
<223> OTHER INFORMATION: Synthetic (DNA encoding the bispecific antibody
      of SEQ ID NO: 124)

<400> SEQUENCE: 125
atgggatggt catgtatcat ccttttctta gtagcaactg caactggagt acattcagag      60
gttcagctgg tggagtctgg cggtggcctg gtgcagccag ggggctcact ccgtttgtcc     120
tgtgcagctt ctggcttcac cttcactgat tactacatga gctgggtgcg tcaggccccg     180
ggtaagggcc tggaatggtt gggttttatt agaaacaaag ctaatggtta cacaacagag     240
tacagtgcat ctgtgaaggg tcgtttcact ataagcagag ataattccaa aaacacactg     300
tacctgcaga tgaacagcct gcgtgctgag gacactgccg tctattattg tctagagat      360 aactggtttg cttactgggg ccaagggact ctggtcaccg tctcctcggg cctgggcggc     420
ctgggcggcg gcggcagcgg cggcggcggc agcggcggca gcggcggcgt gggcagcgat     480
atccagatga cccagtcccc gagctccctg tccgcctctg tgggcgatag ggtcaccatc     540
acctgcaagt ccagtcagag tcttttagct agtggcaacc aaaataacta cttggcctgg     600
caccaacaga aaccaggaaa agctccgaaa atgctgatta tttgggcatc cactagggta     660
tctggagtcc cttctcgctt ctctggctcc gggtctggga cggatttcac tctgaccatc     720
agcagtctgc agccggaaga cttcgcaact tattactgtc agcagtccta cagccgcccg     780
tacacgttcg gacagggtac caaggtggag atcaaacgtg agcccaaatc ttgtgacaaa     840
actcacacat gcccaccgtg cccagcacct gaactcctgg ggggcccgtc agtcttcctc     900
ttccccccaa aacccaagga caccctcatg atctcccgga cccctgaggt cacatgcgtg     960
gtggtggacg tgagccacga agaccctgag gtcaagttca actggtacgt ggacggcgtg    1020
gaggtgcata atgccaagac aaagccgcgg gaggagcagt acaacagcac gtaccgtgtg    1080
gtcagcgtcc tcaccgtcct gcaccaggac tggctgaatg gcaaggagta caagtgcaag    1140
```

```
gtctccaaca aagccctccc agcccccatc gagaaaacca tctccaaagc caaagggcag    1200
ccccgagaac cacaggtgta caccctgccc ccatcccggg aagagatgac caagaaccag    1260
gtcagcctga cctgcctggt caaaggcttc tatcccagcg acatcgccgt ggagtgggag    1320
agcaatgggc agccggagaa caactacaag accacgcctc ccgtgctgga ctccgacggc    1380
tccttcttcc tctacagcaa gctcaccgtg gacaagagca ggtggcagca ggggaacgtc    1440
ttctcatgct ccgtgatgca tgaggctctg cacaaccact acacgcagaa gagcctctcc    1500
ctgtctccgg gtaaaatgca gatcttcgtg aaaaccctga ccggcaagac catcaccctg    1560
gaagtggaac ccagcgacac catcgagaac gtgaaggcca agatccagga caaagagggc    1620
atcccccccg accagcagag actgatcttc gccggcaagc agctggaaga tggcagaacc    1680
ctgagcgact acaacatcca gaaagagtcc accctgcacc tggtgctgcg gctgagaggc    1740
ggaggatccc aggtgcagct ggtgcagagc ggcgccgagg tgaagaagcc cggcgccagc    1800
gtgaaggtga gctgcaaggc cagcggctac accttcaccg gctactacat gcactgggtg    1860
cgccaggccc ccgccaggg cctggagtgg atgggctgga tcaaccccaa cagcggcggc    1920
accaactacg cccagaagtt ccagggccgc gtgaccatga cccgcgacac cagcatcagc    1980
accgcctaca tggagctgag ccgcctgcgc agcgacgaca ccgccgtgta ctactgcgcc    2040
cgcagcccca cccctactac tacgacagc agcggctact actacccgg cgccttcgac    2100 atctggggcc agggcaccat ggtgaccgtg agcgcggcg cgcagcg cggcggcg    2160 agcggcggcg cggcagcca gcccggcctg acccagcccc cagcgtgag cgtggccccc    2220 ggccagaccg cccgcatcac ctgcggcggc aacaacatcg gcagcaagag cgtgcactgg    2280
taccagcaga gcccggcca ggcccccgtg ctggtggtgt acgacgacag cgaccgcccc    2340
agcggcatcc ccgagcgctt cagcggcagc aacagcggca acaccgccac cctgaccatc    2400
agccgcgtgg aggccggcga cgaggccgac tactactgcc aggtgtggga cagcagcagc    2460
gaccactacg tgttcggcac cggcaccaag gtgaccgtgc tggagcccaa atcttgtgac    2520
aaaactcaca catgcccacc gtgcccagca cctgaactcc tggggggacc gtcagtcttc    2580
ctcttccccc caaaacccaa ggacaccctc atgatctccc ggacccctga ggtcacatgc    2640
gtggtggtcg acgtgagcca cgaagaccct gaggtcaagt tcaactggta cgtggacggc    2700
gtggaggtgc ataatgccaa gacaaagccg cgggaggagc agtacaacag cacgtaccgt    2760
gtggtcagcg tcctcaccgt cctgcaccag gactggctga atggcaagga gtacaagtgc    2820
aaggtctcca acaaagccct cccagccccc atcgagaaaa ccatctccaa agccaaaggg    2880
cagccccgag aaccacaggt gtacaccctg cccccatccc gggaagagat gaccaagaac    2940
caggtcagcc tgacctgcct ggtcaaaggc ttctatccca gcgacatcgc cgtggagtgg    3000
gagagcaatg gcagccgga gaacaactac aagaccacgc ctcccgtgct ggactccgac    3060
ggctccttct tcctctacag caagctcacc gtggacaaga gcaggtggca gcagggaaac    3120
gtcttctcat gctccgtgat gcatgaggct ctgcacaacc actacacgca gaagagcctc    3180
tccctgtctc cgggtaaatg a                                              3201
```

<210> SEQ ID NO 126
<211> LENGTH: 1066
<212> TYPE: PRT
<213> ORGANISM: Artificial Sequence
<220> FEATURE:
<223> OTHER INFORMATION: Synthetic (anti-c-Met/anti-Ang2 bispecific antibody with knob and hole)

```
<400> SEQUENCE: 126

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Tyr Met Ser Trp Val Arg Gln Ala Pro Gly Lys Gly Leu
    50                  55                  60

Glu Trp Leu Gly Phe Ile Arg Asn Lys Ala Asn Gly Tyr Thr Thr Glu
65                  70                  75                  80

Tyr Ser Ala Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Asn Trp Phe Ala Tyr Trp Gly Gln
        115                 120                 125

Gly Thr Leu Val Thr Val Ser Ser Gly Leu Gly Gly Leu Gly Gly Gly
    130                 135                 140

Gly Ser Gly Gly Gly Ser Gly Gly Ser Gly Val Gly Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ser Ser Gln Ser Leu Leu Ala Ser Gly
            180                 185                 190

Asn Gln Asn Asn Tyr Leu Ala Trp His Gln Gln Lys Pro Gly Lys Ala
        195                 200                 205

Pro Lys Met Leu Ile Ile Trp Ala Ser Thr Arg Val Ser Gly Val Pro
    210                 215                 220

Ser Arg Phe Ser Gly Ser Gly Ser Gly Thr Asp Phe Thr Leu Thr Ile
225                 230                 235                 240

Ser Ser Leu Gln Pro Glu Asp Phe Ala Thr Tyr Tyr Cys Gln Gln Ser
                245                 250                 255

Tyr Ser Arg Pro Tyr Thr Phe Gly Gln Gly Thr Lys Val Glu Ile Lys
            260                 265                 270

Arg Glu Pro Lys Ser Cys Asp Lys Thr His Thr Cys Pro Pro Cys Pro
        275                 280                 285

Ala Pro Glu Leu Leu Gly Gly Pro Ser Val Phe Leu Phe Pro Pro Lys
    290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
    370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Glu Glu Met
                405                 410                 415
```

-continued

```
Thr Lys Asn Gln Val Ser Leu Tyr Cys Leu Val Lys Gly Phe Tyr Pro
            420                 425                 430

Ser Asp Ile Ala Val Glu Trp Glu Ser Asn Gly Gln Pro Glu Asn Asn
            435                 440                 445

Tyr Lys Thr Thr Pro Pro Val Leu Asp Ser Asp Gly Ser Phe Phe Leu
            450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                    485                 490                 495

Lys Ser Leu Ser Leu Ser Pro Gly Lys Met Gln Ile Phe Val Lys Thr
            500                 505                 510

Leu Thr Gly Lys Thr Ile Thr Leu Glu Val Glu Pro Ser Asp Thr Ile
            515                 520                 525

Glu Asn Val Lys Ala Lys Ile Gln Asp Lys Glu Gly Ile Pro Pro Asp
            530                 535                 540

Gln Gln Arg Leu Ile Phe Ala Gly Lys Gln Leu Glu Asp Gly Arg Thr
545                 550                 555                 560

Leu Ser Asp Tyr Asn Ile Gln Lys Glu Ser Thr Leu His Leu Val Leu
                    565                 570                 575

Arg Leu Arg Gly Gly Ser Gln Val Gln Leu Val Gln Ser Gly Ala
            580                 585                 590

Glu Val Lys Lys Pro Gly Ala Ser Val Lys Val Ser Cys Lys Ala Ser
            595                 600                 605

Gly Tyr Thr Phe Thr Gly Tyr Tyr Met His Trp Val Arg Gln Ala Pro
            610                 615                 620

Gly Gln Gly Leu Glu Trp Met Gly Trp Ile Asn Pro Asn Ser Gly Gly
625                 630                 635                 640

Thr Asn Tyr Ala Gln Lys Phe Gln Gly Arg Val Thr Met Thr Arg Asp
                    645                 650                 655

Thr Ser Ile Ser Thr Ala Tyr Met Glu Leu Ser Arg Leu Arg Ser Asp
            660                 665                 670

Asp Thr Ala Val Tyr Tyr Cys Ala Arg Ser Pro Asn Pro Tyr Tyr Tyr
            675                 680                 685

Asp Ser Ser Gly Tyr Tyr Pro Gly Ala Phe Asp Ile Trp Gly Gln
            690                 695                 700

Gly Thr Met Val Thr Val Ser Gly Gly Gly Ser Gly Gly Gly Gly
705                 710                 715                 720

Ser Gly Gly Gly Gly Ser Gln Pro Gly Leu Thr Gln Pro Pro Ser Val
                    725                 730                 735

Ser Val Ala Pro Gly Gln Thr Ala Arg Ile Thr Cys Gly Gly Asn Asn
            740                 745                 750

Ile Gly Ser Lys Ser Val His Trp Tyr Gln Gln Lys Pro Gly Gln Ala
            755                 760                 765

Pro Val Leu Val Val Tyr Asp Ser Asp Arg Pro Ser Gly Ile Pro
            770                 775                 780

Glu Arg Phe Ser Gly Ser Asn Ser Gly Asn Thr Ala Thr Leu Thr Ile
785                 790                 795                 800

Ser Arg Val Glu Ala Gly Asp Glu Ala Asp Tyr Tyr Cys Gln Val Trp
                    805                 810                 815

Asp Ser Ser Asp His Tyr Val Phe Gly Thr Gly Thr Lys Val Thr
            820                 825                 830
```

```
Val Leu Glu Pro Lys Ser Cys Asp Lys Thr His Thr Cys Pro Pro Cys
        835                 840                 845

Pro Ala Pro Glu Leu Leu Gly Gly Pro Ser Val Phe Leu Phe Pro Pro
        850                 855                 860

Lys Pro Lys Asp Thr Leu Met Ile Ser Arg Thr Pro Glu Val Thr Cys
865                 870                 875                 880

Val Val Val Asp Val Ser His Glu Asp Pro Glu Val Lys Phe Asn Trp
                885                 890                 895

Tyr Val Asp Gly Val Glu Val His Asn Ala Lys Thr Lys Pro Arg Glu
            900                 905                 910

Glu Gln Tyr Asn Ser Thr Tyr Arg Val Val Ser Val Leu Thr Val Leu
        915                 920                 925

His Gln Asp Trp Leu Asn Gly Lys Glu Tyr Lys Cys Lys Val Ser Asn
    930                 935                 940

Lys Ala Leu Pro Ala Pro Ile Glu Lys Thr Ile Ser Lys Ala Lys Gly
945                 950                 955                 960

Gln Pro Arg Glu Pro Gln Val Tyr Thr Leu Pro Pro Ser Arg Glu Glu
                965                 970                 975

Met Thr Lys Asn Gln Val Ser Leu Thr Cys Leu Val Lys Gly Phe Tyr
            980                 985                 990

Pro Ser Asp Ile Ala Val Glu Trp  Glu Ser Asn Gly Gln  Pro Glu Asn
        995                 1000                1005

Asn Tyr  Lys Thr Thr Pro Pro  Val Leu Asp Ser Asp  Gly Ser Phe
    1010                1015                1020

Phe Leu  Thr Ser Lys Leu Thr  Val Asp Lys Ser Arg  Trp Gln Gln
    1025                1030                1035

Gly Asn  Val Phe Ser Cys Ser  Val Met His Glu Ala  Leu His Asn
    1040                1045                1050

His Tyr  Thr Gln Lys Ser Leu  Ser Leu Ser Pro Gly  Lys
    1055                1060                1065

<210> SEQ ID NO 127
<211> LENGTH: 3201
<212> TYPE: DNA
<213> ORGANISM: Artificial Sequence
<220> FEATURE:
<223> OTHER INFORMATION: Synthetic (DNA encoding the bispecific antibody
      of SEQ ID NO 126)

<400> SEQUENCE: 127
atgggatggt catgtatcat ccttttttcta gtagcaactg caactggagt acattcagag    60
gttcagctgg tggagtctgg cggtggcctg gtgcagccag ggggctcact ccgtttgtcc   120
tgtgcagctt ctggcttcac cttcactgat tactacatga gctgggtgcg tcaggccccg   180
ggtaagggcc tggaatggtt gggttttatt agaaacaaag ctaatggtta cacaacagag   240
tacagtgcat ctgtgaaggg tcgtttcact ataagcagag ataattccaa aaacacactg   300
tacctgcaga tgaacagcct gcgtgctgag gacactgccg tctattattg tgctagagat   360
aactggtttg cttactgggg ccaagggact ctggtcaccg tctcctcggg cctgggcggc   420
ctgggcggag gaggctctgg aggcggcgga agcggcggca gcggcggcgt gggcagcgat   480
atccagatga cccagtcccc gagctccctg tccgcctctg tgggcgatag ggtcaccatc   540
acctgcaagt ccagtcagag tctttttagct agtggcaacc aaaataacta cttggcctgg   600
caccaacaga aaccaggaaa agctccgaaa atgctgatta tttgggcatc cactagggta   660
tctggagtcc cttctcgctt ctctgggtcc gggtctggga cggatttcac tctgaccatc   720
```

-continued

```
agcagtctgc agccggaaga cttcgcaact tattactgtc agcagtccta cagccgcccg    780
tacacgttcg gacagggtac caaggtggag atcaaacgtg agcccaagag ctgcgacaag    840
acccacacct gccccccctg ccccgccccc gagctgctgg gcggcccag cgtgttcctg     900 ttcccccca agcccaagga caccctgatg atcagccgca ccccgaggt gacctgcgtg      960 gtggtggacg tgagccacga ggaccccgag gtgaagttca actggtacgt ggacggcgtg    1020
gaggtgcaca cgccaagac caagcccgc gaggagcagt acaacagcac ctaccgcgtg      1080
gtgagcgtgc tgaccgtgct gcaccaggac tggctgaacg gcaaggagta caagtgcaag    1140
gtgagcaaca aggccctgcc cgcccccatc gagaagacca tcagcaaggc caagggccag    1200
ccccgcgagc cccaggtgta caccctgccc ccagccgcg aggagatgac caagaaccag     1260
gtgagcctgt actgcctggt gaagggcttc taccccagcg acatcgccgt ggagtgggag    1320
agcaacggcc agcccgagaa caactacaag accacccccc ccgtgctgga cagcgacggc    1380
agcttcttcc tgtacagcaa gctgaccgtg gacaagagcc gctggcagca gggcaacgtg    1440
ttcagctgca gcgtgatgca cgaggccctg cacaaccact acacccagaa gagcctgagc    1500
ctgagccccg gcaagatgca gatcttcgtg aagaccctga ccggcaagac catcaccctg    1560
gaggtggagc ccagcgacac catcgagaac gtgaaggcca agatccagga caaggagggc    1620 atccccccg accagcagcg cctgatcttc gccggcaagc agctggagga cggccgcacc    1680
ctgagcgact acaacatcca agagagc accctgcacc tggtgctgcg cctgcgcggc      1740
ggcggatccc aggtgcagct ggtgcagagc ggcgccgagg tgaagaagcc cggcgccagc    1800
gtgaaggtga gctgcaaggc cagcggctac accttcaccg gctactacat gcactgggtg    1860
cgccaggccc ccggccaggg cctggagtgg atgggctgga tcaacccaa cagcggcggc    1920 accaactacg cccagaagtt ccaggccgc gtgaccatga cccgcgacac cagcatcagc    1980
accgcctaca tggagctgag ccgcctgcgc agcgacgaca ccgccgtgta ctactgcgcc    2040
cgcagcccca cccctactac tacgacagc agcggctact actaccccgg cgccttcgac    2100
atctggggcc agggcaccat ggtgaccgtg agcggaggcg gcggaagcgg cggaggaggc    2160
tctggcggcg gcggaagcca gcccggcctg acccagcccc ccagcgtgag cgtggccccc    2220
ggccagaccg cccgcatcac ctgcggcggc aacaacatcg gcagcaagag cgtgcactgg    2280
taccagcaga agcccggcca ggccccccgtg ctggtggtgt acgacgacag cgaccgcccc    2340
agcggcatcc ccgagcgctt cagcggcagc aacagcggca acaccgccac cctgaccatc    2400
agccgcgtga aggccggcga cgaggccgac tactactgcc aggtgtggga cagcagcagc    2460
gaccactacg tgttcggcac cggcaccaag gtgaccgtgc tggagcccaa gagctgcgac    2520
aagacccaca cctgcccccc ctgccccgcc ccgagctgc tgggcggccc cagcgtgttc     2580
ctgttccccc ccaagcccaa ggacaccctg atgatcagcc gcaccccga ggtgacctgc     2640 gtggtggtgg acgtgagcca cgaggacccc gaggtgaagt tcaactggta cgtggacggc    2700
gtggaggtgc acaacgccaa gaccaagccc cgcgaggagc agtacaacag cacctaccgc    2760
gtggtgagcg tgctgaccgt gctgcaccag gactggctga acggcaagga gtacaagtgc    2820
aaggtgagca acaaggccct gccccccc atcgagaaga ccatcagcaa ggccaagggc      2880
cagccccgcg agccccaggt gtacaccctg cccccagcc gcgaggagat gaccaagaac     2940
caggtgagcc tgacctgcct ggtgaagggc ttctacccca gcgacatcgc cgtggagtgg    3000
gagagcaacg gccagcccga gaacaactac aagaccaccc cccccgtgct ggacagcgac    3060
```

-continued

```
ggcagcttct tcctgaccag caagctgacc gtggacaaga gccgctggca gcagggcaac    3120
gtgttcagct gcagcgtgat gcacgaggcc ctgcacaacc actacaccca agaagagcctg    3180 agcctgagcc ccggcaagtg a                                               3201
```

<210> SEQ ID NO 128
<211> LENGTH: 254
<212> TYPE: PRT
<213> ORGANISM: Artificial Sequence
<220> FEATURE:
<223> OTHER INFORMATION: Synthetic (C-Met binding region)

<400> SEQUENCE: 128

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Gly Leu Gly Gly Leu Gly Gly Gly Gly Ser Gly
        115                 120                 125

Gly Gly Gly Ser Gly Gly Ser Ser Gly Val Gly Ser Asp Ile Gln Met
    130                 135                 140

Thr Gln Ser Pro Ser Ser Leu Ser Ala Ser Val Gly Asp Arg Val Thr
145                 150                 155                 160

Ile Thr Cys Lys Ser Ser Gln Ser Leu Leu Ala Ser Gly Asn Gln Asn
                165                 170                 175

Asn Tyr Leu Ala Trp His Gln Gln Lys Pro Gly Lys Ala Pro Lys Met
            180                 185                 190

Leu Ile Ile Trp Ala Ser Thr Arg Val Ser Gly Val Pro Ser Arg Phe
        195                 200                 205

Ser Gly Ser Gly Ser Gly Thr Asp Phe Thr Leu Thr Ile Ser Ser Leu
    210                 215                 220

Gln Pro Glu Asp Phe Ala Thr Tyr Tyr Cys Gln Gln Ser Tyr Ser Arg
225                 230                 235                 240

Pro Tyr Thr Phe Gly Gln Gly Thr Lys Val Glu Ile Lys Arg
                245                 250
```

<210> SEQ ID NO 129
<211> LENGTH: 232
<212> TYPE: PRT
<213> ORGANISM: Artificial Sequence
<220> FEATURE:
<223> OTHER INFORMATION: Synthetic (Fc region)

<400> SEQUENCE: 129

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30
```

Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
             100                 105                 110

Leu Pro Ala Pro Ile Glu Lys Thr Ile Ser Lys Ala Lys Gly Gln Pro
         115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 130
<211> LENGTH: 1527
<212> TYPE: DNA
<213> ORGANISM: Artificial Sequence
<220> FEATURE:
<223> OTHER INFORMATION: Synthetic (DNA encoding Anti-Ang2 scFv-Fc)

<400> SEQUENCE: 130
aagcttgcca ccatgggctg agctgcatc atcctgttcc tggtggccac cgccaccggc     60
gtgcacagcc aggtgcagct ggtgcagagc ggcgccgagg tgaagaagcc cggcgccagc    120
gtgaaggtga gctgcaaggc cagcggctac accttcaccg gctactacat gcactgggtg    180
cgccaggccc ccggccaggg cctggagtgg atgggctgga tcaaccccaa cagcggcggc    240
accaactacg cccagaagtt ccagggccgc gtgaccatga cccgcgacac cagcatcagc    300
accgcctaca tggagctgag ccgcctgcgc agcgacgaca ccgccgtgta ctactgcgcc    360
cgcagcccca cccctactac tacgacagc agcggctact actaccccgg cgccttcgac    420
atctggggcc agggcaccat ggtgaccgtg agcggcggcg gcggcagcgg cggcggcggc    480
agcggcggcg gcggcagcca gcccggcctg acccagcccc ccagcgtgag cgtggccccc    540
ggccagaccg cccgcatcac ctgcggcggc aacaacatcg gcagcaagag cgtgcactgg    600
taccagcaga gcccggcca ggccccccgtg ctggtggtgt acgacgacag cgaccgcccc    660
agcggcatcc ccgagcgctt cagcggcagc aacagcggca acaccgccac cctgaccatc    720
agccgcgtgg aggccggcga cgaggccgac tactactgcc aggtgtggga cagcagcagc    780
gaccactacg tgttcggcac cggcaccaag gtgaccgtgc tggagcccaa atcttgtgac    840
aaaactcaca catgcccacc gtgcccagca cctgaactcc tggggggacc gtcagtcttc    900

```
ctcttccccc caaaacccaa ggacaccctc atgatctccc ggacccctga ggtcacatgc    960
gtggtggtgg acgtgagcca cgaagaccct gaggtcaagt tcaactggta cgtggacggc   1020
gtggaggtgc ataatgccaa gacaaagccg cgggaggagc agtacaacag cacgtaccgt   1080
gtggtcagcg tcctcaccgt cctgcaccag gactggctga atggcaagga gtacaagtgc   1140
aaggtctcca acaaagccct cccagccccc atcgagaaaa ccatctccaa agccaaaggg   1200
cagccccgag aaccacaggt gtacaccctg cccccatccc gggaagagat gaccaagaac   1260
caggtcagcc tgacctgcct ggtcaaaggc ttctatccca gcgacatcgc cgtggagtgg   1320
gagagcaatg ggcagccgga gaacaactac aagaccacgc ctcccgtgct ggactccgac   1380
ggctccttct tcctctacag caagctcacc gtggacaaga gcaggtggca gcaggggaac   1440
gtcttctcat gctccgtgat gcatgaggct ctgcacaacc actacacgca gaagagcctc   1500
tccctgtctc cgggtaaatg actcgag                                       1527
```

<210> SEQ ID NO 131
<211> LENGTH: 19
<212> TYPE: PRT
<213> ORGANISM: Artificial Sequence
<220> FEATURE:
<223> OTHER INFORMATION: Synthetic (signal sequence)

<400> SEQUENCE: 131

Met Gly Trp Ser Cys Ile Ile Leu Phe Leu Val Ala Thr Ala Thr Gly
1               5                   10                  15

Val His Ser

<210> SEQ ID NO 132
<211> LENGTH: 63
<212> TYPE: DNA
<213> ORGANISM: Artificial Sequence
<220> FEATURE:
<223> OTHER INFORMATION: Synthetic (coding DNA sequence of signal
      sequence)

<400> SEQUENCE: 132
gccaccatgg gatggtcatg tatcatcctt tttctagtag caactgcaac tggagtacat    60
tca                                                                  63

<210> SEQ ID NO 133
<211> LENGTH: 254
<212> TYPE: PRT
<213> ORGANISM: Artificial Sequence
<220> FEATURE:
<223> OTHER INFORMATION: Synthetic (Anti-cMET scFv)

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
                20                  25                  30

Tyr Met Ser Trp Val Arg Gln Ala Pro Gly Lys Gly Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr

```
                85                  90                  95
Tyr Cys Ala Arg Asp Asn Trp Phe Ala Tyr Trp Gly Gln Gly Thr Leu
            100                 105                 110

Val Thr Val Ser Ser Gly Leu Gly Gly Leu Gly Gly Gly Ser Gly
        115                 120                 125

Gly Gly Gly Ser Gly Gly Ser Ser Gly Val Gly Ser Asp Ile Gln Met
    130                 135                 140

Thr Gln Ser Pro Ser Ser Leu Ser Ala Ser Val Gly Asp Arg Val Thr
145                 150                 155                 160

Ile Thr Cys Lys Ser Ser Gln Ser Leu Leu Ala Ser Gly Asn Gln Asn
                165                 170                 175

Asn Tyr Leu Ala Trp His Gln Gln Lys Pro Gly Lys Ala Pro Lys Met
            180                 185                 190

Leu Ile Ile Trp Ala Ser Thr Arg Val Ser Gly Val Pro Ser Arg Phe
        195                 200                 205

Ser Gly Ser Gly Ser Gly Thr Asp Phe Thr Leu Thr Ile Ser Ser Leu
    210                 215                 220

Gln Pro Glu Asp Phe Ala Thr Tyr Tyr Cys Gln Gln Ser Tyr Ser Arg
225                 230                 235                 240

Pro Tyr Thr Phe Gly Gln Gly Thr Lys Val Glu Ile Lys Arg
                245                 250
```

<210> SEQ ID NO 134
<211> LENGTH: 762
<212> TYPE: DNA
<213> ORGANISM: Artificial Sequence
<220> FEATURE:
<223> OTHER INFORMATION: Synthetic (codign DNA sequence of Anti-cMET scFv)

<400> SEQUENCE: 134

```
gaggttcagc tggtggagtc tggcggtggc ctggtgcagc caggggctc actccgtttg      60
tcctgtgcag cttctggctt caccttcact gattactaca tgagctgggt gcgtcaggcc    120
ccgggtaagg gcctggaatg gttgggtttt attagaaaca aagctaatgg ttacacaaca    180
gagtacagtg catctgtgaa gggtcgtttc actataagca gagataattc caaaacacac    240
ctgtacctgc agatgaacag cctgcgtgct gaggacactg ccgtctatta ttgtgctaga    300
gataactggt ttgcttactg gggccaaggg actctggtca ccgtctcctc gggcctgggc    360
ggcctgggcg gcggcggcag cggcggcggc ggcagcggcg gcagcagcgg cgtgggcagc    420
gatatccaga tgacccagtc cccgagctcc ctgtccgcct ctgtgggcga tagggtcacc    480
atcacctgca gtccagtca gagtcttta gctagtggca accaaaataa ctacttggcc      540
tggcaccaac agaaaccagg aaaagctccg aaaatgctga ttatttgggc atccactagg    600
gtatctggag tcccttctcg cttctctggc tccgggtctg gacggattt cactctgacc     660
atcagcagtc tgcagccgga agacttcgca acttattact gtcagcagtc ctacagccgc    720
ccgtacacgt tcggacaggg taccaaggtg gagatcaaac gt                       762
```

<210> SEQ ID NO 135
<211> LENGTH: 232
<212> TYPE: PRT
<213> ORGANISM: Artificial Sequence
<220> FEATURE:
<223> OTHER INFORMATION: Synthetic (Fc (Hinge-C2-C3) with knob)

<400> SEQUENCE: 135

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50              55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
            130                 135                 140

Lys Asn Gln Val Ser Leu Tyr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 136
<211> LENGTH: 232
<212> TYPE: PRT
<213> ORGANISM: Artificial Sequence
<220> FEATURE:
<223> OTHER INFORMATION: Synthetic (Fc (Hinge-C2-C3) with hole)

<400> SEQUENCE: 136

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50              55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

```
Arg Glu Pro Gln Val Tyr Thr Leu Pro Pro Ser Arg Glu Glu Met Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Thr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 137
<211> LENGTH: 76
<212> TYPE: PRT
<213> ORGANISM: Artificial Sequence
<220> FEATURE:
<223> OTHER INFORMATION: Synthetic (Ubiquitin)

<400> SEQUENCE: 137

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 138
<211> LENGTH: 228
<212> TYPE: DNA
<213> ORGANISM: Artificial Sequence
<220> FEATURE:
<223> OTHER INFORMATION: Synthetic (coding DNA of Ubiquitin)

<400> SEQUENCE: 138
atgcagatct tcgtgaagac cctgaccggc aagaccatca ccctggaggt ggagcccagc      60
gacaccatcg agaacgtgaa ggccaagatc caggacaagg agggcatccc ccccgaccag     120
cagcgcctga tcttcgccgg caagcagctg gaggacggcc gcaccctgag cgactacaac     180
atccagaagg agagcaccct gcacctggtg ctgcgcctgc gcggcggc                  228

<210> SEQ ID NO 139
<211> LENGTH: 244
<212> TYPE: PRT
<213> ORGANISM: Artificial Sequence
<220> FEATURE:
<223> OTHER INFORMATION: Synthetic (Anti-VEGF scFv)

<400> SEQUENCE: 139

Glu Val Gln Leu Val Gln Ser Gly Ala Glu Val Arg Lys Pro Gly Ala
1               5                   10                  15

Ser Val Lys Val Ser Cys Lys Ala Ser Gly Tyr Ser Phe Thr Gly His
            20                  25                  30
```

Tyr Ile His Trp Val Arg Gln Ala Pro Gly Gln Gly Leu Glu Trp Met
            35                  40                  45

Gly Trp Ile Asn Pro Tyr Ser Gly Gly Thr Asn Phe Pro Arg Glu Phe
    50                  55                  60

Gln Gly Arg Val Thr Met Thr Arg Asp Thr Ser Val Asn Thr Val Tyr
65                  70                  75                  80

Met Glu Leu Thr Arg Leu Thr Ser Asp Thr Ser Val Tyr Tyr Cys
                85                  90                  95

Ala Arg Asp His Arg Ile Val Gly Gly Leu Asp Tyr Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Ser Tyr Val Leu Thr Gln Pro Pro Ser Ala
            130                 135                 140

Ser Gly Thr Pro Gly Gln Arg Val Thr Ile Ser Cys Ser Gly Ser Ser
145                 150                 155                 160

Ser Asn Ile Gly Ile Asn Tyr Val Tyr Trp Tyr Gln Gln Leu Pro Gly
                165                 170                 175

Thr Ala Pro Lys Leu Leu Ile Tyr Arg Asn Asp Gln Arg Pro Ser Gly
            180                 185                 190

Val Pro Asp Arg Phe Ser Gly Ser Lys Ser Gly Thr Ser Ala Ser Leu
            195                 200                 205

Ala Ile Ser Gly Leu Arg Ser Glu Asp Glu Ala Asp Tyr Tyr Cys Ala
            210                 215                 220

Thr Trp Asp Asp Ser Leu Ser Gly Val Val Phe Gly Gly Gly Thr Lys
225                 230                 235                 240

Val Thr Val Leu

<210> SEQ ID NO 140
<211> LENGTH: 732
<212> TYPE: DNA
<213> ORGANISM: Artificial Sequence
<220> FEATURE:
<223> OTHER INFORMATION: Synthetic (coding DNA of Anti-VEGF scFv)

<400> SEQUENCE: 140
gaggtgcagc tggtgcagag cggcgccgag gtgcgcaagc ccggcgccag cgtgaaggtg      60
agctgcaagg ccagcggcta cagcttcacc ggccactaca tccactgggt gcgccaggcc    120
cccggccagg gcctggagtg gatgggctgg atcaacccct acagcggcgg caccaacttc    180
ccccgcgagt tccagggccg cgtgaccatg acccgcgaca ccagcgtgaa caccgtgtac    240
atggagctga cccgcctgac cagcgacgac accagcgtgt actactgcgc cgcgaccac    300 cgcatcgtgg gcggcctgga ctactggggc cagggcaccc tggtgaccgt gagcagcggc    360
ggcggcggca gcggcggcgg cggcagcggc ggcggcggca gcagctacgt gctgacccag    420 cccccccagcg ccagcggcac ccccggccag cgcgtgacca tcagctgcag cggcagcagc    480
agcaacatcg gcatcaacta cgtgtactgg taccagcagc tgcccggcac cgcccccaag    540
ctgctgatct accgcaacga ccagcgcccc agcggcgtgc ccgaccgctt cagcggcagc    600
aagagcggca ccagcgccag cctggccatc agcggcctgc gcagcgagga cgaggccgac    660
tactactgcg ccacctggga cgacagcctg agcggcgtgg tgttcggcgg cggcaccaag    720
gtgaccgtgc tg    732

<210> SEQ ID NO 141
<211> LENGTH: 3198
<212> TYPE: DNA
<213> ORGANISM: Artificial Sequence
<220> FEATURE:
<223> OTHER INFORMATION: Synthetic (DNA sequence for preparing anti-cMet/VEGF bispecific antibody)

<400> SEQUENCE: 141

```
aagcttgcca ccatgggatg gtcatgtatc atccttttc tagtagcaac tgcaactgga      60
gtacattcag aggttcagct ggtggagtct ggcggtggcc tggtgcagcc aggggggctca    120
ctccgtttgt cctgtgcagc ttctggcttc accttcactg attactacat gagctgggtg    180
cgtcaggccc cgggtaaggg cctggaatgg ttgggtttta ttagaaacaa agctaatggt    240
tacacaacag agtacagtgc atctgtgaag ggtcgtttca ctataagcag agataattcc    300
aaaaacacac tgtacctgca gatgaacagc ctgcgtgctg aggacactgc cgtctattat    360
tgtgctagag ataactggtt tgcttactgg ggccaaggga ctctggtcac cgtctcctcg    420
ggcctgggcg gcctggcgg cggcggcagc ggcggcggcg gcagcggcgg cagcagcggc    480
gtgggcagcg atatccagat gacccagtcc ccgagctccc tgtccgcctc tgtgggcgat    540
agggtcacca tcacctgcaa gtccagtcag agtcttttag ctagtggcaa ccaaaataac    600
tacttggcct ggcaccaaca gaaaccagga aaagctccga aatgctgat tattgggca     660
tccactaggg tatctggagt cccttctcgc ttctctggct ccgggtctgg gacggatttc    720
actctgacca tcagcagtct gcagccggaa gacttcgcaa cttattactg tcagcagtcc    780
tacagccgcc cgtacacgtt cggacagggt accaaggtgg agatcaaacg tgagcccaaa    840
tcttgtgaca aaactcacac atgcccaccg tgcccagcac ctgaactcct ggggggaccg    900
tcagtcttcc tcttcccccc aaaacccaag gacaccctca tgatctcccg gacccctgag    960
gtcacatgcg tggtggtgga cgtgagccac gaagaccctg aggtcaagtt caactggtac   1020
gtggacggcg tggaggtgca taatgccaag acaaagccgc gggaggagca gtacaacagc   1080
acgtaccgtg tggtcagcgt cctcaccgtc ctgcaccagg actggctgaa tggcaaggag   1140
tacaagtgca aggtctccaa caaagccctc ccagccccca tcgagaaaac catctccaaa   1200
gccaaagggc agccccgaga accacaggtg tacaccctgc ccccatcccg ggaagagatg   1260
accaagaacc aggtcagcct gacctgcctg gtcaaaggct tctatcccag cgacatcgcc   1320
gtggagtggg agagcaatgg gcagccggag aacaactaca agaccacgcc tcccgtgctg   1380
gactccgacg gctccttctt cctctacagc aagctcaccg tggacaagag caggtggcag   1440
caggggaacg tcttctcatg ctccgtgatg catgaggctc tgcacaacca ctacacgcag   1500
aagagcctct ccctgtctcc gggtaaaatg cagatcttcg tgaaacccct gaccggcaag   1560
accatcaccc tggaagtgga accagcgac accatcgaga cgtgaaggc caagatccag   1620
gacaaagagg gcatcccccc cgaccagcag agactgatct cgccggcaa gcagctggaa   1680
gatggcagaa ccctgagcga ctacaacatc cagaaagagt ccaccctgca cctggtgctg   1740
cggctgagag gcggaggatc cgaggtgcag ctggtgcaga gcggcgccga ggtgcgcaag   1800
cccgcgcca gcgtgaaggt gagctgcaag gccagcggct acagcttcac cggccactac   1860
atccactggg tgcgccaggc ccccggccag ggcctggagt ggatgggctg atcaacccc   1920
tacagcggcg gcaccaactt ccccgcgag ttcagggcc gcgtgaccat gacccgcgac   1980
accagcgtga acaccgtgta catggagctg acccgcctga ccagcgacga caccagcgtg   2040
tactactgcg cccgcgacca ccgcatcgtg ggcggcctgg actactgggg ccagggcacc   2100
```

-continued

```
ctggtgaccg tgagcagcgg cggcggcggc agcggcggcg gcggcagcgg cggcggcggc    2160
agcagctacg tgctgaccca gcccccagc gccagcggca cccccggcca gcgcgtgacc    2220
atcagctgca gcggcagcag cagcaacatc ggcatcaact acgtgtactg gtaccagcag    2280
ctgcccggca cgcccccaa gctgctgatc taccgcaacg accagcgccc agcggcgtg    2340 cccgaccgct tcagcggcag caagagcggc accagcgcca gcctggccat cagcggcctg    2400
cgcagcgagg acgaggccga ctactactgc gccacctggg acgacagcct gagcggcgtg    2460
gtgttcggcg gcggcaccaa ggtgaccgtg ctggagccca atcttgtga caaaactcac    2520 acatgcccac cgtgcccagc acctgaactc ctggggggac cgtcagtctt cctcttcccc    2580
ccaaaaccca aggacaccct catgatctcc cggacccctg aggtcacatg cgtggtggtc    2640
gacgtgagcc acgaagaccc tgaggtcaag ttcaactggt acgtggacgg cgtggaggtg    2700
cataatgcca agacaaagcc gcgggaggag cagtacaaca gcacgtaccg tgtggtcagc    2760
gtcctcaccg tcctgcacca ggactggctg aatggcaagg agtacaagtg caaggtctcc    2820
aacaaagccc tcccagcccc catcgagaaa accatctcca aagccaaagg gcagccccga    2880
gaaccacagg tgtacaccct gcccccatcc cgggaagaga tgaccaagaa ccaggtcagc    2940
ctgacctgcc tggtcaaagg cttctatccc agcgacatcg ccgtggagtg ggagagcaat    3000
gggcagccgg agaacaacta caagaccacg cctcccgtgc tggactccga cggctccttc    3060
ttcctctaca gcaagctcac cgtggacaag agcaggtggc agcaggggaa cgtcttctca    3120
tgctccgtga tgcatgaggc tctgcacaac cactacacgc agaagagcct ctccctgtct    3180
ccgggtaaat gactcgag                                                 3198
```

<210> SEQ ID NO 142
<211> LENGTH: 1040
<212> TYPE: PRT
<213> ORGANISM: Artificial Sequence
<220> FEATURE:
<223> OTHER INFORMATION: Synthetic (anti-cMet/VEGF bispecific antibody
     with knob and hole)

<400> SEQUENCE: 142

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Gly Leu Gly Gly Leu Gly Gly Gly Gly Ser Gly
        115                 120                 125

Gly Gly Gly Ser Gly Gly Ser Ser Gly Val Gly Ser Asp Ile Gln Met
    130                 135                 140

Thr Gln Ser Pro Ser Ser Leu Ser Ala Ser Val Gly Asp Arg Val Thr
145                 150                 155                 160
```

-continued

```
Ile Thr Cys Lys Ser Ser Gln Ser Leu Leu Ala Ser Gly Asn Gln Asn
                165                 170                 175

Asn Tyr Leu Ala Trp His Gln Gln Lys Pro Gly Lys Ala Pro Lys Met
            180                 185                 190

Leu Ile Ile Trp Ala Ser Thr Arg Val Ser Gly Val Pro Ser Arg Phe
        195                 200                 205

Ser Gly Ser Gly Ser Gly Thr Asp Phe Thr Leu Thr Ile Ser Ser Leu
    210                 215                 220

Gln Pro Glu Asp Phe Ala Thr Tyr Tyr Cys Gln Gln Ser Tyr Ser Arg
225                 230                 235                 240

Pro Tyr Thr Phe Gly Gln Gly Thr Lys Val Glu Ile Lys Arg Glu Pro
                245                 250                 255

Lys Ser Cys Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
    290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
        355                 360                 365

Ala Pro Ile Glu Lys Thr Ile Ser Lys Ala Lys Gly Gln Pro Arg Glu
    370                 375                 380

Pro Gln Val Tyr Thr Leu Pro Pro Ser Arg Glu Glu Met Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Lys
        435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys Met Gln Ile Phe Val Lys Thr Leu Thr Gly
                485                 490                 495

Lys Thr Ile Thr Leu Glu Val Glu Pro Ser Asp Thr Ile Glu Asn Val
            500                 505                 510

Lys Ala Lys Ile Gln Asp Lys Glu Gly Ile Pro Pro Asp Gln Gln Arg
        515                 520                 525

Leu Ile Phe Ala Gly Lys Gln Leu Glu Asp Gly Arg Thr Leu Ser Asp
    530                 535                 540

Tyr Asn Ile Gln Lys Glu Ser Thr Leu His Leu Val Leu Arg Leu Arg
545                 550                 555                 560

Gly Gly Gly Ser Glu Val Gln Leu Val Gln Ser Gly Ala Glu Val Arg
                565                 570                 575
```

```
Lys Pro Gly Ala Ser Val Lys Val Ser Cys Lys Ala Ser Gly Tyr Ser
            580                 585                 590

Phe Thr Gly His Tyr Ile His Trp Val Arg Gln Ala Pro Gly Gln Gly
            595                 600                 605

Leu Glu Trp Met Gly Trp Ile Asn Pro Tyr Ser Gly Gly Thr Asn Phe
610                 615                 620

Pro Arg Glu Phe Gln Gly Arg Val Thr Met Thr Arg Asp Thr Ser Val
625                 630                 635                 640

Asn Thr Val Tyr Met Glu Leu Thr Arg Leu Thr Ser Asp Asp Thr Ser
            645                 650                 655

Val Tyr Tyr Cys Ala Arg Asp His Arg Ile Val Gly Gly Leu Asp Tyr
            660                 665                 670

Trp Gly Gln Gly Thr Leu Val Thr Val Ser Ser Gly Gly Gly Gly Ser
            675                 680                 685

Gly Gly Gly Gly Ser Gly Gly Gly Ser Ser Tyr Val Leu Thr Gln
            690                 695                 700

Pro Pro Ser Ala Ser Gly Thr Pro Gly Gln Arg Val Thr Ile Ser Cys
705                 710                 715                 720

Ser Gly Ser Ser Ser Asn Ile Gly Ile Asn Tyr Val Tyr Trp Tyr Gln
            725                 730                 735

Gln Leu Pro Gly Thr Ala Pro Lys Leu Leu Ile Tyr Arg Asn Asp Gln
            740                 745                 750

Arg Pro Ser Gly Val Pro Asp Arg Phe Ser Gly Ser Lys Ser Gly Thr
            755                 760                 765

Ser Ala Ser Leu Ala Ile Ser Gly Leu Arg Ser Glu Asp Glu Ala Asp
            770                 775                 780

Tyr Tyr Cys Ala Thr Trp Asp Asp Ser Leu Ser Gly Val Val Phe Gly
785                 790                 795                 800

Gly Gly Thr Lys Val Thr Val Leu Glu Pro Lys Ser Cys Asp Lys Thr
            805                 810                 815

His Thr Cys Pro Pro Cys Pro Ala Pro Glu Leu Leu Gly Gly Pro Ser
            820                 825                 830

Val Phe Leu Phe Pro Pro Lys Pro Lys Asp Thr Leu Met Ile Ser Arg
            835                 840                 845

Thr Pro Glu Val Thr Cys Val Val Val Asp Val Ser His Glu Asp Pro
850                 855                 860

Glu Val Lys Phe Asn Trp Tyr Val Asp Gly Val Glu Val His Asn Ala
865                 870                 875                 880

Lys Thr Lys Pro Arg Glu Glu Gln Tyr Asn Ser Thr Tyr Arg Val Val
            885                 890                 895

Ser Val Leu Thr Val Leu His Gln Asp Trp Leu Asn Gly Lys Glu Tyr
            900                 905                 910

Lys Cys Lys Val Ser Asn Lys Ala Leu Pro Ala Pro Ile Glu Lys Thr
            915                 920                 925

Ile Ser Lys Ala Lys Gly Gln Pro Arg Glu Pro Gln Val Tyr Thr Leu
            930                 935                 940

Pro Pro Ser Arg Glu Glu Met Thr Lys Asn Gln Val Ser Leu Thr Cys
945                 950                 955                 960

Leu Val Lys Gly Phe Tyr Pro Ser Asp Ile Ala Val Glu Trp Glu Ser
            965                 970                 975

Asn Gly Gln Pro Glu Asn Asn Tyr Lys Thr Thr Pro Pro Val Leu Asp
            980                 985                 990

Ser Asp Gly Ser Phe Phe Leu Tyr  Ser Lys Leu Thr Val  Asp Lys Ser
```

```
            995                 1000                1005
Arg Trp Gln Gln Gly Asn Val Phe Ser Cys Ser Val Met His Glu
    1010                1015                1020

Ala Leu His Asn His Tyr Thr Gln Lys Ser Leu Ser Leu Ser Pro
    1025                1030                1035

Gly Lys
    1040

<210> SEQ ID NO 143
<211> LENGTH: 3120
<212> TYPE: DNA
<213> ORGANISM: Artificial Sequence
<220> FEATURE:
<223> OTHER INFORMATION: Synthetic (Coding DNA of anti-cMet/VEGF
      bispecific antibody)

<400> SEQUENCE: 143
```

| | | | | | |
|---|---|---|---|---|---|
| gaggttcagc | tggtggagtc | tggcggtggc | ctggtgcagc | caggggggctc | actccgtttg | 60 |
| tcctgtgcag | cttctggctt | caccttcact | gattactaca | tgagctgggt | gcgtcaggcc | 120 |
| ccgggtaagg | gcctggaatg | gttgggtttt | attagaaaca | aagctaatgg | ttacacaaca | 180 |
| gagtacagtg | catctgtgaa | gggtcgtttc | actataagca | gagataattc | caaaaacaca | 240 |
| ctgtacctgc | agatgaacag | cctgcgtgct | gaggacactg | ccgtctatta | ttgtgctaga | 300 |
| gataactggt | ttgcttactg | gggccaaggg | actctggtca | ccgtctcctc | gggcctgggc | 360 |
| ggcctgggcg | gcggcggcag | cggcggcggc | ggcagcggcg | gcagcagcgg | cgtgggcagc | 420 |
| gatatccaga | tgacccagtc | cccgagctcc | ctgtccgcct | ctgtgggcga | tagggtcacc | 480 |
| atcacctgca | agtccagtca | gagtctttta | gctagtggca | accaaaataa | ctacttggcc | 540 |
| tggcaccaac | agaaaccagg | aaaagctccg | aaaatgctga | ttatttgggc | atccactagg | 600 |
| gtatctggag | tccccttctcg | cttctctggc | tccgggtctg | gacggatttt | cactctgacc | 660 |
| atcagcagtc | tgcagccgga | agacttcgca | acttattact | gtcagcagtc | ctacagccgc | 720 |
| ccgtacacgt | tcggacaggg | taccaaggtg | gagatcaaac | gtgagcccaa | atcttgtgac | 780 |
| aaaactcaca | catgcccacc | gtgcccagca | cctgaactcc | tggggggacc | gtcagtcttc | 840 |
| ctcttccccc | caaaacccaa | ggacaccctc | atgatctccc | ggaccctgag | gtcacatgc | 900 |
| gtggtggtgg | acgtgagcca | cgaagaccct | gaggtcaagt | tcaactggta | cgtgacggc | 960 |
| gtggaggtgc | ataatgccaa | gacaaagccg | cgggaggagc | agtacaacag | cacgtaccgt | 1020 |
| gtggtcagcg | tcctcaccgt | cctgcaccag | gactggctga | atggcaagga | gtacaagtgc | 1080 |
| aaggtctcca | acaaagccct | cccagccccc | atcgagaaaa | ccatctccaa | agccaaaggg | 1140 |
| cagccccgag | aaccacaggt | gtacaccctg | cccccatccc | gggaagagat | gaccaagaac | 1200 |
| caggtcagcc | tgacctgcct | ggtcaaaggc | ttctatccca | gcgacatcgc | cgtggagtgg | 1260 |
| gagagcaatg | ggcagccgga | gaacaactac | aagaccacgc | ctcccgtgct | ggactccgac | 1320 |
| ggctccttct | tcctctacag | caagctcacc | gtggacaaga | gcaggtggca | gcaggggaac | 1380 |
| gtcttctcat | gctccgtgat | gcatgaggct | ctgcacaacc | actacacgca | gaagagcctc | 1440 |
| tccctgtctc | cgggtaaaat | gcagatcttc | gtgaaaaccc | tgaccggcaa | gaccatcacc | 1500 |
| ctggaagtgg | aacccagcga | caccatcgag | aacgtgaagg | ccaagatcca | ggacaaagag | 1560 |
| ggcatccccc | ccgaccagca | gagactgatc | ttcgccggca | agcagctgga | agatggcaga | 1620 |
| accctgagcg | actacaacat | ccagaaagag | tccaccctgc | acctggtgct | gcggctgaga | 1680 |
| ggcggaggat | ccgaggtgca | gctggtgcag | agcggcgccg | aggtgcgcaa | gcccggcgcc | 1740 |

```
agcgtgaagg tgagctgcaa ggccagcggc tacagcttca ccggccacta catccactgg    1800
gtgcgccagg ccccccggcca gggcctggag tggatgggct ggatcaaccc ctacagcggc   1860
ggcaccaact tcccccgcga gttccagggc cgcgtgacca tgacccgcga caccagcgtg    1920
aacaccgtgt acatggagct gacccgcctg accagcgacg acaccagcgt gtactactgc    1980
gcccgcgacc accgcatcgt gggcggcctg gactactggg gccagggcac cctggtgacc    2040
gtgagcagcg gcggcggcgg cagcggcggc ggcggcagcg gcggcggcgg cagcagctac    2100
gtgctgaccc agccccccag cgccagcggc accccccggcc agcgcgtgac catcagctgc    2160
agcggcagca gcagcaacat cggcatcaac tacgtgtact ggtaccagca gctgcccggc    2220
accgccccca gctgctgat ctaccgcaac gaccagcgcc ccagcggcgt gcccgaccgc      2280
ttcagcggca gcaagagcgg caccagcgcc agcctggcca tcagcggcct gcgcagcgag    2340
gacgaggccg actactactg cgccacctgg gacgacagcc tgagcggcgt ggtgttcggc    2400
ggcggcacca aggtgaccgt gctggagccc aaatcttgtg acaaaactca cacatgccca    2460
ccgtgcccag cacctgaact cctggggggga ccgtcagtct tcctcttccc cccaaaaccc   2520
aaggacaccc tcatgatctc ccggaccccct gaggtcacat gcgtggtggt cgacgtgagc   2580
cacgaagacc ctgaggtcaa gttcaactgg tacgtggacg gcgtggaggt gcataatgcc   2640
aagacaaagc cgcgggagga gcagtacaac agcacgtacc gtgtggtcag cgtcctcacc    2700
gtcctgcacc aggactggct gaatggcaag gagtacaagt gcaaggtctc caacaaagcc   2760
ctcccagccc ccatcgagaa aaccatctcc aaagccaaag gcagccccg agaaccacag    2820
gtgtacaccc tgcccccatc ccgggaagag atgaccaaga accaggtcag cctgacctgc    2880
ctggtcaaag gcttctatcc cagcgacatc gccgtggagt gggagagcaa tgggcagccg   2940
gagaacaact acaagaccac gcctcccgtg ctggactccg acggctcctt cttcctctac    3000
agcaagctca ccgtggacaa gagcaggtgg cagcagggga acgtcttctc atgctccgtg    3060
atgcatgagg ctctgcacaa ccactacacg cagaagagcc tctccctgtc tccgggtaaa    3120
```

<210> SEQ ID NO 144
<211> LENGTH: 232
<212> TYPE: PRT
<213> ORGANISM: Artificial Sequence
<220> FEATURE:
<223> OTHER INFORMATION: Synthetic (Fc (Hinge-C2-C3) without knob/hole)

<400> SEQUENCE: 144

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
```

```
                    115                 120                 125
Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 145
<211> LENGTH: 696
<212> TYPE: DNA
<213> ORGANISM: Artificial Sequence
<220> FEATURE:
<223> OTHER INFORMATION: Synthetic (gene coding SEQ ID NO: 144)

<400> SEQUENCE: 145
gagcccaaat cttgtgacaa aactcacaca tgcccaccgt gcccagcacc tgaactcctg      60
gggggcccgt cagtcttcct cttccccccc aaacccaagg acaccctcat gatctcccgg     120
acccctgagg tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagccctcc cagcccccat cgagaaaacc     360
atctccaaag ccaaagggca gccccgagaa ccacaggtgt acaccctgcc cccatcccgg     420
gaagagatga ccaagaacca ggtcagcctg acctgcctgg tcaaaggctt ctatcccagc     480
gacatcgccg tggagtggga gagcaatggg cagccggaga acaactacaa gaccacgcct     540
cccgtgctgg actccgacgg ctccttcttc ctctacagca agctcaccgt ggacaagagc     600
aggtggcagc aggggaacgt cttctcatgc tccgtgatgc atgaggctct gcacaaccac     660
tacacgcaga agagcctctc cctgtctccg ggtaaa                              696

<210> SEQ ID NO 146
<211> LENGTH: 1040
<212> TYPE: PRT
<213> ORGANISM: Artificial Sequence
<220> FEATURE:
<223> OTHER INFORMATION: Synthetic (anti-cMet/VEGF bispecific antibody
      without knob and hole)

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60
```

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Arg Asp Asn Trp Phe Ala Tyr Trp Gly Gln Gly Thr Leu
            100                 105                 110

Val Thr Val Ser Ser Gly Leu Gly Gly Leu Gly Gly Gly Ser Gly
            115                 120                 125

Gly Gly Gly Ser Gly Gly Ser Ser Gly Val Gly Ser Asp Ile Gln Met
        130                 135                 140

Thr Gln Ser Pro Ser Ser Leu Ser Ala Ser Val Gly Asp Arg Val Thr
145                 150                 155                 160

Ile Thr Cys Lys Ser Ser Gln Ser Leu Leu Ala Ser Gly Asn Gln Asn
                165                 170                 175

Asn Tyr Leu Ala Trp His Gln Gln Lys Pro Gly Lys Ala Pro Lys Met
            180                 185                 190

Leu Ile Ile Trp Ala Ser Thr Arg Val Ser Gly Val Pro Ser Arg Phe
            195                 200                 205

Ser Gly Ser Gly Ser Gly Thr Asp Phe Thr Leu Thr Ile Ser Ser Leu
210                 215                 220

Gln Pro Glu Asp Phe Ala Thr Tyr Tyr Cys Gln Gln Ser Tyr Ser Arg
225                 230                 235                 240

Pro Tyr Thr Phe Gly Gln Gly Thr Lys Val Glu Ile Lys Arg Glu Pro
            245                 250                 255

Lys Ser Cys Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
            275                 280                 285

Thr Leu Met Ile Ser Arg Thr Pro Glu Val Thr Cys Val Val Val Asp
            290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
            325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
            355                 360                 365

Ala Pro Ile Glu Lys Thr Ile Ser Lys Ala Lys Gly Gln Pro Arg Glu
            370                 375                 380

Pro Gln Val Tyr Thr Leu Pro Pro Ser Arg Glu Glu Met Thr Lys Asn
385                 390                 395                 400

Gln Val Ser Leu Thr Cys Leu Val Lys Gly Phe Tyr Pro Ser Asp Ile
            405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Lys
            435                 440                 445

Leu Thr Val Asp Lys Ser Arg Trp Gln Gln Gly Asn Val Phe Ser Cys
            450                 455                 460

Ser Val Met His Glu Ala Leu His Asn His Tyr Thr Gln Lys Ser Leu
465                 470                 475                 480

-continued

Ser Leu Ser Pro Gly Lys Met Gln Ile Phe Val Lys Thr Leu Thr Gly
                485                 490                 495

Lys Thr Ile Thr Leu Glu Val Glu Pro Ser Asp Thr Ile Glu Asn Val
            500                 505                 510

Lys Ala Lys Ile Gln Asp Lys Glu Gly Ile Pro Pro Asp Gln Gln Arg
        515                 520                 525

Leu Ile Phe Ala Gly Lys Gln Leu Glu Asp Gly Arg Thr Leu Ser Asp
    530                 535                 540

Tyr Asn Ile Gln Lys Glu Ser Thr Leu His Leu Val Leu Arg Leu Arg
545                 550                 555                 560

Gly Gly Gly Ser Glu Val Gln Leu Val Gln Ser Gly Ala Glu Val Arg
                565                 570                 575

Lys Pro Gly Ala Ser Val Lys Val Ser Cys Lys Ala Ser Gly Tyr Ser
            580                 585                 590

Phe Thr Gly His Tyr Ile His Trp Val Arg Gln Ala Pro Gly Gln Gly
        595                 600                 605

Leu Glu Trp Met Gly Trp Ile Asn Pro Tyr Ser Gly Gly Thr Asn Phe
    610                 615                 620

Pro Arg Glu Phe Gln Gly Arg Val Thr Met Thr Arg Asp Thr Ser Val
625                 630                 635                 640

Asn Thr Val Tyr Met Glu Leu Thr Arg Leu Thr Ser Asp Asp Thr Ser
                645                 650                 655

Val Tyr Tyr Cys Ala Arg Asp His Arg Ile Val Gly Gly Leu Asp Tyr
            660                 665                 670

Trp Gly Gln Gly Thr Leu Val Thr Val Ser Ser Gly Gly Gly Gly Ser
        675                 680                 685

Gly Gly Gly Gly Ser Gly Gly Gly Ser Ser Tyr Val Leu Thr Gln
    690                 695                 700

Pro Pro Ser Ala Ser Gly Thr Pro Gly Gln Arg Val Thr Ile Ser Cys
705                 710                 715                 720

Ser Gly Ser Ser Ser Asn Ile Gly Ile Asn Tyr Val Tyr Trp Tyr Gln
                725                 730                 735

Gln Leu Pro Gly Thr Ala Pro Lys Leu Leu Ile Tyr Arg Asn Asp Gln
            740                 745                 750

Arg Pro Ser Gly Val Pro Asp Arg Phe Ser Gly Ser Lys Ser Gly Thr
        755                 760                 765

Ser Ala Ser Leu Ala Ile Ser Gly Leu Arg Ser Glu Asp Glu Ala Asp
    770                 775                 780

Tyr Tyr Cys Ala Thr Trp Asp Asp Ser Leu Ser Gly Val Val Phe Gly
785                 790                 795                 800

Gly Gly Thr Lys Val Thr Val Leu Glu Pro Lys Ser Cys Asp Lys Thr
                805                 810                 815

His Thr Cys Pro Pro Cys Pro Ala Pro Glu Leu Leu Gly Gly Pro Ser
            820                 825                 830

Val Phe Leu Phe Pro Pro Lys Pro Lys Asp Thr Leu Met Ile Ser Arg
        835                 840                 845

Thr Pro Glu Val Thr Cys Val Val Val Asp Val Ser His Glu Asp Pro
    850                 855                 860

Glu Val Lys Phe Asn Trp Tyr Val Asp Gly Val Glu Val His Asn Ala
865                 870                 875                 880

Lys Thr Lys Pro Arg Glu Glu Gln Tyr Asn Ser Thr Tyr Arg Val Val
                885                 890                 895

Ser Val Leu Thr Val Leu His Gln Asp Trp Leu Asn Gly Lys Glu Tyr

-continued

```
                 900                 905                 910
Lys Cys Lys Val Ser Asn Lys Ala Leu Pro Ala Pro Ile Glu Lys Thr
                915                 920                 925

Ile Ser Lys Ala Lys Gly Gln Pro Arg Glu Pro Gln Val Tyr Thr Leu
            930                 935                 940

Pro Pro Ser Arg Glu Glu Met Thr Lys Asn Gln Val Ser Leu Thr Cys
945                 950                 955                 960

Leu Val Lys Gly Phe Tyr Pro Ser Asp Ile Ala Val Glu Trp Glu Ser
                965                 970                 975

Asn Gly Gln Pro Glu Asn Asn Tyr Lys Thr Thr Pro Pro Val Leu Asp
            980                 985                 990

Ser Asp Gly Ser Phe Phe Leu Tyr Ser Lys Leu Thr Val Asp Lys Ser
        995                1000                1005

Arg Trp Gln Gln Gly Asn Val Phe Ser Cys Ser Val Met His Glu
    1010                1015                1020

Ala Leu His Asn His Tyr Thr Gln Lys Ser Leu Ser Leu Ser Pro
    1025                1030                1035

Gly Lys
   1040

<210> SEQ ID NO 147
<211> LENGTH: 108
<212> TYPE: PRT
<213> ORGANISM: Homo sapiens
<220> FEATURE:
<221> NAME/KEY: MOD_RES
<222> LOCATION: (58)..(58)
<223> OTHER INFORMATION: Xaa is Val or Met
<220> FEATURE:
<221> NAME/KEY: MOD_RES
<222> LOCATION: (70)..(70)
<223> OTHER INFORMATION: Xaa is Lys or Arg

<400> SEQUENCE: 147

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Asp Gly Gln Pro
        35                  40                  45

Glu Asn Asn Tyr Lys Thr Thr Pro Pro Xaa Leu Asp Ser Asp Gly Ser
    50                  55                  60

Phe Phe Leu Tyr Ser Xaa Leu Thr Val Asp Lys Ser Arg Trp Gln Gln
65                  70                  75                  80

Gly Asn Val Phe Ser Cys Ser Val Met His Glu Ala Leu His Asn His
                85                  90                  95

Tyr Thr Gln Lys Ser Leu Ser Leu Ser Pro Gly Lys
            100                 105

<210> SEQ ID NO 148
<211> LENGTH: 113
<212> TYPE: PRT
<213> ORGANISM: Homo sapiens
<220> FEATURE:
<221> NAME/KEY: MOD_RES
<222> LOCATION: (21)..(21)
<223> OTHER INFORMATION: Xaa is Asp or Asn
<220> FEATURE:
<221> NAME/KEY: MOD_RES
<222> LOCATION: (22)..(22)
<223> OTHER INFORMATION: Xaa is Glu or Gln
```

```
<220> FEATURE:
<221> NAME/KEY: MOD_RES
<222> LOCATION: (62)..(62)
<223> OTHER INFORMATION: Xaa is Glu or Gln

<400> SEQUENCE: 148

Gly Asn Thr Phe Arg Pro Gln Val His Leu Leu Pro Pro Ser Glu
1               5                   10                  15

Glu Leu Ala Leu Xaa Xaa Leu Val Thr Leu Thr Cys Leu Ala Arg Gly
            20                  25                  30

Phe Ser Pro Lys Asp Val Leu Val Arg Trp Leu Gln Gly Ser Gln Glu
            35                  40                  45

Leu Pro Arg Glu Lys Tyr Leu Thr Trp Ala Ser Arg Gln Xaa Pro Ser
50                  55                  60

Gln Gly Thr Thr Thr Phe Ala Val Thr Ser Ile Leu Arg Val Ala Ala
65                  70                  75                  80

Glu Asp Trp Lys Lys Gly Asp Thr Phe Ser Cys Met Val Gly His Glu
                85                  90                  95

Ala Leu Pro Leu Ala Phe Thr Gln Lys Thr Ile Asp Arg Leu Ala Gly
            100                 105                 110

Lys

<210> SEQ ID NO 149
<211> LENGTH: 107
<212> TYPE: PRT
<213> ORGANISM: Homo sapiens

<400> SEQUENCE: 149

Gln Ala Pro Val Lys Leu Ser Leu Asn Leu Leu Ala Ser Ser Asp Pro
1               5                   10                  15

Pro Glu Ala Ala Ser Trp Leu Leu Cys Glu Val Ser Gly Phe Ser Pro
            20                  25                  30

Pro Asn Ile Leu Leu Met Trp Leu Glu Asp Gln Arg Glu Val Asn Thr
            35                  40                  45

Ser Gly Phe Ala Pro Ala Arg Pro Pro Gln Pro Gly Ser Thr Thr
50                  55                  60

Phe Trp Ala Trp Ser Val Leu Arg Val Pro Ala Pro Pro Ser Pro Gln
65                  70                  75                  80

Pro Ala Thr Tyr Thr Cys Val Val Ser His Glu Asp Ser Arg Thr Leu
                85                  90                  95

Leu Asn Ala Ser Arg Ser Leu Glu Val Ser Tyr
            100                 105

<210> SEQ ID NO 150
<211> LENGTH: 110
<212> TYPE: PRT
<213> ORGANISM: Homo sapiens

<400> SEQUENCE: 150

Gly Pro Arg Ala Ala Pro Glu Val Tyr Ala Phe Ala Thr Pro Glu Trp
1               5                   10                  15

Pro Gly Ser Arg Asp Lys Arg Thr Leu Ala Cys Leu Ile Gln Asn Phe
            20                  25                  30

Met Pro Glu Asp Ile Ser Val Gln Trp Leu His Asn Glu Val Gln Leu
            35                  40                  45

Pro Asp Ala Arg His Ser Thr Thr Gln Pro Arg Lys Thr Lys Gly Ser
50                  55                  60
```

Gly Phe Phe Val Phe Ser Arg Leu Glu Val Thr Arg Ala Glu Trp Glu
65                  70                  75                  80

Gln Lys Asp Glu Phe Ile Cys Arg Ala Val His Glu Ala Ala Ser Pro
            85                  90                  95

Ser Gln Thr Val Gln Arg Ala Val Ser Val Asn Pro Gly Lys
        100                 105                 110

<210> SEQ ID NO 151
<211> LENGTH: 106
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Xaa is Glu or Gln
<220> FEATURE:
<221> NAME/KEY: MOD_RES
<222> LOCATION: (3)..(3)
<223> OTHER INFORMATION: Xaa is Asp or Asn
<220> FEATURE:
<221> NAME/KEY: MOD_RES
<222> LOCATION: (37)..(37)
<223> OTHER INFORMATION: Xaa is Asp or Asn
<220> FEATURE:
<221> NAME/KEY: MOD_RES
<222> LOCATION: (46)..(46)
<223> OTHER INFORMATION: Xaa is Glu or Gln
<220> FEATURE:
<221> NAME/KEY: MOD_RES
<222> LOCATION: (56)..(56)
<223> OTHER INFORMATION: Xaa is Asp or Asn
<220> FEATURE:
<221> NAME/KEY: MOD_RES
<222> LOCATION: (59)..(59)
<223> OTHER INFORMATION: Xaa is Glu or Gln
<220> FEATURE:
<221> NAME/KEY: MOD_RES
<222> LOCATION: (63)..(63)
<223> OTHER INFORMATION: Xaa is Asp or Asn
<220> FEATURE:
<221> NAME/KEY: MOD_RES
<222> LOCATION: (77)..(77)
<223> OTHER INFORMATION: Xaa is Asp or Asn
<220> FEATURE:
<221> NAME/KEY: MOD_RES
<222> LOCATION: (78)..(78)
<223> OTHER INFORMATION: Xaa is Asp or Asn
<220> FEATURE:
<221> NAME/KEY: MOD_RES
<222> LOCATION: (80)..(80)
<223> OTHER INFORMATION: Xaa is Asp or Asn

<400> SEQUENCE: 151

Asp Xaa Xaa Thr Ala Ile Arg Val Phe Ala Ile Pro Pro Ser Phe Ala
1               5                   10                  15

Ser Ile Phe Leu Thr Lys Ser Thr Lys Leu Thr Cys Leu Val Thr Asp
            20                  25                  30

Leu Thr Thr Tyr Xaa Ser Val Thr Ile Ser Trp Thr Arg Xaa Asp Gly
        35                  40                  45

Glu Ala Val Lys Thr His Thr Xaa Ile Ser Xaa Ser His Pro Xaa Ala
    50                  55                  60

Thr Phe Ser Ala Val Gly Glu Ala Ser Ile Cys Glu Xaa Xaa Trp Xaa
65                  70                  75                  80

Ser Gly Glu Arg Phe Thr Cys Thr Val Thr His Thr Asp Leu Pro Ser
            85                  90                  95

Pro Leu Lys Gln Thr Ile Ser Arg Pro Lys
        100                 105